US010160793B2

(12) United States Patent
Scheer et al.

(10) Patent No.: US 10,160,793 B2
(45) Date of Patent: Dec. 25, 2018

(54) METHODS OF TREATING INFLAMMATORY BOWEL DISEASE USING IL-22 FC FUSION PROTEINS

(71) Applicant: Genentech, Inc., South San Francisco, CA (US)

(72) Inventors: Justin Scheer, Ridgefield, CT (US); Wenjun Ouyang, Foster City, CA (US); Richard Vandlen, Hillsborough, CA (US); Philip E. Hass, Moss Beach, CA (US); Eric Gary Stefanich, Emerald Hills, CA (US); Xiaoting Wang, Berkeley, CA (US)

(73) Assignee: Genentech, Inc., South San Francisco, CA (US)

( * ) Notice: Subject to any disclaimer, the term of this patent is extended or adjusted under 35 U.S.C. 154(b) by 538 days.

(21) Appl. No.: 14/214,161

(22) Filed: Mar. 14, 2014

(65) Prior Publication Data

US 2014/0314711 A1    Oct. 23, 2014

Related U.S. Application Data

(60) Provisional application No. 61/860,176, filed on Jul. 30, 2013, provisional application No. 61/821,062, filed on May 8, 2013, provisional application No. 61/800,148, filed on Mar. 15, 2013, provisional application No. 61/800,795, filed on Mar. 15, 2013, provisional application No. 61/801,144, filed on Mar. 15, 2013.

(51) Int. Cl.
| | |
|---|---|
| *A61K 38/20* | (2006.01) |
| *C07K 14/54* | (2006.01) |
| *C07K 16/28* | (2006.01) |
| *A61K 47/38* | (2006.01) |
| *A61K 38/00* | (2006.01) |

(52) U.S. Cl.
CPC .............. *C07K 14/54* (2013.01); *A61K 38/20* (2013.01); *A61K 47/38* (2013.01); *C07K 16/2866* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,670,417 A | 6/1987 | Iwasaki et al. |
| 4,708,871 A | 11/1987 | Geysen |
| 4,717,717 A | 1/1988 | Finkenaur |
| 4,736,866 A | 4/1988 | Leder et al. |
| 4,791,192 A | 12/1988 | Nakagawa et al. |
| 4,816,567 A | 3/1989 | Cabilly et al. |
| 4,833,092 A | 5/1989 | Geysen |
| 4,873,191 A | 10/1989 | Wagner et al. |
| 5,010,182 A | 4/1991 | Brake et al. |
| 5,130,298 A | 7/1992 | Cini et al. |
| 5,223,409 A | 6/1993 | Ladner et al. |
| 5,364,934 A | 11/1994 | Drayna et al. |
| 5,403,484 A | 4/1995 | Ladner et al. |
| 5,427,778 A | 6/1995 | Finkenaur et al. |
| 5,457,093 A | 10/1995 | Cini et al. |
| 5,500,362 A | 3/1996 | Robinson et al. |
| 5,556,762 A | 9/1996 | Pinilla et al. |
| 5,571,689 A | 11/1996 | Heuckeroth et al. |
| 5,624,821 A | 4/1997 | Winter et al. |
| 5,648,237 A | 7/1997 | Carter |
| 5,648,260 A | 7/1997 | Winter et al. |
| 5,663,143 A | 9/1997 | Ley et al. |
| 5,705,485 A | 1/1998 | Cini et al. |
| 5,750,373 A | 5/1998 | Garrard et al. |
| 5,789,199 A | 8/1998 | Joly et al. |
| 5,821,333 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,267,958 B1 | 7/2001 | Andya et al. |
| 6,331,309 B1 | 12/2001 | Jennings, Jr. et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,737,056 B1 | 5/2004 | Presta |
| 6,939,545 B2 | 9/2005 | Jacobs et al. |
| 7,125,978 B1 | 10/2006 | Vezina et al. |
| 7,265,203 B2 | 9/2007 | Presnell et al. |
| 7,332,581 B2 | 2/2008 | Presta |
| 7,371,826 B2 | 5/2008 | Presta |
| 7,414,024 B2 | 8/2008 | Blay et al. |
| 7,521,541 B2 | 4/2009 | Eigenbrot et al. |
| 7,638,604 B2 | 12/2009 | Li et al. |
| 7,642,228 B2 | 1/2010 | Carter et al. |

(Continued)

FOREIGN PATENT DOCUMENTS

| | | |
|---|---|---|
| CN | 1 260834 A | 7/2000 |
| CN | 1 280497 A | 1/2001 |

(Continued)

OTHER PUBLICATIONS

Beck et al., "Trends in Glycosylation, Glycoanalysis and Glycoengineering of Therapeutic Antibodies and Fc-Fusion Proteins" Current Pharmaceutical Biotechnology 9:482-501 ( 2008).

(Continued)

*Primary Examiner* — Dong Jiang
(74) *Attorney, Agent, or Firm* — Clark & Elbing LLP; Karen L. Elbing

(57) ABSTRACT

The invention relates to IL-22 polypeptides, IL-22 Fc fusion proteins and IL-22 agonists, composition comprising the same, methods of making and methods of using the composition for the treatment of diseases. The invention also relates to IL-22 receptor associated reagents and methods of use thereof.

30 Claims, 69 Drawing Sheets

Specification includes a Sequence Listing.

(56) References Cited

U.S. PATENT DOCUMENTS

| | | | |
|---|---|---|---|
| 8,338,569 B2* | 12/2012 | Marshall | C07K 14/71 424/184.1 |
| 9,815,880 B2 | 11/2017 | Scheer et al. | |
| 2001/0023070 A1 | 9/2001 | Ebner et al. | |
| 2002/0164328 A1 | 11/2002 | Shinkawa et al. | |
| 2003/0099649 A1 | 5/2003 | Jacobs et al. | |
| 2003/0115614 A1 | 6/2003 | Kanda et al. | |
| 2003/0143697 A1 | 7/2003 | Stahl et al. | |
| 2003/0157106 A1 | 8/2003 | Jacobs et al. | |
| 2003/0157108 A1 | 8/2003 | Presta | |
| 2003/0170823 A1 | 9/2003 | Presnell et al. | |
| 2003/0235561 A1 | 12/2003 | Vandenburgh et al. | |
| 2004/0023341 A1 | 2/2004 | Xu et al. | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0042220 A1 | 2/2005 | Li et al. | |
| 2005/0079578 A1 | 4/2005 | Centanni et al. | |
| 2005/0089957 A1 | 4/2005 | Goddard et al. | |
| 2005/0123546 A1 | 6/2005 | Umana et al. | |
| 2005/0158317 A1 | 7/2005 | Blay et al. | |
| 2005/0260186 A1 | 11/2005 | Bookbinder et al. | |
| 2005/0277593 A1 | 12/2005 | Dieckgraefe et al. | |
| 2006/0104968 A1 | 5/2006 | Bookbinder et al. | |
| 2007/0212356 A1 | 9/2007 | Chen et al. | |
| 2008/0031882 A1 | 2/2008 | Liang et al. | |
| 2008/0138314 A1 | 6/2008 | Huang et al. | |
| 2009/0010875 A1 | 1/2009 | Lauder et al. | |
| 2009/0202475 A1 | 8/2009 | Abbas et al. | |
| 2010/0087627 A1* | 4/2010 | Marshall | C07K 14/71 530/362 |
| 2011/0118173 A1 | 5/2011 | Pownall et al. | |
| 2011/0280828 A1 | 11/2011 | Abbas et al. | |
| 2011/0287009 A1 | 11/2011 | Scheer et al. | |
| 2013/0052159 A1 | 2/2013 | Abbas et al. | |
| 2013/0121959 A1* | 5/2013 | Maxwell | C07K 14/54 424/85.2 |
| 2013/0171100 A1 | 7/2013 | Yan et al. | |
| 2014/0286898 A1* | 9/2014 | Gavin | C07K 14/55 424/85.2 |
| 2017/0008942 A1 | 1/2017 | Scheer et al. | |
| 2017/0088596 A1 | 3/2017 | Scheer et al. | |
| 2017/0320926 A1 | 11/2017 | Scheer et al. | |

FOREIGN PATENT DOCUMENTS

| | | |
|---|---|---|
| CN | 1 01225110 A | 7/2008 |
| EP | 0117060 A2 | 8/1984 |
| EP | 0117060 A3 | 8/1984 |
| EP | 0036776 B1 | 5/1988 |
| EP | 0 117 058 B1 | 9/1989 |
| EP | 0 362 179 A2 | 4/1990 |
| EP | 0 362 179 A3 | 4/1990 |
| EP | 0 073 657 B1 | 12/1990 |
| EP | 1748789 B1 | 12/2010 |
| JP | 2008-502317 A | 1/2008 |
| JP | 2008-526740 A | 7/2008 |
| JP | 2011-50310 A | 1/2011 |
| JP | 2012-515165 A | 7/2012 |
| RU | 2006101702 A | 9/2006 |
| RU | 2302460 C1 | 7/2007 |
| RU | 2367471 C2 | 9/2009 |
| WO | 84/03506 | 9/1984 |
| WO | 84/03564 | 9/1984 |
| WO | 87/05330 A1 | 9/1987 |
| WO | 89/05859 A1 | 6/1989 |
| WO | 90/13646 A1 | 11/1990 |
| WO | 94/29351 A2 | 12/1994 |
| WO | 94/29351 A3 | 12/1994 |
| WO | 97/30087 A1 | 8/1997 |
| WO | WO-98/51794 A1 | 11/1998 |
| WO | 98/58964 A1 | 12/1998 |
| WO | WO-99/17786 A1 | 4/1999 |
| WO | 99/22764 A1 | 5/1999 |
| WO | 99/51642 A1 | 10/1999 |
| WO | 99/61617 A1 | 12/1999 |
| WO | 00/00823 | 1/2000 |
| WO | 00/24758 A1 | 5/2000 |
| WO | 00/39585 A1 | 7/2000 |
| WO | 00/61739 A1 | 10/2000 |
| WO | 00/65027 A2 | 11/2000 |
| WO | 00/65027 A3 | 11/2000 |
| WO | 00/73454 A1 | 12/2000 |
| WO | 00/73457 A1 | 12/2000 |
| WO | 01/29246 A1 | 4/2001 |
| WO | 01/046422 A1 | 6/2001 |
| WO | 02/16611 A2 | 2/2002 |
| WO | 02/16611 A3 | 2/2002 |
| WO | 02/031140 A1 | 4/2002 |
| WO | WO-02/29098 A2 | 4/2002 |
| WO | 02/068476 A2 | 9/2002 |
| WO | 02/068476 A3 | 9/2002 |
| WO | 02/077174 A2 | 10/2002 |
| WO | 02/077174 A3 | 10/2002 |
| WO | 03/011878 A2 | 2/2003 |
| WO | 03/011878 A3 | 2/2003 |
| WO | 03/084570 A1 | 10/2003 |
| WO | 03/085107 A1 | 10/2003 |
| WO | 03/085119 A1 | 10/2003 |
| WO | 2004/056312 A2 | 7/2004 |
| WO | 2004/056312 A3 | 7/2004 |
| WO | WO-2004/096273 A1 | 11/2004 |
| WO | 2005/000897 A2 | 1/2005 |
| WO | 2005/000897 A3 | 1/2005 |
| WO | 2005/035586 A1 | 4/2005 |
| WO | 2005/035778 A1 | 4/2005 |
| WO | 2005/053742 A1 | 6/2005 |
| WO | 2005/063820 A2 | 7/2005 |
| WO | 2005/100402 A1 | 10/2005 |
| WO | 2006/029879 A2 | 3/2006 |
| WO | 2006/044908 A2 | 4/2006 |
| WO | 2006/044908 A3 | 4/2006 |
| WO | 2006/073508 A1 | 7/2006 |
| WO | 2006/138468 A2 | 12/2006 |
| WO | 2006/138468 A3 | 12/2006 |
| WO | WO-2007/081608 A2 | 7/2007 |
| WO | 2007/098170 A1 | 8/2007 |
| WO | 2008/112543 A2 | 9/2008 |
| WO | 2008/112543 A3 | 9/2008 |
| WO | 2009/020844 A1 | 2/2009 |
| WO | 2009/062102 A2 | 5/2009 |
| WO | 2009/062102 A3 | 5/2009 |
| WO | 2009/117640 A2 | 9/2009 |
| WO | 2009/117640 A3 | 9/2009 |
| WO | 2010/081112 A1 | 7/2010 |
| WO | 2011/033249 A1 | 3/2011 |
| WO | 2011/087986 A1 | 7/2011 |
| WO | 2012/028089 A1 | 3/2012 |
| WO | 2013/055958 | 4/2013 |
| WO | 2013/097748 A1 | 7/2013 |
| WO | 2013/121959 A1 | 8/2013 |

OTHER PUBLICATIONS

Hamako et al., "Comparative Studies of Asparagine-Linked Sugar Chains of Immunoglobulin G from Eleven Mammalian Species" Comparative Biochemistry and Physiology 106(4):949-954 (1993).

Hristodorov et al., "With or Without Sugar? (A) Glycosylation of Therapeutic Antibodies" Molecular Biotechnology 54(3):1056-1068 (2012).

International Search Report for International Patent Application No. PCT/US2014/029652 dated January 20, 2015

Niwa et al., "IgG Subclass-Independent Improvement of Antibody-Dependent Cellular Cytotoxicity by Fucose Removal from Asn297-Linked Oligosaccharides" Journal of Immunological Methods 306(1-2):151-160 (2005).

Shields et al., Journal of Biological Chemistry 277(30):26733-26740 (2002).

(56) References Cited

OTHER PUBLICATIONS

Xie et al., "Interleukin (IL)-22, a Novel Human Cytokine that Signals Through the Interferon Receptor-Related Proteins CRF2-4 and IL-22R" Journal of Biological Chemistry 275(40):31335-31339 (2000).
Adams et al., "Molecular cloning of mouse immunoglobulin heavy chain messenger ribonucleic acids coding for μ, α, γ1, γ2a, and γ3 chains" Biochem 19:2711-2719 ( 1980).
Andoh et al., "Interleukin-22, a member of the IL-10 subfamily, induces inflammatory responses in colonic subepithelial myofibroblasts" Gastroenterology 129:969-984 (2005).
Apelqvist et al., "What is the most effective way to reduce incidence of amputation in the diabetic foot?" Diabetes Metab Res 16( Suppl 1):S75-S83 ( 2000).
Apelqvist, "What is the value of treating a diabetic foot wound?" Diabetes Care (Consensus Development Conference on Diabetic Foot Wound Care, Apr. 7-8, 1999, Boston, MA, American Diabetes Association), 22(8):1354-1360 (Aug. 1999).
Aplin et al., "Preparation, properties, and applications of carbohydrate conjugates of proteins and lipids" Crit Rev Biochem Molec Biol 10(4):259-306 (May 1981).
Barcia et al., "Triglyceride-rich lipoproteins as agents of innate immunity" Clin Inect Dis 41( Suppl 7):S498-S503 ( 2005).
Bradley Teratocarcinomas and Embryonic Stem Cells: A Practical Approach "Production and analysis of chimaeric mice" (Ch. 5), E. J. Robertson, ed.,IRL, Oxford,:113-151 ( 1987).
Brand et al., "IL-22 increased in active Crohn's disease and promotes proinflammatory gene expression and intestinal epithelial cell migration" Am J Physiol Gastrointest Liver Physiol 290:G827-G838 ( 2006).
Brubaker et al., "Reduced neutrophil chemotaxis and infiltration contributes to delayed resolution of cutaneous wound infection with advanced age" J. Immunol 190:1746-1757 ( 2013).
Brueggemann et al., "Comparison of the effector functions of human immunoglobulins using a matched set of chimeric antibodies" J. Exp. Med. 166:1351-1361 ( 1987).
Buford, Wound Healing and Pressure Sores, HealingWell.com, published on Oct. 24, 2001, pp. 1-5.
Cani et al., "Changes in gut microbiota control metabolic endotoxemia-induced inflammation in high-fat diet-induced obesity and diabetes in mice" Diabetes 57:1470-1481 (Jun. 2008).
Cani et al., "Metabolic endotoxemia initiates obesity and insulin resistance" Diabetes 56(7):1761-1772 (Jul. 2007).
Carter et al., "Improved oligonucleotide site-directed mutagenesis Using M13 vectors" Nucl Acids Res 13(12):4431-4443 ( 1985).
Chang et al., "Phenotypic expression in *E. coli* of a DNA sequence coding for mouse dihydrofolate reductase" Nature 275:617-624 (Oct. 19, 1978).
Charlton, K.A., "Expression and isolation of recombinant antibody fragments in *E. coli*" Method Molec Biol 248:245-254 ( 2003).
Chothia et al., "Canonical structures for the hypervariable regions of immunoglobulins" J Mol Biol 196:901-917 ( 1987).
Clackson et al., "Making antibody fragments using phage display libraries" Nature 352:624-628 (Aug. 15, 1991).
Clynes et al., "Fc receptors are required in passive and active immunity to melanoma" P Natl Acad Sci USA 95(2):652-656 (Jan. 1998).
Couffinhal et al., "Animal Model: Mouse Model of Angiogenesis" Am J Pathol 152(6):1667-1679 ( 1998).
Cox et al., "Opposing consequences of IL-23 signaling mediated by innate and adaptive cells in chemical induced colitis in mice" Mucosal Immunol 5(1):99-109 (Jan. 2012).
Cragg et al., "Antibody specificity controls in vivo effector mechanisms of anti-CD20 reagents" Blood 103(7):2738-2743 ( 2004).
Cragg et al., "Complement-mediated lysis by anti-CD20 mAb correlates with segregation into lipid rafts" Blood 101(3):1045-1052 ( 2003).
Creighton, T. Proteins: Structures and Molecular Principles New York, NY:W.H. Freeman & Co.,:70-87 ( 1984).

Cwirla et al., "Peptides on phage: a vast library of peptides for identifying ligands" P Natl Acad Sci USA 87:6378-6382 (Aug. 1990).
Dargaville et al., "Sensors and imaging for wound healing: A review" Biosensors and Bioelectronics 41:30-42 ( 2013).
De Boer et al., "The tac promoter: A functional hybrid derived from the trp and lac Promoters" P Natl Acad Sci USA 80:21-25 (Jan. 1983).
Dolby et al., "Cloning and partial nucleotide sequence of human immunoglobulin μ chain cDNA from B cells and mouse-human hybridomas" P Natl Acad Sci USA 77(10):6027-6031 (Oct. 1980).
Duncan et al., "The binding site for Clq on IgG" Nature 322:738-740 ( 1988).
Edge et al., "Deglycosylation of glycoproteins by trifluoromethanesulfonic acid" Anal Biochem 118:131-137 ( 1981).
Evan et al., "Isolation of monoclonal antibodies apecific for auman c-myc proto-oncogene product" Mol Cell Biol 5(12):3610-3616 (Dec. 1985).
Falkner et al., "Expression of mouse immunoglobulin genes in monkey cells" Nature 298:286-288 (Jul. 15, 1982).
Field et al., "Purification of a RAS-Responsive Adenylyl Cyclase Complex from *Saccharomyces cerevisiae* by Use of an Epitope Addition Method" Mol Cell Biol 8(5):2159-2165 (May 1988).
Gazzano-Santoro et al., "A non-radioactive complement-dependent cytotoxicity assay for anti-CD20 monoclonal antibody" J Immunol Methods 202(2):163-171 (Mar. 28, 1997).
Gerngross, T. U, "Advances in the production of human therapeutic proteins in yeasts and filamentous fungi" Nat Biotech 22(11):1409-1414 (Nov. 2004).
Gething et al., "Cell-surface expression of influenza haemagglutinin from a cloned DNA copy of the RNA gene" Nature 293:620-625 (Oct. 22, 1981).
Geysen et al. Synthetic Peptides as AntigensJohn Wiley & Sons,:130-149 ( 1986).
Geysen et al., "Small peptides induce antibodies with a sequence and structural requirement for binding antigen comparable to antibodies raised against the native protein" P Natl Acad Sci USA 82:178-182 ( 1985).
Geysen et al., "Strategies for epitope analysis using peptide synthesis" J Immunol Methods 102:259-274 ( 1987).
Geysen et al., "Use of peptide synthesis to probe viral antigens for epitopes to a resolution of a single amino acid" P Natl Acad Sci USA 81:3998-4002 ( 1984).
Goeddel et al., "Direct expression in *Escherichia coli* of a DNA sequence coding for human growth hormone" Nature 281:544-548 (Oct. 18, 1979).
Goeddel et al., "Synthesis of human fibroblast interferon by *E. coli*" Nucleic Acids Res 8(18):4057-4074 ( 1980).
Goshal et al., "Chylomicrons promote intestinal absorption of lipopolysaccharides" J Lipid Res 50(1):90-97 ( 2009).
Gough et al., "Molecular cloning of seven mouse immunoglobulin κ chain messenger ribonucleic acids" Biochemistry—US 19:2702-2710 ( 1980).
Graham et al., "A new technique for the assay of infectivity of human adenovirus 5 DNA" Virology 52:456-467 ( 1973).
Graham et al., "Characteristics of a human cell line transformed by DNA from human adenovirus type 5" J Gen Virol 36:59-72 ( 1977).
Guyer et al "Immunoglobulin binding by mouse intestinal epithelial cell receptors" J. Immunol 117(2):587-593 (Aug. 1976).
Hansson et al., "Inflammation, atherosclerosis and coronary artery disease" N Engl J Med 352(16):1685-1695 ( 2005).
Hansson et al., "The immune system in atherosclerosis" Nature Immmunol 12(3):204-212 ( 2011).
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hess et al., "Cooperation of glycolytic enzymes" Adv Enzyme Regul. 7:149-67 ( 1969).

(56) References Cited

OTHER PUBLICATIONS

Hitzeman et al., "Isolation and characterization of the yeast 3-phosphoglycerokinase gene (PGK) by an immunological screening technique" J Biol Chem 255(24):12073-80 (Dec. 25, 1980).
Holland et al., "Isolation and identification of yeast messenger ribonucleic acids coding for enolase, glyceraldehyde-3-phosphate dehydrogenase, and phosphoglycerate kinase" Biochem 17(23):4900-4907 ( 1978).
Hopp et al., "A short polypeptide marker sequence useful for recombinant protein identification and purification" Bio-Technol 6:1204-1210 ( 1988).
Hsiao et al., "High-frequency transformation of yeast by plasmids containing the cloned yeast ARG4 gene" P Natl Acad Sci USA 76(8):3829-3833 (Aug. 1979).
Idusogie et al., "Mapping of the C1q binding site on Rituxan, a chimeric antibody with a human IgG1 Fc" J Immunol 164:4178-4184 ( 2000).
Isner et al., "Arterial gene transfer for therapeutic angiogenesis in patients with peripheral artery disease" Hum Gene Ther 7:959-988 (May 20, 1996).
Jiang et al., "IL-22 is related to development of human colon cancer by activation of STAT3" BMC Cancer (http://www.biomedcentral.com/1471-2407/13/59), 13:59 ( 2013).
Jones, E., "Proteinase mutants of *Saccharomyces cerevisiae*" Genetics 85(1):23-33 (Jan. 1977).
Kanda et al., "Comparison of cell lines for stable production of fucose-negative antibodies with enhanced ADCC" Biotechnol Bioeng 94(4):680-688 (Jul. 5, 2006).
Kang et al., "Linkage of recognition and replication functions by assembling combinatorial antibody Fab libraries along phage surfaces" Proc Natl Acad Sci U S A. 88(10):4363-6 ( 1991).
Keown et al., "Methods for introducing DNA into mammalian cells" Methods Enzymol 185:527-537 ( 1990).
Kim et al., "Localization of the site of the murine IgG1 molecule that is involved in binding to the murine intestinal Fc receptor" Eur J Immunol 24(10):2429-2434 (Oct. 1994).
Kindt et al. Kuby Immunology Sixth edition, New York: W. H. Freeman and Company,:91 ( 2007).
Kingsman et al., "Replication in *Saccharomyces cerevisiae* of plasmid pBR313 carrying DNA from the yeast trp1 region" Gene 7:141-152 ( 1979).
Kobayashi et al., "A novel core fucose-speciic lectin from the mushroom pholiota squarrosa" J Biol Chem 287(41):33973-33982 (Oct. 5, 2012).
Kumar et al., "IL-22: An evolutionary missing-link authenticating the role of the immune system in tissue regeneration" J Cancer 4:57-65 ( 2013).
Lakso et al., "Targeted oncogene activation by site-specific recombination in transgenic mice" P Natl Acad Sci USA 89:6232-6236 (Jul. 1992).
Lavitrano et al., "Sperm cells as vectors for introducing foreign DNA into eggs: Genetic transformation of mice" Cell 57:717-723 (Jun. 2, 1989).
Lazarus et al., "Deinitions and guidelines for assessment o wounds and evaluation of healing" Arch Derm 130(4):489-493 ( 1994).
Li et al., "Optimization of humanized IgGs in glycoengineered Pichia pastoris" Nat Biotechnol 24(2):210-215 (Feb. 2006).
"Targeted mutation of the DNA methyltransferase gene results in embryonic lethality" Cell 69:915-926 (Jun. 12, 1992).
Lo, C.W., "Transformation by iontophoretic microinjection of DNA: Multiple integrations without tandem insertions" Mol Cell Biol 3(10):1803-1814 (Oct. 1983).
Lowman et al., "Selecting High-Affinity Binding Proteins by Monovalent Phage Display" !Biochem 30(45):10832-10838 ( 1991).
Lutz-Freyermuth et al., "Quantitative determination that one of two potential RNA-binding domains of the A protein component of the U1 small nuclear ribonucleoprotein complex binds with high affinity to stem-loop II of U1 RNA" P Natl Acad Sci USA 87:6393-6397 (Aug. 1990).

Manco et al., "Gut microbiota, lipopolysaccharides and innate immunity in the pathogenesis of obesity and cardiovascular risk" Endocr Rev 31(6):817-844 (Dec. 2010).
Mansour et al., "Disruption of the proto-oncogene int-2 in mouse embryo-derived stem cells: A general strategy for targeting mutations to non-selectable genes" Nature 336:348-352 (Nov. 24, 1988).
Mantei et al., "Rabbit β-globin mRNA production in mouse L cells transformed with cloned rabbit β-globin chromosomal DNA" Nature 281:40-46 (Sep. 6, 1979).
Marks et al., "By-passing immunization, human antibodies from V-gene libraries displayed on phage" J Mol Biol 222:581-597 ( 1991).
Martin et al., "GAP domains responsible for Ras p21-dependent inhibition of muscarinic atrial $K^+$ channel currents" Science 255:192-194 (Jan. 10, 1992).
Mather, "Establishment and characterization of two distinct mouse testicular epithelial cell lines" Biol Reprod 23:243-252 ( 1980).
McGee et al., "IL-22 promotes fibroblast-mediated wound repair in the skin" J Invest Derm 133:1321-1329 ( 2013).
Merrifield, "Solid phase peptide synthesis: The synthesis of a tetrapeptide" J Am Chem Soc 85:2149-2154 ( 1963).
Mizoguchi et al., "Healing of intestinal inflammation by IL-22" Inflamm Bowel Dis 18(9):1777-1784 ( 2012).
Morrison et al., "Transfer and expression of immunoglobulin genes" Annu Rev Immunol 2:239-256 ( 1984).
Okazaki et al., "Fucose depletion from human IgG1 oligosaccharide enhances binding enthalpy and association rate between IgG1 and FcγRIIIa" J Molec Biol 336:1239-1249 ( 2004).
Ota et al., "IL-22 bridges the lymphotoxin pathway with the maintenance of colonic lymphoid structures during infection with Citrobacter rodentium" Nature Immmunol 12:941-948 (2011).
Ouyang et al., "Regulation and functions of the IL-10 family of cytokines in inflamation and disease" Ann Rev Immunol 29:71-109 ( 2011).
Paborsky et al., "Mammalian cell transient expression of tissue factor for the production of antigen" Protein Eng 3(6):547-553 (May 1990).
Pastorelli et al., "Emerging drugs for the treatment of ulcerative colitis" Expert Opinion On Emerging Drugs 14:505-521 ( 2009).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pickert et al., "STAT3 links IL-22 signaling in intestinal epithelial cells to mucosal would healing" J Exp Med 206(7):1465-1472 ( 2009).
Portolano et al., "Lack of promiscuity in autoantigen-specific H and L chain combinations as revealed by human H and L chanin 'Roulette'" J Immunol 150(3):880-887 (Feb. 1, 1993).
Powell-Braxton et al., "A mouse model of human familial hypercholesterolemia: Markedly elevated low density lipoprotein cholesterol levels and severe atherosclerosis on a low-fat chow diet" Nature Med 4(8):934-938 (Aug. 1998).
Ravetch and Kinet, "Fc receptors" Annu Rev Immunol 9:457-492 ( 1991).
Rice et al., "Regulated expression of an immunoglobulin κ gene introduced into a mouse lymphoid cell line" P Natl Acad Sci USA 79:7862-7865 ( 1982).
Ripka et al., "Two chinese hamster ovary glycosylation mutants affected in the conversion of GDP-mannose to GDP-fucose" Arch Biochem Biophys 249(2):533-545 (Sep. 1986).
Ross, R., "Atherosclerosis is an inflammatory disease" Am Heart J 138(5 Pt 2):S419-20 (Nov. 1999).
Sa et al., "The effects of IL-20 subfamily cytokines on reconstituted human epidermis suggest potential roles in cutaneous innate defense and pathogenic adaptive immunity in psoriasis" J Immunol 178:2229-2240 ( 2007).
Sabat et al., "IL-22 and IL-17: An Overview" Prog Inflamm Res:11-35 ( 2013).
Schoofs et al., "Epitopes of an influenza viral peptide recognized by antibody at single amino acid resolution" J Immunol 140:611-616 ( 1988).

(56) References Cited

OTHER PUBLICATIONS

Shaw et al., "A general method for the transfer of cloned genes to plant cells" Gene 23:315-330 ( 1983).
Shields et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Shoji-Hosaka et al., "Enhanced Fc-dependent dellular cytotoxicity of Fc Fusion proteins derived from TNF receptor II and LFA-3 by fucose removal from Asn-linked oligosaccharides" J Biochem 140:777-783 ( 2006).
Singer et al., "Cutaneous wound healing" New Engl J Med 341:738-746 (Sep. 2, 1999).
Skinner et al., "Use of the Glu-Glu-Phe C-terminal Epitope for Rapid Purification of the Catalytic Domain of Normal and Mutant ras GTPase-activating Proteins" J Biol Chem 266(22):14163-14166 (Aug. 5, 1991).
Smith, G. P., "Surface presentation of protein epitopes using bacteriophage expression systems" Current Opin Biotechnol 2:668-673 ( 1991).
Soj ar et al., "A chemical method for the deglycosylation of proteins" Arch Biochem Biophys 259(1):52-57 ( 1987).
Stinchcomb et al., "Isolation and characterisation of a yeast chromosomal replicator" Nature 282(5734):39-43 (Nov. 1, 1979).
Sugimoto et al., "IL-22 ameliorates intestinal inflammation in a mouse model of ulcerative colitis" J Clin Invest 118(2):534-544 (Feb. 2008).
Takeshita et al., "Gene transer of naked DNA encoding for three isoforms of vascular endothelial growth factor stimulates collateral development in vivo" Lab Invest 75(4):487-501 (Oct. 1996).
Tan et al., "MRI of the diabetic foot: differentiation of infection from neuropathic change" Br J Radiol 80:939-948 ( 2007).
Thomas et al., "Site-directed mutagenesis by gene targeting in mouse embryo-derived stem cells." Cell 51:503-512 (Nov. 6, 1987).
Thomas, P., "Hybridization of denatured RNA and small DNA fragments transferred to nitrocellulose" P Natl Acad Sci USA 77(9):5201-5205 (Sep. 1980).
Thompson et al., "Germ Line Transmission and Expression of a Corrected HPRT Gene Produced by Gene Targeting in Embryonic Stem Cells" Cell 56:313-321 (Jan. 27, 1989).
Thotakura et al., "Enzymatic deglycosylation of glycoproteins" Methods Enzymol 138:350-359 ( 1987).
Tschumper et al., "Sequence of a yeast DNA fragment containing a chromosomal replicator and the TRP1 gene" Gene 10:157-166 ( 1980).
Turnbaugh et al., "The core gut microbiome, energy balance and obesity" J Physiol (Lond) 587((Pt 17)):4153-4158 ( 2009).
Urlaub et al., "Isolation of chinese hamster cell mutants deficient in dihydrofolate reductase activity" P Natl Acad Sci USA 77(7):4216-4220 (Jul 1980).
Van der Putten et al., "Efficient insertion of genes into the mouse germ line via retroviral vectors" P Natl Acad Sci USA 82:6148-6152 (Sep. 1985).
Van Solingen et al., "Fusion of yeast spheroplasts" J Bact 130(2):946-947 (May 1977).
Weber et al., "Inhibition of interleukin-22 attenuates bacterial load and organ failure during acute polymicrobial sepsis" Infect Immun 75(4):1690-1697 ( 2007).
Wells et al., "Cassette mutagenesis: An efficient method for generation of multiple mutations at defined sites" Gene 34:315-323 ( 1985).
Wells et al., "Importance of hydrogen-bond formation in stabilizing the transition state of subtilisin" Phil Trans R Soc London A 317:415-423 ( 1986).
Wolk et al., "IL-22 Increases the innate immunity of tissues" Immunity 21(2):241-254 ( 2004).
Wolk et al., "IL-22 induces lipopolysaccharide-binding protein in hepatocytes: A potential systemic role of IL-22 in Crohn's disease" J. Immunol 178:5973-5981 ( 2007).

Wright and Morrison, "Effect of glycosylation on antibody function: Implications for genetic engineering" Trends Biotechnol 15:26-32 ( 1997).
Wu et al., "Amelioration of type 2 diabetes by antibody-mediated activation of fibroblast growth factor receptor 1" Science Translational Medicine 3:113ra-126 ( 2011).
Xavier et al., "Unravelling the pathogenesis of inflammatory bowel disease" Nature :448:427-434 ( 2007).
Xue et al., "Aryl hydrocarbon receptor regulates pancreatic L-22 production and protects mice from acute pancreatitis" Gastroenterology 143:1670-1680 ( 2012).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki et al. Methods in Molecular Biology "Expression of recombinant antibodies in mammalian cell lines" Lo, B.K.C. (ed.), Totowa, NJ:Humana Press, vol. 248:255-268 ( 2004).
Zhao et al., "Time course study of delayed wound healing in a biofllm-challenged diabetic mouse model" Wound Rep Reg 20:342-352 ( 2012).
Zheng et al., "Interleukin-22 mediates early host defense against attaching and effacing bacterial pathogens" Nature Med 14(3):282-289 (Mar. 2008).
Zheng et al., "Interleukin-22, a T$_{H}$17 Cytokine, Mediates IL-23-Induced Dermal Inflammation and Acanthosis" Nature 445(7128):648-651 (Feb. 8, 2007).
Zoller et al., "Oligonucleotide-directed mutagenesis using M13-derived vectors: An efficient and general procedure for the production of point mutations in any fragment of DNA" Nucl Acids Res 10:6487-6504 ( 1987).
Hristodorov et al., "With or without sugar? (A)glycosylation of therapeutic antibodies," Mol Biotechnol. 54(3):1056-68 (2013).
Written Opinion for Singaporean application No. 11201507429T, dated Oct. 13, 2016 (8 pages).
Office Action for U.S. Appl. No. 15/217,790, dated Jan. 30, 2017 (11 pages).
Brandi et al., "MyD88-mediated signals induce the bactericidal lectin RegIII gamma and protect mice against intestinal Listeria monocytogenes infection," J Exp Med. 204(8):1891-900 (2007).
Bry et al., "Critical role of T cell-dependent serum antibody, but not the gut-associated lymphoid tissue, for surviving acute mucosal infection with Citrobacter rodentium, an attaching and effacing pathogen," J Immunol. 172(1):433-41 (2004).
Cash et al., "Refolding, purification, and characterization of human and murine RegIII proteins expressed in *Escherichia coli*," available in PMC Sep. 8, 2009, published in final edited form as: Protein Expr Purif. 48(1):151-9 (2006).
Cash et al., "Symbiotic bacteria direct expression of an intestinal bactericidal lectin," available in PMC Jul. 28, 2009, published in final edited form as: Science. 313(5790):1126-30 (2006).
Domschke et al., "Preface," Ann N Y Acad Sci. 1072:xi (2006).
Dumoutier et al., "Cloning and characterization of IL-22 binding protein, a natural antagonist of IL-10-related T cell-derived inducible factor/IL-22," J Immunol. 166(12):7090-5 (2001).
Eckmann, "Animal models of inflammatory bowel disease: lessons from enteric infections," Ann N Y Acad Sci. 1072:28-38 (2006).
Fisher et al., "mda-7/IL-24, a novel cancer selective apoptosis inducing cytokine gene: from the laboratory into the clinic," Cancer Biol Ther. 2(4 Suppl 1):523-37 (2003).
Ganz, "Defensins and host defense," Science. 286(5439):420-1 (1999).
Gironella et al., "Anti-inflammatory effects of pancreatitis associated protein in inflammatory bowel disease," Gut. 54(9):1244-53 (2005) (11 pages).
Happel et al., "Divergent roles of IL-23 and IL-12 in host defense against Klebsiella pneumoniae," J Exp Med. 202(6):761-9 (2005).
Higgins et al., "Citrobacter rodentium infection in mice elicits a mucosal Th1 cytokine response and lesions similar to those in murine inflammatory bowel disease," Infect Immun. 67(6):3031-9 (1999).

(56) References Cited

OTHER PUBLICATIONS

Iovanna et al., "Messenger RNA sequence and expression of rat pancreatitis-associated protein, a lectin-related protein overexpressed during acute experimental pancreatitis," J Biol Chem. 266(36):24664-9 (1991).
Jurjus et al., "Animal models of inflammatory bowel disease," J Pharmacol Toxicol Methods. 50(2):81-92 (2004).
Kaistha et al., "Homology modeling of phosphoryl thymidine kinase of enterohemorrhagic *Escherichia coli* OH: 157," Bioinformation. 3(6):240-3 (2009).
Kawada et al., "Insights from advances in research of chemically induced experimental models of human inflammatory bowel disease," World J Gastroenterol. 13(42):5581-93 (2007).
Keilbaugh et al., "Activation of RegIIIbeta/gamma and interferon gamma expression in the intestinal tract of SCID mice: an innate response to bacterial colonisation of the gut," Gut. 54(5):623-9 (2005) (8 pages).
Kreis et al., "Recombinant interleukin-24 lacks apoptosis-inducing properties in melanoma cells," PLoS One. 2(12):e1300 (2007) (15 pages).
Kreymborg et al., "IL-22 is expressed by Th17 cells in an IL-23-dependent fashion, but not required for the development of autoimmune encephalomyelitis," J Immunol. 179(12):8098-104 (2007).
Levillayer et al., "Interleukin 22 is a candidate gene for Tmevp3, a locus controlling Theiler's virus-induced neurological diseases," Genetics. 176(3):1835-44 (2007).
Liang et al., "Interleukin (IL)-22 and IL-17 are coexpressed by Th17 cells and cooperatively enhance expression of antimicrobial peptides," J Exp Med. 203(10):2271-9 (2006).
Lécart et al., "IL-22, in contrast to IL-10, does not induce Ig production, due to absence of a functional IL-22 receptor on activated human B cells," Int Immunol. 14(11):1351-6 (2002).
Maaser et al., "Clearance of Citrobacter rodentium requires B cells but not secretory immunoglobulin A (IgA) or IgM antibodies," Infect Immun. 72(6):3315-24 (2004).
Mangan et al., "Transforming growth factor-beta induces development of the T(H)17 lineage," Nature. 441(7090):231-4 (2006).
Missé et al., "IL-22 participates in an innate anti-HIV-1 host-resistance network through acute-phase protein induction," J Immunol. 178(1):407-15 (2007).
Moucadel et al., "Cdx1 promotes cellular growth of epithelial intestinal cells through induction of the secretory protein PAP I," Eur J Cell Biol. 80(2):156-63 (2001).
Mundy et al., "Citrobacter rodentium of mice and man," Cell Microbiol. 7(12):1697-706 (2005).
NCBI GenBank Accession No. AAH67509.1, dated Jul. 15, 2006, accessed Mar. 29, 2018 (2 pages).
NCBI GenBank Accession No. AY358890.1, dated Oct. 3, 2003, accessed Mar. 29, 2018 (2 pages).
NCBI GenBank Accession No. NP_940850, dated Jun. 26, 2017, accessed Apr. 10, 2018 (2 pages).
Ogawa et al., "Identification of genes involved in mucosal defense and inflammation associated with normal enteric bacteria," Am J Physiol Gastrointest Liver Physiol. 279(3):G492-9 (2000).
Ogawa et al., "Increased expression of HIP/PAP and regenerating gene III in human inflammatory bowel disease and a murine bacterial reconstitution model," Inflamm Bowel Dis. 9(3):162-70 (2003).
Pull et al., "Activated macrophages are an adaptive element of the colonic epithelial progenitor niche necessary for regenerative responses to injury," Proc Natl Acad Sci U S A. 102(1):99-104 (2005).
Renauld, "Class II cytokine receptors and their ligands: key antiviral and inflammatory modulators," Nat Rev Immunol. 3(8):667-76 (2003).
Simmons et al., "Impaired resistance and enhanced pathology during infection with a noninvasive, attaching-effacing enteric bacterial pathogen, Citrobacter rodentium, in mice lacking IL-12 or IFN-gamma," J Immunol. 168(4):1804-12 (2002).
Sugimoto et al., "Innate Cell-Targeting Therapeutic Effect of IL-22 on Experimental Colitis," AGA Abstracts, Gastroenterology. 130(4 Suppl 2):A41 Abstract 232 (2006).
Sugimoto et al., "Local IL-22 Gene Delivery Targeting Inflamed Mucosa Induces the Rapid Attenuation with Goblet Cell Restitution," Gastroenterology. 132(4 Suppl 2):A-153 Abstract 1012 (2007).
Sun et al., "IL-22 is involved in atherosclerosis lesions by regulated impaired proliferation ability of oxidized low density lipoprotein treated CRL-1730," Chin J Microbiol Immunol. 32:995-9 (2012) (English language abstract included).
Toy et al., "Cutting edge: interleukin 17 signals through a heteromeric receptor complex," J Immunol. 177(1):36-9 (2006).
Wolk et al., "IL-22 regulates the expression of genes responsible for antimicrobial defense, cellular differentiation, and mobility in keratinocytes: a potential role in psoriasis," Eur J Immunol. 36(5):1309-23 (2006).
Xu et al., "A soluble class II cytokine receptor, IL-22RA2, is a naturally occurring IL-22 antagonist," Proc Natl Acad Sci U S A. 98(17):9511-6 (2001).
Zenewicz et al., "Interleukin-22 but not interleukin-17 provides protection to hepatocytes during acute liver inflammation," Immunity. 27(4):647-59 (2007).
International Preliminary Report on Patentability for International Patent Application No. PCT/US2008/082890, dated May 11, 2010 (13 pages).
Notice of Reasons for Rejection for Japanese Patent Application No. 2016-503181, dated May 8, 2018 (10 pages).
Written Opinion for International Patent Application No. PCT/US2008/082890, dated Aug. 19, 2009 (12 pages).

\* cited by examiner

IL-22 Amino Acid Sequences Alignment

```
Human (Q9GZX6)           apisshcrldksnfqqpyitnrtfmlakeasladnntdvrligeklfhgvsmsercylmk   60
Chimpanzee (XP_003313906) apisshcrldkssfqqpyitnrtfmlakeasladnntdvrligeklfhgvsmsercylmk
Orangutan (XP_002823544) apisshcrldksnfqqpyitnrtfmlakeasladnntdvrligeklfrgvsmsercylmk
Mouse (Q9JJY9)           lpvntrcklevsnfqqpyivnrtfmlakeasladnntdvrligeklfrgvsakdqcylmk
Dog (XP_538274)          lpisshcrldksnfqqpyitnrtfmlakeasladnntdvrligeklfhgvnmgercylml
                         *  * ****** *********** *********************** **  ******

Human (Q9GZX6)           qvlnftleevlfpqsdrfqpymqevvpflarlsnrlstchiegddlhiqrnvqklkdtvk   120
Chimpanzee (XP_003313906) qvlnftleevlfpqsdrfqpymqevvpflarlsnrlstchiegddlhiqrnvqklkdtvk
Orangutan (XP_002823544) qvlnftleevlfpqsdrfqpymqevvpflarlsnrlstchiegddlhiqrnvqklkdtvk
Mouse (Q9JJY9)           qvlnftledvllpqsdrfqpymqevvpflktklsnqlsschisgddqniqknvrrlketvk
Dog (XP_538274)          evlnftleevllpqsdrfqpymqevvpflarlsnrklsqchienddghiqrnvqklkdtvg
                          ******* ** ****************   ** *   **  **   ** ** *****

Human (Q9GZX6)           klgesgeikaigeldlllfmslrnlrnaci   146   (SEQ ID NO:4)
Chimpanzee (XP_003313906) klgengeikaigeldlllfmslrnlrnaci         (SEQ ID NO:48)
Orangutan (XP_002823544) klgesgeikaigeldlllfmslrnlrnaci         (SEQ ID NO:49)
Mouse (Q9JJY9)           klgesgeikaigeldlllfmslrnlrnacv         (SEQ ID NO:50)
Dog (XP_538274)          klgengeikaigeldlllfmalrnlrnacv         (SEQ ID NO:51)
                         **** *************** ***** *****
```

FIG. 1

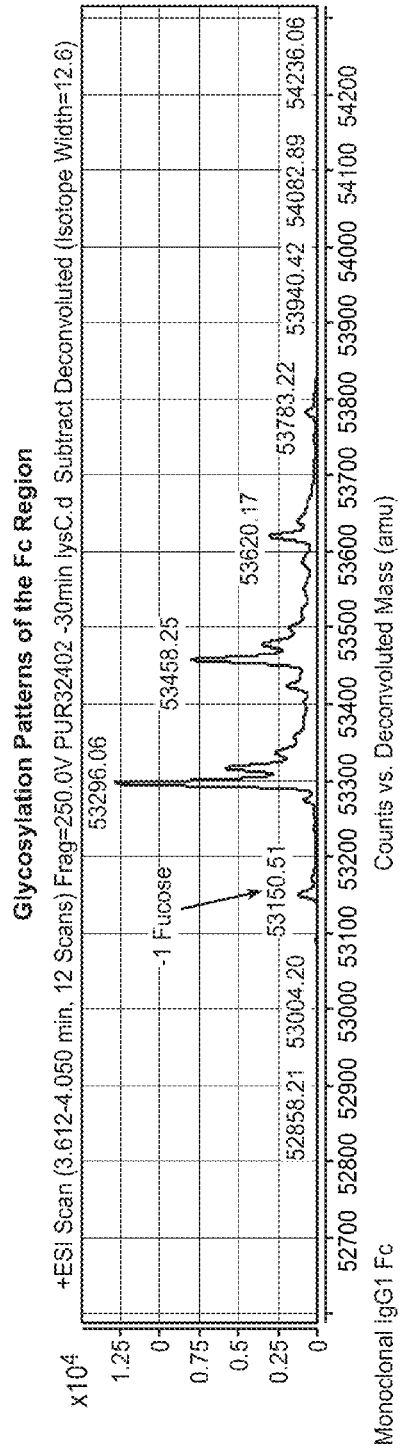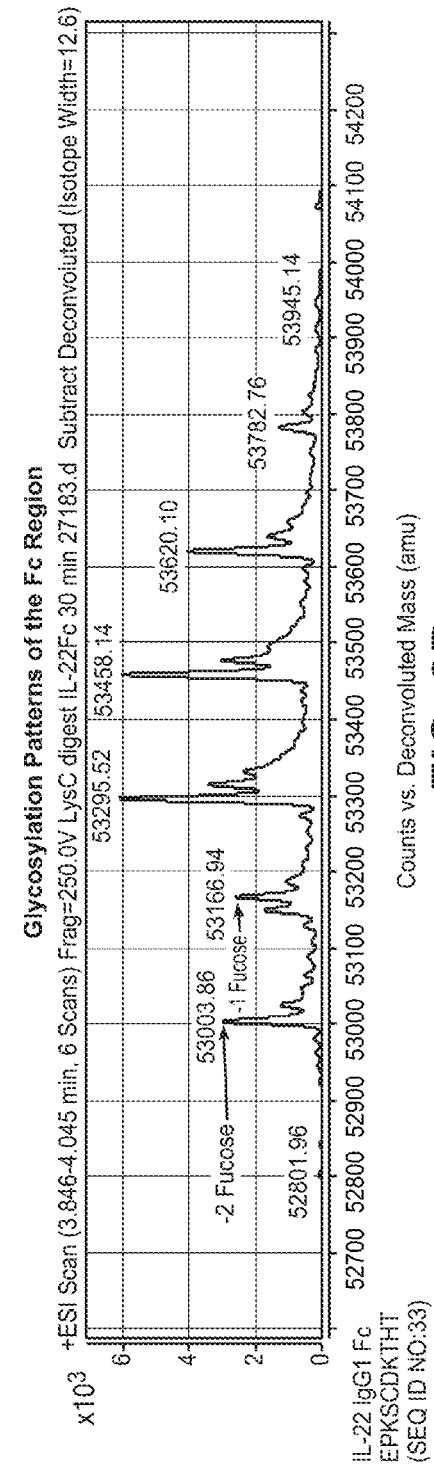

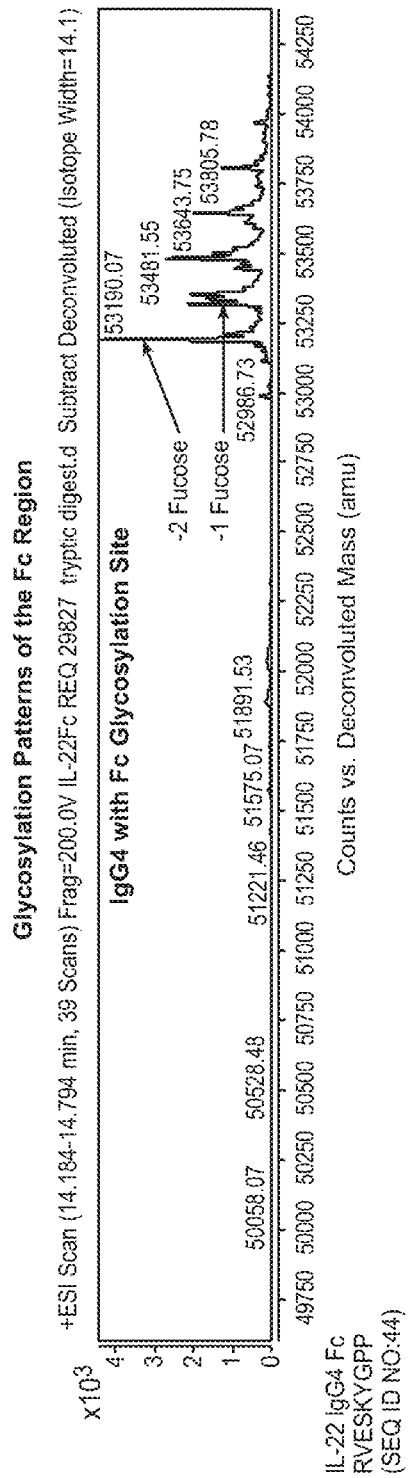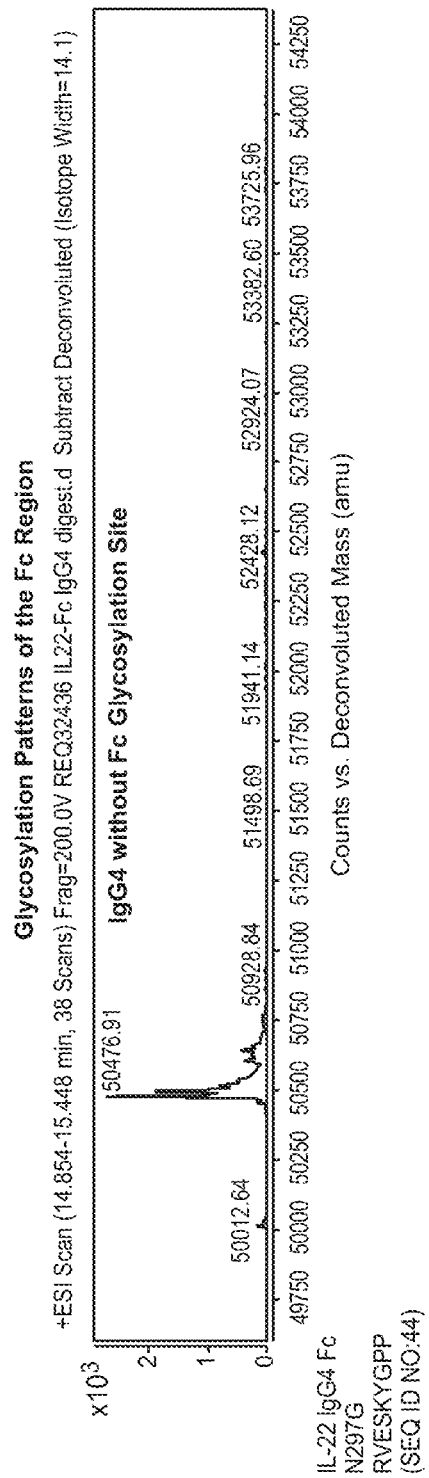
FIG. 2E
FIG. 2F

FIG. 3

[Mature N-term IL-22]

| | | Position |
|---|---|---|
| IL-22 IgG4 Fc | APISSHCRLDKSNFQQPYITNRTFMLAKEASLADNNTDVRLIGEKLFHGV | 50 |
| IL-22 IgG1 Fc | APISSHCRLDKSNFQQPYITNRTFMLAKEASLADNNTDVRLIGEKLFHGV | 50 |
| IL-22 | APISSHCRLDKSNFQQPYITNRTFMLAKEASLADNNTDVRLIGEKLFHGV | 50 |
| IL-22 IgG4 Fc | SMSERCYLMKQVLNFTLEEVLFPQSDRFQPYMQEVVPFLARLSNRLSTCH | 100 |
| IL-22 IgG1 Fc | SMSERCYLMKQVLNFTLEEVLFPQSDRFQPYMQEVVPFLARLSNRLSTCH | 100 |
| IL-22 | SMSERCYLMKQVLNFTLEEVLFPQSDRFQPYMQEVVPFLARLSNRLSTCH | 100 |

[C-term] [Linker]

| | | |
|---|---|---|
| IL-22 IgG4 Fc | IEGDDLHIQRNVQKLKDTVKKLGESGEIKAIGELDLLFMSLRNACIRVES | 150 |
| IL-22 IgG1 Fc | IEGDDLHIQRNVQKLKDTVKKLGESGEIKAIGELDLLFMSLRNACIEPKS | 150 |
| IL-22 | IEGDDLHIQRNVQKLKDTVKKLGESGEIKAIGELDLLFMSLRNACI (SEQ ID NO:4) | 146 |

[Fc]

| | | |
|---|---|---|
| IL-22 IgG4 Fc | K-YGPPCPPCPAPEFLGGPSVFLFPPKPKDTLMISRTPEVTCVVVDVSQE | 199 |
| IL-22 IgG1 Fc | SDKTHTCPPCPAPELLGGPSVFLFPPKPKDTLMISRTPEVTCVVVDVSHE | 200 |

N297G

| | | |
|---|---|---|
| IL-22 IgG4 Fc | DPEVQFNWYVDGVEVHNAKTKPREEQFGSTYRVVSVLTVLHQDWLNGKEY | 249 |
| IL-22 IgG1 Fc | DPEVKFNWYVDGVEVHNAKTKPREEQYGSTYRVVSVLTVLHQDWLNGKEY | 250 |
| IL-22 IgG4 Fc | KCKVSNKGLPSSIEKTISKAKGQPREPQVYTLPPSQEEMTKNQVSLTCLV | 299 |
| IL-22 IgG1 Fc | KCKVSNKALPAPIEKTISKAKGQPREPQVYTLPPSREEMTKNQVSLTCLV | 300 |
| IL-22 IgG4 Fc | KGFYPSDIAVEWESNGQPENNYKTTPPVLDSDGSFFLYSRLTVDKSRWQE | 349 |
| IL-22 IgG1 Fc | KGFYPSDIAVEWESNGQPENNYKTTPPVLDSDGSFFLYSKLTVDKSRWQQ | 350 |
| IL-22 IgG4 Fc | GNVFSCSVMHEALHNHYTQKSLSLSLGK (SEQ ID NO:16/SEQ ID NO:8) | 377 |
| IL-22 IgG1 Fc | GNVFSCSVMHEALHNHYTQKSLSLSPGK (SEQ ID NO:20/SEQ ID NO:12) | 378 |

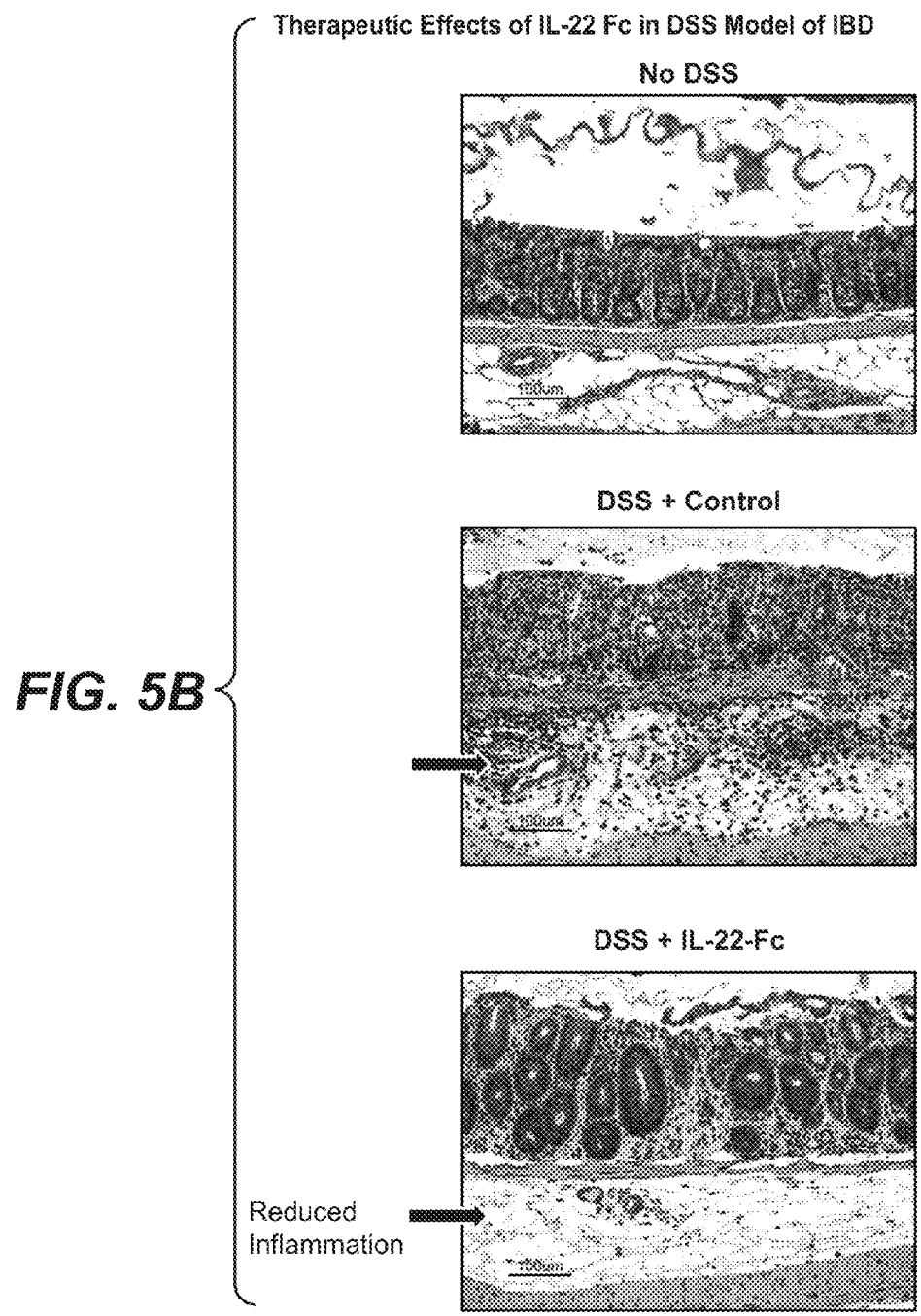

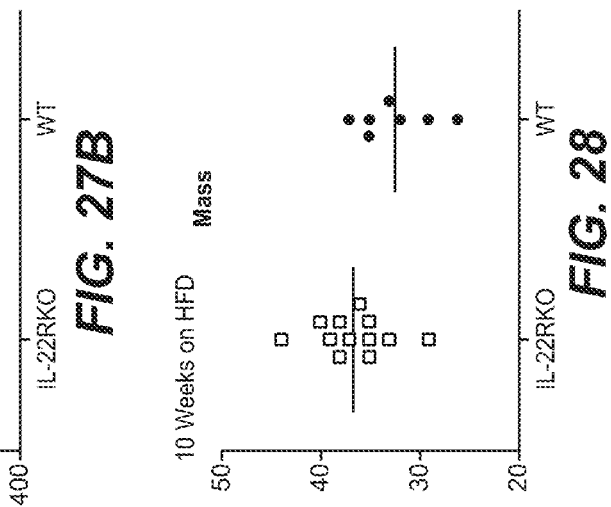
FIG. 27B
FIG. 28
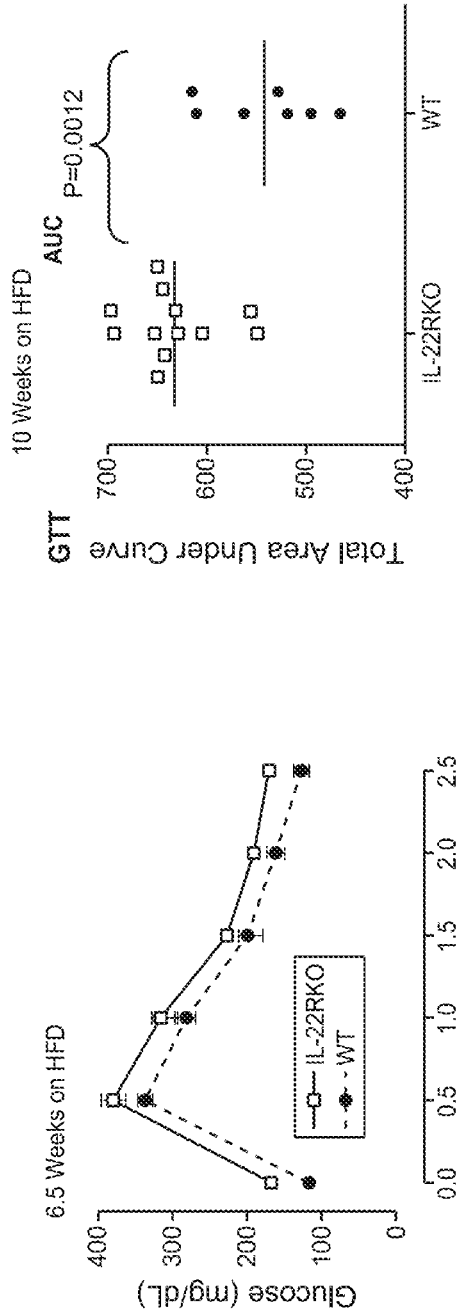
FIG. 27A

CTTCAGAACAGGTTCTCCTTCCCCAGTCACCAGTTGCTCGAGTTAGAATTGTCTGCAATGGCCGCCC
TGCAGAAATCTGTGAGCTCTTTCCTTATGGGGACCCTGGCCACCAGCTGCCTCCTTCTCTTGGCCCT
CTTGGTACAGGGAGGAGCAGCTGCGCCCATCAGCTCCCACTGCAGGCTTGACAAGTCCAACTTCCAG
CAGCCCTATATCACCAACCGCACCTTCATGCTGGCTAAGGAGGCTAGCTTGGCTGATAACAACACAG
ACGTTCGTCTCATTGGGGAGAAACTGTTCCACGGAGTCAGTATGAGTGAGCGCTGCTATCTGATGA
AGCAGGTGCTGAACTTCACCCTTGAAGAAGTGCTGTTCCCTCAATCTGATAGGTTCCAGCCTTATAT
GCAGGAGGTGGTGCCCTTCCTGGCCAGGCTCAGCAACAGGCTAAGCACATGTCATATTGAAGGTGA
TGACCTGCATATCCAGAGGAATGTGCAAAAGCTGAAGGACACAGTGAAAAAGCTTGGAGAGAGTGG
AGAGATCAAAGCAATTGGAGAACTGGATTTGCTGTTTATGTCTCTGAGAAATGCCTGCATTTGACC
AGAGCAAAGCTGAAAAATGAATAACTAACCCCCTTTCCCTGCTAGAAATAACAATTAGATGCCCCA
AAGCGATTTTTTTTAACCAAAAGGAAGATGGGAAGCCAAACTCCATCATGATGGGTGGATTCCAAA
TGAACCCCTGCGTTAGTTACAAAGGAAACCAATGCCACTTTTGTTTATAAGACCAGAAGGTAGACT
TTCTAAGCATAGATATTTATTGATAACATTTCATTGTAACTGGTGTTCTATACACAGAAAACAATT
TATTTTTTAAATAATTGTCTTTTTCCATAAAAAAGATTACTTTCCATTCCTTTAGGGGAAAAAACC
CCTAAATAGCTTCATGTTTCCATAATCAGTACTTTATATTTATAAATGTATTTATTATTATTATAA
GACTGCATTTTATTTATATCATTTTATTAATATGGATTTATTTATAGAAACATCATTCGATATTGC
TACTTGAGTGTAAGGCTAATATTGATATTTATGACAATAATTATAGAGCTATAACATGTTTATTTG
ACCTCAATAAACACTTGGATATCCC

SEQ ID NO. 70

FIG. 30

MAALQKSVSSFLMGTLATSCLLLLALLVQGGAAAPISSHCRLDKSNFQQPVITNRTFMLAKEASLADN
NTDVRLIGEKLFHGVSMSERCYLMKQVLNFTLEEVLFPQSDRFQPYMQEVVPFLARLSNRLSTCHIE
GDDLHIQRNVQKLKDTVKKLGESGEIKAIGELDLLFMSLRNACI

SEQIDNO.71

Signal peptide: amino acids 1-33

FIG. 31 mIL22mIgG2a

Protein
MAVLQKSMSFSLMGTLAASCLLLIALWAQEANALPVNTRCKLEVSNFQQPYIVNRTFMLA
KEASLADNNTDVRLIGEKLFRGVSAKDQCYLMKQVLNFTLEDVLLPQSDRFQPYMQEVVP
FLTKLSNQLSSCHISGDDQNIQKNVRRLKETVKKLGESGEIKAIGELDLLFMSLRNACVAR
GPTIKPCPPCKCPAPNLLGGPSVFIFPPKIKDVLMISLSPIVTCVVVDVSEDDPDVQISWFVN
NVEVHTAQTQTHREDYNSTLRVVSALPIQHQDWMSGKEFKCKVNNKDLPAPIERTISKPK
GSVRAPQVYVLPPPEEEMTKKQVTLTCMYTDFMPEDIYVEWTNNGKTELNYKNTEPVLD
SDGSYFMYSKLRVEKKNWVERNSYSCSVHEGLHNHHTTKSFSRTPGK

SEQ. ID. NO. 73

*FIG. 32A* mIL22mIgG2a
DNA sequence:
ATGGCTGTCCTGCAGAAATCTATGAGTTTTTCCCTTATGGGGACTTTGGCCGCCAGCTG
CCTGCTTCTCATTGCCCTGTGGGCCCAGGAGGCAAATGCGC
TGCCCGTCAACACCCGGTGCAAGCTTGAGGTGTCCAACTTCCAGCAGCCATACATCGT
CAACCGCACCTTTATGCTGGCCAAGGAGGCCAGCCTTGCAGA
TAACAACACAGATGTCCGGCTCATCGGGGAGAAACTGTTCCGAGGAGTCAGTGCTAAG
GATCAGTGCTACCTGATGAAGCAGGTGCTCAACTTCACCCTG
GAAGACGTTCTGCTCCCCAGTCAGACAGGTTCCAGCCCTACATGCAGGAGGTGGTGC
CTTTCCTGACCAAACTCAGCAATCAGCTCAGCTCCTGTCACA
TCAGCGGTGACGACCAGAACATCCAGAAGAATGTCAGAAGGCTGAAGGAGACAGTGA
AAAAGCTTGGAGAGAGTGGAGAGATCAAGGCGATTGGGGAACT
GGACCTGCTGTTTATGTCTCTGAGAAATGCTTGCGTCGCTCGAGGACCCACAATCAAG
CCCTGTCCTCCATGCAAATGCCCAGCACCTAACCTCTTGGGT
GGACCATCCGTCTTCATCTTCCCTCCAAAGATCAAGGATGTACTCATGATCTCCCTGAG
CCCCATAGTCACATGTGTGGTGGTGGATGTGAGCGAGGATG
ACCCAGATGTCCAGATCAGCTGGTTTGTGAACAACGTGGAAGTACACACAGCTCAGAC
ACAAACCCATAGAGAGGATTACAACAGTACTCTACGCGTGGT
CAGTGCCCTCCCCATCCAGCACCAGGACTGGATGAGTGGCAAGGAGTTCAAATGCAAG
GTCAACAACAAAGACCTCCCAGCGCCCATCGAGAGAACCATC
TCAAAACCCAAAGGGTCAGTAAGAGCTCCACAGGTATATGTCTTGCCTCCACCAGAAG
AAGAGATGACTAAGAAACAGGTCACTCTGACCTGCATGGTCA
CAGACTTCATGCCTGAAGACATTTACGTGGAGTGGACCAACAACGGGAAAACAGAGC
TAAACTACAAGAACACTGAACCAGTCCTGGACTCTGATGGTTC
TTACTTCATGTACAGCAAGCTGAGAGTGGAAAAGAAGAACTGGGTGGAAAGAAATAG
CTACTCCTGTTCAGTGGTCCACGAGGGTCTGCACAATCACCAC
ACGACTAAGAGCTTCTCCCGGACTCCGGGTAAATGA

SEQ. ID. NO. 72

*FIG. 32B*

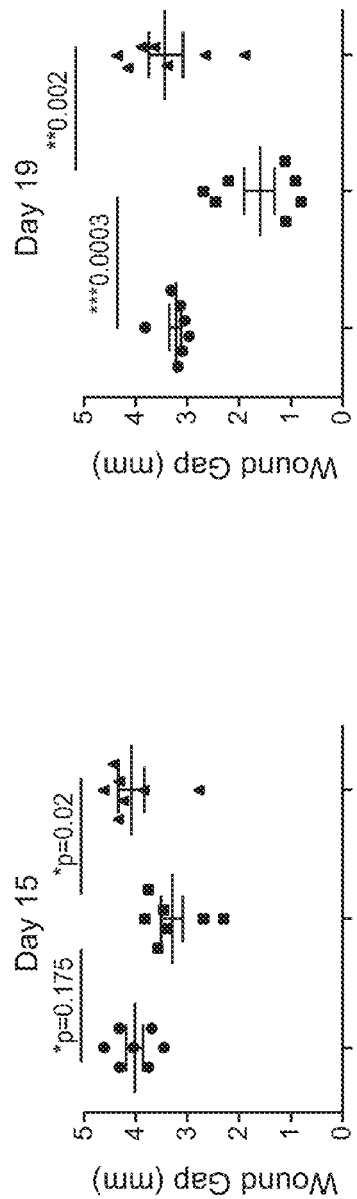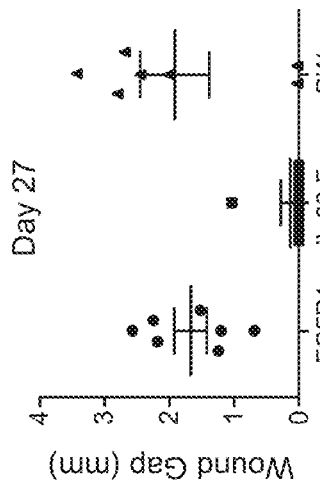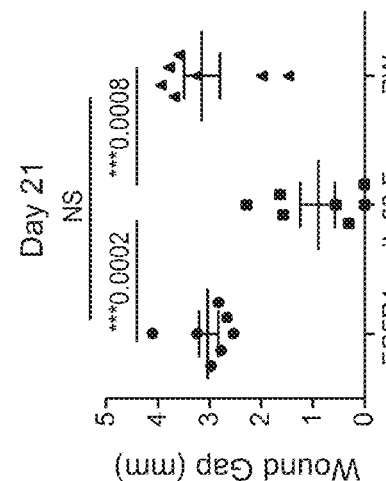
FIG. 39A  FIG. 39B  FIG. 39C  FIG. 39D

Lean db/db

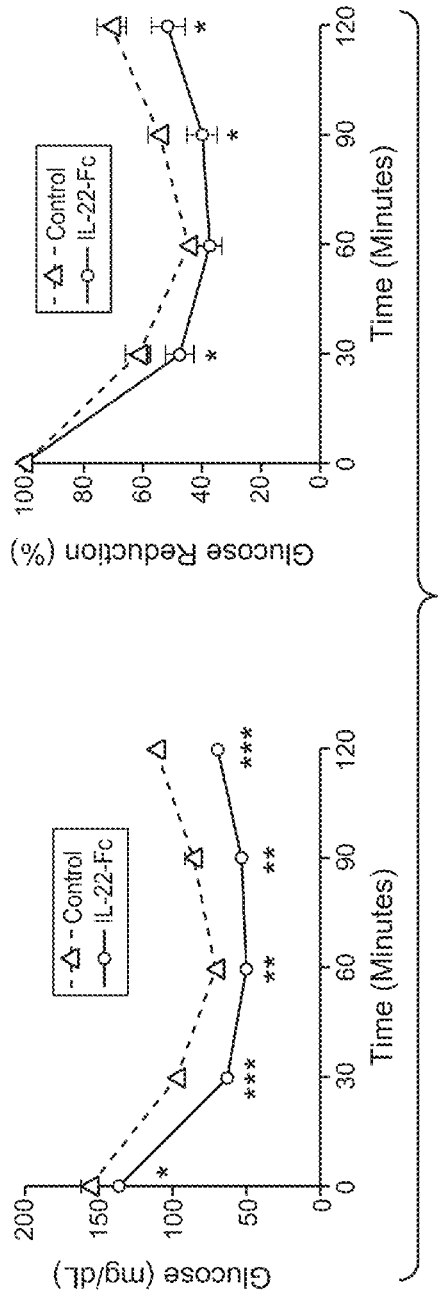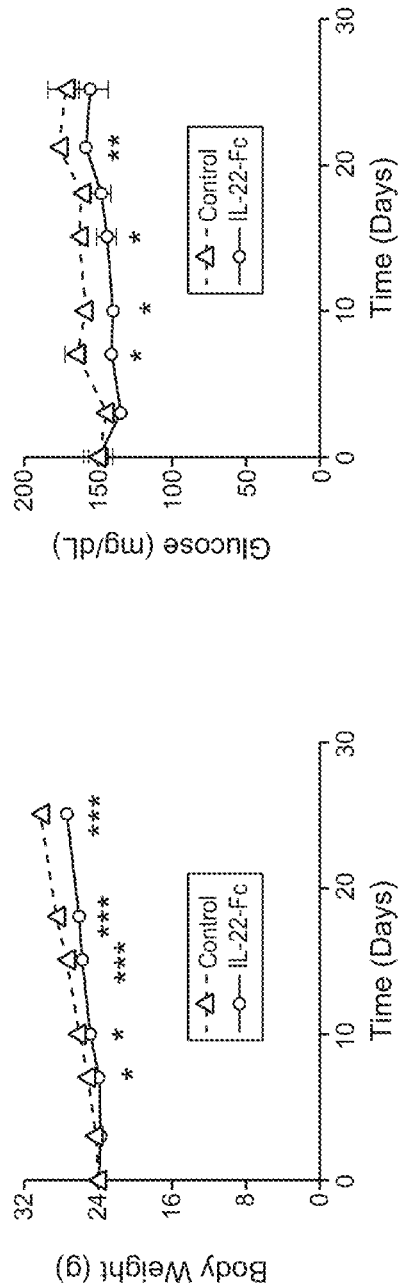

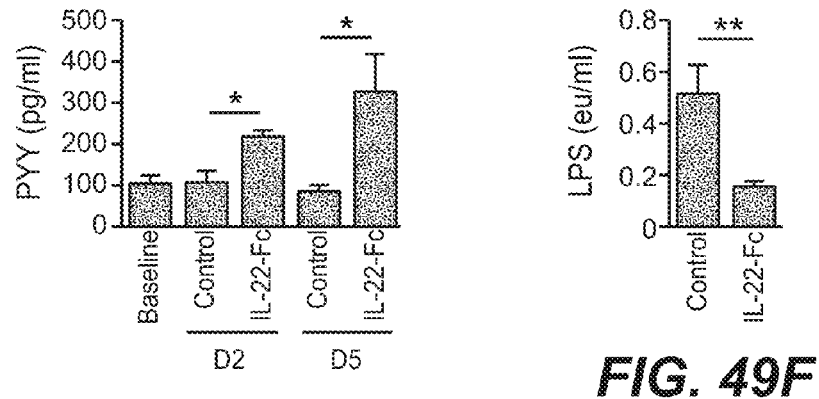
FIG. 49E
FIG. 49F
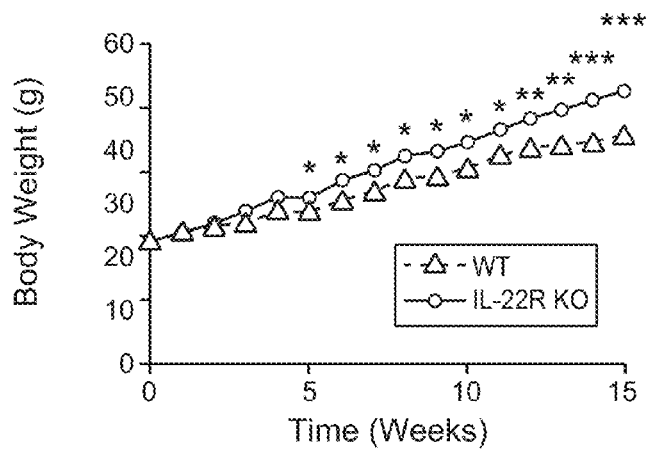
FIG. 49G
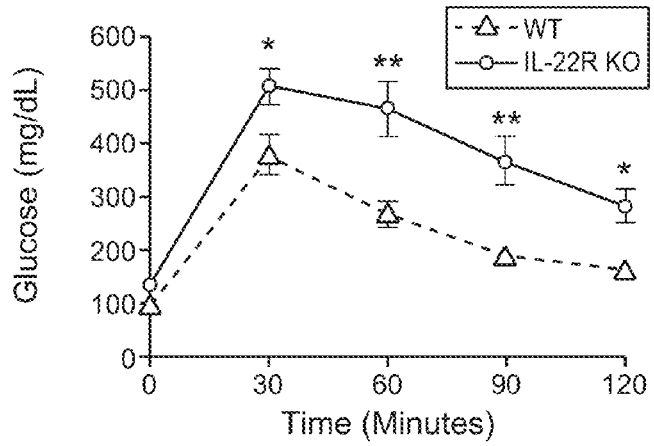
FIG. 49H

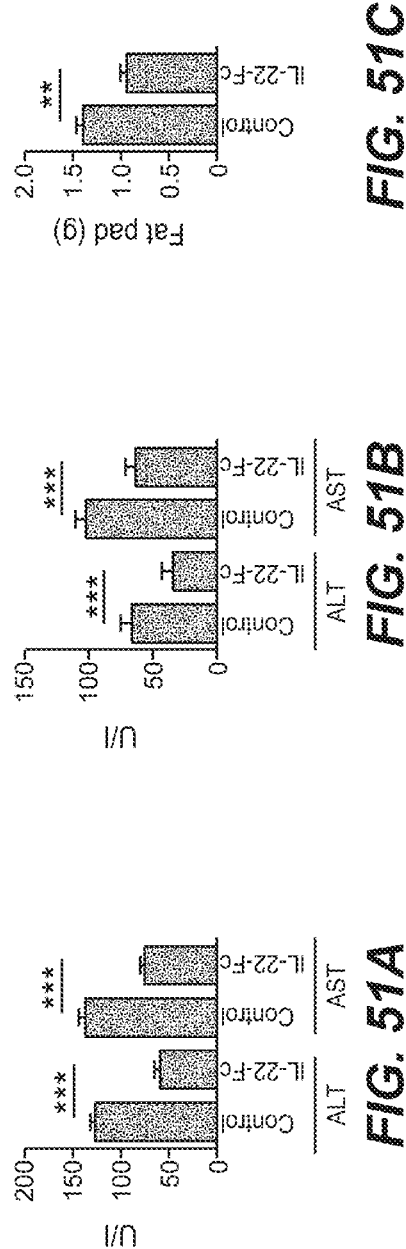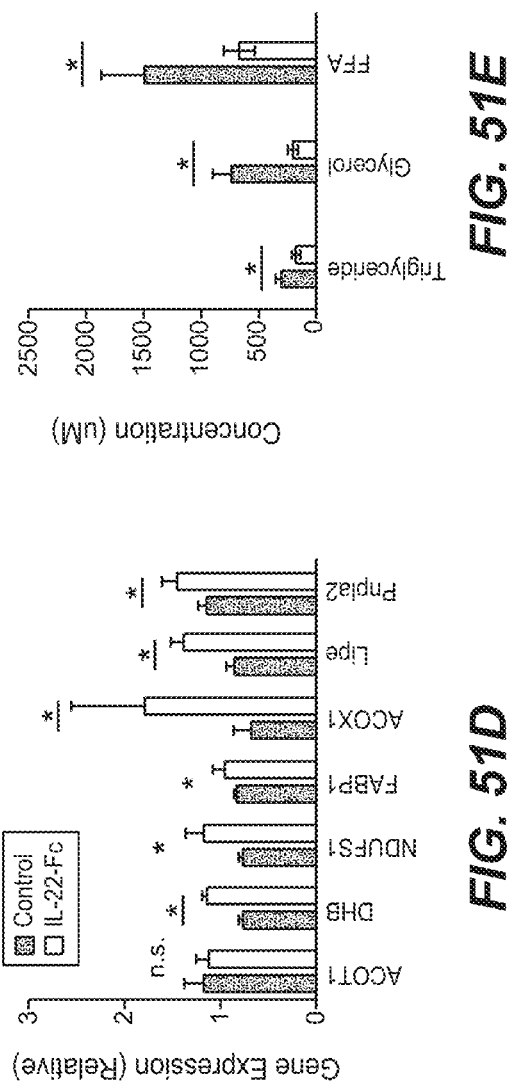

```
                         SEQUENCE LISTING

<160> NUMBER OF SEQ ID NOS: 80

<210> SEQ ID NO 1
<211> LENGTH: 495
<212> TYPE: DNA
<213> ORGANISM: Homo sapiens
<220> FEATURE:
<223> OTHER INFORMATION: Human IL-22

<400> SEQUENCE: 1
atgggatggt catgtatcat ccttttctta gtagcaactg caactggagt acattcagcg      60
cccatcagct cccactgcag gcttgacaag tccaacttcc agcagcccta tatcaccaac     120
cgcaccttca tgctggctaa ggaggctagc ttggctgata caacacaga cgttcgtctc     180 attggggaga aactgttcca cggagtcagt atgagtgagc gctgctatct gatgaagcag     240
gtgctgaact tcacccttga agaagtgctg ttccctcaat ctgataggtt ccagccttat     300
atgcaggagg tggtgcccct cctggccagg ctcagcaaca ggctaagcac atgtcatatt     360
gaaggtgatg acctgcatat ccagaggaat gtgcaaaagc tgaaggacac agtgaaaaag     420
cttggagaga gtggagagat caaagcaatt ggagaactgg atttgctgtt tatgtctctg     480
agaaatgcct gcatt                                                     495

<210> SEQ ID NO 2
<211> LENGTH: 165
<212> TYPE: PRT
<213> ORGANISM: Homo sapiens
<220> FEATURE:
<223> OTHER INFORMATION: Human IL-22

<400> SEQUENCE: 2

Met Gly Trp Ser Cys Ile Ile Leu Phe Leu Val Ala Thr Ala Thr Gly
1               5                   10                  15

Val His Ser Ala Pro Ile Ser Ser His Cys Arg Leu Asp Lys Ser Asn
            20                  25                  30

Phe Gln Gln Pro Tyr Ile Thr Asn Arg Thr Phe Met Leu Ala Lys Glu
        35                  40                  45

Ala Ser Leu Ala Asp Asn Asn Thr Asp Val Arg Leu Ile Gly Glu Lys
    50                  55                  60

Leu Phe His Gly Val Ser Met Ser Glu Arg Cys Tyr Leu Met Lys Gln
```

```
                65                  70                  75                  80
Val Leu Asn Phe Thr Leu Glu Glu Val Leu Phe Pro Gln Ser Asp Arg
                    85                  90                  95

Phe Gln Pro Tyr Met Gln Glu Val Val Pro Phe Leu Ala Arg Leu Ser
                100                 105                 110

Asn Arg Leu Ser Thr Cys His Ile Glu Gly Asp Asp Leu His Ile Gln
                115                 120                 125

Arg Asn Val Gln Lys Leu Lys Asp Thr Val Lys Lys Leu Gly Glu Ser
                130                 135                 140

Gly Glu Ile Lys Ala Ile Gly Glu Leu Asp Leu Leu Phe Met Ser Leu
145                 150                 155                 160

Arg Asn Ala Cys Ile
                165

<210> SEQ ID NO 3
<211> LENGTH: 438
<212> TYPE: DNA
<213> ORGANISM: Homo sapiens
<220> FEATURE:
<223> OTHER INFORMATION: IL-22 DNA (mature)

<400> SEQUENCE: 3
gcgcccatca gctcccactg caggcttgac aagtccaact tccagcagcc ctatatcacc      60
aaccgcacct tcatgctggc taaggaggct agcttggctg ataacaacac agacgttcgt    120
ctcattgggg agaaactgtt ccacggagtc agtatgagtg agcgctgcta tctgatgaag    180
caggtgctga acttcaccct tgaagaagtg ctgttccctc aatctgatag gttccagcct    240
tatatgcagg aggtggtgcc cttcctggcc aggctcagca acaggctaag cacatgtcat    300
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcatt                                                  438

<210> SEQ ID NO 4
<211> LENGTH: 146
<212> TYPE: PRT
<213> ORGANISM: Homo sapiens
<220> FEATURE:
<223> OTHER INFORMATION: IL-22 (mature)

<400> SEQUENCE: 4

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
                35                  40                  45

Gly Val Ser Met Ser Glu Arg Cys Tyr Leu Met Lys Gln Val Leu Asn
                50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
                100                 105                 110

Gln Lys Leu Lys Asp Thr Val Lys Lys Leu Gly Glu Ser Gly Glu Ile
                115                 120                 125
```

Lys Ala Ile Gly Glu Leu Asp Leu Leu Phe Met Ser Leu Arg Asn Ala
            130                 135                 140

Cys Ile
145

<210> SEQ ID NO 5
<211> LENGTH: 57
<212> TYPE: DNA
<213> ORGANISM: Homo sapiens
<220> FEATURE:
<223> OTHER INFORMATION: IL-22 leader sequence

<400> SEQUENCE: 5
atgggatggt catgtatcat ccttttttcta gtagcaactg caactggagt acattca      57

<210> SEQ ID NO 6
<211> LENGTH: 19
<212> TYPE: PRT
<213> ORGANISM: Homo sapiens
<220> FEATURE:
<223> OTHER INFORMATION: IL-22 leader sequence

<400> SEQUENCE: 6

Met Gly Trp Ser Cys Ile Ile Leu Phe Leu Val Ala Thr Ala Thr Gly
1               5                   10                  15

Val His Ser

<210> SEQ ID NO 7
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (minus C-terminal Lys)
      N297G

<400> SEQUENCE: 7

| | | |
|---|---|---|
| gcgcccatca gctcccactg caggcttgac aagtccaact tccagcagcc ctatatcacc | 60 |
| aaccgcacct tcatgctggc taaggaggct agcttggctg ataacaacac agacgttcgt | 120 |
| ctcattgggg agaaactgtt ccacggagtc agtatgagtg agcgctgcta tctgatgaag | 180 |
| caggtgctga acttcacccct tgaagaagtg ctgttccctc aatctgatag gttccagcct | 240 |
| tatatgcagg aggtggtgcc cttcctggcc aggctcagca caggctaag cacatgtcat | 300 |
| attgaaggtg atgacctgca tatccagagg aatgtgcaaa agctgaagga cacagtgaaa | 360 |
| aagcttggag agagtggaga gatcaaagca attggagaac tggatttgct gtttatgtct | 420 |
| ctgagaaatg cctgcattcg cgttgagtcc aaatatggtc ccccatgccc accatgccca | 480 |
| gcacctgagt tcctgggggg accatcagtc ttcctgttcc ccccaaaacc caaggacact | 540 |
| ctcatgatct cccggacccc tgaggtcacg tgcgtggtgg tggacgtgag ccaggaagac | 600 |
| cccgaggtcc agttcaactg gtacgtggat ggcgtggagg tgcataatgc caagacaaag | 660 |
| ccgcgggagg agcagttcgg aagcacgtac cgtgtggtca gcgtcctcac cgtcctgcac | 720 |
| caggactggc tgaacggcaa ggagtacaag tgcaaggtct ccaacaaagg cctcccgtcc | 780 |
| tccatcgaga aaaccatctc caaagccaaa gggcagcccc gagagccaca ggtgtacacc | 840 |
| ctgcccccat cccaggagga gatgaccaag aaccaggtca gcctgacctg cctggtcaaa | 900 |
| ggcttctacc ccagcgacat cgccgtggag tgggagagca atgggcagcc ggagaacaac | 960 |

```
tacaagacca cgcctcccgt gctggactcc gacggctcct tcttcctcta cagcaggcta    1020
accgtggaca agagcaggtg gcaggagggg aatgtcttct catgctccgt gatgcatgag    1080
gctctgcaca accactacac acagaagagc ctctccctgt ctctgggt                1128
```

<210> SEQ ID NO 8
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (minus C-terminal Lys)
      N297G

<400> SEQUENCE: 8

```
Ala Pro Ile Ser Ser His Cys Arg Leu Asp Lys Ser Asn Phe Gln Gln
 1               5                  10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Gly Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
```

```
                305                 310                 315                 320
Tyr Lys Thr Thr Pro Pro Val Leu Asp Ser Asp Gly Ser Phe Phe Leu
                    325                 330                 335
Tyr Ser Arg Leu Thr Val Asp Lys Ser Arg Trp Gln Glu Gly Asn Val
                    340                 345                 350
Phe Ser Cys Ser Val Met His Glu Ala Leu His Asn His Tyr Thr Gln
                    355                 360                 365
Lys Ser Leu Ser Leu Ser Leu Gly
            370                 375
```

<210> SEQ ID NO 9
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (minus C-terminal Lys)
      N297A

<400> SEQUENCE: 9

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat     300
attgaaggtg atgacctgca tatccagagg aatgtgcaaa agctgaagga cacagtgaaa     360
agcttggag agagtggaga gatcaaagca attggagaac tggatttgct gtttatgtct     420
ctgagaaatg cctgcattcg cgttgagtcc aaatatggtc cccatgccc accatgccca     480
gcacctgagt tcctgggggg accatcagtc ttcctgttcc ccccaaaacc caaggacact     540
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag     660
ccgcgggagg agcagttcgc tagcacgtac cgtgtggtca gcgtcctcac cgtcctgcac     720
caggactggc tgaacggcaa ggagtacaag tgcaaggtct ccaacaaagg cctcccgtcc     780
tccatcgaga aaaccatctc caaagccaaa gggcagcccc gagagccaca ggtgtacacc     840
ctgcccccat cccaggagga gatgaccaag aaccaggtca gcctgacctg cctggtcaaa     900
ggcttctacc ccagcgacat cgccgtggag tgggagagca atgggcagcc ggagaacaac     960
tacaagacca cgcctcccgt gctggactcc gacggctcct tcttcctcta cagcaggcta    1020
accgtggaca agagcaggtg gcaggagggg aatgtcttct catgctccgt gatgcatgag    1080
gctctgcaca accactacac acagaagagc ctctccctgt ctctgggt                1128
```

<210> SEQ ID NO 10
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (minus C-terminal Lys)
      N297A

<400> SEQUENCE: 10

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
            115                 120                 125

Lys Ala Ile Gly Glu Leu Asp Leu Leu Phe Met Ser Leu Arg Asn Ala
130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
            195                 200                 205

Val Asp Gly Val Glu Val His Asn Ala Lys Thr Lys Pro Arg Glu Glu
210                 215                 220

Gln Phe Ala Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
            325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
            355                 360                 365

Lys Ser Leu Ser Leu Ser Leu Gly
    370                 375

<210> SEQ ID NO 11
<211> LENGTH: 1131
<212> TYPE: DNA
<213> ORGANISM: Artificial Sequence
<220> FEATURE:
```

<223> OTHER INFORMATION: Description of Artificial Sequence: Synthetic
polynucleotide
<220> FEATURE:
<223> OTHER INFORMATION: IL-22 Fc fusion IgG1 (minus C-terminal Lys)
N297G

<400> SEQUENCE: 11

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat      300
attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattga gcccaaatct agtgacaaaa ctcacacatg cccaccgtgc     480
ccagcacctg aactcctggg gggaccgtca gtcttcctct ccccccaaa acccaaggac      540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta cggaagcacg taccgtgtgg tcagcgtcct caccgtcctg     720
caccaggact ggctgaatgg caaggagtac aagtgcaagg tctccaacaa agccctccca     780
gcccccatcg agaaaaccat ctccaaagcc aagggcagc cccgagaacc acaggtgtac      840
accctgcccc catcccggga agagatgacc aagaaccagg tcagcctgac ctgcctggtc     900
aaaggcttct atcccagcga catcgccgtg gagtgggaga gcaatgggca gccggagaac     960
aactacaaga ccacgcctcc cgtgctggac tccgacggct ccttcttcct ctacagcaag    1020
ctcaccgtgg acaagagcag gtggcagcag gggaacgtct tctcatgctc cgtgatgcat    1080
gaggctctgc acaaccacta cacgcagaag agcctctccc tgtctccggg t             1131
```

<210> SEQ ID NO 12
<211> LENGTH: 377
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: IL-22 Fc fusion IgG1 (minus C-terminal Lys)
N297G

<400> SEQUENCE: 12

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
```

```
                100             105             110
Gln Lys Leu Lys Asp Thr Val Lys Lys Leu Gly Glu Ser Gly Glu Ile
            115                 120                 125
Lys Ala Ile Gly Glu Leu Asp Leu Leu Phe Met Ser Leu Arg Asn Ala
        130                 135                 140
Cys Ile Glu Pro Lys Ser Ser Asp Lys Thr His Thr Cys Pro Pro Cys
145                 150                 155                 160
Pro Ala Pro Glu Leu Leu Gly Gly Pro Ser Val Phe Leu Phe Pro Pro
                165                 170                 175
Lys Pro Lys Asp Thr Leu Met Ile Ser Arg Thr Pro Glu Val Thr Cys
            180                 185                 190
Val Val Val Asp Val Ser His Glu Asp Pro Glu Val Lys Phe Asn Trp
        195                 200                 205
Tyr Val Asp Gly Val Glu Val His Asn Ala Lys Thr Lys Pro Arg Glu
    210                 215                 220
Glu Gln Tyr Gly Ser Thr Tyr Arg Val Val Ser Val Leu Thr Val Leu
225                 230                 235                 240
His Gln Asp Trp Leu Asn Gly Lys Glu Tyr Lys Cys Lys Val Ser Asn
                245                 250                 255
Lys Ala Leu Pro Ala Pro Ile Glu Lys Thr Ile Ser Lys Ala Lys Gly
            260                 265                 270
Gln Pro Arg Glu Pro Gln Val Tyr Thr Leu Pro Pro Ser Arg Glu Glu
        275                 280                 285
Met Thr Lys Asn Gln Val Ser Leu Thr Cys Leu Val Lys Gly Phe Tyr
    290                 295                 300
Pro Ser Asp Ile Ala Val Glu Trp Glu Ser Asn Gly Gln Pro Glu Asn
305                 310                 315                 320
Asn Tyr Lys Thr Thr Pro Pro Val Leu Asp Ser Asp Gly Ser Phe Phe
                325                 330                 335
Leu Tyr Ser Lys Leu Thr Val Asp Lys Ser Arg Trp Gln Gln Gly Asn
            340                 345                 350
Val Phe Ser Cys Ser Val Met His Glu Ala Leu His Asn His Tyr Thr
        355                 360                 365
Gln Lys Ser Leu Ser Leu Ser Pro Gly
    370                 375
```

<210> SEQ ID NO 13
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (minus C-terminal Lys)
      N297A

<400> SEQUENCE: 13
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcacct tgaagaagtg ctgttccctc aatctgatag gttccagcct     240
tatatgcagg aggtggtgcc cttcctggcc aggctcagca acaggctaag cacatgtcat     300
attgaaggtg atgacctgca tatccagagg aatgtgcaaa agctgaagga cacagtgaaa     360

-continued

```
aagcttggag agagtggaga gatcaaagca attggagaac tggatttgct gtttatgtct      420
ctgagaaatg cctgcattga gcccaaatct agtgacaaaa ctcacacatg cccaccgtgc      480
ccagcacctg aactcctggg gggaccgtca gtcttcctct tccccccaaa acccaaggac      540
accctcatga tctcccggac ccctgaggtc acatgcgtgg tggtggacgt gagccacgaa      600
gaccctgagg tcaagttcaa ctggtacgtg gacggcgtgg aggtgcataa tgccaagaca      660
aagccgcggg aggagcagta cgctagcacg taccgtgtgg tcagcgtcct caccgtcctg      720
caccaggact ggctgaatgg caaggagtac aagtgcaagg tctccaacaa agccctccca      780
gccccatcg agaaaaccat ctccaaagcc aagggcagc cccgagaacc acaggtgtac      840
accctgcccc catcccggga agatgacc aagaaccagg tcagcctgac ctgcctggtc      900
aaaggcttct atcccagcga catcgccgtg gagtgggaga gcaatgggca gccggagaac      960
aactacaaga ccacgcctcc cgtgctggac tccgacggct ccttcttcct ctacagcaag     1020
ctcaccgtgg acaagagcag gtggcagcag gggaacgtct tctcatgctc cgtgatgcat     1080
gaggctctgc acaaccacta cacgcagaag agcctctccc tgtctccggg t             1131
```

<210> SEQ ID NO 14
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-22 Fc fusion IgG1 (minus C-terminal Lys) N297A

<400> SEQUENCE: 14

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205
```

```
Tyr Val Asp Gly Val Glu Val His Asn Ala Lys Thr Lys Pro Arg Glu
    210                 215                 220
Glu Gln Tyr Ala Ser Thr Tyr Arg Val Val Ser Val Leu Thr Val Leu
225                 230                 235                 240
His Gln Asp Trp Leu Asn Gly Lys Glu Tyr Lys Cys Lys Val Ser Asn
                245                 250                 255
Lys Ala Leu Pro Ala Pro Ile Glu Lys Thr Ile Ser Lys Ala Lys Gly
                260                 265                 270
Gln Pro Arg Glu Pro Gln Val Tyr Thr Leu Pro Pro Ser Arg Glu Glu
            275                 280                 285
Met Thr Lys Asn Gln Val Ser Leu Thr Cys Leu Val Lys Gly Phe Tyr
    290                 295                 300
Pro Ser Asp Ile Ala Val Glu Trp Glu Ser Asn Gly Gln Pro Glu Asn
305                 310                 315                 320
Asn Tyr Lys Thr Thr Pro Pro Val Leu Asp Ser Asp Gly Ser Phe Phe
                325                 330                 335
Leu Tyr Ser Lys Leu Thr Val Asp Lys Ser Arg Trp Gln Gln Gly Asn
                340                 345                 350
Val Phe Ser Cys Ser Val Met His Glu Ala Leu His Asn His Tyr Thr
            355                 360                 365
Gln Lys Ser Leu Ser Leu Ser Pro Gly
    370                 375
```

<210> SEQ ID NO 15
<211> LENGTH: 1131
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: IL-22 Fc fusion IgG4 (full) N297G

<400> SEQUENCE: 15

```
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag    180
caggtgctga acttcaccct tgaagaagtg ctgttccctc aatctgatag gttccagcct    240
tatatgcagg aggtggtgcc cttcctggcc aggctcagca acaggctaag cacatgtcat    300
attgaaggtg atgacctgca tatccagagg aatgtgcaaa agctgaagga cagtgaaa     360
aagcttggag agagtggaga gatcaaagca attggagaac tggatttgct gtttatgtct    420
ctgagaaatg cctgcattcg cgttgagtcc aaatatggtc ccccatgccc accatgccca    480
gcacctgagt tcctgggggg accatcagtc ttcctgttcc cccaaaaacc caaggacact    540
ctcatgatct cccggacccc tgaggtcacg tgcgtggtgg tggacgtgag ccaggaagac    600
cccgaggtcc agttcaactg gtacgtggat ggcgtggagt gcataatgc caagacaaag    660
ccgcgggagg agcagttcgg aagcacgtac cgtgtggtca gcgtcctcac cgtcctgcac    720
caggactggc tgaacggcaa ggagtacaag tgcaaggtct ccaacaaagg cctcccgtcc    780
tccatcgaga aaaccatctc caaagccaaa gggcagcccc gagagccaca ggtgtacacc    840
ctgcccccat cccaggagga gatgaccaag aaccaggtca gcctgacctg cctggtcaaa    900
ggcttctacc ccagcgacat cgccgtggag tgggagagca tgggcagcc ggagaacaac    960
tacaagacca cgcctcccgt gctggactcc gacggctcct tcttcctcta cagcaggcta   1020
```

```
accgtggaca agagcaggtg gcaggagggg aatgtcttct catgctccgt gatgcatgag    1080
gctctgcaca accactacac acagaagagc ctctccctgt ctctgggtaa a             1131
```

<210> SEQ ID NO 16
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (full) N297G

<400> SEQUENCE: 16

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
    210                 215                 220

Gln Phe Gly Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
```

```
                    325                 330                 335
Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
            355                 360                 365

Lys Ser Leu Ser Leu Ser Leu Gly Lys
            370                 375

<210> SEQ ID NO 17
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (full) N297A

<400> SEQUENCE: 17
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcacccT tgaagaagtg ctgttccctc aatctgatag gttccagcct     240
tatatgcagg aggtggtgcc cttcctggcc aggctcagca caggctaag cacatgtcat      300 attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattcg cgttgagtcc aaatatggtc ccccatgccc accatgccca     480
gcacctgagt tcctgggggg accatcagtc ttcctgttcc cccaaaaacc caaggacact     540
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag     660
ccgcgggagg agcagttcgc tagcacgtac cgtgtggtca gcgtcctcac cgtcctgcac     720
caggactggc tgaacggcaa ggagtacaag tgcaaggtct ccaacaaagg cctcccgtcc     780
tccatcgaga aaaccatctc caaagccaaa gggcagcccc gagagccaca ggtgtacacc     840
ctgcccccat cccaggagga gatgaccaag aaccaggtca gcctgacctg cctggtcaaa     900
ggcttctacc ccagcgacat cgccgtggag tgggagagca atgggcagcc ggagaacaac     960
tacaagacca cgcctcccgt gctggactcc gacggctcct tcttcctcta cagcaggcta    1020
accgtggaca agagcaggtg gcaggagggg aatgtcttct catgctccgt gatgcatgag    1080
gctctgcaca accactacac acagaagagc ctctccctgt ctctgggtaa a             1131

<210> SEQ ID NO 18
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (full) N297A

<400> SEQUENCE: 18

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
```

```
            20                  25                  30
Ala Asp Asn Asn Thr Asp Val Arg Leu Ile Gly Glu Lys Leu Phe His
        35                  40                  45
Gly Val Ser Met Ser Glu Arg Cys Tyr Leu Met Lys Gln Val Leu Asn
    50                  55                  60
Phe Thr Leu Glu Glu Val Leu Phe Pro Gln Ser Asp Arg Phe Gln Pro
65                  70                  75                  80
Tyr Met Gln Glu Val Val Pro Phe Leu Ala Arg Leu Ser Asn Arg Leu
                85                  90                  95
Ser Thr Cys His Ile Glu Gly Asp Asp Leu His Ile Gln Arg Asn Val
            100                 105                 110
Gln Lys Leu Lys Asp Thr Val Lys Lys Leu Gly Glu Ser Gly Glu Ile
        115                 120                 125
Lys Ala Ile Gly Glu Leu Asp Leu Leu Phe Met Ser Leu Arg Asn Ala
    130                 135                 140
Cys Ile Arg Val Glu Ser Lys Tyr Gly Pro Pro Cys Pro Pro Cys Pro
145                 150                 155                 160
Ala Pro Glu Phe Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser Gln Glu Asp Pro Glu Val Gln Phe Asn Trp Tyr
        195                 200                 205
Val Asp Gly Val Glu Val His Asn Ala Lys Thr Lys Pro Arg Glu Glu
    210                 215                 220
Gln Phe Ala Ser Thr Tyr Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Gly Leu Pro Ser Ser Ile Glu Lys Thr Ile Ser Lys Ala Lys Gly Gln
            260                 265                 270
Pro Arg Glu Pro Gln Val Tyr Thr Leu Pro Pro Ser Gln Glu Glu Met
        275                 280                 285
Thr Lys Asn Gln Val Ser Leu Thr Cys Leu Val Lys Gly Phe Tyr Pro
    290                 295                 300
Ser Asp Ile Ala Val Glu Trp Glu Ser Asn Gly Gln Pro Glu Asn Asn
305                 310                 315                 320
Tyr Lys Thr Thr Pro Pro Val Leu Asp Ser Asp Gly Ser Phe Phe Leu
                325                 330                 335
Tyr Ser Arg Leu Thr Val Asp Lys Ser Arg Trp Gln Glu Gly Asn Val
            340                 345                 350
Phe Ser Cys Ser Val Met His Glu Ala Leu His Asn His Tyr Thr Gln
        355                 360                 365
Lys Ser Leu Ser Leu Ser Leu Gly Lys
    370                 375

<210> SEQ ID NO 19
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (full) N297G
```

-continued

```
<400> SEQUENCE: 19
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca acaggctaag cacatgtcat     300
attgaaggtg atgacctgca tatccagagg aatgtgcaaa agctgaagga cacagtgaaa     360
aagcttggag agagtggaga gatcaaagca attggagaac tggatttgct gtttatgtct     420
ctgagaaatg cctgcattga gcccaaatct agtgacaaaa ctcacacatg cccaccgtgc     480
ccagcacctg aactcctggg gggaccgtca gtcttcctct tccccccaaa acccaaggac     540
accctcatga tctcccggac ccctgaggtc acatgcgtgg tggtggacgt gagccacgaa     600
gaccctgagg tcaagttcaa ctggtacgtg gacggcgtgg aggtgcataa tgccaagaca     660
aagccgcggg aggagcagta cggaagcacg taccgtgtgt cagcgtcct caccgtcctg     720
caccaggact ggctgaatgg caaggagtac aagtgcaagg tctccaacaa agccctccca     780
gcccccatcg agaaaaccat ctccaaagcc aagggcagc cccgagaacc acaggtgtac     840
accctgcccc catcccggga agagatgacc aagaaccagg tcagcctgac ctgcctggtc     900
aaaggcttct atcccagcga catcgccgtg gagtgggaga gcaatgggca gccggagaac     960
aactacaaga ccacgcctcc cgtgctggac tccgacggct ccttcttcct ctacagcaag    1020
ctcaccgtgg acaagagcag gtggcagcag gggaacgtct tctcatgctc cgtgatgcat    1080
gaggctctgc acaaccacta cacgcagaag agcctctccc tgtctccggg taaa          1134
```

<210> SEQ ID NO 20
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (full) N297G

<400> SEQUENCE: 20

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140
```

```
Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
            165                 170                 175

Lys Pro Lys Asp Thr Leu Met Ile Ser Arg Thr Pro Glu Val Thr Cys
        180                 185                 190

Val Val Val Asp Val Ser His Glu Asp Pro Glu Val Lys Phe Asn Trp
    195                 200                 205

Tyr Val Asp Gly Val Glu Val His Asn Ala Lys Thr Lys Pro Arg Glu
210                 215                 220

Glu Gln Tyr Gly Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375
```

<210> SEQ ID NO 21
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (full) N297A

<400> SEQUENCE: 21

```
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca acaggctaag cacatgtcat   300
attgaaggtg atgacctgca tatccagagg aatgtgcaaa agctgaagga cacagtgaaa   360
aagcttggag agagtggaga gatcaaagca attggagaac tggatttgct gtttatgtct   420
ctgagaaatg cctgcattga gcccaaatct agtgacaaaa ctcacacatg cccaccgtgc   480
ccagcacctg aactcctggg gggaccgtca gtcttcctct ccccccaaa acccaaggac   540 accctcatga tctcccggac ccctgaggtc acatgcgtgg tggtggacgt gagccacgaa   600
```

-continued

```
gaccctgagg tcaagttcaa ctggtacgtg gacggcgtgg aggtgcataa tgccaagaca    660
aagccgcggg aggagcagta cgctagcacg taccgtgtgg tcagcgtcct caccgtcctg    720
caccaggact ggctgaatgg caaggagtac aagtgcaagg tctccaacaa agccctccca    780
gcccccatcg agaaaaccat ctccaaagcc aaagggcagc cccgagaacc acaggtgtac    840
accctgcccc catcccggga agagatgacc aagaaccagg tcagcctgac ctgcctggtc    900
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg taaa         1134
```

<210> SEQ ID NO 22
<211> LENGTH: 378
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-22 Fc fusion IgG1 (full) N297A

<400> SEQUENCE: 22

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Ala Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255
```

-continued

| | | | | | | | | | | | | |
|---|---|---|---|---|---|---|---|---|---|---|---|---|
|Lys|Ala|Leu|Pro|Ala|Pro|Ile|Glu|Lys|Thr|Ile|Ser|Lys|Ala|Lys|Gly|
| | | |260| | | |265| | | |270| |

Gln Pro Arg Glu Pro Gln Val Tyr Thr Leu Pro Ser Arg Glu Glu
        275                 280                 285

Met Thr Lys Asn Gln Val Ser Leu Thr Cys Leu Val Lys Gly Phe Tyr
    290                 295                 300

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
                325                 330                 335

Leu Tyr Ser Lys Leu Thr Val Asp Lys Ser Arg Trp Gln Gln Gly Asn
            340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375

```
<210> SEQ ID NO 23
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (wt N297, minus Lys)

<400> SEQUENCE: 23
gcgcccatca gctcccactg caggcttgac aagtccaact tccagcagcc ctatatcacc      60
aaccgcacct tcatgctggc taaggaggct agcttggctg ataacaacac agacgttcgt     120
ctcattgggg agaaactgtt ccacggagtc agtatgagtg agcgctgcta tctgatgaag     180
caggtgctga acttcaccct tgaagaagtg ctgttccctc aatctgatag gttccagcct     240
tatatgcagg aggtggtgcc cttcctggcc aggctcagca caggctaag cacatgtcat     300 attgaaggtg atgacctgca tatccagagg aatgtgcaaa agctgaagga cacagtgaaa     360
aagcttggag agagtggaga gatcaaagca attggagaac tggatttgct gttttatgtct     420 ctgagaaatg cctgcattcg cgttgagtcc aaatatggtc ccccatgccc accatgccca     480
gcacctgagt tcctgggggg accatcagtc ttcctgttcc ccccaaaacc caaggacact     540
ctcatgatct cccggacccc tgaggtcacg tgcgtggtgg tggacgtgag ccaggaagac     600
cccgaggtcc agttcaactg gtacgtggat ggcgtggagg tgcataatgc caagacaaag     660
ccgcgggagg agcagttcaa cagcacgtac cgtgtggtca gcgtcctcac cgtcctgcac     720
caggactggc tgaacggcaa ggagtacaag tgcaaggtct ccaacaaagg cctcccgtcc     780
tccatcgaga aaaccatctc caaagccaaa gggcagcccc gagagccaca ggtgtacacc     840
ctgcccccat cccaggagga gatgaccaag aaccaggtca gcctgacctg cctggtcaaa     900
ggcttctacc ccagcgacat cgccgtggag tgggagagca atgggcagcc ggagaacaac     960
tacaagacca cgcctcccgt gctggactcc gacggctcct tcttcctcta cagcaggcta    1020
accgtggaca gagcaggtg gcaggaggg aatgtcttct catgctccgt gatgcatgag    1080
gctctgcaca accactacac acagaagagc ctctcccctgt ctctgggt             1128

<210> SEQ ID NO 24
<211> LENGTH: 376
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (wt N297, minus Lys)

<400> SEQUENCE: 24

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Arg Val Glu Ser Lys Tyr Gly Pro Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
210                 215                 220

Gln Phe Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
            260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
            340                 345                 350

Phe Ser Cys Ser Val Met His Glu Ala Leu His Asn His Tyr Thr Gln
        355                 360                 365

Lys Ser Leu Ser Leu Ser Leu Gly
```

<210> SEQ ID NO 25
<211> LENGTH: 1131
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: IL-22 Fc fusion IgG1 (wt N297, minus Lys)

<400> SEQUENCE: 25

| | |
|---|---|
| gcgcccatca gctcccactg caggcttgac aagtccaact tccagcagcc ctatatcacc | 60 |
| aaccgcacct tcatgctggc taaggaggct agcttggctg ataacaacac agacgttcgt | 120 |
| ctcattgggg agaaactgtt ccacggagtc agtatgagtg agcgctgcta tctgatgaag | 180 |
| caggtgctga acttcaccct tgaagaagtg ctgttccctc aatctgatag gttccagcct | 240 |
| tatatgcagg aggtggtgcc cttcctggcc aggctcagca acaggctaag cacatgtcat | 300 |
| attgaaggtg atgacctgca tatccagagg aatgtgcaaa agctgaagga cacagtgaaa | 360 |
| aagcttggag agagtggaga gatcaaagca attggagaac tggatttgct gtttatgtct | 420 |
| ctgagaaatg cctgcattga gcccaaatct agtgacaaaa ctcacacatg cccaccgtgc | 480 |
| ccagcacctg aactcctggg gggaccgtca gtcttcctct tccccccaaa acccaaggac | 540 |
| accctcatga tctcccggac ccctgaggtc acatgcgtgg tggtggacgt gagccacgaa | 600 |
| gaccctgagg tcaagttcaa ctggtacgtg gacggcgtgg aggtgcataa tgccaagaca | 660 |
| aagccgcggg aggagcagta caacagcacg taccgtgtgg tcagcgtcct caccgtcctg | 720 |
| caccaggact ggctgaatgg caaggagtac aagtgcaagg tctccaacaa agccctccca | 780 |
| gcccccatcg agaaaaccat ctccaaagcc aaagggcagc cccgagaacc acaggtgtac | 840 |
| accctgcccc catcccggga agagatgacc aagaaccagg tcagcctgac ctgcctggtc | 900 |
| aaaggcttct atcccagcga catcgccgtg gagtgggaga gcaatgggca gccggagaac | 960 |
| aactacaaga ccacgcctcc cgtgctggac tccgacggct ccttcttcct ctacagcaag | 1020 |
| ctcaccgtgg acaagagcag gtggcagcag gggaacgtct tctcatgctc cgtgatgcat | 1080 |
| gaggctctgc acaaccacta cacgcagaag agcctctccc tgtctccggg t | 1131 |

<210> SEQ ID NO 26
<211> LENGTH: 377
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: IL-22 Fc fusion IgG1 (wt N297, minus Lys)

<400> SEQUENCE: 26

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro

```
                65                  70                  75                  80
Tyr Met Gln Glu Val Val Pro Phe Leu Ala Arg Leu Ser Asn Arg Leu
                    85                  90                  95
Ser Thr Cys His Ile Glu Gly Asp Asp Leu His Ile Gln Arg Asn Val
                100                 105                 110
Gln Lys Leu Lys Asp Thr Val Lys Leu Gly Glu Ser Gly Glu Ile
            115                 120                 125
Lys Ala Ile Gly Glu Leu Asp Leu Leu Phe Met Ser Leu Arg Asn Ala
            130                 135                 140
Cys Ile Glu Pro Lys Ser Ser Asp Lys Thr His Thr Cys Pro Pro Cys
145                 150                 155                 160
Pro Ala Pro Glu Leu Leu Gly Gly Pro Ser Val Phe Leu Phe Pro Pro
                165                 170                 175
Lys Pro Lys Asp Thr Leu Met Ile Ser Arg Thr Pro Glu Val Thr Cys
                180                 185                 190
Val Val Val Asp Val Ser His Glu Asp Pro Glu Val Lys Phe Asn Trp
            195                 200                 205
Tyr Val Asp Gly Val Glu Val His Asn Ala Lys Thr Lys Pro Arg Glu
            210                 215                 220
Glu Gln Tyr Asn Ser Thr Tyr Arg Val Val Ser Val Leu Thr Val Leu
225                 230                 235                 240
His Gln Asp Trp Leu Asn Gly Lys Glu Tyr Lys Cys Lys Val Ser Asn
                245                 250                 255
Lys Ala Leu Pro Ala Pro Ile Glu Lys Thr Ile Ser Lys Ala Lys Gly
                260                 265                 270
Gln Pro Arg Glu Pro Gln Val Tyr Thr Leu Pro Pro Ser Arg Glu Glu
            275                 280                 285
Met Thr Lys Asn Gln Val Ser Leu Thr Cys Leu Val Lys Gly Phe Tyr
            290                 295                 300
Pro Ser Asp Ile Ala Val Glu Trp Glu Ser Asn Gly Gln Pro Glu Asn
305                 310                 315                 320
Asn Tyr Lys Thr Thr Pro Pro Val Leu Asp Ser Asp Gly Ser Phe Phe
                325                 330                 335
Leu Tyr Ser Lys Leu Thr Val Asp Lys Ser Arg Trp Gln Gln Gly Asn
                340                 345                 350
Val Phe Ser Cys Ser Val Met His Glu Ala Leu His Asn His Tyr Thr
            355                 360                 365
Gln Lys Ser Leu Ser Leu Ser Pro Gly
            370                 375

<210> SEQ ID NO 27
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG4 (N297 wt)

<400> SEQUENCE: 27
gcgcccatca gctcccactg caggcttgac aagtccaact tccagcagcc ctatatcacc     60
aaccgcacct tcatgctggc taaggaggct agcttggctg ataacaacac agacgttcgt    120
ctcattgggg agaaactgtt ccacggagtc agtatgagtg agcgctgcta tctgatgaag    180
caggtgctga acttcaccct tgaagaagtg ctgttccctc aatctgatag gttccagcct    240
```

```
tatatgcagg aggtggtgcc cttcctggcc aggctcagca acaggctaag cacatgtcat    300
attgaaggtg atgacctgca tatccagagg aatgtgcaaa agctgaagga cacagtgaaa    360
aagcttggag agagtggaga gatcaaagca attggagaac tggatttgct gtttatgtct    420
ctgagaaatg cctgcattcg cgttgagtcc aaatatggtc ccccatgccc accatgccca    480
gcacctgagt tcctgggggg accatcagtc ttcctgttcc ccccaaaacc caaggacact    540
ctcatgatct cccggacccc tgaggtcacg tgcgtggtgg tggacgtgag ccaggaagac    600
cccgaggtcc agttcaactg gtacgtggat ggcgtggagg tgcataatgc caagacaaag    660
ccgcgggagg agcagttcaa cagcacgtac cgtgtggtca gcgtcctcac cgtcctgcac    720
caggactggc tgaacggcaa ggagtacaag tgcaaggtct ccaacaaagg cctcccgtcc    780
tccatcgaga aaaccatctc caaagccaaa gggcagcccc gagagccaca ggtgtacacc    840
ctgcccccat cccaggagga gatgaccaag aaccaggtca gcctgacctg cctggtcaaa    900
ggcttctacc ccagcgacat cgccgtggag tgggagagca atgggcagcc ggagaacaac    960
tacaagacca cgcctcccgt gctggactcc gacggctcct tcttcctcta cagcaggcta   1020
accgtggaca agagcaggtg gcaggagggg aatgtcttct catgctccgt gatgcatgag   1080
gctctgcaca accactacac acagaagagc ctctccctgt ctctgggtaa a            1131
```

<210> SEQ ID NO 28
<211> LENGTH: 377
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG4 (N297 wt)

<400> SEQUENCE: 28

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Arg Val Glu Ser Lys Tyr Gly Pro Cys Pro Pro Cys Pro
145                 150                 155                 160

Ala Pro Glu Phe Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

```
Val Val Asp Val Ser Gln Glu Asp Pro Glu Val Gln Phe Asn Trp Tyr
        195                 200                 205

Val Asp Gly Val Glu Val His Asn Ala Lys Thr Lys Pro Arg Glu Glu
        210                 215                 220

Gln Phe Asn Ser Thr Tyr Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Gly Leu Pro Ser Ser Ile Glu Lys Thr Ile Ser Lys Ala Lys Gly Gln
                260                 265                 270

Pro Arg Glu Pro Gln Val Tyr Thr Leu Pro Pro Ser Gln Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Asn Gly Gln Pro Glu Asn Asn
305                 310                 315                 320

Tyr Lys Thr Thr Pro Pro Val Leu Asp Ser Asp Gly Ser Phe Phe Leu
                325                 330                 335

Tyr Ser Arg Leu Thr Val Asp Lys Ser Arg Trp Gln Glu Gly Asn Val
                340                 345                 350

Phe Ser Cys Ser Val Met His Glu Ala Leu His Asn His Tyr Thr Gln
        355                 360                 365

Lys Ser Leu Ser Leu Ser Leu Gly Lys
        370                 375

<210> SEQ ID NO 29
<211> LENGTH: 1134
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IL-22 Fc fusion IgG1 (N297 wt)

<400> SEQUENCE: 29
gcgcccatca gctcccactg caggcttgac aagtccaact tccagcagcc ctatatcacc    60
aaccgcacct tcatgctggc taaggaggct agcttggctg ataacaacac agacgttcgt   120
ctcattgggg agaaactgtt ccacggagtc agtatgagtg agcgctgcta tctgatgaag   180
caggtgctga acttcaccct tgaagaagtg ctgttccctc aatctgatag gttccagcct   240
tatatgcagg aggtggtgcc cttcctggcc aggctcagca acaggctaag cacatgtcat   300
attgaaggtg atgacctgca tatccagagg aatgtgcaaa agctgaagga cacagtgaaa   360
aagcttggag agagtggaga gatcaaagca attggagaac tggatttgct gtttatgtct   420
ctgagaaatg cctgcattga gcccaaatct agtgacaaaa ctcacacatg cccaccgtgc   480
ccagcacctg aactcctggg gggaccgtca gtcttcctct tccccccaaa acccaaggac   540
accctcatga tctcccggac ccctgaggtc acatgcgtgg tggtggacgt gagccacgaa   600
gaccctgagg tcaagttcaa ctggtacgtg gacggcgtgg aggtgcataa tgccaagaca   660
aagccgcggg aggagcagta caacagcacg taccgtgtgg tcagcgtcct caccgtcctg   720
caccaggact ggctgaatgg caaggagtac aagtgcaagg tctccaacaa agccctccca   780
gcccccatcg agaaaaccat ctccaaagcc aaagggcagc ccgagaacc acaggtgtac   840 accctgcccc catcccggga agagatgacc aagaaccagg tcagcctgac ctgcctggtc   900
```

```
aaaggcttct atcccagcga catcgccgtg gagtgggaga gcaatgggca gccggagaac    960
aactacaaga ccacgcctcc cgtgctggac tccgacggct ccttcttcct ctacagcaag   1020
ctcaccgtgg acaagagcag gtggcagcag gggaacgtct tctcatgctc cgtgatgcat   1080
gaggctctgc acaaccacta cacgcagaag agcctctccc tgtctccggg taaa         1134
```

<210> SEQ ID NO 30
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG1 (N297 wt)

<400> SEQUENCE: 30

```
Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile Glu Pro Lys Ser Ser Asp Lys Thr His Thr Cys Pro Pro Cys
145                 150                 155                 160

Pro Ala Pro Glu Leu Leu Gly Gly Pro Ser Val Phe Leu Phe Pro Pro
                165                 170                 175

Lys Pro Lys Asp Thr Leu Met Ile Ser Arg Thr Pro Glu Val Thr Cys
            180                 185                 190

Val Val Val Asp Val Ser His Glu Asp Pro Glu Val Lys Phe Asn Trp
        195                 200                 205

Tyr Val Asp Gly Val Glu Val His Asn Ala Lys Thr Lys Pro Arg Glu
    210                 215                 220

Glu Gln Tyr Asn Ser Thr Tyr Arg Val Val Ser Val Leu Thr Val Leu
225                 230                 235                 240

His Gln Asp Trp Leu Asn Gly Lys Glu Tyr Lys Cys Lys Val Ser Asn
                245                 250                 255

Lys Ala Leu Pro Ala Pro Ile Glu Lys Thr Ile Ser Lys Ala Lys Gly
            260                 265                 270

Gln Pro Arg Glu Pro Gln Val Tyr Thr Leu Pro Pro Ser Arg Glu Glu
        275                 280                 285

Met Thr Lys Asn Gln Val Ser Leu Thr Cys Leu Val Lys Gly Phe Tyr
    290                 295                 300
```

Pro Ser Asp Ile Ala Val Glu Trp Glu Ser Asn Gly Gln Pro Glu Asn
305                 310                 315                 320

Asn Tyr Lys Thr Thr Pro Pro Val Leu Asp Ser Asp Gly Ser Phe Phe
            325                 330                 335

Leu Tyr Ser Lys Leu Thr Val Asp Lys Ser Arg Trp Gln Gln Gly Asn
        340                 345                 350

Val Phe Ser Cys Ser Val Met His Glu Ala Leu His Asn His Tyr Thr
        355                 360                 365

Gln Lys Ser Leu Ser Leu Ser Pro Gly Lys
    370                 375

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      hinge peptide

<400> SEQUENCE: 31

Cys Pro Pro Cys Pro
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 32

Asp Lys Thr His Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 33

Glu Pro Lys Ser Cys Asp Lys Thr His Thr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 34

Val Glu Pro Lys Ser Cys Asp Lys Thr His Thr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 35

Lys Val Glu Pro Lys Ser Cys Asp Lys Thr His Thr
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 36

Lys Lys Val Glu Pro Lys Ser Cys Asp Lys Thr His Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 37

Asp Lys Lys Val Glu Pro Lys Ser Cys Asp Lys Thr His Thr
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 38

Val Asp Lys Lys Val Glu Pro Lys Ser Cys Asp Lys Thr His Thr
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 39

Lys Val Asp Lys Lys Val Glu Pro Lys Ser Cys Asp Lys Thr His Thr
1               5                   10                  15

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 40

Glu Pro Lys Ser Ser Asp Lys Thr His Thr
1               5                   10

<210> SEQ ID NO 41
<211> LENGTH: 8

```
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 41

Gly Gly Gly Asp Lys Thr His Thr
1               5

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      linker (IgG3) peptide

<400> SEQUENCE: 42

Glu Leu Lys Thr Pro Leu Gly Asp Thr Thr His Thr
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 43

Ser Lys Tyr Gly Pro Pro
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 44

Arg Val Glu Ser Lys Tyr Gly Pro Pro
1               5

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 45

Gly Gly Ser
1

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 46

Gly Gly Gly Ser
```

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 47

Gly Gly Gly Gly Ser
1               5

<210> SEQ ID NO 48
<211> LENGTH: 146
<212> TYPE: PRT
<213> ORGANISM: Pan troglodytes

<400> SEQUENCE: 48

Ala Pro Ile Ser Ser His Cys Arg Leu Asp Lys Ser Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Asn Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 49
<211> LENGTH: 146
<212> TYPE: PRT
<213> ORGANISM: Pongo abelii

<400> SEQUENCE: 49

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
                20                  25                  30

Ala Asp Asn Asn Thr Asp Val Arg Leu Ile Gly Glu Lys Leu Phe Arg
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

```
Ser Thr Cys His Ile Glu Gly Asp Asp Leu His Ile Gln Arg Asn Val
            100                 105                 110

Gln Lys Leu Lys Asp Thr Val Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile
145

<210> SEQ ID NO 50
<211> LENGTH: 146
<212> TYPE: PRT
<213> ORGANISM: Mus musculus

<400> SEQUENCE: 50

Leu Pro Val Asn Thr Arg Cys Lys Leu Glu Val Ser Asn Phe Gln Gln
1               5                   10                  15

Pro Tyr Ile Val Asn Arg Thr Phe Met Leu Ala Lys Glu Ala Ser Leu
            20                  25                  30

Ala Asp Asn Asn Thr Asp Val Arg Leu Ile Gly Glu Lys Leu Phe Arg
        35                  40                  45

Gly Val Ser Ala Lys Asp Gln Cys Tyr Leu Met Lys Gln Val Leu Asn
50                  55                  60

Phe Thr Leu Glu Asp Val Leu Leu Pro Gln Ser Asp Arg Phe Gln Pro
65                  70                  75                  80

Tyr Met Gln Glu Val Val Pro Phe Leu Thr Lys Leu Ser Asn Gln Leu
                85                  90                  95

Ser Ser Cys His Ile Ser Gly Asp Asp Gln Asn Ile Gln Lys Asn Val
            100                 105                 110

Arg Arg Leu Lys Glu Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Val
145

<210> SEQ ID NO 51
<211> LENGTH: 146
<212> TYPE: PRT
<213> ORGANISM: Canis familiaris

<400> SEQUENCE: 51

Leu Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Asn Met Gly Glu Arg Cys Tyr Leu Met Lys Glu Val Leu Asn
50                  55                  60

Phe Thr Leu Glu Glu Val Leu Leu Pro Gln Ser Asp Arg Phe Gln Pro
65                  70                  75                  80

Tyr Met Gln Glu Val Val Pro Phe Leu Ala Arg Leu Ser Asn Lys Leu
                85                  90                  95

Ser Gln Cys His Ile Glu Asn Asp Asp Gln His Ile Gln Arg Asn Val
            100                 105                 110
```

Gln Lys Leu Lys Asp Thr Val Gln Lys Leu Gly Glu Asn Gly Glu Ile
            115                 120                 125

Lys Ala Ile Gly Glu Leu Asp Leu Leu Phe Met Ala Leu Arg Asn Ala
    130                 135                 140

Cys Val
145

<210> SEQ ID NO 52
<211> LENGTH: 94
<212> TYPE: DNA
<213> ORGANISM: Artificial Sequence
<220> FEATURE:
<223> OTHER INFORMATION: Description of Artificial Sequence: Synthetic
      IL-22 Fc fusion protein IgG1 forward primer

<400> SEQUENCE: 52
ttgaattcca ccatgggatg gtcatgtatc atcctttttc tagtagcaac tgcaactgga      60
gtacattcag cgcccatcag ctcccactgc aggc                                 94

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      IL-22 Fc fusion IgG1 reverse primer

<400> SEQUENCE: 53
aggtcgactc atttacccgg agacagggag agg                                  33

<210> SEQ ID NO 54
<211> LENGTH: 94
<212> TYPE: DNA
<213> ORGANISM: Artificial Sequence
<220> FEATURE:
<223> OTHER INFORMATION: Description of Artificial Sequence: Synthetic
      IL-22 Fc fusion IgG4 forward primer

<400> SEQUENCE: 54
ttgaattcca ccatgggatg gtcatgtatc atcctttttc tagtagcaac tgcaactgga      60
gtacattcag cgcccatcag ctcccactgc aggc                                 94

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Synthetic
      IL-22 Fc fusion IgG4 reverse primer

<400> SEQUENCE: 55
aggtcgactt atttacccag agacagggag agg                                  33

<210> SEQ ID NO 56
<211> LENGTH: 35
<212> TYPE: DNA
<213> ORGANISM: Artificial Sequence
<220> FEATURE:
<223> OTHER INFORMATION: Description of Artificial Sequence: Synthetic
      IgG1 N297G forward primer

<400> SEQUENCE: 56
gcgggaggag cagtacggaa gcacgtaccg tgtgg                                35

<210> SEQ ID NO 57
<211> LENGTH: 35
<212> TYPE: DNA
<213> ORGANISM: Artificial Sequence
<220> FEATURE:
<223> OTHER INFORMATION: Description of Artificial Sequence: Synthetic
      IgG1 N297G reverse primer

<400> SEQUENCE: 57
ccacacggta cgtgcttccg tactgctcct cccgc                                35

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
      IgG4 N297G forward primer

<400> SEQUENCE: 58
acaaagccgc gggaggagca gttcggaagc acgtaccgtg tggtcagcgt c              51

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      IgG4 N297G reverse primer

<400> SEQUENCE: 59
gacgctgacc acacggtacg tgcttccgaa ctgctcctcc cgcggctttg t              51

<210> SEQ ID NO 60
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 Fc fusion IgG2a

<400> SEQUENCE: 60

Met Ala Val Leu Gln Lys Ser Met Ser Phe Ser Leu Met Gly Thr Leu
 1               5                  10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

```
Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Ala Arg Gly Pro Thr Ile Lys Pro Cys Pro Pro Cys Lys
            180                 185                 190

Cys Pro Ala Pro Asn Leu Leu Gly Gly Pro Ser Val Phe Ile Phe Pro
        195                 200                 205

Pro Lys Ile Lys Asp Val Leu Met Ile Ser Leu Ser Pro Ile Val Thr
    210                 215                 220

Cys Val Val Val Asp Val Ser Glu Asp Asp Pro Asp Val Gln Ile Ser
225                 230                 235                 240

Trp Phe Val Asn Asn Val Glu Val His Thr Ala Gln Thr Gln Thr His
                245                 250                 255

Arg Glu Asp Tyr Asn Ser Thr Leu Arg Val Val Ser Ala Leu Pro Ile
                260                 265                 270

Gln His Gln Asp Trp Met Ser Gly Lys Glu Phe Lys Cys Lys Val Asn
            275                 280                 285

Asn Lys Asp Leu Pro Ala Pro Ile Glu Arg Thr Ile Ser Lys Pro Lys
        290                 295                 300

Gly Ser Val Arg Ala Pro Gln Val Tyr Val Leu Pro Pro Glu Glu
305                 310                 315                 320

Glu Met Thr Lys Lys Gln Val Thr Leu Thr Cys Met Val Thr Asp Phe
                325                 330                 335

Met Pro Glu Asp Ile Tyr Val Glu Trp Thr Asn Asn Gly Lys Thr Glu
            340                 345                 350

Leu Asn Tyr Lys Asn Thr Glu Pro Val Leu Asp Ser Asp Gly Ser Tyr
        355                 360                 365

Phe Met Tyr Ser Lys Leu Arg Val Glu Lys Lys Asn Trp Val Glu Arg
370                 375                 380

Asn Ser Tyr Ser Cys Ser Val Val His Glu Gly Leu His Asn His His
385                 390                 395                 400

Thr Thr Lys Ser Phe Ser Arg Thr Pro Gly Lys
                405                 410

<210> SEQ ID NO 61
<211> LENGTH: 372
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IL-22 IgG1 fusion knob (T366W) minus Lys

<400> SEQUENCE: 61

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80
```

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Trp Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly
        370

<210> SEQ ID NO 62
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Monomeric Fc hole

<400> SEQUENCE: 62

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 63

Gly Gly Gly Ser Thr His Thr
1               5

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 64

Asp Lys Lys Val Glu Pro Lys Ser Ser Asp Lys Thr His Thr
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 65

Lys Val Asp Lys Lys Val Glu Pro Lys Ser Ser Asp Lys Thr His Thr
1               5                   10                  15

-continued

```
<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 66

Lys Lys Val Glu Pro Lys Ser Ser Asp Lys Thr His Thr
1               5                  10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 67

Val Glu Pro Lys Ser Ser Asp Lys Thr His Thr
1               5                  10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 68

Lys Val Glu Pro Lys Ser Ser Asp Lys Thr His Thr
1               5                  10

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 69

Val Asp Lys Lys Val Glu Pro Lys Ser Ser Asp Lys Thr His Thr
1               5                  10                  15

<210> SEQ ID NO 70
<211> LENGTH: 1152
<212> TYPE: DNA
<213> ORGANISM: Homo sapiens
<220> FEATURE:
<221> NAME/KEY: CDS
<222> LOCATION: (58)..(597)

<400> SEQUENCE: 70
cttcagaaca ggttctcctt ccccagtcac cagttgctcg agttagaatt gtctgca          57 atg gcc gcc ctg cag aaa tct gtg agc tct ttc ctt atg ggg acc ctg        105
Met Ala Ala Leu Gln Lys Ser Val Ser Ser Phe Leu Met Gly Thr Leu
  1               5                  10                  15 gcc acc agc tgc ctc ctt ctc ttg gcc ctc ttg gta cag gga gga gca        153
Ala Thr Ser Cys Leu Leu Leu Leu Ala Leu Leu Val Gln Gly Gly Ala
             20                  25                  30 gct gcg ccc atc agc tcc cac tgc agg ctt gac aag tcc aac ttc cag        201
Ala Ala Pro Ile Ser Ser His Cys Arg Leu Asp Lys Ser Asn Phe Gln
         35                  40                  45
```

```
cag ccc tat atc acc aac cgc acc ttc atg ctg gct aag gag gct agc      249
Gln Pro Tyr Ile Thr Asn Arg Thr Phe Met Leu Ala Lys Glu Ala Ser
    50                  55                  60 ttg gct gat aac aac aca gac gtt cgt ctc att ggg gag aaa ctg ttc      297
Leu Ala Asp Asn Asn Thr Asp Val Arg Leu Ile Gly Glu Lys Leu Phe
65                  70                  75                  80 cac gga gtc agt atg agt gag cgc tgc tat ctg atg aag cag gtg ctg      345
His Gly Val Ser Met Ser Glu Arg Cys Tyr Leu Met Lys Gln Val Leu
                85                  90                  95 aac ttc acc ctt gaa gaa gtg ctg ttc cct caa tct gat agg ttc cag      393
Asn Phe Thr Leu Glu Glu Val Leu Phe Pro Gln Ser Asp Arg Phe Gln
            100                 105                 110 cct tat atg cag gag gtg gtg ccc ttc ctg gcc agg ctc agc aac agg      441
Pro Tyr Met Gln Glu Val Val Pro Phe Leu Ala Arg Leu Ser Asn Arg
        115                 120                 125 cta agc aca tgt cat att gaa ggt gat gac ctg cat atc cag agg aat      489
Leu Ser Thr Cys His Ile Glu Gly Asp Asp Leu His Ile Gln Arg Asn
    130                 135                 140 gtg caa aag ctg aag gac aca gtg aaa aag ctt gga gag agt gga gag      537
Val Gln Lys Leu Lys Asp Thr Val Lys Lys Leu Gly Glu Ser Gly Glu
145                 150                 155                 160 atc aaa gca att gga gaa ctg gat ttg ctg ttt atg tct ctg aga aat      585
Ile Lys Ala Ile Gly Glu Leu Asp Leu Leu Phe Met Ser Leu Arg Asn
                165                 170                 175 gcc tgc att tga ccagagcaaa gctgaaaaat gaataactaa cccccttttcc         637
Ala Cys Ile ctgctagaaa taacaattag atgccccaaa gcgattttt ttaaccaaaa ggaagatggg     697
aagccaaact ccatcatgat gggtggattc caaatgaacc cctgcgttag ttacaaagga   757
aaccaatgcc acttttgttt ataagaccag aaggtagact ttctaagcat agatattttat  817 tgataacatt tcattgtaac tggtgttcta tacacagaaa acaatttatt ttttaaataa   877
ttgtcttttt ccataaaaaa gattactttc cattcctttta ggggaaaaaa ccctaaata   937 gcttcatgtt tccataatca gtactttata tttataaatg tatttattat tattataaga   997
ctgcatttta tttatatcat tttattaata tggatttatt tatagaaaca tcattcgata  1057
ttgctacttg agtgtaaggc taatattgat atttatgaca ataattatag agctataaca  1117 tgttttatttg acctcaataa acacttggat atccc                             1152

<210> SEQ ID NO 71
<211> LENGTH: 179
<212> TYPE: PRT
<213> ORGANISM: Homo sapiens

<400> SEQUENCE: 71

Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95
```

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
130                 135                 140

Val Gln Lys Leu Lys Asp Thr Val Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile

<210> SEQ ID NO 72
<211> LENGTH: 1236
<212> TYPE: DNA
<213> ORGANISM: Artificial Sequence
<220> FEATURE:
<223> OTHER INFORMATION: Synthetic polypeptide

<400> SEQUENCE: 72

```
atggctgtcc tgcagaaatc tatgagtttt tcccttatgg ggactttggc cgccagctgc      60
ctgcttctca ttgccctgtg ggcccaggag gcaaatgcgc tgcccgtcaa cacccggtgc     120
aagcttgagg tgtccaactt ccagcagcca tacatcgtca accgcacctt tatgctggcc     180
aaggaggcca gccttgcaga taacaacaca gatgtccggc tcatcgggga gaaactgttc     240
cgaggagtca gtgctaagga tcagtgctac ctgatgaagc aggtgctcaa cttcacctg      300
gaagacgttc tgctccccca gtcagacagg ttccagccct acatgcagga ggtggtgcct     360
ttcctgacca aactcagcaa tcagctcagc tcctgtcaca tcagcggtga cgaccagaac     420
atccagaaga atgtcagaag gctgaaggag acagtgaaaa agcttggaga gagtggagag     480
atcaaggcga ttggggaact ggacctgctg tttatgtctc tgagaaatgc ttgcgtcgct     540
cgaggaccca caatcaagcc ctgtcctcca tgcaaatgcc agcacctaa cctcttgggt      600
ggaccatccg tcttcatctt ccctccaaag atcaaggatg tactcatgat ctccctgagc     660
cccatagtca catgtgtggt ggtggatgtg agcgaggatg acccagatgt ccagatcagc     720
tggtttgtga caacgtgga agtacacaca gctcagacac aaacccatag agaggattac     780
aacagtactc tacgcgtggt cagtgccctc cccatccagc accaggactg gatgagtggc     840
aaggagttca atgcaaggt caacaacaaa gacctccag cgcccatcga gagaaccatc       900
tcaaaaccca agggtcagt aagagctcca caggtatatg tcttgcctcc accagaagaa      960
gagatgacta gaaacaggt cactctgacc tgcatggtca cagacttcat gcctgaagac     1020
atttacgtgg agtggaccaa caacgggaaa acagagctaa actacaagaa cactgaacca     1080
gtcctggact ctgatggttc ttacttcatg tacagcaagc tgagagtgga aaagaagaac     1140
tgggtggaaa gaaatagcta ctcctgttca gtggtccacg agggtctgca caatcaccac     1200
acgactaaga gcttctcccg gactccgggt aaatga                              1236
```

<210> SEQ ID NO 73
<211> LENGTH: 411
<212> TYPE: PRT
<213> ORGANISM: Artificial Sequence
<220> FEATURE:
<223> OTHER INFORMATION: Synthetic polypeptide

<400> SEQUENCE: 73

-continued

```
Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
            35                  40                  45

Gln Pro Tyr Ile Val Asn Arg Thr Phe Met Leu Ala Lys Glu Ala Ser
        50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
                100                 105                 110

Pro Tyr Met Gln Glu Val Val Pro Phe Leu Thr Lys Leu Ser Asn Gln
            115                 120                 125

Leu Ser Ser Cys His Ile Ser Gly Asp Asp Gln Asn Ile Gln Lys Asn
        130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val Ala Arg Gly Pro Thr Ile Lys Pro Cys Pro Pro Cys Lys
            180                 185                 190

Cys Pro Ala Pro Asn Leu Leu Gly Gly Pro Ser Val Phe Ile Phe Pro
        195                 200                 205

Pro Lys Ile Lys Asp Val Leu Met Ile Ser Leu Ser Pro Ile Val Thr
    210                 215                 220

Cys Val Val Asp Val Ser Glu Asp Asp Pro Asp Val Gln Ile Ser
225                 230                 235                 240

Trp Phe Val Asn Asn Val Glu Val His Thr Ala Gln Thr Gln Thr His
                245                 250                 255

Arg Glu Asp Tyr Asn Ser Thr Leu Arg Val Val Ser Ala Leu Pro Ile
            260                 265                 270

Gln His Gln Asp Trp Met Ser Gly Lys Glu Phe Lys Cys Lys Val Asn
        275                 280                 285

Asn Lys Asp Leu Pro Ala Pro Ile Glu Arg Thr Ile Ser Lys Pro Lys
    290                 295                 300

Gly Ser Val Arg Ala Pro Gln Val Tyr Val Leu Pro Pro Pro Glu Glu
305                 310                 315                 320

Glu Met Thr Lys Lys Gln Val Thr Leu Thr Cys Met Val Thr Asp Phe
                325                 330                 335

Met Pro Glu Asp Ile Tyr Val Glu Trp Thr Asn Asn Gly Lys Thr Glu
            340                 345                 350

Leu Asn Tyr Lys Asn Thr Glu Pro Val Leu Asp Ser Asp Gly Ser Tyr
        355                 360                 365

Phe Met Tyr Ser Lys Leu Arg Val Glu Lys Lys Asn Trp Val Glu Arg
    370                 375                 380

Asn Ser Tyr Ser Cys Ser Val Val His Glu Gly Leu His Asn His His
385                 390                 395                 400

Thr Thr Lys Ser Phe Ser Arg Thr Pro Gly Lys
                405                 410
```

<210> SEQ ID NO 74
<211> LENGTH: 20
<212> TYPE: DNA
<213> ORGANISM: Artificial Sequence
<220> FEATURE:
<223> OTHER INFORMATION: Synthetic primer

<400> SEQUENCE: 74
aggtccattc agatgctggt                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic primer

<400> SEQUENCE: 75
taggtgtggt tgacgtggag                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic primer

<400> SEQUENCE: 76
ccaccccaca ctcacaccgg                                               20

<210> SEQ ID NO 77
<211> LENGTH: 177
<212> TYPE: PRT
<213> ORGANISM: Homo sapiens

<400> SEQUENCE: 77

Met Lys Leu Gln Cys Val Ser Leu Trp Leu Leu Gly Thr Ile Leu Ile
1               5                   10                  15

Leu Cys Ser Val Asp Asn His Gly Leu Arg Arg Cys Leu Ile Ser Thr
                20                  25                  30

Asp Met His Ile Glu Glu Ser Phe Gln Glu Ile Lys Arg Ala Ile
        35                  40                  45

Gln Ala Lys Asp Thr Phe Pro Asn Val Thr Ile Leu Ser Thr Leu Glu
    50                  55                  60

Thr Leu Gln Ile Ile Lys Pro Leu Asp Val Cys Cys Val Thr Lys Asn
65                  70                  75                  80

Leu Leu Ala Phe Tyr Val Asp Arg Val Phe Lys Asp His Gln Glu Pro
                85                  90                  95

Asn Pro Lys Ile Leu Arg Lys Ile Ser Ser Ile Ala Asn Ser Phe Leu
            100                 105                 110

Tyr Met Gln Lys Thr Leu Arg Gln Cys Gln Glu Gln Arg Gln Cys His
        115                 120                 125

Cys Arg Gln Glu Ala Thr Asn Ala Thr Arg Val Ile His Asp Asn Tyr
    130                 135                 140

Asp Gln Leu Glu Val His Ala Ala Ala Ile Lys Ser Leu Gly Glu Leu
145                 150                 155                 160

Asp Val Phe Leu Ala Trp Ile Asn Lys Asn His Glu Val Met Ser Ser
                165                 170                 175

Ala

<210> SEQ ID NO 78
<211> LENGTH: 176
<212> TYPE: PRT
<213> ORGANISM: Homo sapiens

<400> SEQUENCE: 78

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Thr Glu
                165                 170                 175

<210> SEQ ID NO 79
<211> LENGTH: 207
<212> TYPE: PRT
<213> ORGANISM: Homo sapiens

<400> SEQUENCE: 79

Met Asn Phe Gln Gln Arg Leu Gln Ser Leu Trp Thr Leu Ala Ser Arg
1               5                   10                  15

Pro Phe Cys Pro Pro Leu Leu Ala Thr Ala Ser Gln Met Gln Met Val
            20                  25                  30

Val Leu Pro Cys Leu Gly Phe Thr Leu Leu Leu Trp Ser Gln Val Ser
            35                  40                  45

Gly Ala Gln Gly Gln Glu Phe His Phe Gly Pro Cys Gln Val Lys Gly
    50                  55                  60

Val Val Pro Gln Lys Leu Trp Glu Ala Phe Trp Ala Val Lys Asp Thr
65                  70                  75                  80

Met Gln Ala Gln Asp Asn Ile Thr Ser Ala Arg Leu Leu Gln Gln Glu
                85                  90                  95

Val Leu Gln Asn Val Ser Asp Ala Glu Ser Cys Tyr Leu Val His Thr
            100                 105                 110

Leu Leu Glu Phe Tyr Leu Lys Thr Val Phe Lys Asn Tyr His Asn Arg
        115                 120                 125

Thr Val Glu Val Arg Thr Leu Lys Ser Phe Ser Thr Leu Ala Asn Asn
    130                 135                 140

Phe Val Leu Ile Val Ser Gln Leu Gln Pro Ser Gln Glu Asn Glu Met
145                 150                 155                 160

```
Phe Ser Ile Arg Asp Ser Ala His Arg Arg Phe Leu Leu Phe Arg Arg
                165             170                 175

Ala Phe Lys Gln Leu Asp Val Glu Ala Ala Leu Thr Lys Ala Leu Gly
            180             185                 190

Glu Val Asp Ile Leu Leu Thr Trp Met Gln Lys Phe Tyr Lys Leu
        195             200                 205

<210> SEQ ID NO 80
<211> LENGTH: 171
<212> TYPE: PRT
<213> ORGANISM: Homo sapiens

<400> SEQUENCE: 80

Met Leu Val Asn Phe Ile Leu Arg Cys Gly Leu Leu Val Thr Leu
1               5                   10                  15

Ser Leu Ala Ile Ala Lys His Lys Gln Ser Ser Phe Thr Lys Ser Cys
            20              25                  30

Tyr Pro Arg Gly Thr Leu Ser Gln Ala Val Asp Ala Leu Tyr Ile Lys
            35              40                  45

Ala Ala Trp Leu Lys Ala Thr Ile Pro Glu Asp Arg Ile Lys Asn Ile
    50              55                  60

Arg Leu Leu Lys Lys Thr Lys Lys Gln Phe Met Lys Asn Cys Gln
65              70                  75                  80

Phe Gln Glu Gln Leu Leu Ser Phe Phe Met Glu Asp Val Phe Gly Gln
                85                  90                  95

Leu Gln Leu Gln Gly Cys Lys Lys Ile Arg Phe Val Glu Asp Phe His
                100             105                 110

Ser Leu Arg Gln Lys Leu Ser His Cys Ile Ser Cys Ala Ser Ser Ala
            115             120                 125

Arg Glu Met Lys Ser Ile Thr Arg Met Lys Arg Ile Phe Tyr Arg Ile
        130             135                 140

Gly Asn Lys Gly Ile Tyr Lys Ala Ile Ser Glu Leu Asp Ile Leu Leu
145             150                 155                 160

Ser Trp Ile Lys Lys Leu Leu Glu Ser Ser Gln
                165             170
```

METHODS OF TREATING INFLAMMATORY BOWEL DISEASE USING IL-22 FC FUSION PROTEINS

The instant application claims the benefit of priority to U.S. provisional application Ser. Nos. 61/800,148, 61/800,795 and 61/801,144, all of which were filed on Mar. 15, 2013, U.S. provisional application Ser. No. 61/821,062, filed on May 8, 2013, and U.S. provisional application Ser. No. 61/860,176, filed on Jul. 30, 2013, the contents of all of which are herein incorporated by reference in their entirety.

SEQUENCE LISTING

The instant application contains a Sequence Listing submitted via EFS-Web and hereby incorporated by reference in its entirety. Said ASCII copy, created on Mar. 14, 2014, is named P5580R1_Seq_Listing.txt, and is 106,757 bytes in size.

FIELD

The present invention relates to IL-22 and IL-22 Fc fusion proteins, IL-22 agonists, compositions comprising the same, and methods of making and method of using the same.

BACKGROUND

Interleukin-22 (IL-22) is a member of the IL-10 family of cytokine that is produced by Th22 cells, NK cells, lymphoid tissue inducer (LTi) cells, dendritic cells and Th17 cells. IL-22 binds to the IL-22R1/IL-10R2 receptor complex, which is expressed in innate cells such as epithelial cells, hepatocytes, and keratinocytes and in barrier epithelial tissues of several organs including dermis, pancreas, intestine and the respiratory system.

IL-22 plays an important role in mucosal immunity, mediating early host defense against attaching and effacing bacterial pathogens. See Zheng et al., 2008, Nat. Med. 14:282-89. IL-22 promotes the production of anti-microbial peptides and proinflammatory cytokines from epithelial cells and stimulates proliferation and migration of colonic epithelial cells in the gut. See Kumar et al., 2013, J. Cancer, 4:57-65. Upon bacterial infection, IL-22 knock-out mice displayed impaired gut epithelial regeneration, high bacterial load and increased mortality. Kumar et al., supra. Similarly, infection of IL-22 knock-out mice with influenza virus resulted in severe weight loss and impaired regeneration of tracheal and bronchial epithelial cells. Thus, IL-22 plays a pro-inflammatory role in suppressing microbial infection as well as an anti-inflammatory protective role in epithelial regeneration in inflammatory responses. Much of IL-22's biological action promoting pathological inflammation and tissue repair remains to be determined. The seemingly conflicting reports on the effects of IL-22 on epithelial cells are not yet thoroughly understood. Kumar et al., supra.

The regulation of antimicrobial defensins, which limits bacterial replication and dissemination, would help to stabilize intestinal microbiota by reducing subsequent LPS production, and preserving mucosal integrity. IL-22 upregulates expression of acute phase proteins, including SAA, and contributes to the expression of a range of genes associated with acute inflammatory responses, including IL-6, G-CSF, and IL-1a. Systemic administration of IL-22 to healthy mice also up regulates LPS binding proteins to physiologically relevant concentrations for neutralizing LPS in response to bacterial infection.

Increased expression of IL-22 is detected in inflammatory bowel disorder (IBD) patients. See e.g., Wolk et al., 2007, J. Immunology, 178:5973; Andoh et al., 2005, Gastroenterology, 129:969. IBDs such as Crohn's disease (CD) and ulcerative colitis (UC) are thought to result from a dysregulated immune response to the commensal microflora present in the gut. Cox et al., 2012, Mucosal Immunol. 5:99-109. Both UC and CD are complex diseases that occur in genetically susceptible individuals who are exposed to as yet poorly-defined environmental stimuli. CD and UC are mediated by both common and distinct mechanisms and exhibit distinct clinical features. See Sugimoto et al. 2008, J. Clinical Investigation, 118:534-544.

In UC, inflammation occurs primarily in the mucosa of the colon and the rectum, leading to debilitating conditions including diarrhea, rectal bleeding, and weight loss. It is thought that UC is largely caused by an inappropriate inflammatory response by the host to intestinal microbes penetrating through a damaged epithelial barrier (Xavier and Podolsky, 2007, Nature 448:427-434). Crohn's disease is characterized by intestinal infilatratoin of activated immune cells and distortion of the intestinal architechture. See Wolk et al., supra.

In recent years, a number of drugs based on various strategies to regulate the immune response have been tested to treat IBD, including steroids, immunomodulators, and antibodies against inflammatory cytokines, with variable success (Pastorelli et al., Expert opinion on emerging drugs, 2009, 14:505-521). The complex variety of gut flora contributes to the heterogeneity of the disease. Thus, there is a need for a better therapeutics for IBD.

Cardiovascular disease (CVD) is a leading cause of mortality that results, in part, from atherosclerotic disease of large blood vessels. Atherosclerosis is the major culprit in CVD events and is a slow and progressive disease that results from hypercholesterolemia and chronically inflamed blood vessels. Atherosclerotic lesions are characterized as lipid laden with infiltration of immunocytes, especially macrophages and T cells. It is now acknowledged that both the innate and adaptive immune mechanisms contribute to the progression and eventual thrombosis of the atherogenic plaque (Ross, Am Heart J. 1999 November; 138 (5 Pt 2):5419-20; Hansson 2005 N Engl J Med 352(16): 1685-95; Hansson and Hermansson 2011 Nature Immunology 12(3): 204-12).

Acute pancreatitis (AP) is an acute inflammatory process of the pancreas. Acute kidney injury (AKI) is an abrupt loss of kidney function, resulting in the retention of urea and other nitrogenous waste products and in the dysregulation of extracellular volume and electrolytes. AKI was previously known as acute kidney failure. The change reflects recent recognition that even smaller decreases in kidney function that do not result in overt organ failure are of substantial clinical relevance and are associated with increased morbidity and mortality. There remains a need for better treatment for AP and AKI.

Metabolic syndrome is a complex state characterized by a series of risk factors that contribute to thrombosis, hypertension, dyslipidemia, and inflammation. Insulin resistance and obesity are major pathogenic mechanisms underlying the metabolic syndrome.

Insulin resistance increases CVD risk because it induces endothelial dysfunction which, in combination with atherogenic dyslipidemia, inflammation, and hypertension, contributes to the mortality from coronary artery disease (CAD). Persistent insulin resistance also increases the chance of developing diabetes mellitus type 2 (T2DM) although the atherogenic state occurs many years before the onset of T2DM. It is likely therefore that the natural history of CAD lies in the same pathway as T2DM but begins much earlier in life in a subclinical form, taking longer to manifest clinically, with or without the presence of diabetes.

The term metabolic endotoxemia was coined to describe the condition of increased plasma LPS induced by, for example, high-fat high-calorie diet (HFD) (Cani et al. 2007. Diabetes 56(7): 1761-72). Mice fed with HFD have increased plasma levels of bacterial lipopolysaccharide (LPS) and this elevation appears to be a direct consequence of the increased dietary fat (Cani et al. 2007 supra; Cani et al. 2008 Diabetes 57(6): 1470-81; Ghoshal et al. 2009, J Lipid Res 50(1): 90-7). There is compelling evidence that gut microbiota play an integral part in the host's energy balance and harvest of dietary nutrients and carbohydrate metabolism, through modulation of gut mucosal epithelial cell function (Turnbaugh et al. 2009, Physiol (Lond) 587(Pt 17): 4153-8; Manco et al. 2010, Endocr Rev 31(6): 817-44). Alteration in gut microbiota that occurs through disproportionate dietary fat composition or excess dietary caloric consumption is a recognized initiator of obesity and insulin resistance, the established sequela of cardiovascular disease. Lipopolysaccharides are found in outer membrane of gram-negative bacteria and act as a source of endotoxin that can elicit a strong immune response (Barcia et al. Clin Infect Dis 41 Suppl 7: S498-503). Alterations in the population, species and regional distribution of intestinal microbiota can lead to changes in catabolism of LPS and a high fat diet will facilities adsorption of LPS across the intestinal barrier. Under these conditions, increased LPS in systemic circulation will induce low grade chronic inflammation, activating the endogenous protective host response to elevate plasma lipids that, in the chronic condition, contributes to diet induced obesity, insulin resistance and atherosclerosis, and eventual CVD events.

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of carbohydrate energy as glycogen. Glucose is stored in the body as glycogen, a form of polymerized glucose, which can be converted back into glucose to meet metabolism requirements. Under normal conditions, insulin is secreted at both a basal rate and at enhanced rates following glucose stimulation, all to maintain metabolic homeostasis by the conversion of glucose into glycogen. There remains a need for new treatment paradigms for atherosclerosis and prevention of CVD events, metabolic syndrome, acute endotoxemia and sepsis, and insulin-related disorders.

Wound healing is a complex process, involving an inflammation phase, a granulation tissue formation phase, and a tissue remodeling phase (see, e.g., Singer and Clark, Cutaneous Wound Healing, *N. Engl. J. Med.* 341:738-46 (1999)). These events are triggered by cytokines and growth factors that are released at the site of injury. Many factors can complicate or interfere with normal adequate wound healing. For example, such factors include age, infection, poor nutrition, immunosuppression, medications, radiation, diabetes, peripheral vascular disease, systemic illness, smoking, and stress.

For subjects with diabetes, a chronic, debilitating disease, development of a diabetic foot ulcer (also referred to as a wound) is a common complication. A chronic ulcer is defined as a wound that does not proceed through an orderly and timely repair process to produce anatomic and functional integrity (see, e.g., Lazarus et al., Definitions and guidelines for assessment of wounds and evaluation of healing, *Arch. Dermatol.* 130:489-93 (1994)). By its nature, the diabetic foot ulcer is a chronic wound (American Diabetes Association, Consensus development conference on diabetic foot wound care, *Diabetes Care*, 22(8):1354-60 (1999)). Because the skin serves as the primary barrier again the environment, an open refractory wound can be catastrophic; a major disability (including limb loss) and even death can result. Foot ulceration is the precursor to about 85% of lower extremity amputations in persons with diabetes (see, e.g., Apelqvist, et al., What is the most effective way to reduce incidence of amputation in the diabetic foot? *Diabetes Metab Res. Rev.,* 16(1 Suppl.): S75-S83 (2000)). Thus, there is a need for accelerating or improving wound healing, including diabetic wound healing.

SUMMARY

In one aspect, the invention provides IL-22 Fc fusion proteins, compositions comprising the same, and methods of using the same.

In one aspect, the invention provides an IL-22 Fc fusion protein that binds to IL-22 receptor, said IL-22 Fc fusion protein comprising an IL-22 polypeptide linked to an Fc region by a linker, wherein the Fc region comprises a hinge region, an IgG CH2 domain and an IgG CH3 domain, wherein the IL-22 Fc fusion protein comprises an amino acid sequence having at least 95%, at least 96%, at least 97%, at least 98%, preferably at least 99% sequence identity to the amino acid sequence selected from the group consisting of SEQ ID NO:8, SEQ ID NO:10, SEQ ID NO:12 and SEQ ID NO:14, and wherein the Fc region is not glycosylated. In certain embodiments, the N297 residue of the CH2 domain is changed to glycine or alanine. In certain other embodiments, the N297 residue is changed to Gly; while in other embodiments, the N297 residue is changed to Ala. In certain embodiments, the binding to IL-22 receptor triggers IL-22 receptor downstream signaling, including activating STAT3.

In certain embodiments, the IL-22 Fc fusion protein comprises an amino acid sequence having at least 98% sequence identity to the amino acid sequence of SEQ ID NO:8 or SEQ ID NO:12. In certain other embodiments, the IL-22 Fc fusion protein comprises an amino acid sequence having at least 99% sequence identity to the amino acid sequence of SEQ ID NO:8 or SEQ ID NO:12. In certain other embodiments, the IL-22 Fc fusion protein comprises an amino acid sequence having at least 99% sequence identity to the amino acid sequence of SEQ ID NO:8. In certain other embodiments, the IL-22 Fc fusion protein comprises an amino acid sequence having at least 99% sequence identity to the amino acid sequence of SEQ ID NO:12. In certain embodiments, the functions and/or activities of the IL-22 Fc fusion protein can be assayed by in vitro or in vivo methods, for example, IL-22 receptor binding assay, Stat3 luciferase reporter activity assay, etc. In certain embodiments, the IL-22 Fc fusion protein comprises the amino acid sequence of SEQ ID NO:8 or SEQ ID NO:12. In certain particular embodiments, the IL-22 Fc fusion protein comprises the amino acid sequence of SEQ ID NO:8. In certain embodiments, the invention provides the IL-22 Fc fusion protein produced by the method comprising the step of culturing a host cell capable of expressing the IL-22 Fc fusion protein under conditions suitable for expression of the IL-22 Fc fusion protein. In certain embodiments, the method further comprises the step of obtaining the IL-22 Fc fusion protein from the cell culture or culture medium. In certain embodiments, the host cell is a Chinese hamster ovary (CHO) cell; while in other embodiments, the host cell is an *E. coli* cell.

In another aspect, the invention provides an IL-22 Fc fusion protein comprising an IL-22 polypeptide linked to an IgG Fc region by a linker, wherein the Fc region comprises a hinge region, an IgG CH2 domain and an IgG CH3 domain, and wherein the Fc region is not glycosylated. In certain embodiments, the hinge region comprises the amino acid sequence of CPPCP (SEQ ID NO:31). In certain other embodiments, the N297 residue in the Fc region is changed and/or the T299 residue in the Fc region is changed. In certain embodiments, the N297 residue in the CH2 domain is changed, preferably to glycine or alanine. In certain particular embodiments, the N297 residue is changed to glycine. In certain other embodiments, the N297 residue is changed to alanine. In yet other embodiments, the T299 residue is changed to Ala, Gly or Val. In certain other embodiments, the linker is 8-20 amino acids long, 8-16 amino acids long, or 10-16 amino acids long.

In certain embodiments, the Fc region comprises the CH2 and CH3 domain of IgG1. In certain particular embodiments, the linker comprises the amino acid sequence DKTHT (SEQ ID NO:32). In certain embodiments, the linker comprises the amino acid sequence GGGDKTHT (SEQ ID NO:41). In certain embodiments, the linker is at least 11 amino acids long and comprises the amino acid sequence EPKSCDKTHT (SEQ ID NO:33). In certain other embodiments, the linker comprises the amino acid sequence VEPKSCDKTHT (SEQ ID NO:34), KVEPKSCDKTHT (SEQ ID NO:35), KKVEPKSCDKTHT (SEQ ID NO:36), DKKVEPKSCDKTHT (SEQ ID NO:37), VDKKVEPKSCDKTHT (SEQ ID NO:38), or KVDKKVEPKSCDKTHT (SEQ ID NO:39). In certain particular embodiments, the linker comprises the amino acid sequence EPKSSDKTHT (SEQ ID NO:40). In certain embodiments, the linker comprises the amino acid sequence VEPKSSDKTHT (SEQ ID NO:67), KVEPKSSDKTHT (SEQ ID NO:68), KKVEPKSSDKTHT (SEQ ID NO:66), DKKVEPKSSDKTHT (SEQ ID NO:64), VDKKVEPKSSDKTHT (SEQ ID NO:69), or KVDKKVEPKSSDKTHT (SEQ ID NO:65). In certain particular embodiments, the linker does not comprise the amino acid sequence of GGS (SEQ ID NO: 45), GGGS (SEQ ID NO:46) or GGGGS (SEQ ID NO:47). In separate embodiments, the IL-22 IgG1 Fc fusion protein comprises a linker sequence of GGGSTHT (SEQ ID NO:63). In other particular embodiments, the IL-22 Fc fusion protein comprises the amino acid sequence of SEQ ID NO:12 or SE ID NO:14. In certain other particular embodiments, the IL-22 Fc fusion protein comprises the amino acid sequence of SEQ ID NO:12.

In certain embodiments, the IL-22 Fc fusion protein comprises the CH2 and CH3 domain of IgG4. In certain other embodiments, the linker comprises the amino acid sequence SKYGPP (SEQ ID NO:43). In certain particular embodiments, the linker comprises the amino acid sequence RVESKYGPP (SEQ ID NO:44). In certain embodiments, none of the linkers comprise the amino acid sequence GGS (SEQ ID NO:45), GGGS (SEQ ID NO:46) or GGGGS (SEQ ID NO:47). In other particular embodiments, the IL-22 Fc fusion protein comprises the amino acid sequence of SEQ ID NO:8 or SE ID NO:10. In particular embodiments, the IL-22 Fc fusion protein comprises the amino acid sequence of SEQ ID NO:8. In another embodiment, the IL-22 Fc fusion protein is produced by the method comprising the step of culturing a host cell capable of expressing the IL-22 Fc fusion protein under conditions suitable for expression of the IL-22 Fc fusion protein. In certain embodiments, the IL-22 Fc fusion protein is produced by the method that further comprises the step of obtaining the IL-22 Fc fusion protein from the cell culture or culture medium. In certain embodiments, the host cell is a Chinese hamster ovary (CHO) cell. In certain other embodiments, the host cell is an *E. coli* cell.

In yet another aspect, the invention provides a composition comprising an IL-22 Fc fusion protein, said IL-22 Fc fusion protein comprising an IL-22 polypeptide linked to an Fc region by a linker, wherein the Fc region comprises a hinge region, an IgG CH2 domain and an IgG CH3 domain, and wherein the composition has an afucosylation level in the CH2 domain of no more than 5%. In certain embodiments, the afucosylation level is no more than 2%, more preferably less than 1%. In certain embodiments, the afucosylation level is measured by mass spectrometry. In certain embodiments, the Fc region comprises the CH2 and CH3 domain of IgG4. In certain embodiments, the Fc region comprises a CH2 and CH3 domain of IgG1. In certain other embodiments, the hinge region comprises the amino acid sequence of CPPCP (SEQ ID NO:31). In certain embodiments, the IL-22 Fc fusion protein comprises the amino acid sequence of SEQ ID NO:24 or SEQ ID NO:26. In certain embodiments, the IL-22 Fc fusion protein comprises the amino acid sequence of SEQ ID NO:24. In certain embodiments, the composition is produced by the process comprising the steps of culturing a host cell capable of expressing the IL-22 Fc fusion protein under conditions suitable for expression of the IL-22 Fc fusion protein, and obtaining the IL-22 Fc fusion protein from the cell culture or culture medium, wherein the composition has an afucosylation level in the CH2 domain of the Fc region of no more than 5%. In certain embodiments, the afucosylation level is no more than 2%, more preferably less than 1%. In certain embodiments, the IL-22 Fc fusion protein is obtained by purification, preferably purifying fucosylated species away from afucosylated species. In certain embodiments, the IL-22 Fc fusion protein is purified by affinity chromatography. In certain embodiments, the host cell is a CHO cell.

In a further aspect, the invention provides an IL-22 Fc fusion protein, or a composition comprising IL-22 Fc fusion proteins, said IL-22 Fc fusion protein is produced by the process comprising the step of culturing a host cell capable of expressing the IL-22 Fc fusion protein under conditions suitable for expression of the IL-22 Fc fusion protein. In certain embodiments, the process further comprises the step of obtaining the IL-22 Fc fusion protein from the cell culture or culture medium. In certain embodiments, the host cell is a CHO cell; while in other embodiments, the host cell is an *E. coli* cell.

In a further aspect, the invention provides a composition comprising an IL-22 Fc fusion protein described herein. In yet another aspect, the invention provides a pharmaceutical composition comprising an IL-22 Fc fusion protein described herein, and at least one pharmaceutically acceptable carrier. In certain embodiments, the composition or pharmaceutical composition comprises an IL-22 Fc fusion protein comprising an amino acid sequence of SEQ ID NO:8, SEQ ID NO:10, SEQ ID NO:12, SEQ ID NO:14, SEQ ID NO:24 or SEQ ID NO:26. In certain particular embodiments, the composition or pharmaceutical composition comprises an IL-22 Fc fusion protein comprising the amino acid sequence of SEQ ID NO:8. In certain particular embodiments, the IL-22 Fc fusion protein is produced by *E. coli*. In certain other embodiments, the Fc region of the IL-22 Fc fusion protein is not glycosylated. In certain further embodiments, the IL-22 Fc fusion protein does not induce antibody dependent cellular cytotoxicity (ADCC). In certain embodiments, the pharmaceutical composition further comprises a suboptimal amount of a therapeutic agent such as dexamethasone. In certain embodiments, the IL-22 polypeptide comprises the amino acid sequence of SEQ ID NO:4.

Further, according to each and every aspect of the invention, in certain embodiments, the IL-22 Fc fusion protein can be a dimeric IL-22 Fc fusion protein (with respect to IL-22); while in other embodiments, the IL-22 Fc fusion protein can be a monomeric Fc fusion protein (with respect to IL22).

In a further aspect, the invention provides a monomeric IL-22 Fc fusion protein. In certain particular embodiments, the monomeric fusion protein comprises an IL-22 Fc fusion arm and an Fc arm. In certain embodiments, the IL-22 Fc fusion arm and the Fc arm comprises either a knob or a hole in the Fc region. In certain embodiments, the Fc region of the IL-22 Fc fusion arm (the monomer IL-22 Fc fusion) comprises a knob and the Fc region of the Fc arm (the monomer Fc without linking to IL-22) comprises a hole. In certain embodiments, the Fc region of the IL-22 Fc fusion arm (the monomer IL-22 Fc fusion) comprises a hole and the Fc region of the Fc arm (the monomer Fc without linking to IL-22) comprises a knob. In certain other embodiments, the monomeric IL-22 Fc fusion protein comprises the amino acid sequence of SEQ ID NO:61 and SEQ ID NO:62. In certain other embodiments, the Fc region of both arms further comprises an N297G mutation. In certain embodiments, the monomeric IL-22 Fc is produced by the process comprising the step of culturing one or more host cells comprising one or more nucleic acid molecules capable of expressing the first polypeptide comprising the amino acid sequence of SEQ ID NO:61 and the second polypeptide comprising the amino acid sequence of SEQ ID NO:62. In certain other embodiments, the method further comprises the step of obtaining the monomeric IL-22 Fc fusion protein from the cell culture or culture medium. In certain embodiments, the host cell is an *E. coli* cell. In a related aspect, the invention provides a composition or pharmaceutical composition comprising the monomeric IL-22 Fc fusion protein.

In yet another aspect, the invention provides an isolated nucleic acid encoding the IL-22 Fc fusion protein described herein. In certain embodiments, the nucleic acid encodes the IL-22 Fc fusion protein comprising the amino acid sequence of SEQ ID NO:8, SEQ ID NO:10, SEQ ID NO:12, SEQ ID NO:14, SEQ ID NO:24 or SEQ ID NO:26, preferably SEQ ID NO:8 or SEQ ID NO:12, more preferably SEQ ID NO:8. In certain other embodiments, the nucleic acid comprises the polynucleotide sequence of SEQ ID NO:7, SEQ ID NO:9, SEQ ID NO:11, SEQ ID NO:13, SEQ ID NO:23 or SEQ ID NO:25. In certain particular embodiments, the nucleic acid comprises the polynucleotide sequence of SEQ ID NO:7 or SEQ ID NO:11, preferably SEQ ID NO:7. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25, wherein the isolated nucleic acid is capable of encoding an IL-22 Fc fusion protein that is capable of binding to IL-22R and/or triggering IL-22R activity and wherein the Fc region of the IL-22 Fc fusion protein is not glycosylated. In certain embodiments, the isolated nucleic acid comprises a polynucleotide sequence that is at least 80%, 85%, 86%, 87%, 88%, 89%, 90%, 91%, 92%, 93%, 94%, 95%, 96%, 97%, 98%, 99% or 100% sequence identity to the polynucleotide sequence of SEQ ID NO:7, SEQ ID NO:9, SEQ ID NO:11, SEQ ID NO:13; SEQ ID NO:23 or SEQ ID NO:25, wherein the isolated nucleic acid is capable of encoding an IL-22 Fc fusion protein comprising the amino acid sequence of SEQ ID NO:8, 10, 12, or 14. In related aspects, the invention provides vectors comprising the nucleic acid described above, and a host cell comprising the vector. In certain embodiments, the host cell is a prokaryotic cell or eukaryotic cell. In certain particular embodiments, the host cell is a prokaryotic cell, including without limitation, an *E. coli* cell. In certain other embodiments, the host cell is a eukaryotic cell, including without limitation, a CHO cell. In certain embodiments, the host cell comprises a vector comprising a nucleic acid encoding the IL-22 Fc fusion protein comprising the amino acid sequence of SEQ ID NO:8.

In a further related aspect, the invention provides methods of making the IL-22 Fc fusion protein comprising the step of culturing the host cell under conditions suitable for expression of the IL-22 Fc fusion protein. In certain embodiments, the method further comprises the step of obtaining the IL-22 Fc fusion protein from the cell culture or culture medium. The IL-22 Fc fusion protein can be obtained from the cell culture or culture medium by any methods of protein isolation or purification known in the art, including without limitation, collecting culture medium, freezing/thawing, centrifugation, cell lysis, homogenization, ammonium sulfate precipitation, HPLC, and affinity, gel filtration, and ion exchanger column chromatography. In certain embodiments, the method further comprises the step of removing afucosylated IL-22 Fc fusion protein. In certain other embodiments, the afucosylated IL-22 Fc fusion protein is removed by affinity column chromatography. In certain embodiments, the host cell is an *E. coli* cell. In other embodiments, the host cell is a CHO cell.

In yet another aspect, the invention provides a composition or pharmaceutical composition comprising an IL-22 Fc fusion protein of the invention and at least one pharmaceutically acceptable carrier. In certain embodiments, the IL-22 Fc fusion protein comprises the amino acid sequence of SEQ ID NO:8, SEQ ID NO:10, SEQ ID NO:12, SEQ ID NO:14, SEQ ID NO:24, or SEQ ID NO:26. In other embodiments, the Fc region of the IL-22 Fc fusion protein is not glycosylated. In certain embodiments, the Fc region of the IL-22 Fc fusion protein is not glycosylated while the IL-22 polypeptide is glycosylated. In certain such embodiments, the IL-22 Fc fusion protein is produced in CHO cells. In certain embodiments, the IL-22 Fc fusion protein does not induce antibody dependent cellular cytotoxicity. In yet other embodiments, the pharmaceutical composition further comprises dexamethasone or a TNF antagonist. In certain particular embodiments, the dexamethasone or a TNF antagonist is present at a suboptimal amount.

In certain other embodiments, the pharmaceutical composition comprising IL-22 Fc fusion proteins has an afucosylation level in the CH2 domain of no more than 5%, preferably no more than 2%, more preferably less than 1%.

In certain particular embodiments, the IL-22 Fc fusion protein comprises the amino acid sequence of SEQ ID NO:24 or SEQ ID NO:26, preferably SEQ ID NO:24. In certain other embodiments, the IL-22 Fc fusion protein is produced in CHO cells. In certain particular embodiments, the subject is a human. In certain embodiments, the pharmaceutical composition is administered systematically or topically. In certain other embodiments, the pharmaceutical composition is administered intravenously, subcutaneously, intraperitoneally or topically.

In a further aspect, the invention provides a pharmaceutical composition comprising an IL-22 polypeptide or IL-22 Fc fusion protein described herein and at least one pharmaceutically acceptable carrier. In certain embodiments, the pharmaceutically acceptable carrier is a gelling agent. In certain embodiments, the gelling agent is a polysaccharide. In some embodiments, the gelling agent is, without limitation, methylcellulose, hydroxyethyl cellulose, carboxymethyl cellulose, hydroxypropyl cellulose, POE-POP block polymers, alginate, hyaluronic acid, polyacrylic acid, hydroxyethyl methylcellulose or hydroxypropyl methylcellulose. In some embodiments, the polysaccharide is a cellulosic agent such as, without limitation, hydroxyethyl methylcellulose or hydroxypropyl methylcellulose. In certain embodiments, the gelling agent is hydroxypropyl methylcellulose. In some embodiments, the pharmaceutical composition is for topical administration. In certain embodiments, the pharmaceutical composition for topical administration comprises an IL-22 polypeptide. In some embodiments, the pharmaceutical composition for topical administration comprises an IL-22 Fc fusion protein. In certain embodiments, the pharmaceutical composition for topical administration comprises an IL-22 polypeptide without an Fc fusion.

In another aspect, the invention provides methods of treating IBD in a subject in need thereof comprising administering to the subject the pharmaceutical composition comprising an IL-22 Fc fusion protein of the invention. In certain embodiments, the IBD is ulcerative colitis. In certain other embodiments, the IBD is Crohn's disease. In certain particular embodiments, the Fc region of the IL-22 Fc fusion protein is not glycosylated. In certain embodiments, the N297 residue and/or the T299 residue of the Fc region is changed. In certain embodiments, the N297 residue of the Fc region is changed. In certain other embodiments, the N297 residue is changed to Gly or Ala, preferably Gly. In certain other embodiments, the T299 residue is changed, preferably to Val, Gly or Ala. In certain particular embodiments, the IL-22 Fc fusion protein comprises the amino acid sequence of SEQ ID NO:8, SEQ ID NO:10, SEQ ID NO:12 or SEQ ID NO:14, preferably SEQ ID NO:8. In certain embodiments, the IL-22 Fc fusion protein is produced in E. coli or a CHO cell. In certain embodiments, the subject is a human. In certain other embodiments, the pharmaceutical composition is administered intravenously, subcutaneously, intraperitoneally or topically.

In another aspect, the invention provides methods of treating any one or combination of the following diseases using an IL-22 polypeptide or an IL-22 Fc fusion protein of this invention: Type II diabetes, Type II diabetes with morbid obesity, wounds (including diabetic wounds and diabetic ulcers), burns, ulcers (including pressure ulcer and venous ulcer), graft versus host disease (GVHD), atherosclerosis, cardiovascular disease, metabolic syndrome, endotoxemia (acute and mild), sepsis, acute coronary heart disease, hypertension, dyslipemia, obesity, hyperglycemia, lipid metabolism disorders, hepatitis, acute hepatitis, renal failure, acute renal failure, acute kidney injury, renal draft failure, post cadaveric renal transplant delayed graft function, contrast induced nephropathy, pancreatitis, acute pancreatitis, liver fibrosis and lung fibrosis. In certain embodiments, acute pancreatitis can be mild to moderate to severe disease. In certain embodiments, acute pancreatitis includes disease post ERCP (endoscopic retrograde cholangiopancreatography). In some further embodiments, the patient to be treated for the above disease is in need of a change in his HDL/LDL lipid profile, which IL-22 polypeptide or IL-22 Fc fusion proteins can alter in the patient to increase HDL and decrease LDL. In a related aspect, the invention provides uses of an IL-22 polypeptide or an IL-22 Fc fusion protein in the preparation of a medicament for the treatment of any one or combinations of the above diseases.

In a further aspect, the invention provides methods of inhibiting microbial infection in the intestine, or preserving goblet cells in the intestine during a microbial infection, of a subject in need thereof comprising the step of administering to the subject the pharmaceutical composition comprising the IL-22 Fc fusion protein of the invention. In other related aspects, the invention provides methods of enhancing epithelial cell integrity, mucosal healing, epithelial cell proliferation, epithelial cell differentiation, epithelial cell migration or epithelial wound healing in the intestine in a subject in need thereof comprising administering to the subject the pharmaceutical composition comprising the IL-22 Fc fusion protein of the invention. In certain embodiments, the epithelial cell is intestinal epithelial cell.

In another aspect, a method for preventing or treating a cardiovascular condition, which condition includes a pathology of atherosclerotic plaque formation, is provided. The method includes administering to a subject in need thereof a therapeutically effective amount of an IL-22 polypeptide or an IL-22 Fc fusion protein. The cardiovascular condition includes, for example, coronary artery disease, coronary microvascular disease, stroke, carotid artery disease, peripheral arterial disease, and chronic kidney disease. The method can include further slowing down the progression of atherosclerotic plaque formation. The method can further include administering one or more additional therapeutic agent to the subject for the prevention or treatment of the cardiovascular condition.

In another aspect, a method for treating metabolic syndrome is provided. The method includes administering to a subject in need thereof a therapeutically effective amount of an IL-22 polypeptide or an IL-22 Fc fusion protein. The method can further include reducing one or more risk factors associated with metabolic syndrome, including one or more of abdominal obesity, hyperglycemia, dyslipidemia, and hypertension. The method can further include reducing the level of bacterial lipopolysaccharide (LPS) in the subject. The method can further include administering one or more additional agent to the subject for the prevention or treatment of metabolic syndrome.

In another aspect, a method for delaying or slowing down the progression of atherosclerosis is provided. The method includes administering to a subject in need thereof a therapeutically effective amount of an IL-22 polypeptide or an IL-22 Fc fusion protein. The method can further include administering one or more additional agent to the subject for delaying or slowing down the progression of atherosclerosis.

In another aspect, a method of preventing indicia of atherosclerosis is provided. The method includes administering a therapeutically effective amount of an IL-22 polypeptide or an IL-22 Fc fusion protein to a subject at risk of atherosclerosis, wherein the IL-22 polypeptide of IL-22 Fc fusion protein is effective against the development of indicia of atherosclerosis. In certain embodiments, the subject has been identified to be at risk to develop a cardiovascular condition. In certain embodiments, the subject is genetically at risk of developing a cardiovascular condition. In one or more embodiments, the indicia of atherosclerosis include plaque accumulation. In some embodiments, the indicia of atherosclerosis include vascular inflammation. The method can further include administering one or more additional agent to the subject for preventing indicia of atherosclerosis.

In yet another aspect, a method of treating one or more of acute endotoxemia and sepsis is provided. The method includes administering to a subject in need thereof a therapeutically effective amount of an IL-22 polypeptide or an IL-22 Fc fusion protein. The method can further include administering one or more additional agent to the subject for treating one or more of acute endotoxemia and sepsis.

In one other aspect, a method is provided for accelerating or improving wound healing, or both, in a subject. The method includes administering to a subject in need thereof a therapeutically effective amount of an IL-22 polypeptide, an IL-22 Fc fusion protein or an IL-22 agonist. In certain embodiments, the wound is a chronic wound. In certain other embodiments, the wound is an infected wound. In certain embodiments, the subject is diabetic, including a subject with type II diabetes. In one or more embodiments, the wound is a diabetic foot ulcer. In certain embodiments, the therapeutically effective amount of an IL-22 polypeptide, IL-22 Fc fusion protein or IL-22 agonist is administered until there is complete wound closure. In some embodiments, the administration is systemic; and in other embodiments, the administration is topical. In certain embodiments, the IL-22 polypeptide, IL-22 Fc fusion protein or IL-22 agonist is in a formulation for topical administration. In certain embodiments, the topical formulation comprises an IL-22 polypeptide without an Fc fusion. In certain embodiments, the IL22 agonist is selected from the group consisting of an IL-22 polypeptide, an IL-22 Fc fusion protein, an IL-22 agonist, an IL-19 polypeptide, an IL-19 Fc fusion protein, an IL-19 agonist, an IL-20 polypeptide, an IL-20 Fc fusion protein, an IL-20 agonist, an IL-24 polypeptide, an IL-24 Fc fusion protein, an IL-24 agonist, an IL-26 polypeptide, an IL-26 Fc fusion protein, an IL-26 agonist, and an IL-22R1 agonist. In certain other embodiments, the IL-22 agonist is selected from the group consisting of an IL-22 polypeptide, an IL-22 Fc fusion protein, an IL-22 agonist, an IL-20 polypeptide, an IL-20 Fc fusion protein, an IL-20 agonist, an IL-24 polypeptide, an IL-24 Fc fusion protein, an IL-24 agonist and an IL-22R1 agonist. In certain embodiments, the IL-22R1 agonist is an anti-IL22R1 agonistic antibody.

In a further aspect, the invention provides methods of treating a metabolic syndrome comprising the step of administering to a subject in need thereof a therapeutically effective amount of one or more IL-22 agonists. In certain embodiments, the IL22 agonist is selected from the group consisting of an IL-22 polypeptide, an IL-22 Fc fusion protein, an IL-22 agonist, an IL-19 polypeptide, an IL-19 Fc fusion protein, an IL-19 agonist, an IL-20 polypeptide, an IL-20 Fc fusion protein, an IL-20 agonist, an IL-24 polypeptide, an IL-24 Fc fusion protein, an IL-24 agonist, an IL-26 polypeptide, an IL-26 Fc fusion protein, an IL-26 agonist, and an IL-22R1 agonist. In certain other embodiments, the IL-22 agonist is selected from the group consisting of an IL-22 polypeptide, an IL-22 Fc fusion protein, an IL-22 agonist, an IL-20 polypeptide, an IL-20 Fc fusion protein, an IL-20 agonist, an IL-24 polypeptide, an IL-24 Fc fusion protein, an IL-24 agonist and an IL-22R1 agonist. In certain embodiments, the IL-22R1 agonist is an anti-IL22R1 agonistic antibody. In certain other embodiments, the metabolic syndrome is diabetes. In certain particular embodiments, the metabolic syndrome is type II diabetes.

According to another embodiment, the subject is administered an IL-22 Fc fusion protein of the invention. In certain embodiments, the subject is a human. In certain embodiments, the IL-22 polypeptide or IL22 Fc fusion protein is administered intravenously, subcutaneously, intraperitoneally, systemically or topically.

In certain embodiments of these aspects, the Fc region of the IL-22 Fc fusion protein is not glycosylated. In certain embodiments, the N297 residue and/or the T299 residue of the Fc region is changed. In certain embodiments, the N297 residue of the Fc region is changed. In certain other embodiments, the N297 residue is changed to Gly or Ala, preferably Gly. In certain other embodiments, the T299 residue is changed, preferably to Val, Gly or Ala. In certain particular embodiments, the IL-22 Fc fusion protein comprises the amino acid sequence of SEQ ID NO:8, SEQ ID NO:10, SEQ ID NO:12 or SEQ ID NO:14, preferably SEQ ID NO:8. In certain embodiments, the IL-22 Fc fusion protein is produced in *E. coli*. In certain embodiments, the subject is a human. In certain other embodiments, the pharmaceutical composition is administered intravenously, subcutaneously or topically.

In certain other embodiments, the pharmaceutical composition comprising IL-22 Fc fusion proteins has an afucosylation level in the CH2 domain of no more than 5%, preferably no more than 2%, more preferably less than 1%. In certain particular embodiments, the IL-22 Fc fusion protein comprises the amino acid sequence of SEQ ID NO:24 or SEQ ID NO:26, preferably SEQ ID NO:24. In certain other embodiments, the IL-22 Fc fusion protein is produced in CHO cells. In certain particular embodiments, the subject is a human. In certain other embodiments, the pharmaceutical composition is administered intravenously, subcutaneously or topically.

In yet other embodiments of the above aspects, the N-glycan attached to the Fc region of the IL-22 Fc fusion protein is enzymatically removed by a glycolytic enzyme. In certain embodiments, the glycolytic enzyme is peptide-N-glycosidase (PNGase). In certain particular embodiments, the subject is a human.

In yet a further aspect, the invention also provides uses of an IL-22 Fc fusion protein described herein in the preparation of a medicament for the treatment of IBD, including UC and CD, in a subject in need thereof. In a related aspect, the invention provides uses of an IL-22 Fc fusion protein described herein in the preparation of a medicament for inhibiting microbial infection in the intestine, or preserving goblet cells in the intestine during a microbial infection in a subject in need thereof. In yet another aspect, the invention provides uses of an IL-22 Fc fusion protein described herein in the preparation of a medicament for enhancing epithelial cell integrity, epithelial cell proliferation, epithelial cell differentiation, epithelial cell migration or epithelial wound healing in the intestine, in a subject in need thereof. In other related aspects, the invention provides uses of an IL-22 polypeptide or IL-22 Fc fusion protein in the preparation of a medicament for treating a cardiovascular condition, metabolic syndrome, atherosclerosis, acute kidney injury, acute pancreatitis, accelerating, promoting or improving wound healing, including without limitation, healing of a chronic wound, diabetic wound, infected wound, pressure ulcer or diabetic foot ulcer, in a subject in need thereof.

Each and every embodiment can be combined unless the context clearly suggests otherwise. Each and every embodiment can be applied to each and every aspect of the invention unless the context clearly suggests otherwise.

Specific embodiments of the present invention will become evident from the following more detailed description of certain preferred embodiments and the claims.

BRIEF DESCRIPTION OF THE FIGURES

FIG. 1 shows amino acid sequence alignment of mature IL-22 from different mammalian species: human (GenBank Accession No. Q9GZX6, SEQ ID NO:4), chimpanzee (GenBank Accession No. XP_003313906, SEQ ID NO:48), orangutan (GenBank Accession No. XP_002823544, SEQ ID NO:49), mouse (GenBank Accession No. Q9JJY9, SEQ ID NO:50) and dog (GenBank Accession No. XP_538274, SEQ ID NO:51).

FIG. 3 shows sequence alignment of human IL-22 IgG4 Fc fusion (N297G, full length Fc sequence with the C-terminal Lys, SEQ ID NO:16, without Lys SEQ ID NO:8), IL-22 IgG1 Fc fusion (N297G, full length Fc sequence with the C-terminal Lys, SEQ ID NO:20, without Lys SEQ ID NO:12) and IL-22 (SEQ ID NO:4). The IL-22 sequence shown is the matured form without the leader sequence. The hinge sequence CPPCP (SEQ ID NO:31) is shown in the box, followed by the CH2 and CH3 domains. The N297G substitution and the optional C-terminus Lys residue are marked.

IL-22 Fc reversed insulin insensitivity in HFD-fed mice. P<0.01, *P<0.001. Error bars, s.e.m.

Figure 24A:
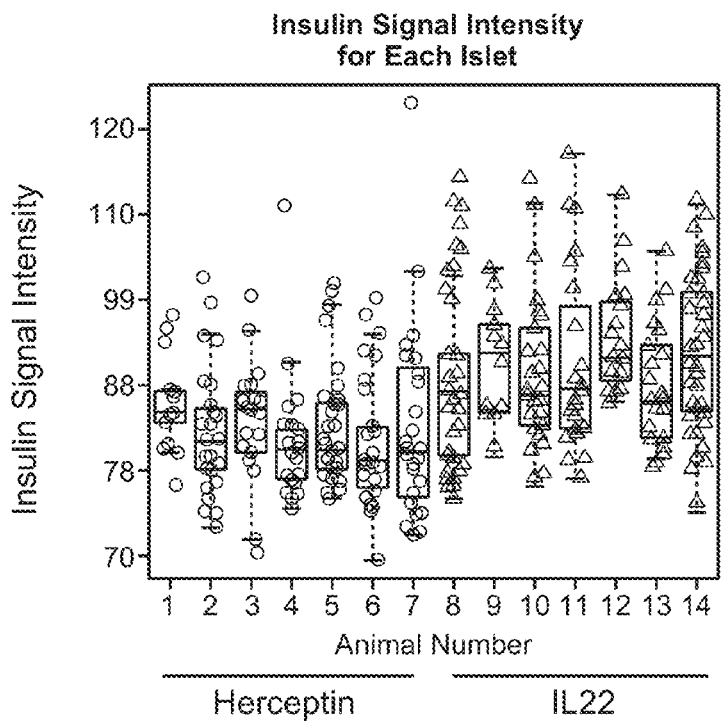
Figure 24B:
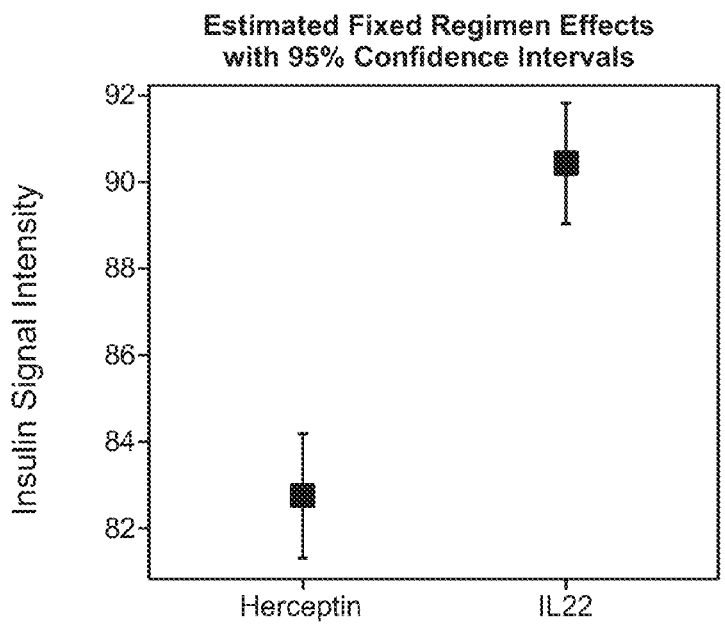

FIGS. 24A-B depict quantitative analysis of insulin-signal intensity in IL-22-Fc treated animals.

Figure 25A:
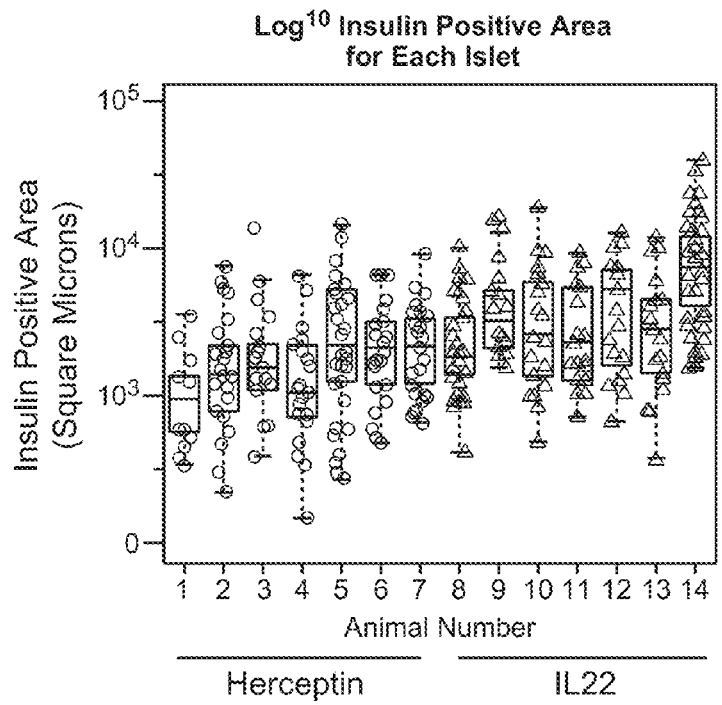
Figure 25B:
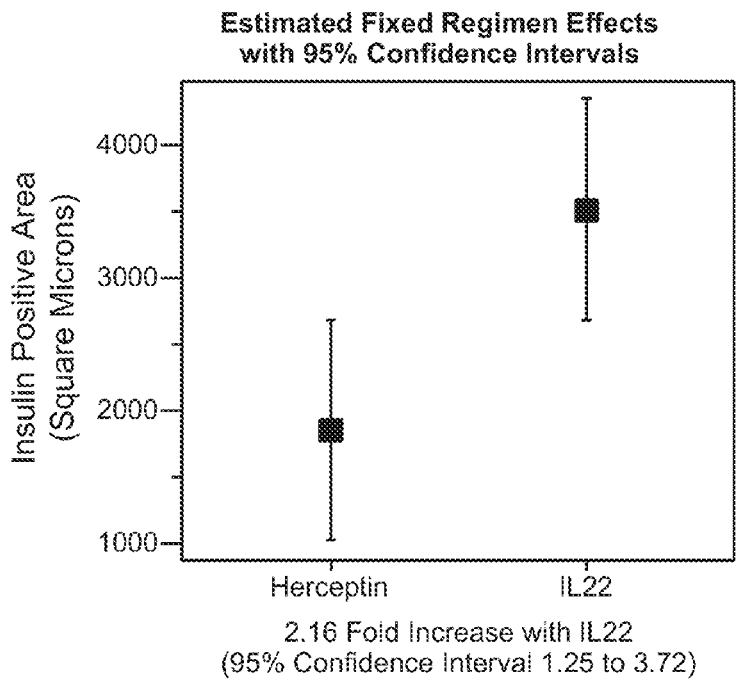

FIGS. 25A-B show that the insulin-positive area was increased in IL-22-Fc treated animals compared to control.

Figure 26B:
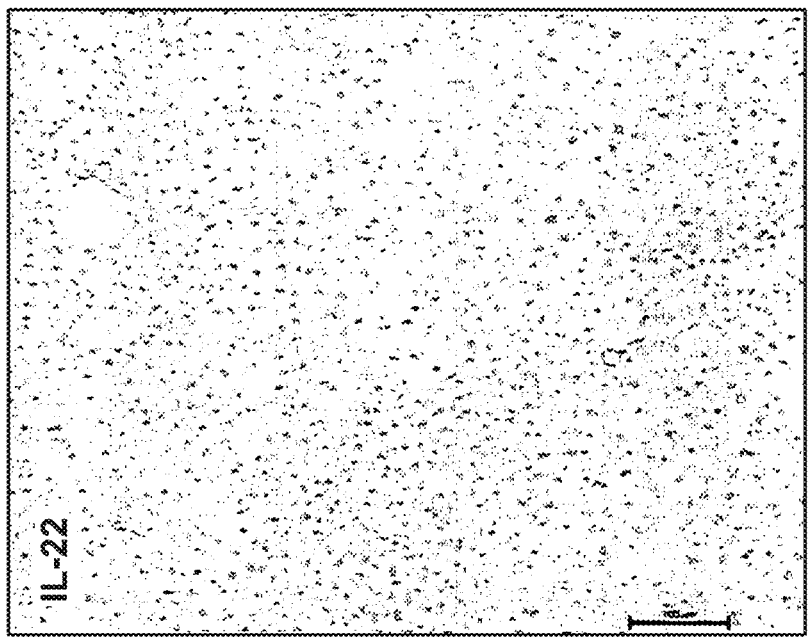
Figure 26A:
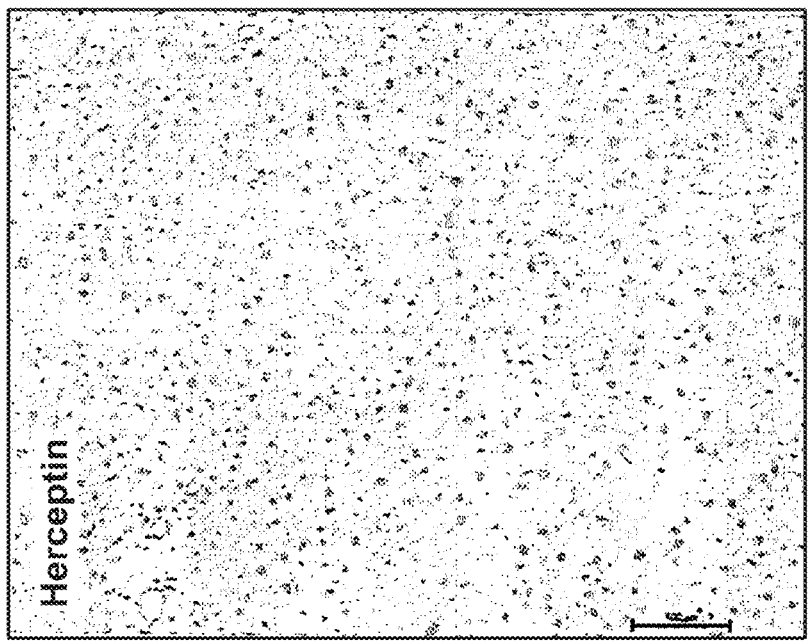
Figure 29B:
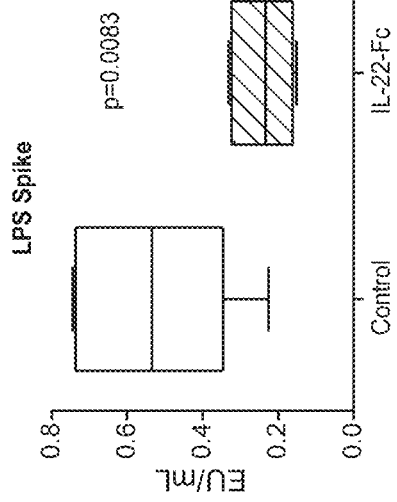
Figure 29D:
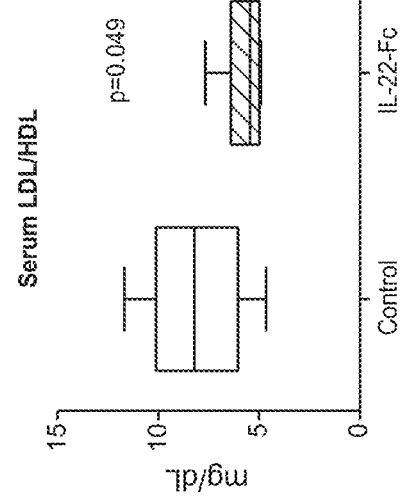
Figure 29A:
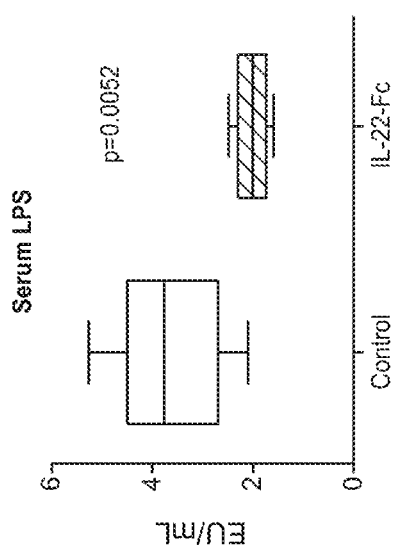
Figure 29C:
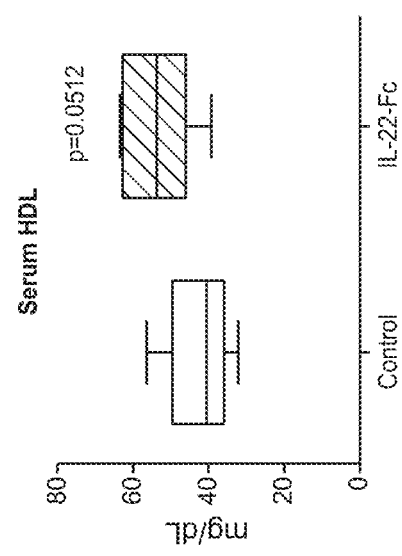

FIGS. 26A-B show histological sections demonstrating a decrease in hepatic periportal steatosis with IL-22-Fc treatment (B) as compared to control (A).

FIGS. 27A-B show an assessment of IL-22R in HFD induced glucose tolerance. (A) glucose levels (mg/dL) over time post glucose ip injection. (B) Calculation of the total area under the curve (AUC).

FIG. 28 shows mass of IL-22 receptor KO mice compared to littermate control.

FIGS. 29A-D Ldlr−/−, Apobec1−/− (dko) mice were treated with 50 ug IL-22Fc or 50 ug anti-ragweed (n=6 per group) for 48 hours. Serum LPS was reduced by 50% (p=0.0052) and serum LDL/HDL was reduced by 30% (p=0.049) in IL-22Fc treated mice.

FIG. 30 shows a nucleotide sequence of a cDNA encoding a native human IL-22 (SEQ ID NO:70).

FIG. 31 shows the amino acid sequence derived from the coding sequence shown in FIG. 30 (SEQ ID NO:71).

FIG. 32A shows the amino acid sequence of a mouse IL-22-mouse-IgG2a fusion protein (SEQ ID NO:73). FIG. 32B shows the nucleotide sequence encoding mouse IL-22-mouse IgG2a fusion protein (SEQ ID NO:72).

Figure 33:
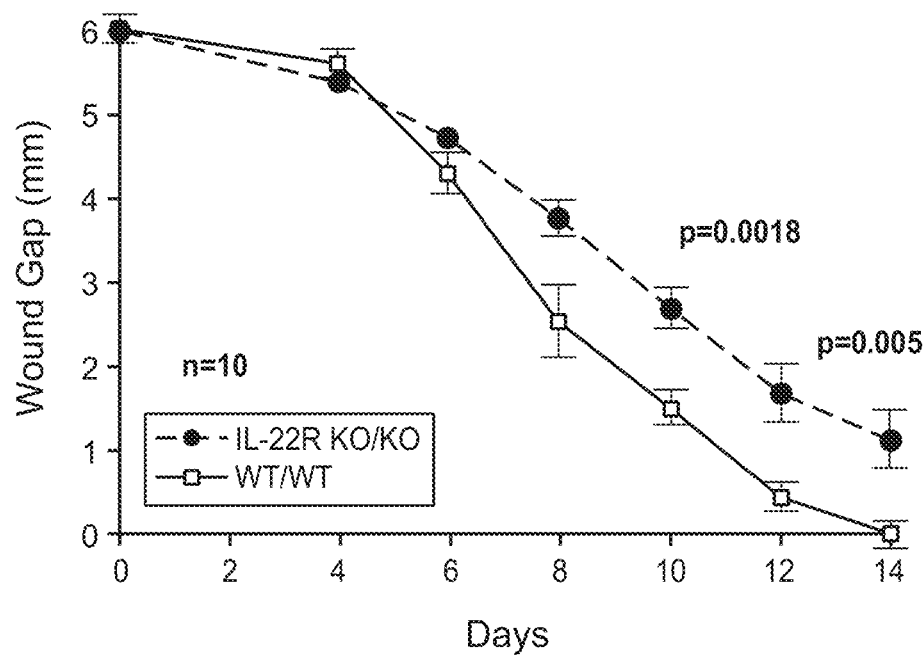

FIG. 33 shows that lack of signaling through IL-22R results in delayed wound healing. IL-22R KO mice wounds were significantly delayed (p=0.0018 on day 10 & p=0.005 on day 12) in healing compared to WT littermate control mice.

Figure 34A:
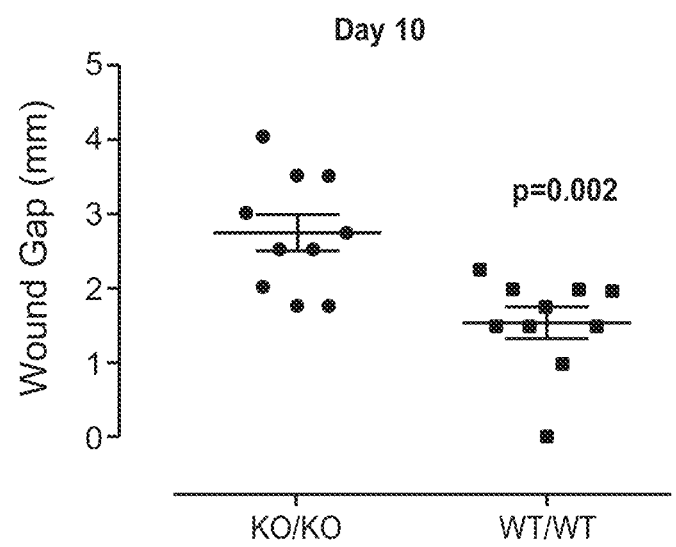
Figure 34B:
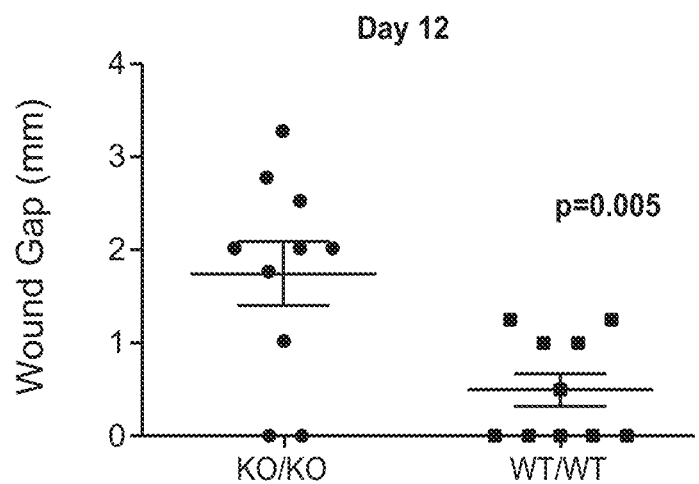
Figure 34C:
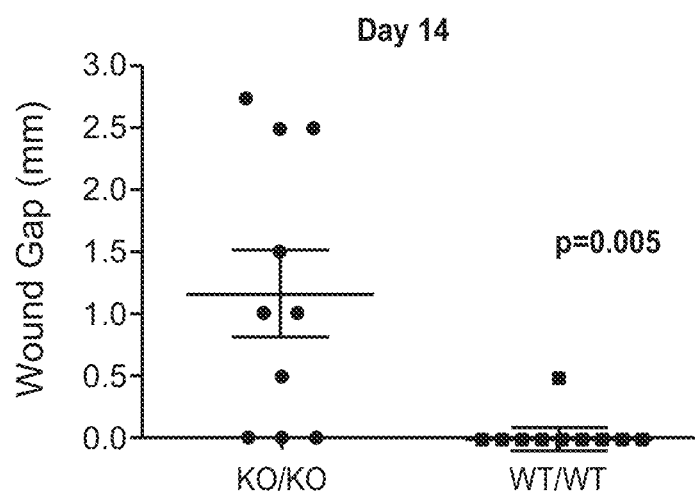
Figure 34D:
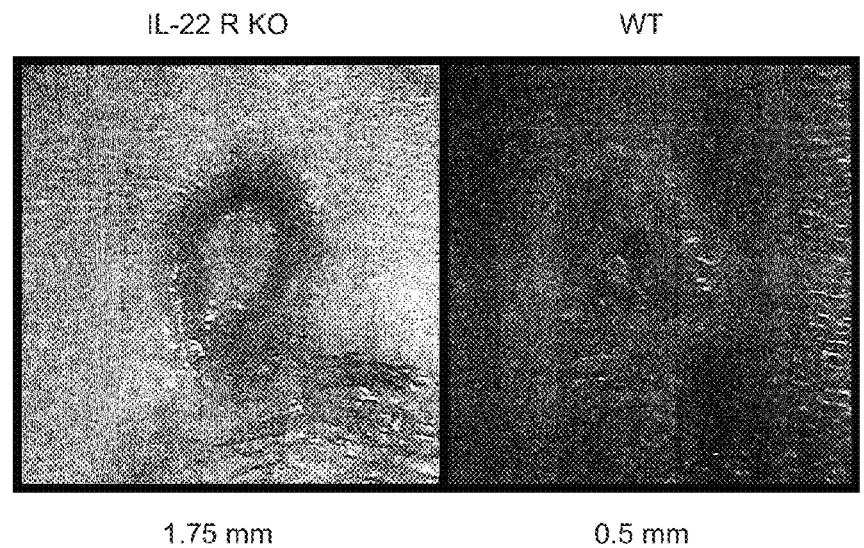

FIGS. 34A-C represent individual mice (n=10) wound gap at days 10, 12 and 15. Representative photo images of the wounds for both IL-22R KO mice and WT at day 14 are shown (D).

Figure 35A:
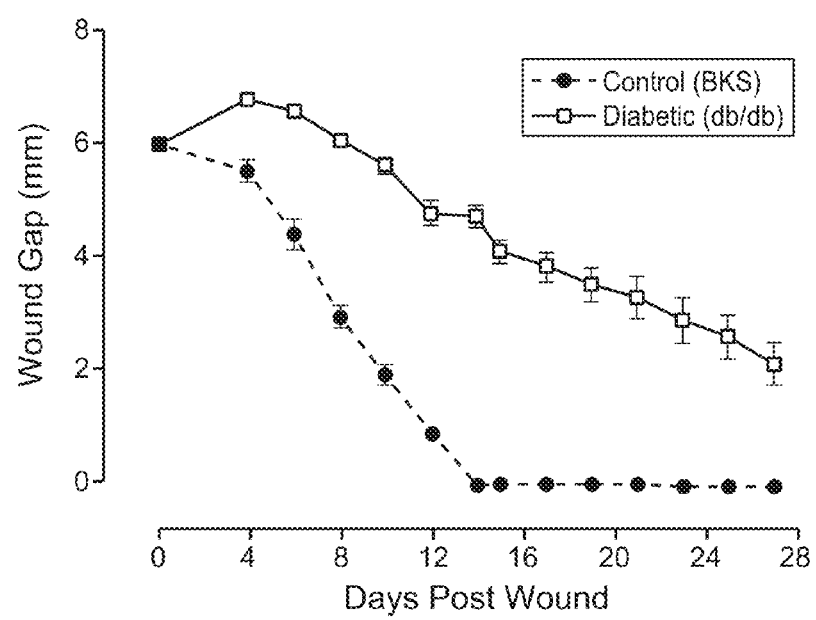
Figure 35B:
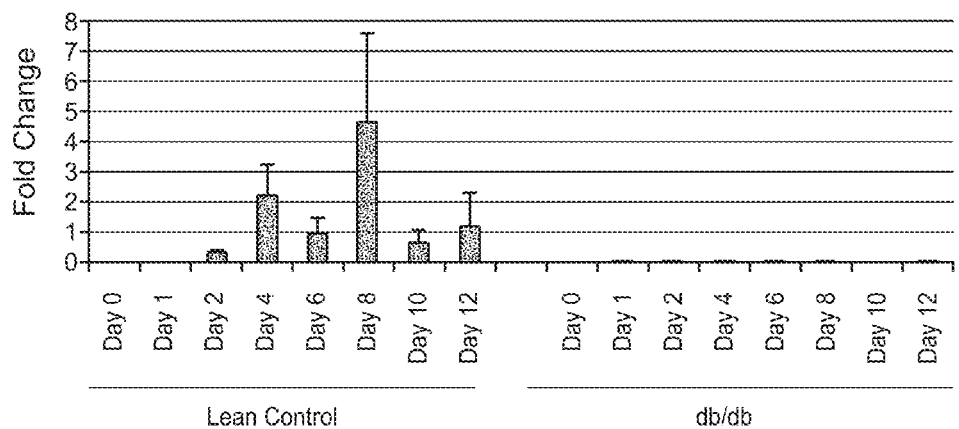

FIGS. 35A-B illustrate wound healing comparison between Control WT mice (BKS) and Diabetic db/db mice. (A) Wound healing in the db/db mice was considerably delayed throughout the period of study and did not heal fully even at day 28. The bar graph in (B) shows the level of IL-22 expression as fold change in wild type or db/db mice days after wound excision.

Figure 36:
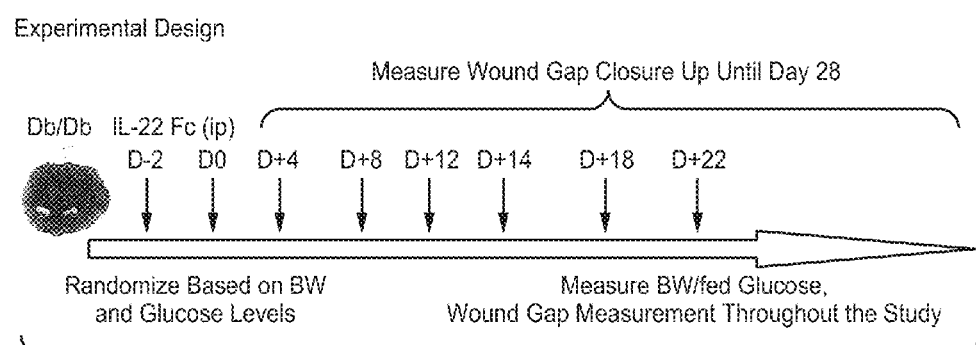

FIG. 36 is a schematic representation of the study design for testing IL-22-Fc in db/db mice in a total of 3 groups (n=7). Anti-ragweed was used for control Fc protein and anti-FGFR1 antibody was used as positive control for glucose regulation.

Figure 37:
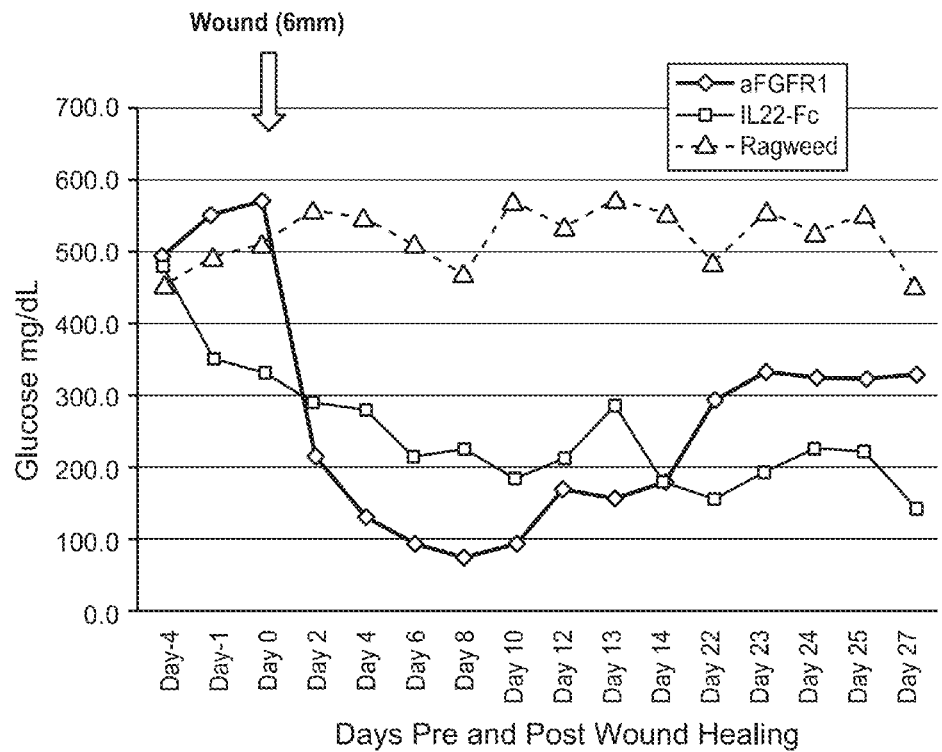

FIG. 37 shows IL-22 Fc normalized fed glucose level of treated mice as compared to controls from days 4 until day 27. Glucose levels were recorded using an Onetouch® glucometer.

Figure 38:
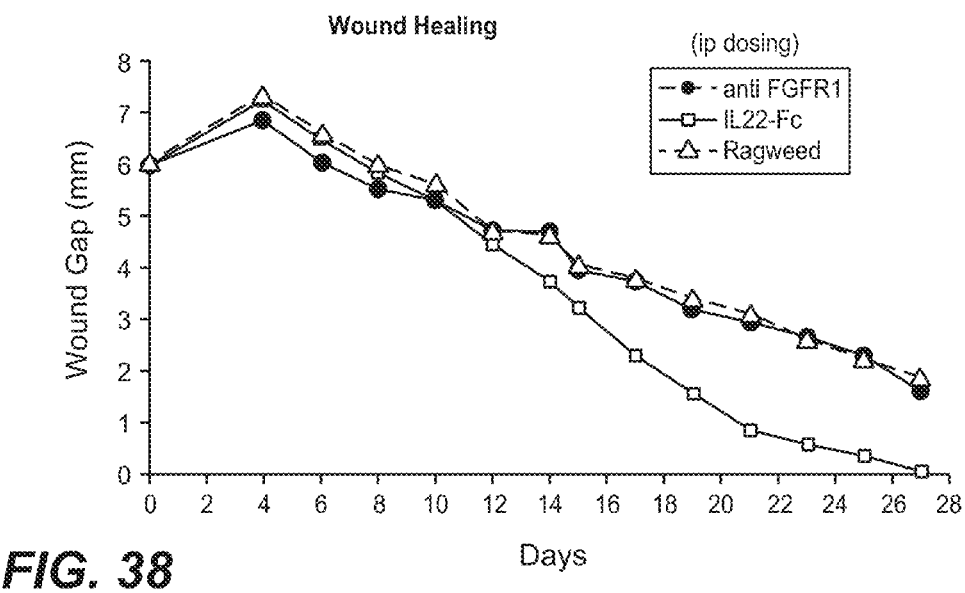

FIG. 38 shows graphically comparative wound gap measurement of IL-22-Fc compared to 2 control antibodies: anti-ragweed and anti-FGFR1. Each data point represents an average of 7 mice/group.

FIGS. 39A-D show individual wound gap measurements at days 15, 19, 21, and day 27. The photographs of representative mice at day 27 are shown (E).

Figures 39E, 40:
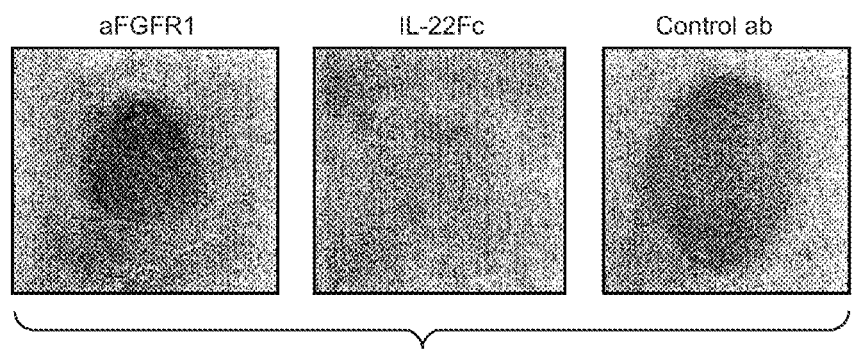

FIG. 40 is a schematic representation of the study design for testing topical vs. systemic dosing of IL-22-Fc compared to control antibody treatment in db/db mice; Total 3 groups (n=7).

Figure 41A:
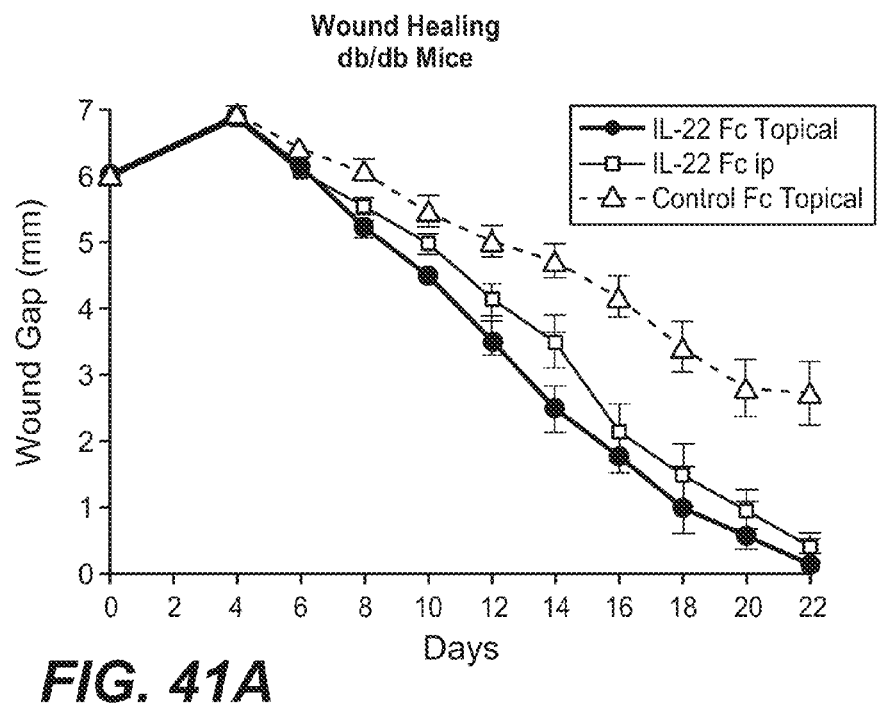
Figure 41B:
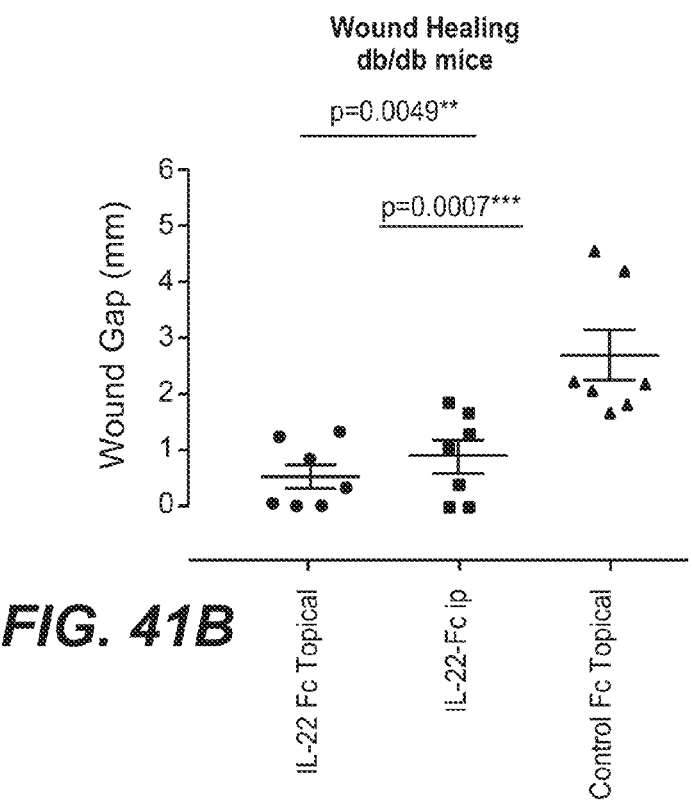

FIG. 41A-B show graphically comparative wound gap measurement of IL-22-Fc topical vs. systemic dosing with control Fc topical treatment. Anti-ragweed antibody was used as an Fc control antibody. Each data point represents an average of 7 mice/group.

Figure 42A:
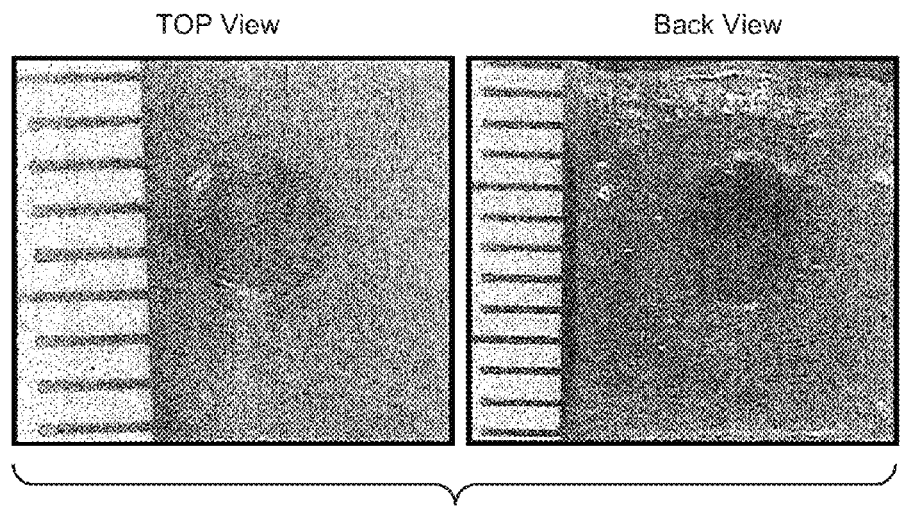
Figure 42B:
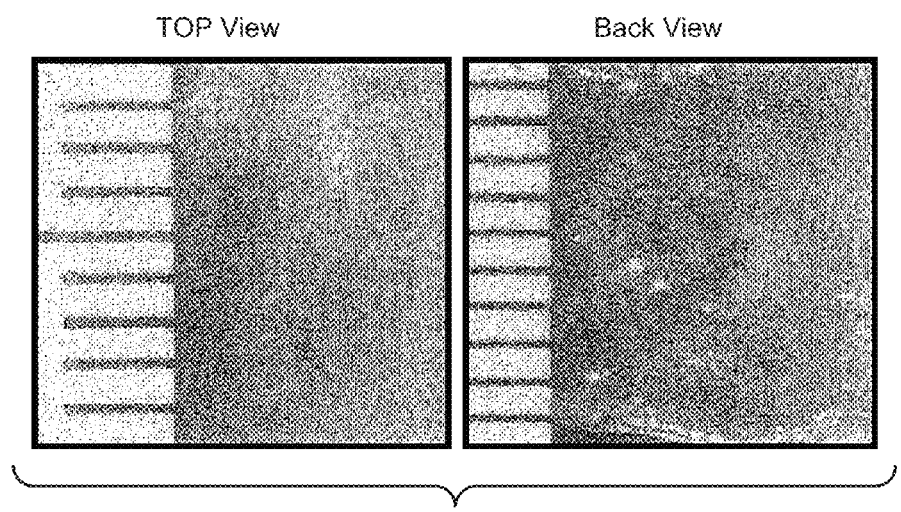

FIGS. 42A-B show photographically surgically removed wound tissue from representative mice showing both top as well as back view on day 22 from IL-22-Fc (B) and control antibody (A).

Figure 43A:
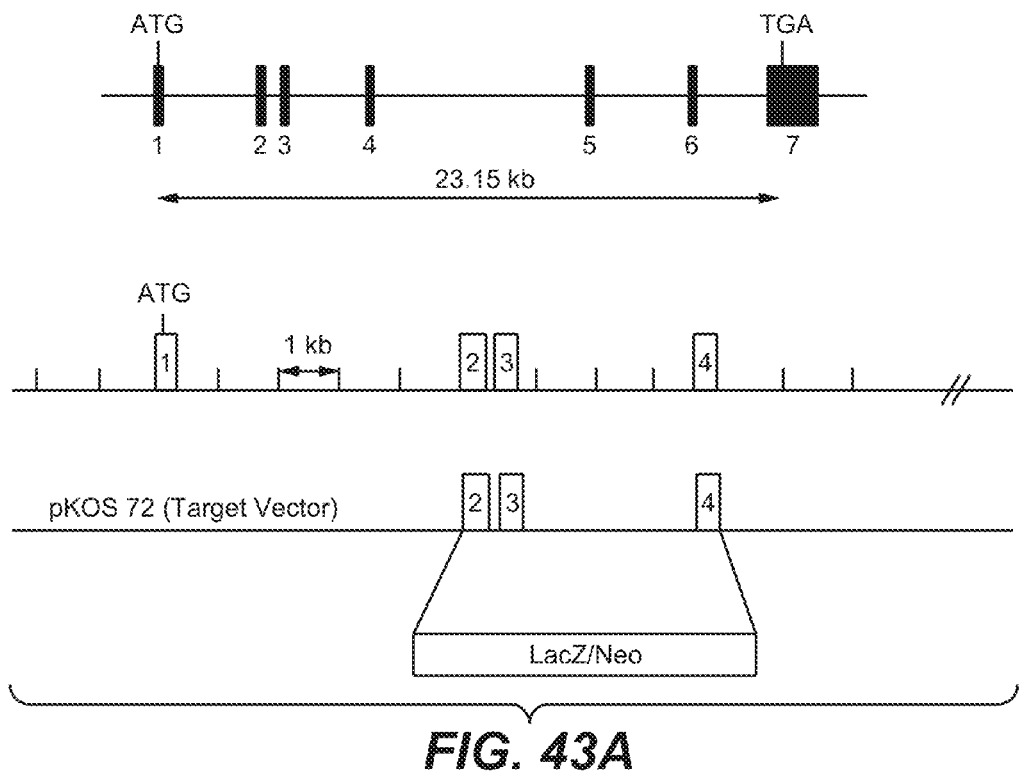
Figure 43B:
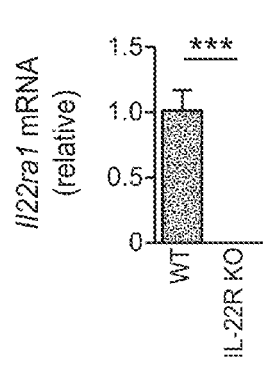
Figure 43C:
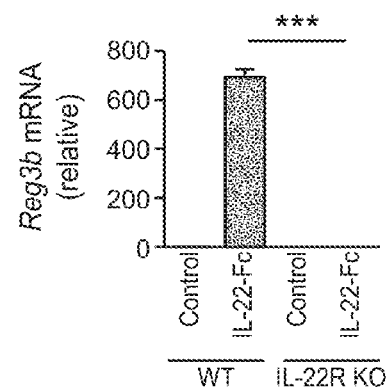
Figure 44A:
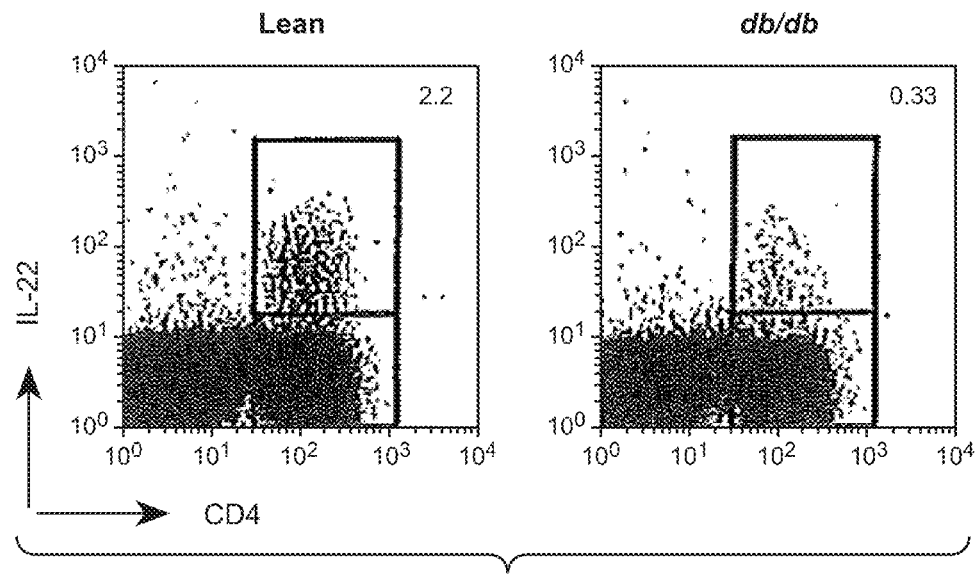
Figure 44C:
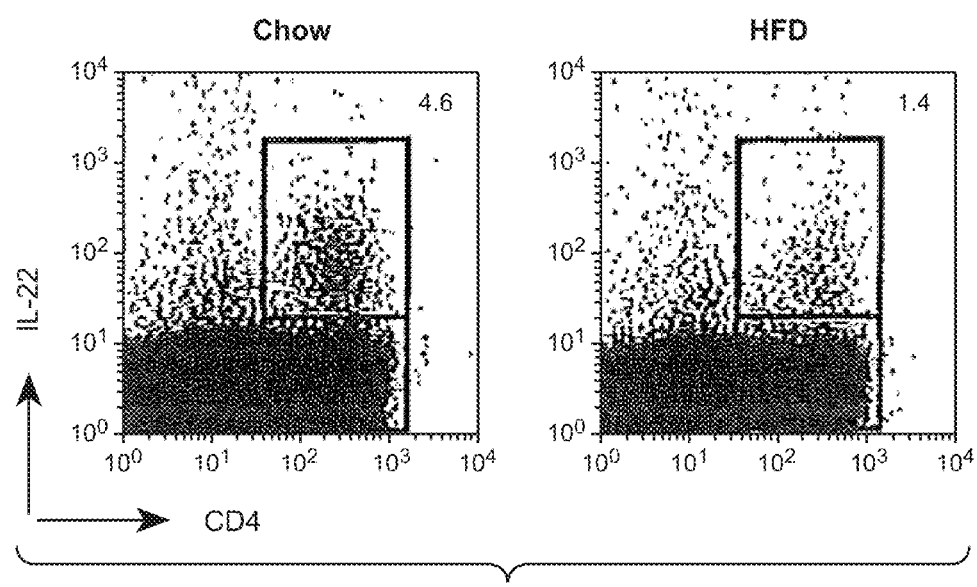
Figure 44B:
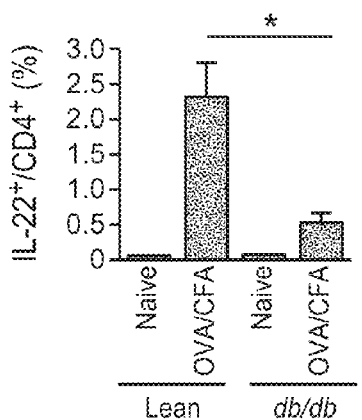
Figure 44D:
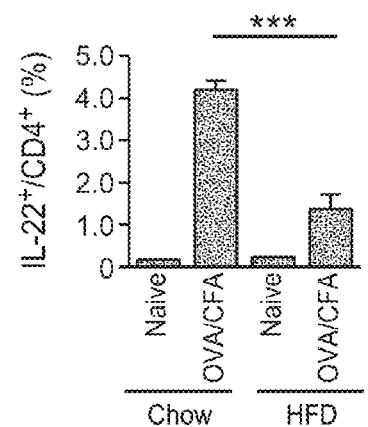
Figure 44E:
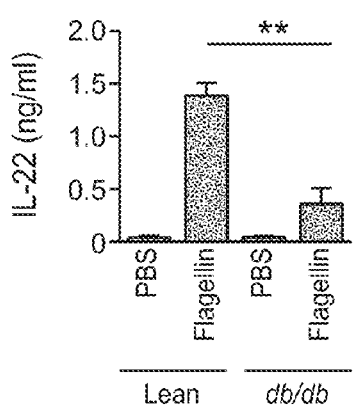
Figure 44F:
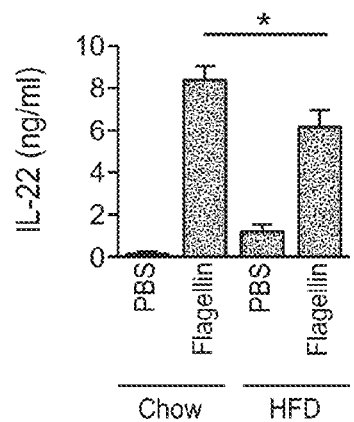

FIG. 43A shows the strategy for generation of IL-22R KO mice. FIG. 43B shows RT-PCR results of IL-22Ra1 mRNA expression in colon from IL-22R KO and WT mice. FIG. 43C shows RT-PCR results of Reg3b mRNA expression in colon from IL-22R KO and WT mice 2 days after a single dose injection of IL-22 Fc or control IgG. ***P<0.001. Error bars, s.e.m.

FIGS. 44A-F show results demonstrating that obese mice mounted defective IL-22 responses. (A-D) Lymphocytes in draining lymph nodes of db/db (A-B), DIO (C-D) and control mice immunized with OVA/CFA were analyzed for IL-22 expression on day 7 by flow cytometry. Numbers on the FACS plots in (A, C) are percentage of IL-22$^+$ cells within CD4$^+$ T cells. (E-F) db/db, lean controls, HFD and chow diet-fed normal mice were injected with flagellin or PBS. Serum was harvested after 2 h. ELISA of IL-22 from db/db and lean controls (E), and HFD and chow diet-fed mice (F). Data shown are representative of three (A-B) or two (C-F) independent experiments. N=4 in all experiments. *P<0.05, P<0.01, *P<0.001, Error bars, s.e.m.

FIGS. 45A-E show defects in IL-17 and IL-22 production in leptin signal-deficient mice. (A-B) IL-17A and IL-22 expression were analyzed on day 7 as percentage within CD4+ cells in db/db and ob/ob mice immunized with OVA/CFA. (C) IL-22 ELISA from culture supernatant of purified naïve WT CD4+ T cells that were stimulated under IL-22 producing conditions with or without recombinant mouse leptin (1 μg/ml). (D) IL-22 ELISA from culture supernatant of Rag2 KO splenocytes stimulated with IL-23 with or without recombinant mouse leptin (1 μg/ml). (E) ELISA of serum IL-22 from ob/ob or lean controls 2 hours after flagellin stimulation. *P<0.05, P<0.01, *P<0.001, Error bars, s.e.m.

FIGS. 46A-J show results demonstrating that the susceptibility of db/db (ob/ob) mice to *C. rodentium* infection was associated with defective IL-22 production and rescued by exogenous IL-22-Fc. (A) IL-22 mRNA expression in colons from WT, db/db and ob/ob mice (n=5) after *C. rodentium* infection. (B) Body weight and (C) survival of db/db and lean control mice (n=10) infected with *C. rodentium*. (D-E) Colon histology of lean control (D) and db/db (E) mice on day 10, showing epithelial hyperplasia, enterocyte shedding into the gut lumen, bacterial colonies (arrows) and submucosal edema (vertical bar). Horizontal bar, 200 μm. (F) Clinical score determined by colon histology (n=5). (G-H) Bacterial burden of db/db and lean control mice (n=5) in liver (G) and spleen (H) on day 10. (I) ELISA of anti-*C. rodentium* IgG in lean control and db/db mice (n=5) on day 10. (J). Survival of lean control or db/db mice (n=10) treated with IL-22-Fc or control IgG after infection. Data shown are representative of three independent experiments. *P<0.05, P<0.01, *P<0.001, Error bars, s.e.m.

FIGS. 47A-D show results demonstrating that diabetic disorders were reduced by IL-22-Fc treatment. (A-D) HFD-fed mice were treated with IL-22-Fc twice per week (n=10). (A) Blood glucose on day 20 (fed) and day 21 (16-hour fasting). (B) Body weight on day 30. (C) Glucose tolerance test on day 21. (D) Insulin tolerance test on day 28. Data shown are representative of two independent experiments. *P<0.05, P<0.01, *P<0.001, Error bars, s.e.m.

FIGS. 48A-E show results demonstrating that IL-22 prevents the diabetic disorders of mice fed with HFD. (A) body weight, (B) blood glucose, (C) glucose tolerance test on day 23, (D) blood glucose on day 23 after 16 h fast, and (E) abdominal fat pad on day 25. *P<0.05, P<0.01, *P<0.001, Error bars, s.e.m.

FIGS. 49A-I show results demonstrating that IL-22 regulates metabolic syndrome through multiple mechanisms. (A-C) Two groups of db/db mice (n=8) were fed with food ad libitum and treated with control IgG or IL-22-Fc twice per week. One group of db/db mice (n=8) was fed with restricted food that matched the food intake of IL-22-Fc treated group, and treated with control IgG. Accumulative food intake of first eight days of ad lib fed mice is shown in (A), blood glucose in (B), and glucose tolerance test on day 25 in (C). (D-E) show PYY levels in db/db (D) and HFD (E) mice treated with IL-22-Fc or control IgG on day 0 and day 2. Serum was collected on day 2 before the $2^{nd}$ treatment and on day 5, and analyzed for PYY. (F) shows serum LPS of db/db mice treated with IL-22-Fc or control IgG for 3 weeks. (G-I) IL-22R KO (n=9) and WT mice (n=6) were fed with HFD starting at 6 weeks of age. The results of body weight are shown in (G), results of glucose tolerance test at 3 months with HFD are shown in (H) and results of Insulin tolerance test at 4 months with HFD are shown in (I). Data shown are representative of two (A-C) or three (D-I) independent experiments. *P<0.05, P<0.01, *P<0.001, Error bars, s.e.m.

Figure 49A:
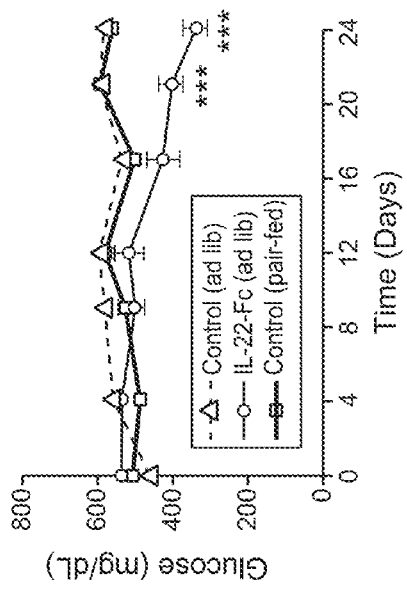
Figure 49C:
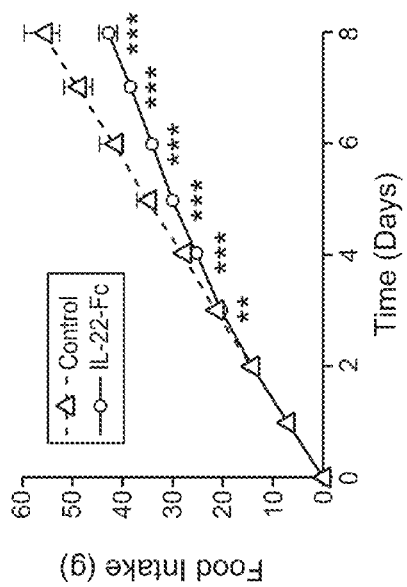
Figure 49B:
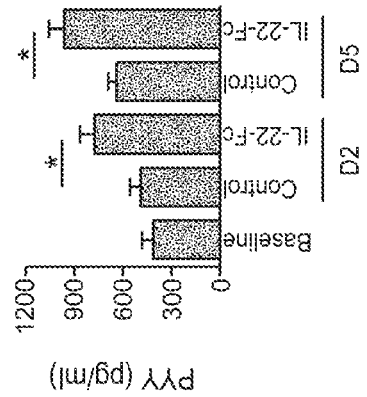
Figure 49D:
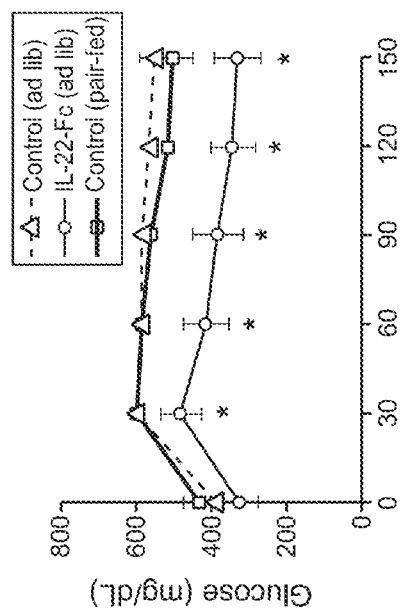
Figure 49I:
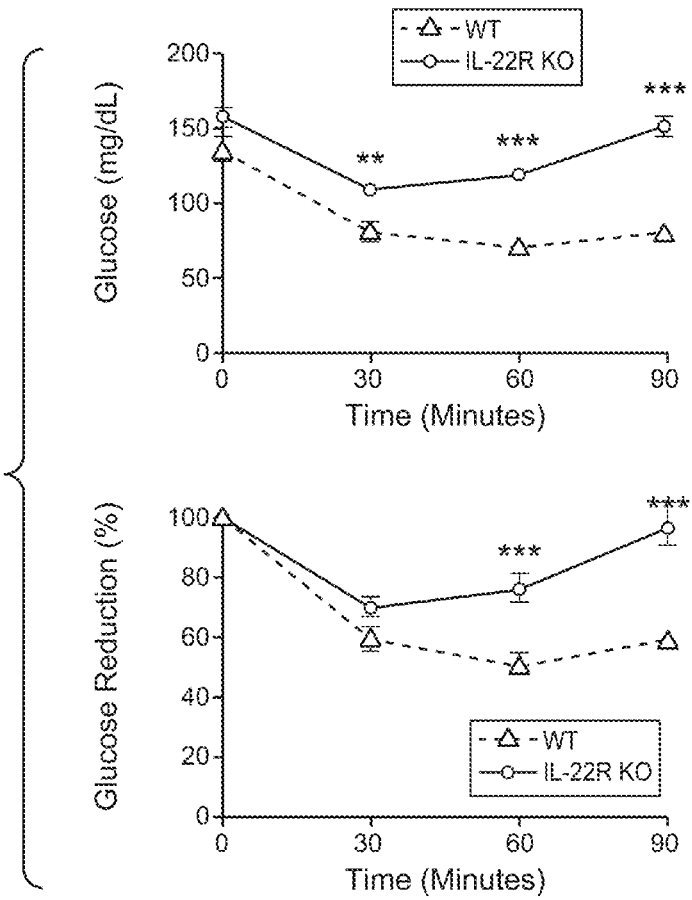
Figure 50:
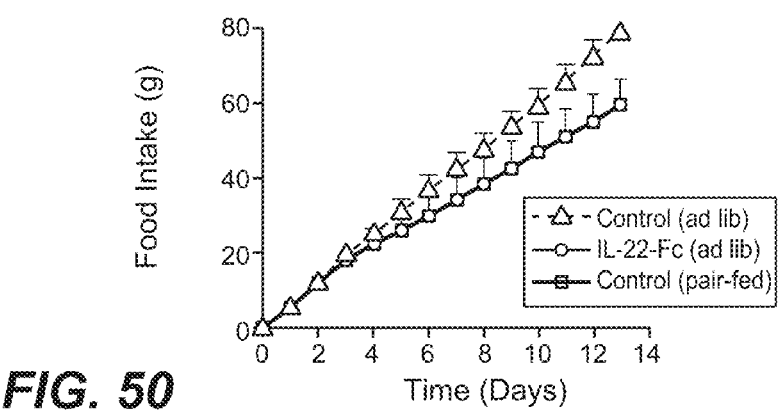

FIG. 50 shows results of pair-feeding restricted food intake. Three groups of db/db mice were fed and treated as in FIG. 49A. Accumulative food intake was measured.

FIGS. 51A-J show results demonstrating IL-22 improved liver function and reduced fat pad. (A) db/db mice treated with IL-22 Fc or control IgG as in FIG. 20A. Liver enzymes were measured at one month. (B-C) HFD-fed mice were treated with IL-22 Fc or control IgG as in FIG. 47A. Liver enzymes (B) and abdominal fat pad (C) were measured at one month. P<0.01, *P<0.001, Error bars, s.e.m. (D-H) mice were fed with HFD for 10 weeks, and then treated with IL-22 Fc or control twice per week for 6 weeks. (D) Lipid metabolic gene expression from white adipose tissue. (E) Serum triglyceride, glycerol and free fatty acid. (F) Hepatic triglyceride. (G) Hepatic cholesterol. (H) White adipose tissue triglyceride. (1-J) db/db mice treated with IL-22 Fc or control IgG for 4 weeks. (I) Hepatic triglyceride. (J) White adipose tissue triglyceride. *P<0.05. Error bars, s.e.m.

Figure 20A:
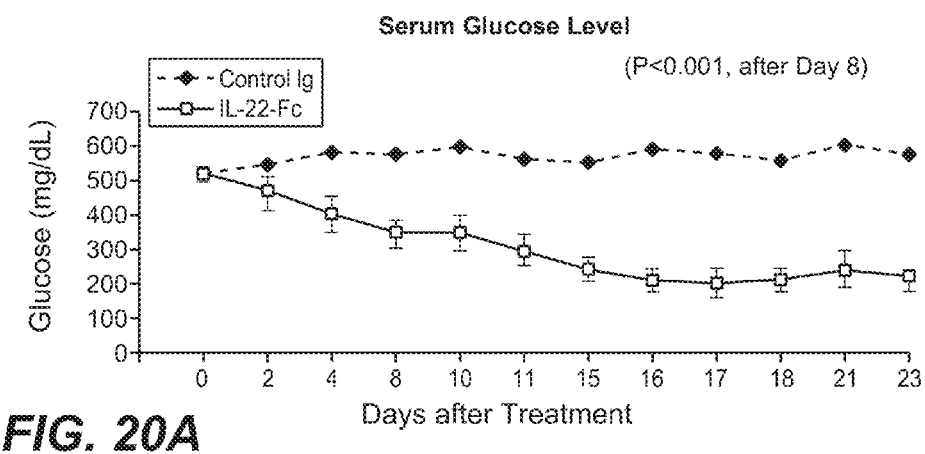
FIGS. 20A-C show body weight and serum glucose levels in db/db mice demonstrating that IL-22-Fc significantly reduced glucose in the obese mice.
Figure 52A:
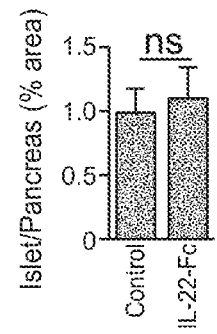
Figure 52B:
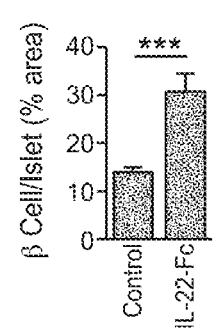
Figure 52C:
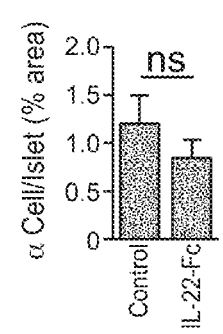

FIGS. 52A-C show results demonstrating that IL-22 increased insulin secretion of 13 cells. db/db mice were treated with IL-22 Fc as in FIG. 20A, Pancreases were harvested on day 30 and stained for insulin and glucagon. (A) Percentage of islet area within total pancreas area. (B) Percentage of β cell area within total islet area. (C) Percentage of a cell area within total islet area.

Figure 53:
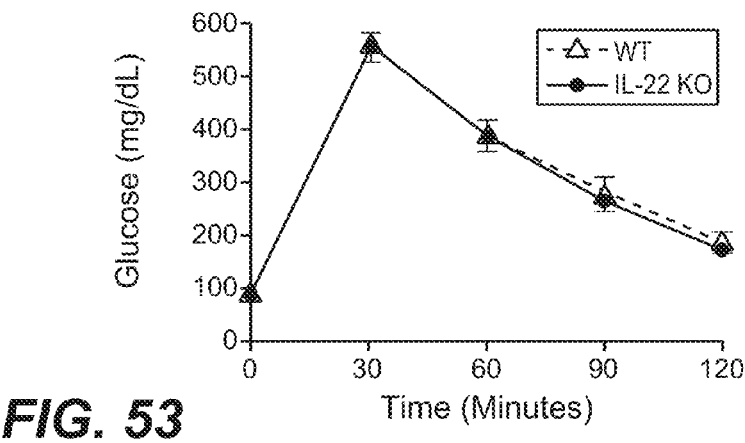
Figure 54A:
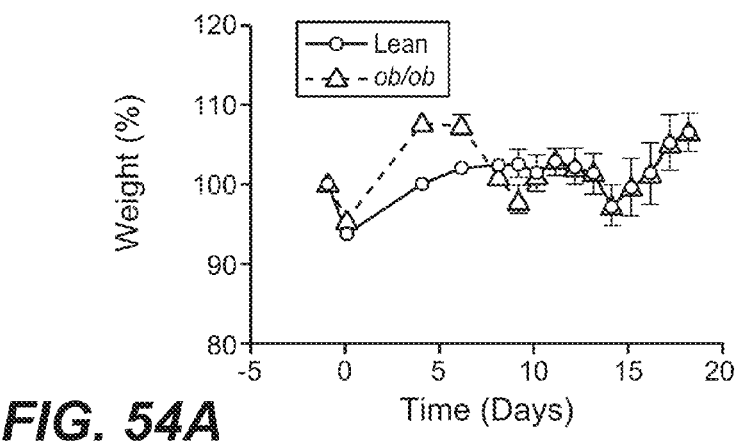
Figure 54B:
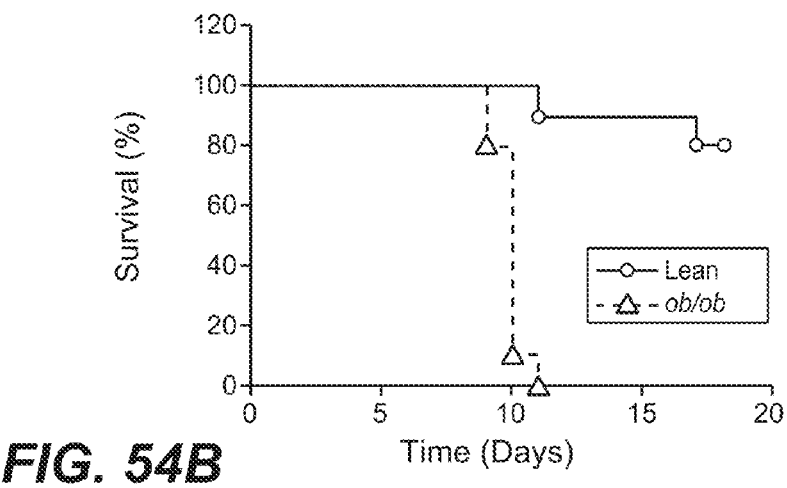
Figure 54C:
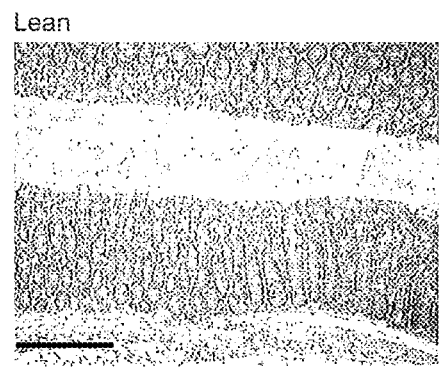
Figure 54D:
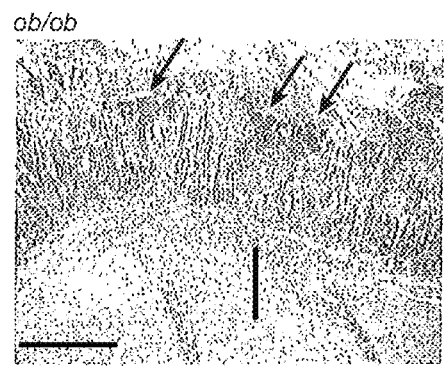
Figure 54E:
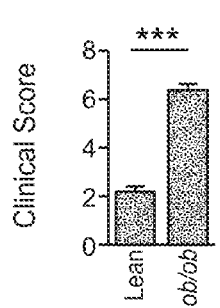
Figure 54F:
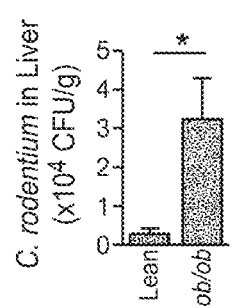
Figure 54G:
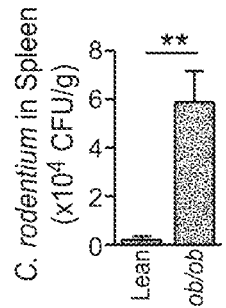

FIG. 53 IL-22 KO mice did not develop glucose intolerance with HFD. IL-22 KO mice were fed with HFD starting at 6 weeks of age. Glucose tolerance test was done 3 months after HFD. Error bars, s.e.m.

FIGS. 54A-G show results demonstrating susceptibility of ob/ob mice to *C. rodentium* infection: (A) body weight and (B) survival of ob/ob and lean mice (n=10) infected with *C. rodentium*; (C-D) colon histology of lean control (C) and ob/ob mice (D) on day 8, showing epithelial hyperplasia, enterocyte shedding into the gut lumen, bacterial colonies (arrows) and submucosal edema (vertical bar) (horizontal bar, 200 μm); (E) clinical score determined by colon histology (n=5); and (F-G) bacterial burden of ob/ob and lean control mice (n=5) in liver (F) and spleen (G) on day 8. *P<0.05, P<0.01, *P<0.001. Error bards, s.e.m.

Figure 55A:
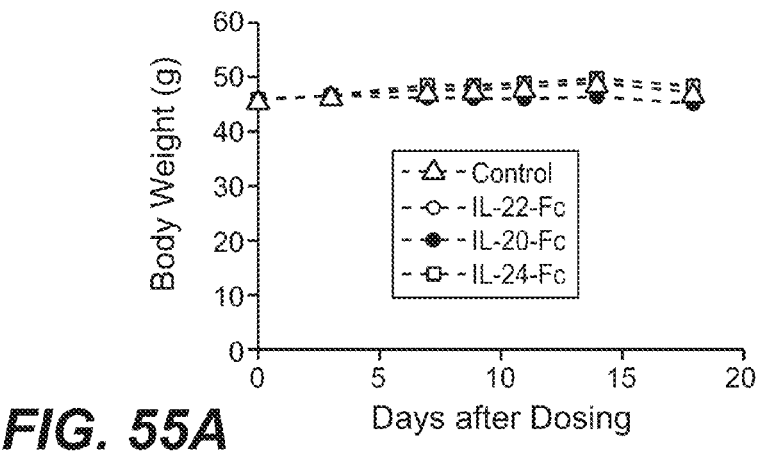
Figure 55B:
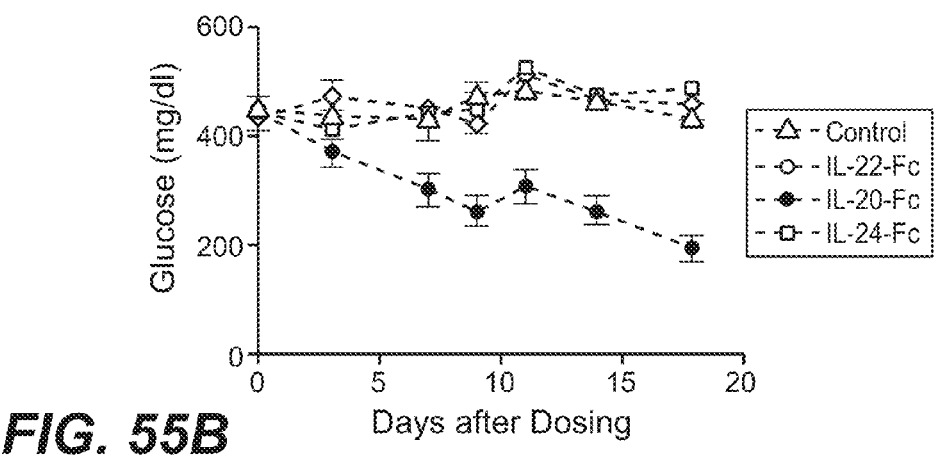
Figure 55C:
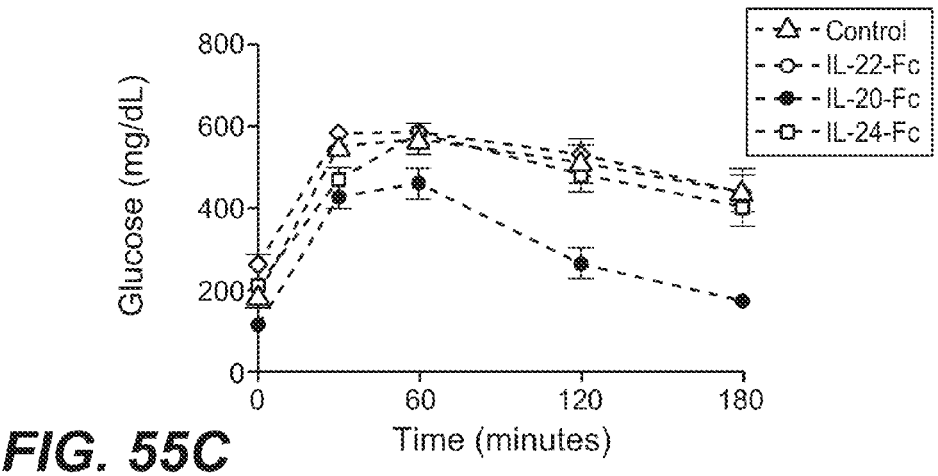

FIGS. 55A-C show results of db/db mice treated with IL-22 Fc, IL-20 Fc or IL-24 Fc in (A) body weight, (B) serum glucose and (C) glucose tolerance test on day 20 of treatment.

Figure 56A:
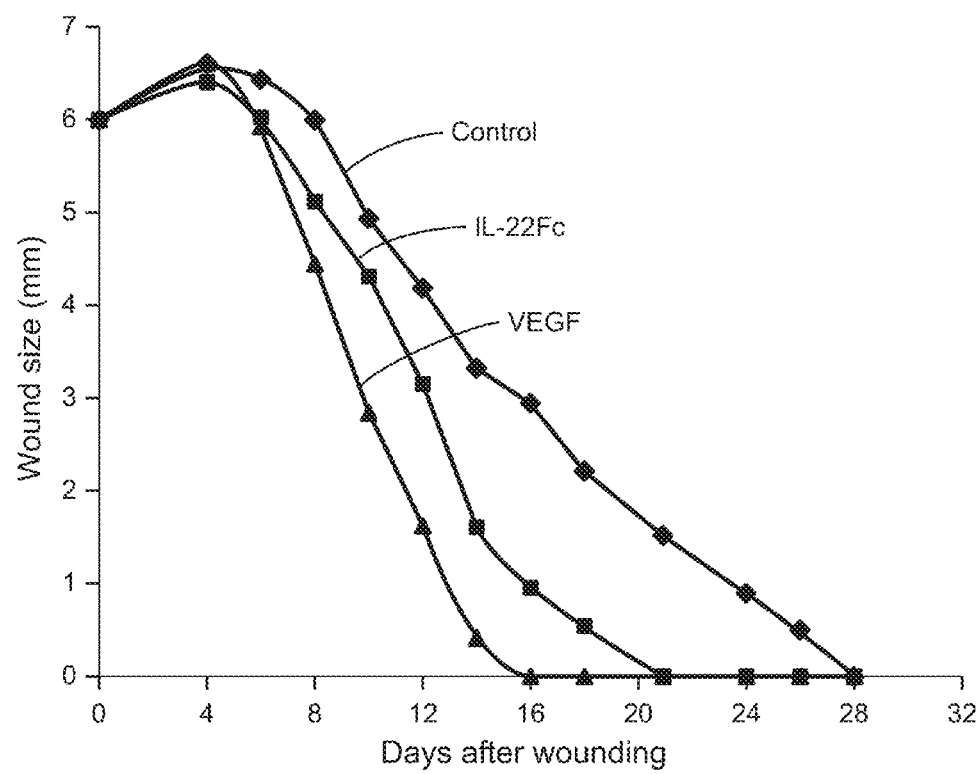

FIGS. 56A and B show results comparing wound healing efficacy in db/db mice treated with VEGF or IL-22 Fc.

FIGS. 57 A-E show cytokine or chemokine induction by IL-22 Fc in reconstituted epidermis.

Figure 58:
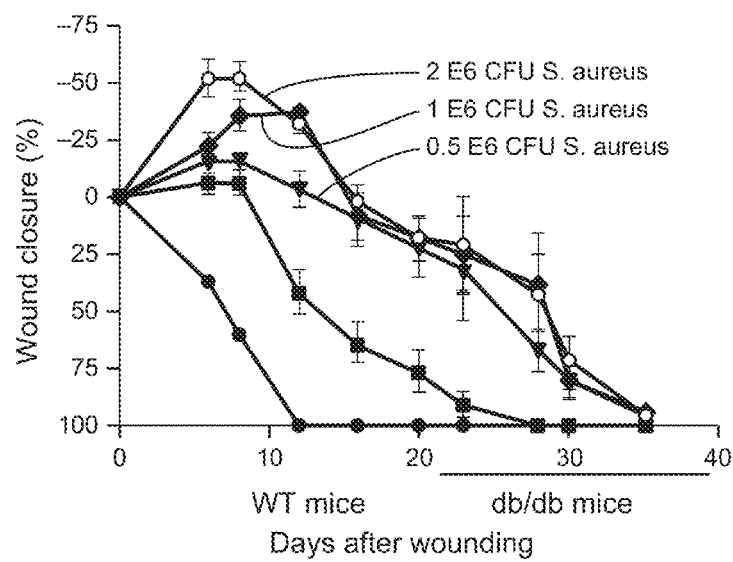

FIG. 58 shows results comparing wound closure using a splinted wound model in wild type mice and db/db mice with or without *S. aureus* infection.

Figure 59A:
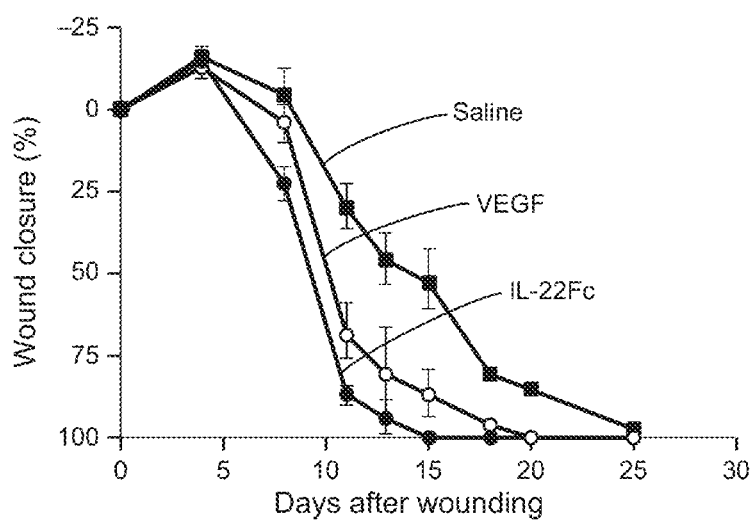
Figure 59B:
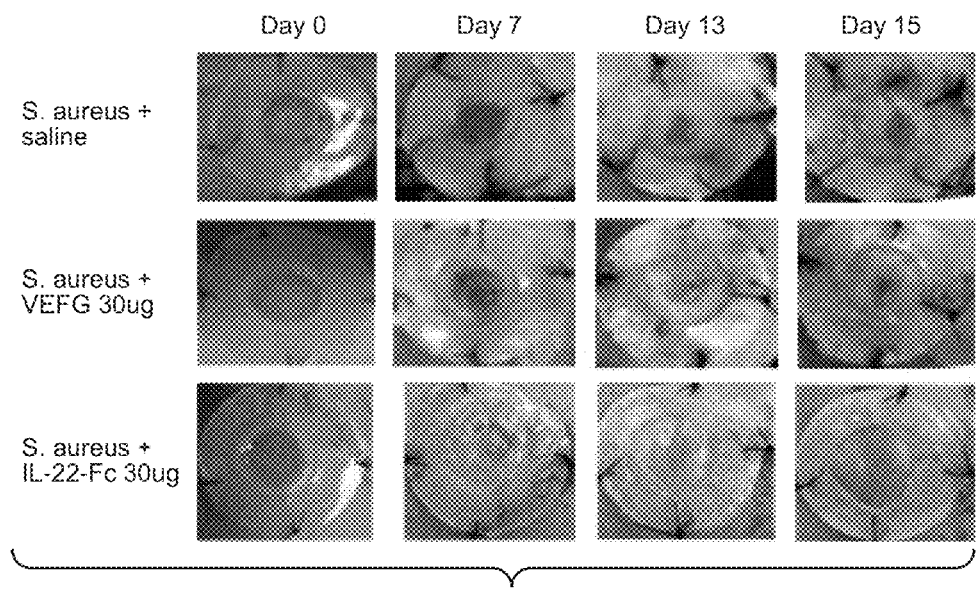

FIGS. 59 A and B show results comparing wound healing efficacy between VEGF and IL-22 Fc in a splinted infected wound model.

Figure 60:
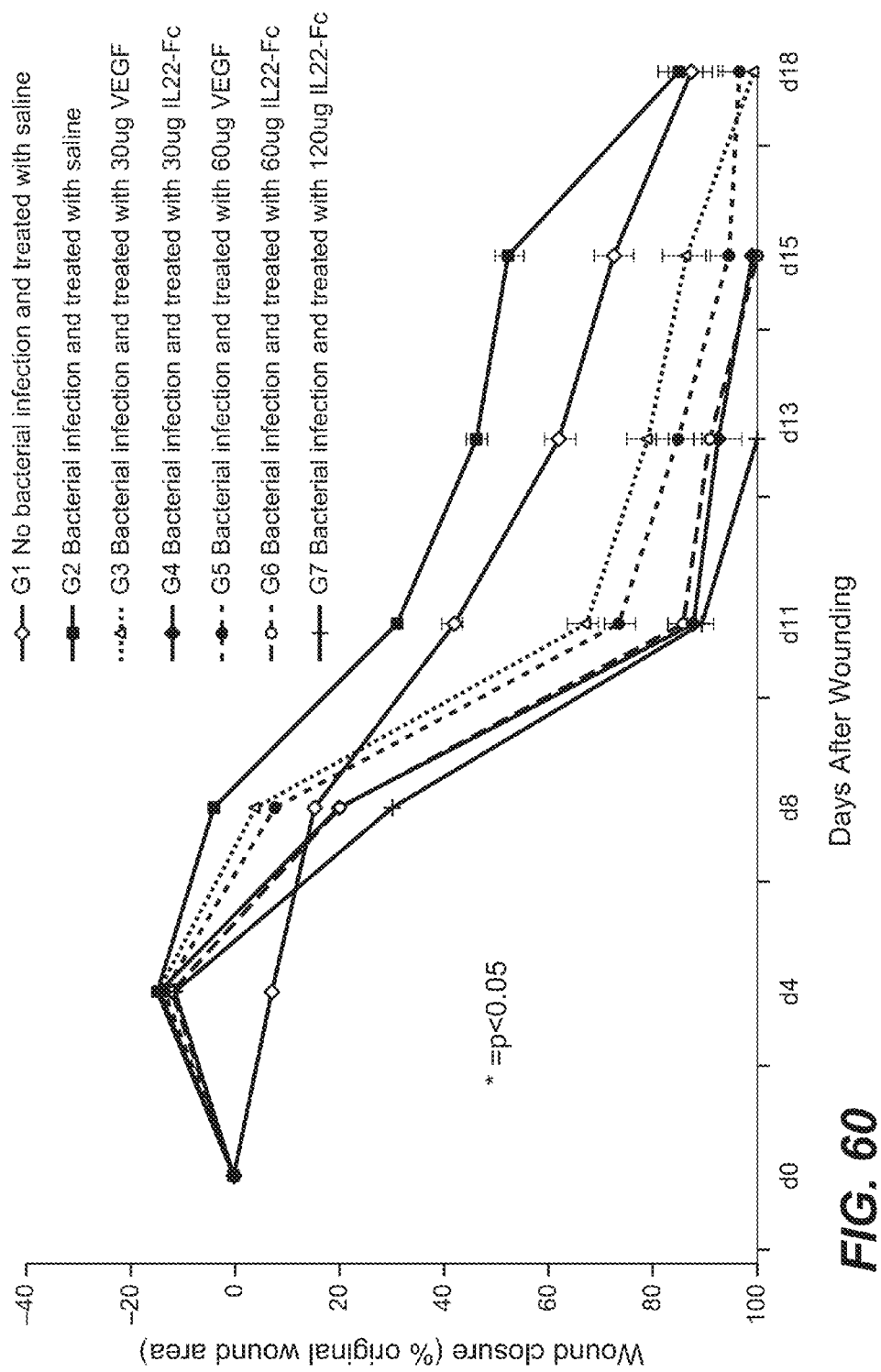

FIG. 60 shows results comparing wound healing efficacy between VEGF and IL-22 Fc at different concentrations in a splinted infected wound model.

Figure 61:
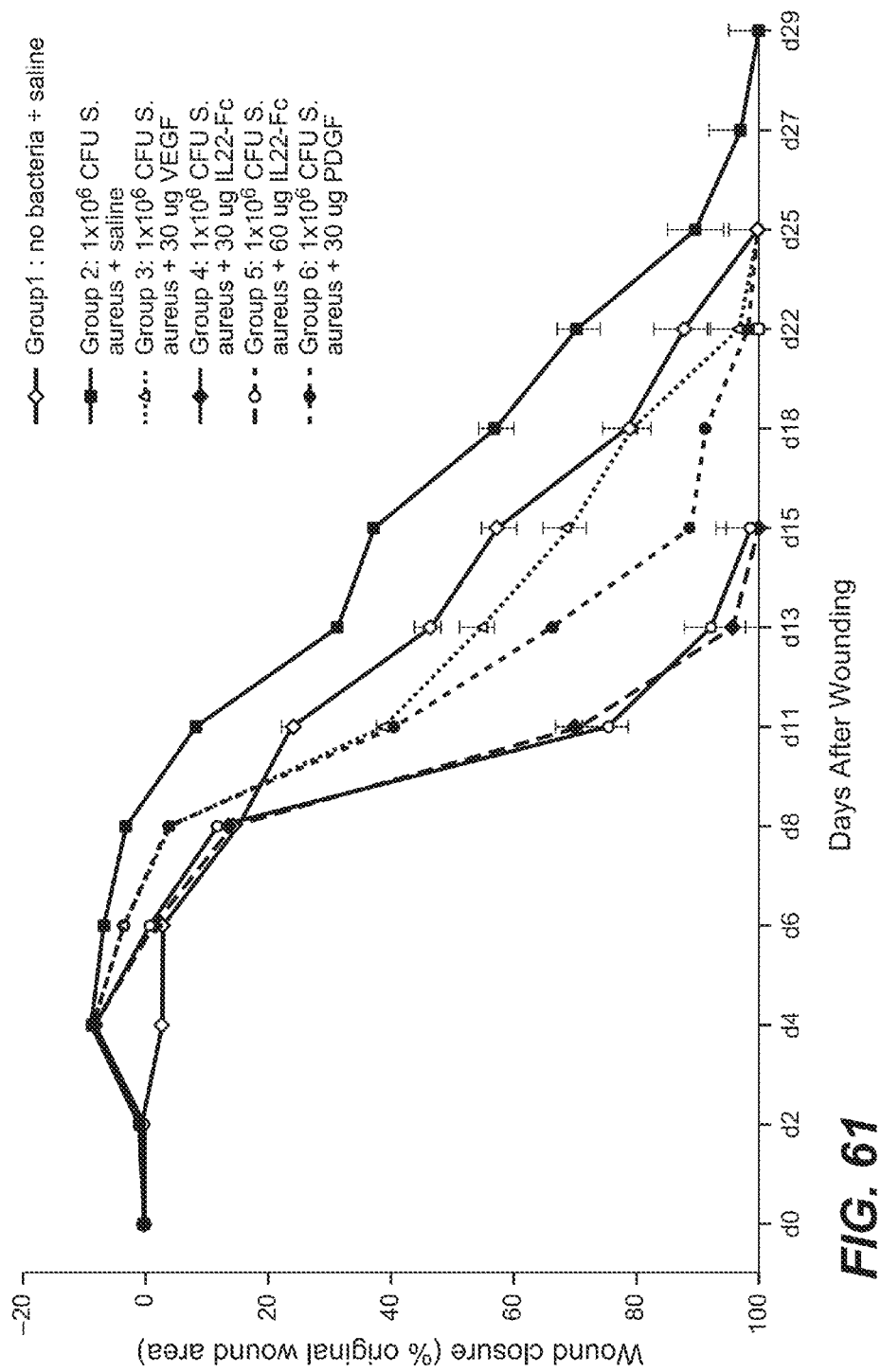

FIG. 61 shows results comparing wound healing efficacy between VEGF, PDGF and IL-22 Fc at different concentrations in a splinted infected wound model.

Figure 62:
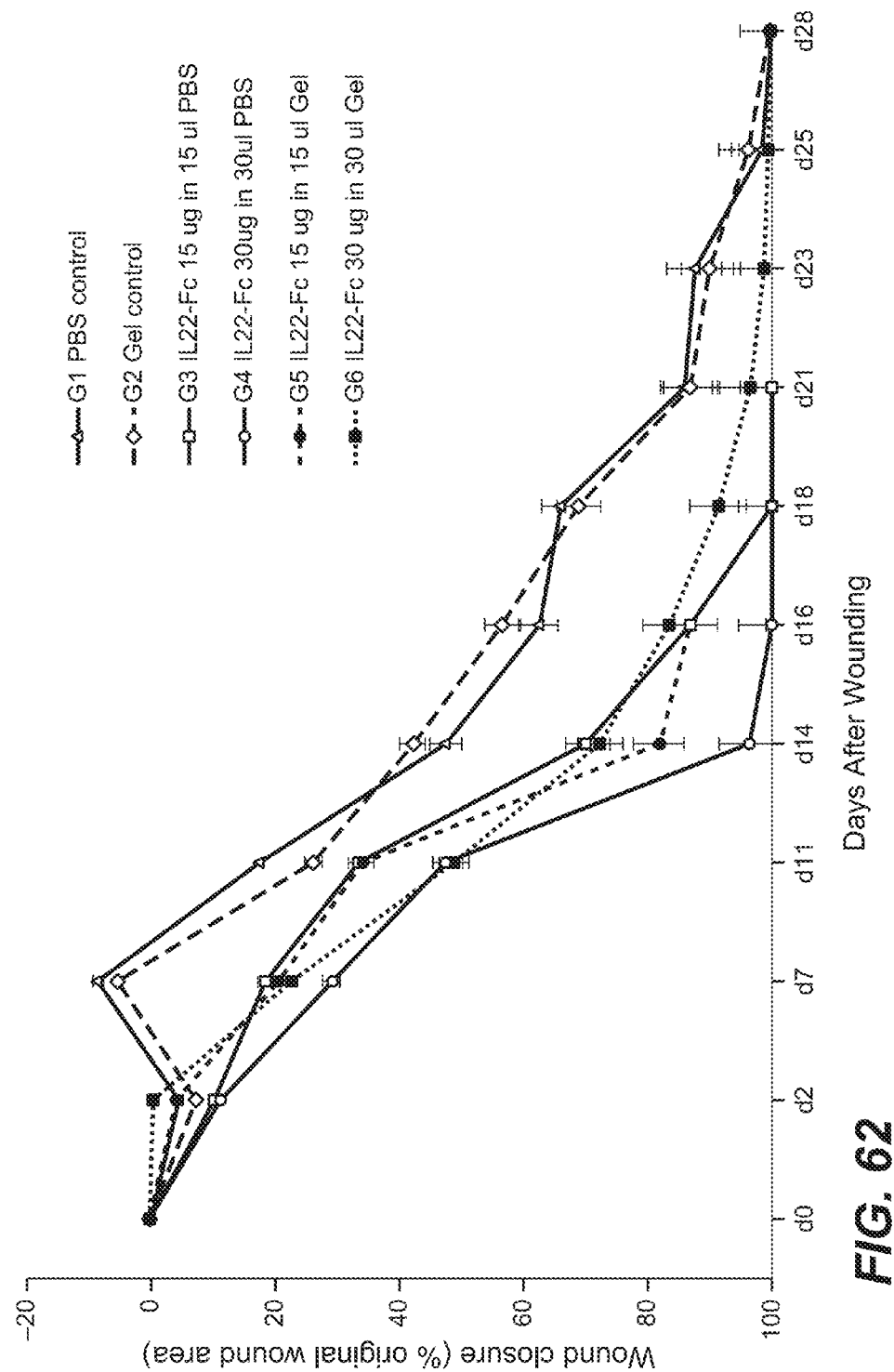

FIG. 62 shows that IL-22 Fc accelerated wound healing in a solution as well as in a gel formulation in a splinted wound model.

DETAILED DESCRIPTION OF EMBODIMENTS OF THE INVENTION

All publications, patents and patent applications cited herein are hereby expressly incorporated by reference for all purposes.

In one aspect, the present invention concerns the IL-22 protein or IL-22 Fc fusion proteins, composition comprising the same, and methods of using the same. In particular, the invention concerns using IL-22 Fc fusion proteins or IL-22 polypeptide in the prevention and treatment of IBD, atherosclerosis, cardiovascular diseases and conditions characterized by atherosclerotic plaque formation, metabolic syndrome, mild and acute endotoxemia and sepsis, acute kidney injury, acute pancreatitis, moderate acute pancreatitis, and insulin-related disorders. Further, the invention concerns using IL-22 Fc fusion proteins or IL-22 polypeptides in the prevention and treatment of diabetic foot ulcer, accelerating wound healing and in particular diabetic wound healing.

In one aspect, it is believed that this is the first disclosure showing IL-22 polypeptide treating cardiovascular disease per se. The data herein supports the notion that an IL-22 polypeptide or IL-22 Fc fusion protein can reduce the growth of atherosclerotic plaques, reduce the frequency of rupture of atherosclerotic plaques and reduce endotoxemia. This invention is particularly useful in treating subjects suffering from metabolic syndrome, mild or acute endotoxemia, sepsis and insulin-related disorders, such as insulin-resistance (no responsive to insulin) who need a change to their HDL/LDL lipid profile, as can be determined by a doctor or clinician. The application shows data that indicate that IL-22 polypeptide or IL-22 Fc fusion protein can increase high density lipoproteins (HDL) and decrease low density lipoproteins (LDL) in those subjects suffering from metabolic syndrome. The data, without being bound by theory, also indicate gut-derived LPS a driver behind endotoxemia and atherosclerosis. Mice treated with mIL-22 Fc fusion protein had reduced hyperlipidemia, improved glucose tolerance with restored vascular function and these changes culminated in a reduction in atherosclerotic plaque.

IL-22 polypeptide or IL-22 Fc fusion protein can attenuate the progression of cardiovascular disease.

Further, diabetes is a chronic disorder affecting carbohydrate, fat and protein metabolism in animals. Diabetes is the leading cause of blindness, renal failure, and lower limb amputations in adults and is a major risk factor for cardiovascular disease and stroke. Type I diabetes mellitus (or insulin-dependent diabetes mellitus ("IDDM") or juvenile-onset diabetes) comprises approximately 10% of all diabetes cases. The disease is characterized by a progressive loss of insulin secretory function by beta cells of the pancreas. This characteristic is also shared by non-idiopathic, or "secondary", diabetes having its origins in pancreatic disease. Type I diabetes mellitus is associated with the following clinical signs or symptoms, e.g., persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM, also referred to as type II diabetes) is a metabolic disorder (or metabolic syndrome) involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms, e.g., persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

I. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *PCR Protocols: A Guide to Methods and Applications* (Innis, et al. 1990. Academic Press, San Diego, Calif.), and Harlow and Lane (1988) *Antibodies: A Laboratory Manual* ch. 14 (Cold Spring Harbor Laboratory, Cold Spring Harbor, N.Y.).

As appropriate, procedures involving the use of commercially available kits and reagents are generally carried out in accordance with manufacturer defined protocols and/or parameters unless otherwise noted. Before the present methods and uses therefore are described, it is to be understood that this invention is not limited to the particular methodology, protocols, cell lines, animal species or genera, constructs, and reagents described as such can, of course, vary. It is also to be understood that the terminology used herein is for the purpose of describing particular embodiments only, and is not intended to limit the scope of the present invention which will be limited only by the appended claims.

As used herein, the singular forms "a", "an" and "the" include plural referents unless the context clearly dictates otherwise. For example, reference to "an isolated peptide" means one or more isolated peptides.

Throughout this specification and claims, the word "comprise," or variations such as "comprises" or "comprising," will be understood to imply the inclusion of a stated integer or group of integers but not the exclusion of any other integer or group of integers.

The term "IL-22 Fc fusion protein" or "IL-22 fusion protein" or "IL-22 Ig fusion protein" as used herein refers to a fusion protein in which IL-22 protein or polypeptide is linked, directly or indirectly, to an IgG Fc region. In certain preferred embodiments, the IL-22 Fc fusion protein of the invention comprises a human IL-22 protein or polypeptide linked to a human IgG Fc region. In certain embodiments, the human IL-22 protein comprises the amino acid sequence of SEQ ID NO:4. However, it is understood that minor sequence variations such as insertions, deletions, substitutions, especially conservative amino acid substitutions of IL-22 or Fc that do not affect the function and/or activity of IL-22 or IL-22 Fc fusion protein are also contemplated by the invention. The IL-22 Fc fusion protein of the invention can bind to IL-22 receptor, which can lead to IL-22 receptor downstream signaling. In certain embodiments, the IL-22 Fc fusion protein is capable of binding to IL-22 receptor, and/or is capable of leading to IL-22 receptor downstream signaling. The functions and/or activities of the IL-22 Fc fusion protein can be assayed by methods known in the art, including without limitation, ELISA, ligand-receptor binding assay and Stat3 luciferase assay. In certain embodiments, the invention provides an IL-22 Fc fusion protein that binds to IL-22 receptor, the binding can lead to IL-22 receptor downstream signaling, said IL-22 Fc fusion protein comprising an amino acid sequence having at least 95% sequence identity to the amino acid sequence selected from the group consisting of SEQ ID NO:8, SEQ ID NO:10, SEQ ID NO:12 and SEQ ID NO:14, and wherein the Fc region is not glycosylated. In certain particular embodiments, the Fc region of the IL-22 fusion protein does not possess effector activities (e.g., does not bind to FcγIIIR) or exhibits substantially lower effector activity than a whole (e.g., wild type) IgG antibody. In certain other embodiments, the Fc region of the IL-22 Fc fusion protein does not trigger cytotoxicity such as antibody-dependent cellular cytotoxicity (ADCC) or complement dependent cytotoxicity (CDC). Unless otherwise specified, "IL-22 fusion protein," "IL-22 Fc fusion," "IL-22 Ig fusion protein," "IL-22 Fc fusion protein" or "IL-22 Fc" are used interchangeably throughout this application.

The term "IL-22" or "IL-22 polypeptide" or "IL-22 protein" as used herein, broadly refers to any native IL-22 from any mammalian source, including primates (e.g. humans) and rodents (e.g., mice and rats), unless otherwise indicated. The term encompasses "full-length," unprocessed IL-22 as well as any forms of IL-22 that result from processing in the cell. For example, both full-length IL-22 containing the N-terminal leader sequence and the mature form IL-22 are encompassed by the current invention. The leader sequence (or signal peptide) can be the endogenous IL-22 leader sequence or an exogenous leader sequence of another mammalian secretary protein. In certain embodiments, the leader sequence can be from a eukaryotic or prokaryotic secretary protein. The term also encompasses naturally occurring variants of IL-22, e.g., splice variants or allelic variants. The amino acid sequence of an exemplary human IL-22 is shown in SEQ ID NO:4 (mature form, without a signal peptide). In certain embodiments, the amino acid sequence of full-length IL-22 protein with the endogenous leader sequence is provided in SEQ ID NO:71; while in other embodiments, the amino acid sequence of mature IL-22 protein with an exogenous leader sequence is provided in SEQ ID NO:2. Minor sequence variations especially conservative amino acid substitutions of IL-22 that do not affect the IL-22's function and/or activity (e.g., binding to IL-22 receptor) are also contemplated by the invention. FIG. 1 shows an amino acid sequence alignment of mature IL-22 from several exemplary mammalian species. The asterisks indicate highly conserved amino acid residues across species that are likely important for the functions and/or activities of IL-22. Accordingly, in certain embodiments, the IL-22 Fc fusion protein of the invention comprises an IL-22 polypeptide comprising an amino acid sequence having at least 95%, at least 96%, at least 97%, at least 98% or at least 99% sequence identity to SEQ ID NO:4. In certain other embodiments, the IL-22 protein has 95% or more sequence identity to SEQ ID NO:71, 96% or more sequence identity to SEQ ID NO:71, 97% or more sequence identity to SEQ ID NO:71; 98% or more sequence identity to SEQ ID NO:71; 99% or more sequence identity to SEQ ID NO:71. The IL-22 polypeptides described herein can be isolated from a variety of sources, such as from human tissue or from another source, or prepared by recombinant or synthetic methods.

The term "IL-22 receptor" or "IL-22R" refers to a heterodimer consisting of IL-22R1 and IL-10R2 or naturally occurring allelic variants thereof. See Ouyang et al., 2011, Annu Rev. Immunol. 29:159-63. IL-10R2 is ubiquitously expressed by many cell types, and IL-22R1 is expressed only in innate cells such as epithelial cells, hepatocytes and keratinocytes. IL-22R1 is also known as IL-22Ra1 or IL-22Ra1. IL-22R1 may be paired with other polypeptides to form heterodimeric receptors for other IL-10 family members, for example IL-20 or IL-24. See e.g., Ouyang et al., 2011, supra.

A "native sequence IL-22 polypeptide" or a "native sequence IL-22R polypeptide" refers to a polypeptide comprising the same amino acid sequence as a corresponding IL-22 or IL-22R polypeptide derived from nature. Such native sequence IL-22 or IL-22R polypeptides can be isolated from nature or can be produced by recombinant or synthetic means. The terms specifically encompass naturally-occurring truncated or secreted forms of the specific IL-22 or IL-22R polypeptide (e.g., an IL-22 lacking its associated signal peptide), naturally-occurring variant forms (e.g., alternatively spliced forms), and naturally-occurring allelic variants of the polypeptide. In various embodiments of the invention, the native sequence IL-22 or IL-22R polypeptides disclosed herein are mature or full-length native sequence polypeptides. An exemplary full length native human IL-22 is shown in FIG. 30 (DNA, SEQ ID NO:70) and FIG. 31 (protein, SEQ ID NO:71). The start and stop codons are shown in bold font and underlined in FIG. 30. While the IL-22 and IL-22R polypeptide sequences disclosed in the accompanying figures are shown to begin with methionine residues designated herein as amino acid position 1, it is conceivable and possible that other methionine residues located either upstream or downstream from the amino acid position 1 in the figures can be employed as the starting amino acid residue for the IL-22 or IL-22R polypeptides.

An "IL-22 variant," an "IL-22R variant," an "IL-22 variant polypeptide," or an "IL-22R variant polypeptide" means an active IL-22 or IL-22R polypeptide as defined above having at least about 80% amino acid sequence identity with a full-length native sequence IL-22 or IL-22R polypeptide sequence. Ordinarily, an IL-22 or IL-22R polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity, and alternatively at least about 99% amino acid sequence identity to a full-length or mature native sequence IL-22 or IL-22R polypeptide sequence.

The term "Fc region," "Fc domain" or "Fc" refers to a C-terminal non-antigen binding region of an immunoglobulin heavy chain that contains at least a portion of the constant region. The term includes native Fc regions and variant Fc regions. In certain embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., *Sequences of Proteins of Immunological Interest*, 5th Ed. Public Health Service, National Institutes of Health, Bethesda, Md., 1991.

In certain embodiments, Fc region refers to an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In certain embodiments, the hinge region comprises the amino acid sequence CPPCP (SEQ ID NO:31). In certain embodiments, the hinge region for IL-22 IgG4 Fc fusion protein comprises the CPPCP sequence (SEQ ID NO:31), a sequence found in the native IgG1 hinge region, to facilitate dimerization. In certain other embodiments, the Fc region starts at the hinge region and extends to the C-terminus of the IgG heavy chain. In certain particular embodiments, the Fc region comprises the Fc region of human IgG1, IgG2, IgG3 or IgG4. In certain particular embodiments, the Fc region comprises the CH2 and CH3 domain of IgG4. In certain other particular embodiments, the Fc region comprises the CH2 and CH3 domain of IgG1. As described in the Example section, it was unexpectedly discovered by the applicants that IL-22 IgG4 Fc fusion protein exhibited even superior pharmacokinetic properties than IL-22 IgG1 Fc fusion protein.

In certain embodiments, the IgG CH2 domain starts at Ala 231. In certain other embodiments, the CH3 domain starts at Gly 341. It is understood that the C-terminus Lys residue of human IgG can be optionally absent. It is also understood that conservative amino acid substitutions of the Fc region without affecting the desired structure and/or stability of Fc is contemplated within the scope of the invention.

In certain embodiments, the IL-22 is linked to the Fc region via a linker. In certain particular embodiments, the linker is a peptide that connects the C-terminus of IL-22 to the Fc region as described herein. In certain embodiments, native IgG sequences are present in the linker and/or hinge region to minimize and/or avoid the risk of immunogenicity. In other embodiments, minor sequence variations can be introduced to the native sequences to facilitate manufacturing. IL-22 Fc fusion constructs comprising exogenous linker or hinge sequences that exhibit high activity (as measured, e.g., by a luciferase assay) are also within the scope of the invention. In certain embodiments, the linker comprises an amino acid sequence that is 8-20 amino acids, 8-16, 8-15, 8-14, 8-13, 8-12, 8-11, 8-10, 8-9, 10-11, 10-12, 10-13, 10-14, 10-15, 10-16, 11-16, 8, 9, 10, 11, 12, 13, 14, 15 or 16 amino acids long. In certain other embodiments, the linker comprises the amino acid sequence DKTHT (SEQ ID NO:32).

In certain particular embodiments, the linker does not comprise the sequence Gly-Gly-Ser (SEQ ID NO:45), Gly-Gly-Gly-Ser (SEQ ID NO:46) or Gly-Gly-Gly-Gly-Ser (SEQ ID NO:47).

In certain embodiments, the IL-22 Fc fusion protein comprises an IL-22 polypeptide linked to an Fc region by a linker. The term "linked to" or "fused to" refers to a covalent bond, e.g., a peptide bond, formed between two moieties.

The term "afucosylation," "afucosylated," "defucosylation," or "defucosylated" refers to the absence or removal of core-fucose from the N-glycan attached to the CH2 domain of Fc.

It was unexpectedly discovered by the applicants that IL-22 IgG1 Fc fusion proteins, unlike other Fc fusion proteins or antibodies comprising Fc, exhibited high levels (e.g., 30%) of afucosylation in the N-glycans attached to the Fc region. The N-glycans attached to the CH2 domain of Fc is heterogeneous. Antibodies or Fc fusion proteins generated in CHO cells are fucosylated by fucosyltransferase activity. See Shoji-Hosaka et al., J. Biochem. 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance antibody-dependent cellular cytotoxicity (ADCC), which can be advantageous in certain antibody therapeutic applications in which cytotoxicity is desirable. See Shoji-Hosaka et al., supra. Such an enhanced effector function, however, can be detrimental when Fc-mediated cytotoxicity is undesirable such as in the case of IL-22 Fc fusion.

IgG4 Fc is known to exhibit less effector activity than IgG1 Fc. Applicants unexpectedly discovered that IL-22 IgG4 Fc fusion protein also showed high levels of afucosylation in the Fc region. The high-level of afucosylated N-glycan attached to the Fc of IgG4 can increase the undesirable effector activity.

Thus, in one aspect, the invention provides an IL-22 Fc fusion protein in which the Fc region or CH2 domain is not glycosylated. In certain embodiments, the N-glycosylation site in the CH2 domain is mutated to prevent from glycosylation.

In certain other embodiments, the glycosylation in the CH2 domain of the Fc region can be eliminated by altering the glycosylation consensus site, i.e., Asn at position 297 followed by any amino acid residue (in the case of human IgG, Ser) and Thr (see FIG. 3). The glycosylation site can be altered by amino acid insertions, deletions and/or substitutions. For example, one or more amino acid residues can be inserted between Asn and Ser or between Ser and Thr to alter the original glycosylation site, wherein the insertions do not regenerate an N-glycosylation site. In certain particular embodiments, the N297 residue (e.g., the N-glycosylated site in Fc, see FIG. 3) within the CH2 domain of human IgG Fc is mutated to abolish the glycosylation site. In certain particular embodiments, the N297 residue is changed to Gly, Ala, Gln, Asp or Glu. In some particular embodiments, the N297 residue is changed to Gly or Ala. In other particular embodiments, the N297 residue is changed to Gly. In certain other embodiments, the T299 residue can be substituted with another amino acid, for example Ala, Val or Gly. In certain particular embodiments, the mutations that result in an aglycosylated Fc do not affect the structure and/or stability of the IL-22 Fc fusion protein.

In a related aspect, the invention provides a method of treating IBD, including UC and CD, methods of inhibiting bacterial infection in the intestine, and methods of improving epithelial integrity, epithelial proliferation, differentiation and/or migration in the intestine, and methods of treating metabolic disorders or metabolic syndrome, type II diabetes, atherosclerosis and diabetic wound healing in a patient in need thereof comprising administering to the patient a pharmaceutical composition comprising an IL-22 Fc fusion protein wherein the Fc region is not glycosylated.

In a further aspect, the invention provides a composition comprising IL-22 Fc fusion proteins having low level of or no afucosylation in the Fc region. Specifically, the invention provides a composition comprising IL-22 Fc fusion proteins having an overall afucosylation level in the Fc region of no more than 10%, preferably no more than 5%, more preferably no more than 2%, and most preferably less than 1%. In another aspect, the invention provides methods of treating IBD, including UC and CD, methods of inhibiting bacterial infection in the intestine, and methods of improving epithelial integrity, epithelial proliferation, differentiation and/or migration in the intestine, and methods of treating metabolic disorders, type II diabetes, type II diabetes with morbid obesity, graft versus host disease (GVHD), atherosclerosis, cardiovascular disease, metabolic syndrome, endotoxemia (acute and mild), sepsis, acute coronary heart disease, hypertension, dyslipemia, obesity, hyperglycemia, lipid metabolism disorders, hepatitis, acute hepatitis, renal failure, acute renal failure, acute kidney injury, rental draft failure, pancreatitis, acute pancreatitis, liver fibrosis and lung fibrosis, wound, infected wound, accelerating wound healing, including diabetic wound healing, in a patient in need thereof comprising administering to the patient a pharmaceutical composition comprising IL-22 Fc fusion proteins having an afucosylation level in the Fc region of no more than 10%, preferably no more than 5%, more preferably no more than 2%, and most preferably less than 1%.

The term "% afucosylation" refers to the level of afucosylation in the Fc region in a composition of IL-22 Fc fusion proteins. The % afucosylation can be measured by mass spectrometry (MS) and presented as the percentage of afucosylated glycan species (species without the fucose on one Fc domain (minus 1) and on both Fc domains (minus 2) combined) over the entire population of IL-22 Fc fusion proteins. For example, % afucosylation can be calculated as the percentage of the combined area under the minus 1 fucose peak and minus 2 fucose peak over the total area of all glycan species analyzed by MS, such as determined by an Agilent 6520B TOF Mass Spectrometer as described in FIG. 2 and in the examples shown below. The level of afucosylation can be measured by any other suitable methods known in the art, including without limitation HPLC-Chip Cube MS (Agilent) and reverse phase-HPLC. The % afucosylation of IL-22 Fc composition can be used as an indication for determining whether the composition will likely trigger unacceptable level of ADCC, unsuitable for the intended purposes. Accordingly, in certain particular embodiments, the composition comprises IL-22 Fc fusion proteins having an afucosylation level of no more than 10%, preferably no more than 5%, more preferably no more than 3%, and most preferably no more than 1%. In certain embodiments, the composition comprises IL-22 Fc fusion proteins having an afucosylation level of no more than 10%, no more than 9%, no more than 8%, no more than 7%, no more than 6%, no more than 5%, no more than 4%, no more than 3%, no more than 2%, or no more than 1%.

In certain embodiments, the desired level of afucosylation of an IL-22 Fc composition can be achieved by methods known in the art, including without limitation, by purification. For example, the fucosylated species in a composition can be enriched by affinity chromatography having resins conjugated with a fucose binding moiety, such as an antibody or lectin specific for fucose, especially fucose present in the 1-6 linkage. See e.g., Kobayashi et al, 2012, J. Biol. Chem. 287:33973-82. In certain other embodiments, the fucosylated species can be enriched and separated from afucosylated species using an anti-fucose specific antibody in an affinity column. Alternatively or additionally, afucosylated species can be separated from fucosylated species based on the differential binding affinity to FcγRIIIa using affinity chromatography.

In certain other embodiments, the IL-22 Fc fusion protein comprises an Fc region in which the N297 residue in the CH2 domain is mutated. In certain embodiments, the N297 residue is changed to Gly or Ala, preferably to Gly. In certain other embodiments, the N297 residue is deleted. In certain embodiments, the IL-22 Fc fusion protein comprising an Fc having an amino acid substitution at N297 is aglycosylated or not glycosylated. The term "aglycosylated" as used herein refers to a protein or a portion of a protein of interest that is not glycosylated. For example, an IL-22 Fc fusion protein with an aglycosylated Fc region can be made by mutagenizing the N297 residue in the CH2 domain of the Fc region.

In other embodiments, the N-glycan attached to the wild type N297 residue can be removed enzymatically, e.g., by deglycosylation. Suitable glycolytic enzymes include without limitation, peptide-N-glycosidase (PNGase).

The term "dimeric IL-22 Fc fusion protein" refers to a dimer in which each monomer comprises an IL-22 Fc fusion protein. The term "monomeric IL-22 Fc fusion protein" refers to a dimer in which one monomer comprises an IL-22 Fc fusion protein (the IL-22 Fc arm), while the other monomer comprises an Fc region without the IL-22 polypeptide (the Fc arm). Accordingly, the dimeric IL-22 Fc fusion protein is bivalent with respect to IL-22R binding, whereas the monomeric IL-22 Fc fusion protein is monovalent with respect to IL-22R binding. The heterodimerization of the monomeric IL-22 Fc fusion protein can be facilitated by methods known in the art, including without limitation, heterodimerization by the knob-into-hole technology. The structure and assembly method of the knob-into-hole technology can be found in, e.g., U.S. Pat. No. 5,821,333, U.S. Pat. No. 7,642,228, US 2011/0287009 and PCT/US2012/059810, hereby incorporated by reference in their entireties. This technology was developed by introducing a "knob" (or a protuberance) by replacing a small amino acid residue with a large one in the CH3 domain of one Fc, and introducing a "hole" (or a cavity) in the CH3 domain of the other Fc by replacing one or more large amino acid residues with smaller ones. In certain embodiments, the IL-22 Fc fusion arm comprises a knob, and the Fc only arm comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the CH3 domain for generating the hole include without limitation the T366S, L368A, F405A, Y407A, Y407T and Y407V substitutions. In certain embodiments, the knob comprises T366W substitution, and the hole comprises the T366S/L368A/Y407V substitutions. In certain particular embodiments, the Fc region of the monomeric IL-22 Fc fusion protein comprises an IgG1 Fc region. In certain particular embodiments, the monomeric IL-22 IgG1 Fc fusion comprises an IL-22 Fc knob arm and an Fc hole arm. In certain embodiments, the IL-22 Fc knob arm comprises a T366W substitution (SEQ ID NO:61), and the Fc hole arm comprises T366S, L368A and Y407V (SEQ ID NO:62). In certain other embodiments, the Fc region of both arms further comprises an N297G or N297A mutation. In certain embodiments, the monomeric IL-22 Fc fusion protein is expressed in E. coli cells. It is understood that other modifications to the Fc region known in the art that facilitate heterodimerization are also contemplated and encompassed by the instant application.

The term "wound" refers to an injury, especially one in which the skin or another external surface is torn, pierced, cut, or otherwise broken.

The term "ulcer" is a site of damage to the skin or mucous membrane that is often characterized by the formation of pus, death of tissue, and is frequently accompanied by an inflammatory reaction.

The term "intestine" or "gut" as used herein broadly encompasses the small intestine and large intestine.

The term "accelerating wound healing" or "acceleration of wound healing" refers to the increase in the rate of healing, e.g., a reduction in time until complete wound closure occurs or a reduction in time until a % reduction in wound area occurs.

A "diabetic wound" is a wound that associated with diabetes.

A "diabetic ulcer" is an ulcer that is associated with diabetes.

A "chronic wound" refers to a wound that does not heal. See, e.g., Lazarus et al., Definitions and guidelines for assessment of wounds and evaluation of healing, *Arch. Dermatol.* 130:489-93 (1994). Chronic wounds include, but are not limited to, e.g., arterial ulcers, diabetic ulcers, pressure ulcers or bed sores, venous ulcers, etc. An acute wound can develop into a chronic wound. Acute wounds include, but are not limited to, wounds caused by, e.g., thermal injury (e.g., burn), trauma, surgery, excision of extensive skin cancer, deep fungal and bacterial infections, vasculitis, scleroderma, pemphigus, toxic epidermal necrolysis, etc. See, e.g., Buford, Wound Healing and Pressure Sores, HealingWell.com, published on: Oct. 24, 2001. Thus, in certain embodiments, a chronic wound is an infected wound. A "normal wound" refers to a wound that undergoes normal wound healing repair.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., a ligand or an antibody) and its binding partner (e.g., a receptor or an antigen). Unless indicated otherwise, as used herein, "binding affinity" refers to intrinsic binding affinity which reflects a 1:1 interaction between members of a binding pair (e.g., IL-22 Fc fusion protein and IL-22 receptor). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" or "effector activities" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation. In certain embodiments, the IL-22 Fc fusion protein does not exhibit any effector function or any detectable effector function. In certain other embodiments, the IL-22 Fc fusion protein exhibits substantially reduced effector function, e.g., about 50%, 60%, 70% 80%, or 90% reduced effector function.

An "effective amount" or "therapeutically effective amount" of an agent, e.g., a pharmaceutical formulation, refers to an amount effective, at dosages and for periods of time necessary, to achieve the desired therapeutic or prophylactic result.

For example, in the case of a cardiovascular disease or condition, the therapeutically effective amount of the IL-22 polypeptide, fusion protein or agonist can reduce the degree of atherosclerotic plaque formation; reduce the size of the atherosclerotic plaque(s); inhibit (i.e., slow to some extent and preferably stop) atherosclerotic plaque; inhibit (i.e., slow to some extent and preferably stop) thrombosis or rupture of an atherosclerotic plaque; and/or relieve to some extent one or more of the symptoms associated with the disease or condition.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of atherosclerotic plaques, or the number of atherosclerotic plaque(s).

A "suboptimal amount" refers to the amount less than the optimal amount of a therapeutic agent typically used for a certain treatment. When two therapeutic agents are given to a subject, either concurrently or sequentially, each therapeutic agent can be given at a suboptimal amount as compared to the treatment when each therapeutic agent is given alone. For example, in certain embodiments, the subject in need of IBD treatment is administered with the pharmaceutical composition comprising the IL-22 Fc fusion protein of the invention and a dexamethasone at a suboptimal amount.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. The transformed cell includes transiently or stably transformed cell. Progeny may not be completely identical in nucleic acid content to a parent cell, but may contain mutations. Mutant progeny that have the same function or biological activity as screened or selected for in the originally transformed cell are included herein. In certain embodiments, the host cell is transiently transfected with the exogenous nucleic acid. In certain other embodiments, the host cell is stably transfected with the exogenous nucleic acid.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody or a fragment of an antibody conjugated to one or more heterologous molecule(s), including but not limited to a cytotoxic agent.

An "individual," "subject" or "patient" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual, subject or patient is a human.

An "isolated" IL-22 fusion protein is one which has been separated from the environment of a host cell that recombinantly produces the fusion protein. In some embodiments, an IL-22 fusion protein is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding IL-22 Fc fusion protein" refers to one or more nucleic acid molecules encoding the IL-22 Fc fusion protein, including such nucleic acid molecule(s) in a single vector or separate vectors, such nucleic acid molecule(s) transiently or stably transfected into a host cell and such nucleic acid molecule(s) present at one or more locations in a host cell.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N— to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "native sequence Fc region" comprises an amino acid sequence identical to the amino acid sequence of an Fc region found in nature. Native sequence human Fc regions include, without limitation, a native sequence human IgG1 Fc region (non-A and A allotypes); native sequence human IgG2 Fc region; native sequence human IgG3 Fc region; and native sequence human IgG4 Fc region, as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith. In certain embodiments, the variant Fc region is not glycosylated.

The term "inflammatory bowel disorder," "inflammatory bowel disease" or IBD is used herein in the broadest sense and includes all diseases and pathological conditions the pathogenesis of which involves recurrent inflammation in the intestine, including small intestine and colon. Commonly seen IBD includes ulcerative colitis and Crohn's disease. IBD is not limited to UC and CD. The manifestations of the disease include but not limited to inflammation and a decrease in epithelial integrity in the intestine.

The term "cardiovascular disease" or "cardiovascular disorder" is used herein in the broadest sense and includes all diseases and pathological conditions the pathogenesis of which involves abnormalities of the blood vessels, such as, for example, atherosclerotic plaque formation (including stable or unstable/vulnerable plaques), atherosclerosis, arteriosclerosis, arteriolosclerosis, and elevated systemic lipopolysaccharide (LPS) exposure. The term additionally includes diseases and pathological conditions that benefit from the inhibition of the formation of atherosclerotic plaques. Cardiovascular diseases include, without limitation, coronary artery atherosclerosis, coronary microvascular disease, stroke, carotid artery disease, peripheral arterial disease, ischemia, coronary artery disease (CAD), acute coronary syndrome (ACS), coronary heart disease (CHD), conditions associated with CAD and CHD, cerebrovascular disease, peripheral vascular disease, aneurysm, vasculitis, venous thrombosis, diabetes mellitus, and metabolic syndromechronic kidney disease, remote tissue injury after ischemia and reperfusion, cardiopulmonary bypass. Specifically included within this group are all cardiovascular diseases associated with the occurrence, development, or progression of which can be controlled by the inhibition of the atherosclerotic plaque formation.

The term "cardiovascular condition" is used herein in the broadest sense and includes all cardiovascular conditions and diseases the pathology of which involves atherosclerotic plaque formation (including stable or unstable/vulnerable plaques), atherosclerosis, arteriosclerosis, arteriolosclerosis, and elevated systemic lipopolysaccharide (LPS) exposure. Specifically included within this group are all cardiovascular conditions and diseases associated with the atherosclerotic plaque formation, the occurrence, development, or progression of which can be controlled by the inhibition of the atherosclerotic plaque formation. The term specifically includes diseases and pathological conditions that benefit from the inhibition of the formation of atherosclerotic plaques. Cardiovascular conditions include, without limitation, coronary artery atherosclerosis, coronary microvascular disease, stroke, carotid artery disease, peripheral arterial disease, ischemia, coronary artery disease (CAD), coronary heart disease (CHD), conditions associated with CAD and CHD, cerebrovascular disease and conditions associated with cerebrovascular disease, peripheral vascular disease and conditions associated with peripheral vascular disease, aneurysm, vasculitis, venous thrombosis, diabetes mellitus, and metabolic syndromechronic kidney disease, remote tissue injury after ischemia and reperfusion, and cardiopulmonary bypass. "Conditions associated with cerebrovascular disease" as used herein include, for example, transient ischemic attack (TIA) and stroke. "Conditions associated with peripheral vascular disease" as used herein include, for example, claudication. Specifically included within this group are all cardiovascular diseases and conditions associated with the occurrence, development, or progression of which can be controlled by the inhibition of the atherosclerostic plaque formation.

Atherosclerotic plaque formation can occur as a result of an innate immune response to metabolic endotoxemia, which is characterized by elevated levels of systemic lipopolysaccharides (LPS) that originate from gut microbiota and a loss of functional integrity in the gut mucosal barrier. The innate immune response to endotoxemia results in the low-grade chronic inflammation that is responsible for plaque formation.

The term "metabolic syndrome" is used herein in the broadest sense. Metabolic syndrome includes the co-occurrence in an adult subject of several metabolic risk factors, including at least three of the following five traits: abdominal obesity, which can be, for example, a waist circumference in men of greater than or equal to 90 cm and in women greater than or equal to 80 cm; elevated serum triglycerides, which can be, for example, greater than or equal to 150 mg/dL, or drug treatment for elevated triglycerides; reduced serum HDL cholesterol level, which can be, for example, below 40 mg/dL in men and below 50 mg/dL in women, or drug treatment for low HDL cholesterol; hypertension, which can be, for example, systolic blood pressure greater than 130 mmHg and diastolic blood pressure greater than 85 mmHg, or drug treatment for hypertension; and elevated fasting plasma glucose, which can be, for example, greater than or equal to 100 mg/dL, drug treatment for elevated glucose, or previously diagnosed type 2 diabetes. See also Meigs, the Metabolic Syndrome (Insulin Resistance Syndrome or Syndrome X), http://www.uptodate.com/contents/the-metabolic-syndrome-insulin-resistance-syndrome-or-syndrome-x, the disclosure of which is hereby incorporated by reference herein.

For children over 16 years old, the above criteria for adults can be used. For children between 10-16 year old, metabolic syndrome includes the co-occurrence in a subject of several metabolic risk factors, including at least three of the following five traits: abdominal obesity, which can be, for example, a waist circumference greater than $90^{th}$ percentile; elevated serum triglycerides, which can be, for example, greater than or equal to 110 mg/dL, greater than $95^{th}$ percentile, or drug treatment for elevated triglycerides; reduced serum HDL cholesterol level, which can be, for example, below 40 mg/dL, less than $5^{th}$ percentile, or drug treatment for low HDL cholesterol; hypertension, which can be, for example, systolic blood pressure greater than 130 mmHg and diastolic blood pressure greater than 85 mmHg, greater than $90^{th}$ percentile, or drug treatment for hypertension; and elevated fasting plasma glucose, which can be, for example, greater than or equal to 100 mg/dL, impaired glucose tolerance, drug treatment for elevated glucose, or previously diagnosed type 2 diabetes.

Generally speaking, the risk factors that co-occur in metabolic syndrome include obesity (such as abdominal obesity), hyperglycemia, dyslipidemia, insulin resistance, and/or hypertension. All these risk factors promote the development of atherosclerotic cardiovascular disease, diabetes, or both. Metabolic syndrome can also feature chronic adipose tissue inflammation.

Metabolic syndrome can be recognized as a proinflammatory, prothrombic state, and can be associated with elevated levels of one or more of C-reactive protein, IL-6, LPS, and plasminogen activator inhibitor 1; such markers can be associated with an increased risk for subsequent development of atherosclerotic cardiovascular disease, diabetes, or both.

Metabolic syndrome can be associated with several obesity-related disorders, including one or more of fatty liver disease with steatosis, fibrosis, and cirrhosis, hepatocellular and intrahepatic cholangiocarcinoma, chronic kidney disease, polycystic ovary syndrome, sleep disordered breathing, including obstructive sleep apnea, and hyperuricemia and gout.

The term "insulin-related disorder" encompasses diseases or conditions characterized by impaired glucose tolerance. In one embodiment, the insulin-related disorder is diabetes mellitus including, without limitation, Type I (insulin-dependent diabetes mellitus or IDDM), Type II (non-insulin dependent diabetes mellitus or NIDDM) diabetes, gestational diabetes, and any other disorder that would be benefited by agents that stimulate insulin secretion. In another embodiment, the insulin-related disorder is characterized by insulin resistance.

The term "sepsis" is used in its broadest sense and can encompass a systemic inflammatory state caused by severe infection. Sepsis can caused by the immune system's response to a serious infection, most commonly bacteria, but also fungi, viruses, and parasites in the blood, urinary tract, lungs, skin, or other tissues.

The term "acute endotoxemia" is used in its broadest sense and can encompass the condition of increased plasma bacterial lipopolysaccharide (LPS). Acute endotoxemia in turn could result in sepsis. Increased LPS in systemic circulation will induce low grade chronic inflammation, activating the endogenous protective host response to elevate plasma lipids that, in the chronic condition contributes to diet induced obesity, insulin resistance and atherosclerosis, and eventual CVD events.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

For example, with regard to IBD, "treatment" can refer to a decrease in the likelihood of developing IBD, a decrease in the rate of developing IBD and a decrease in the severity of the disease. As another example, with regard to atherosclerotic plaque formation, "treatment" can refer to a decrease in the likelihood of developing atherosclerotic plaque deposits, a decrease in the rate of development of deposits, a decrease in the number or size of existing deposits, or improved plaque stability. Those in need of treatment include those already with the disorder as well as those in which the disorder is to be prevented. Desirable effects of treatment include, but are not limited to, preventing occurrence or recurrence of disease, alleviating symptoms, diminishing any direct or indirect pathological consequences of the disease, preventing the disease, decreasing the rate of disease progression, ameliorating or palliating the disease state, and causing remission or improved prognosis. In some embodiments, an IL-22 polypeptide or IL-22 Fc fusion protein of the invention are used to delay development of a disease or to slow the progression of a disease.

In certain embodiments, a "subject in need thereof" in the context of preventing or treating a cardiovascular condition refers to a subject diagnosed with a cardiovascular disease or cardiovascular condition (CVD) or metabolic syndrome or exhibiting one or more conditions associated with CVD or metabolic syndrome, a subject who has been diagnosed with or exhibited one or more conditions associated with CVD or metabolic syndrome in the past, or a subject who has been deemed at risk of developing CVD or metabolic syndrome or one or more conditions associated with CVD or metabolic syndrome in the future due to hereditary or environmental factors. Therefore, in certain embodiments, a subject in need thereof can be a subject exhibiting a CVD or metabolic syndrome or a condition associated with a CVD or metabolic syndrome or a subject that has exhibited a CVD or metabolic syndrome or a condition associated with a CVD or metabolic syndrome in the past or has been deemed at risk for developing a CVD or metabolic syndrome or a condition associated with a CVD or metabolic syndrome in the future.

In treatment of a cardiovascular disease or condition, a therapeutic agent can directly alter the magnitude of response of a component of the immune response, or render the disease more susceptible to treatment by other therapeutic agents, e.g., antibiotics, antifungals, anti-inflammatory agents, chemotherapeutics, etc. In treatment of an arterial disease, treatment might, for example, prevent or slow down the progression of a disease. Thus, treatment of an arterial disease specifically includes the prevention, inhibition, or slowing down of the development of the condition, or of the progression from one stage of the condition to another, more advanced stage, or into a more severe, related condition.

The "pathology" of a disease or condition includes all phenomena that compromise the well-being of the subject. In the case of a cardiovascular disease or condition, this includes, without limitation, atherosclerotic plaque formation (including stable or unstable/vulnerable plaques), atherosclerosis, arteriosclerosis, arteriolosclerosis, and elevated systemic lipopolysaccharide (LPS) exposure.

"Alleviation", "alleviating" or equivalents thereof, refers to both therapeutic treatment and prophylactic or preventative measures, wherein the object is to ameliorate, prevent, slow down (lessen), decrease or inhibit a disease or condition, e.g., the formation of atherosclerotic plaques. Those in need of treatment include those already with the disease or condition as well as those prone to having the disease or condition or those in whom the disease or condition is to be prevented.

"Chronic" administration refers to administration of an agent(s) in a continuous mode as opposed to an acute mode, so as to maintain the initial therapeutic effect for an extended period of time.

"Intermittent" administration is treatment that is not consecutively done without interruption, but rather is cyclic in nature.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. As further examples of % amino acid sequence identity calculations using this method, below demonstrate how to calculate the % amino acid sequence identity of the amino acid sequence designated "Comparison Protein" or "Reference Protein" to the amino acid sequence designated "IL-22", wherein "IL-22" represents the amino acid sequence of an IL-22 polypeptide of interest, "Comparison Protein" represents the amino acid sequence of a polypeptide against which the "IL-22" polypeptide of interest is being compared, and "X", "Y" and "Z" each represent different amino acid residues.

As examples of % amino acid sequence identity calculations using this method, Tables 1 and 2 demonstrate how to calculate the % amino acid sequence identity of the amino acid sequence designated "Comparison Protein" to the amino acid sequence designated "IL-22", wherein "IL-22" represents the amino acid sequence of an IL-22 polypeptide of interest, "Comparison Protein" represents the amino acid sequence of a polypeptide against which the "IL-22" polypeptide of interest is being compared, and "X", "Y" and "Z" each represent different amino acid residues.

```
IL-22        XXXXXXXXXXXX  (Length = 15 amino acids)
             XXX

Reference    XXXXXXYYYYYY  (Length = 12 amino acids)
Protein

% amino acid sequence identity =
(the number of identically matching amino acid
residues between the two polypeptide sequences)
divided by (the total number of amino acid
residues of the IL-22 polypeptide) =
5 divided by 15 = 33.3%

IL-22        XXXXXXXXXX    (Length = 10 amino acids)

Reference    XXXXXYYYYYYZ  (Length = 15 amino acids)
Protein      ZYZ

% amino acid sequence identity =
(the number of identically matching amino acid
residues between the two polypeptide sequences)
divided by (the total number of amino acid
residues of the IL-22 polypeptide) =
5 divided by 10 = 50%
```

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/ 0.1% sodium dodecyl sulfate at 5OC; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

"Moderately stringent conditions" can be identified as described by Sambrook et al., Molecular Cloning: A Laboratory Manual. New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-500 C. The skilled artisan will recognize how to adjust the temperature, ionic strength, etc. as necessary to accommodate factors such as probe length and the like.

The term "agonist" is used in the broadest sense and includes any molecule that partially or fully mimics a biological activity of an IL-22 polypeptide. Also encompassed by "agonist" are molecules that stimulate the transcription or translation of mRNA encoding the polypeptide.

Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

The term "IL-22 agonist" is used in the broadest sense, and includes any molecule that mimics a qualitative biological activity (as hereinabove defined) of a native sequence IL-22 polypeptide. IL-22 agonists specifically include IL-22-Fc or IL-221 g polypeptides (immunoadhesins), but also small molecules mimicking at least one IL-22 biological activity. Preferably, the biological activity is binding of the IL-22 receptor, interacting with IL-22BP, facilitating an innate immune response pathway, or in the case of a cardiovascular disease or condition, to affect the formation of atherosclerotic plaques, in particular to inhibit formation of atherosclerotic plaque formation Inhibition of plaque formation can be assessed by any suitable imaging method known to those of ordinary skill in the art.

IL-22R1 pairs with other proteins to form heterodimers as the receptors for certain IL-10 family members. See Quyang et al., 2011, supra. Thus, in certain embodiments, IL-22 agonists may include an IL-22 receptor agonist, including a cytokine (or a fusion protein or agonist thereof) that binds to and triggers downstream signaling of the IL-22R1. In certain embodiments, the IL-22 agonists include an IL-22R1 agonist, including without limitation an anti-IL-22R1 agonist antibody; an IL-20 agonist, including without limitation IL-20 polypeptide or IL-20 Fc fusion protein; and an IL-24 agonist, including without limitation IL-24 polypeptide or IL-24 fusion protein. In certain other embodiments, the IL-22R1 agonists include an IL-19 agonist, including without limitation IL-19 polypeptide or IL-19 Fc fusion protein; and an IL-26 agonist, including without limitation IL-26 polypeptide or IL-26 Fc fusion protein. Exemplary sequences for IL-19 (GenBank Accession No. AAG16755.1, SEQ ID NO:77), IL-20 (GenBank Accession No. AAH69311.1, SEQ ID NO:78), IL-24 (GenBank Accession No. AAH09681.1, SEQ ID NO:79) and IL-26 (GenBank Accession No. NP_060872.1, SEQ ID NO:80) are provided herein. In certain embodiments, an IL-19 polypeptide comprises the amino acid sequence of SEQ ID NO:77 or the mature protein without the signal peptide. In certain other embodiments, an IL-20 polypeptide comprises the amino acid sequence of SEQ ID NO:78 or the mature protein without the signal peptide. In yet other embodiments, an IL-24 polypeptide comprises the amino acid sequence of SEQ ID NO:79 or the mature protein without the signal peptide. In certain other embodiments, an IL-26 polypeptide comprises the amino acid sequence of SEQ ID NO:80 or the mature protein without the signal peptide.

A "small molecule" is defined herein to have a molecular weight below about 600, preferably below about 1000 daltons.

An "agonist antibody," as used herein, is an antibody which partially or fully mimics a biological activity of an IL-22 polypeptide.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, diluent, stabilizer, or preservative.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on compositions comprising therapeutics that ameliorate IL-22 associated diseases or disorders by increasing IL-22 activities or signaling. In certain embodiments, IL-22 polypeptide and IL-22 Fc fusion proteins that bind to and activate IL-22 receptor are provided. IL-22 Fc fusion proteins of the invention are useful, e.g., for the diagnosis or treatment of IL-22 associated diseases such as inflammatory bowel disease and accelerating wound healing. In addition, IL-22 polypeptide and IL-22 Fc fusion proteins for the treatment of other IL-22 associated diseases for example cardiovascular conditions, metabolic syndrome and accelerating diabetic wound healing are also provided.

A. Exemplary IL-22 Polypeptide

IL-22 polypeptide as used herein includes a polypeptide comprising an amino acid sequence comprising SEQ ID NO:71 (human IL-22 with the endogenous IL-22 leader sequence) (see FIG. 31), or a polypeptide comprising an amino acid sequence that has at least 95% sequence identity with SEQ ID NO:71. In certain embodiments, the IL-22 polypeptide comprises an amino acid sequence comprising SEQ ID NO:4 (human IL-22 without a leader sequence) or a polypeptide comprising an amino acid sequence that has at least 95% sequence identity. In certain embodiments, the IL-22 polypeptide comprises an amino acid sequence comprising SEQ ID NO:4. In certain embodiments, the IL-22 polypeptide does not comprise an Fc fusion.

The preparation of native IL-22 molecules, along with their nucleic acid and polypeptide sequences, can be achieved through methods known to those of ordinary skill in the art. For example, IL-22 polypeptides can be produced by culturing cells transformed or transfected with a vector containing IL-22 nucleic acid. It is, of course, contemplated that alternative methods, which are well known in the art, can be employed to prepare IL-22. For instance, the IL-22 sequence, or portions thereof, can be produced by direct peptide synthesis using solid-phase techniques (see, e.g., Stewart et al., 1969, Solid-Phase Peptide Synthesis, W.H. Freeman Co., San Francisco, Calif. (1969); Merrifield, J. Am. Chem. Soc., 1963, 85:2149-2154). In vitro protein synthesis can be performed using manual techniques or by automation. Automated synthesis can be accomplished, for instance, using an Applied Biosystems Peptide Synthesizer (Foster City, Calif.) using manufacturer's instructions. Various portions of IL-22 can be chemically synthesized separately and combined using chemical or enzymatic methods to produce the full-length IL-22.

IL-22 variants can be prepared by introducing appropriate nucleotide changes into the DNA encoding a native sequence IL-22 polypeptide, or by synthesis of the desired IL-22 polypeptide. Those skilled in the art will appreciate that amino acid changes can alter post-translational processes of IL-22, such as changing the number or position of glycosylation sites or altering the membrane anchoring characteristics.

Variations in the native sequence IL-22 polypeptides described herein can be made, for example, using any of the techniques and guidelines for conservative and non-conservative mutations set forth, for instance, in U.S. Pat. No. 5,364,934. Variations can be a substitution, deletion or insertion of one or more codons encoding a native sequence or variant IL-22 that results in a change in its amino acid sequence as compared with a corresponding native sequence or variant IL-22. Optionally the variation is by substitution of at least one amino acid with any other amino acid in one or more of the domains of a native sequence IL-22 polypeptide. Guidance in determining which amino acid residue can be inserted, substituted or deleted without adversely affecting the desired activity can be found by comparing the sequence of the IL-22 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of 1 to 5 amino acids. The variation allowed can be determined by systematically making insertions, deletions or substitutions of amino acids in the sequence and testing the resulting variants for activity in the in vitro assay described in the Examples below.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

The variations can be made using methods known in the art such as oligonucleotide-mediated (site-directed) mutagenesis, alanine scanning, and PCR mutagenesis. Site-directed mutagenesis (Carter et al., 1986, Nucl. Acids Res, 13:4331; Zoller et al., 1987, Nucl. Acids Res., 10:6487), cassette mutagenesis (Wells et al., 1985, Gene, 34:315), restriction selection mutagenesis (Wells et al., 1986, Philos. Trans. R. Soc. London SerA, 317:415) or other known techniques can be performed on the cloned DNA to produce the IL-22 variant DNA.

Fragments of an IL-22 polypeptide of the present invention are also provided herein. Such fragments can be truncated at the N-terminus or C-terminus, or can lack internal residues, for example, when compared with a full length native protein. Certain fragments lack amino acid residues that are not essential for a desired biological activity of an IL-22 polypeptide of the present invention. Accordingly, in certain embodiments, a fragment of an IL-22 polypeptide is biologically active. In certain embodiments, a fragment of full length IL-22 lacks the N-terminal signal peptide sequence.

Covalent modifications of native sequence and variant IL-22 polypeptides are included within the scope of this invention. One type of covalent modification includes reacting targeted amino acid residues of IL-22 with an organic derivatizing agent that is capable of reacting with selected side chains or the N- or C-terminal residues of the IL-22 polypeptide. Derivatization with bifunctional agents is useful, for instance, for crosslinking IL-22 to a water-insoluble support matrix or surface, for example, for use in the method for purifying anti-IL-22 antibodies. Commonly used cross-linking agents include, e.g., 1,1-bis(diazo-acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the .alpha.-amino groups of lysine, arginine, and histidine side chains (T. E. Creighton, 1983, Proteins: Structure and Molecular Properties, W. H. Freeman & Co., San Francisco, pp. 79-86i), acetylation of the N-terminal amine, and amidation of any C-terminal carboxyl group.

Another type of covalent modification of the IL-22 polypeptides included within the scope of this invention comprises altering the native glycosylation pattern of the polypeptides. "Altering the native glycosylation pattern" is intended for purposes herein to mean deleting one or more carbohydrate moieties found in native sequence IL-22, and/or adding one or more glycosylation sites that are not present in the native sequence IL-22, and/or alteration of the ratio and/or composition of the sugar residues attached to the glycosylation site(s).

Glycosylation of polypeptides is typically either N-linked or O-linked. N-linked glycosylation refers to the attachment of the carbohydrate moiety to the side-chain of an asparagine residue. The tripeptide sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5-hydroxyproline or 5-hydroxylysine can also be involved in O-linked glycosylation. Addition of glycosylation sites to the IL-22 polypeptide can be accomplished by altering the amino acid sequence. The alteration can be made, for example, by the addition of, or substitution by, one or more serine or threonine residues to the native sequence IL-22 (for N-linked glycosylation sites), or the addition of a recognition sequence for O-linked glycosylation. The IL-22 amino acid sequence can optionally be altered through changes at the DNA level, particularly by mutating the DNA encoding the IL-22 polypeptide at preselected bases such that codons are generated that will translate into the desired amino acids.

Another means of increasing the number of carbohydrate moieties on the IL-22 polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on an IL-22 polypeptide can be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of IL-22 comprises linking the IL-22 polypeptide to one of a variety of non-proteinaceous polymers, e.g., polyethylene glycol, polypropylene glycol, or polyoxyalkylenes, for example in the manner set forth in U.S. Pat. No. 4,640,835; 4,496,689; 4,301,144; 4,670,417; 4,791,192 or 4,179,337. The native sequence and variant IL-22 can also be modified in a way to form a chimeric molecule comprising IL-22, including fragments of IL-22, fused to another, heterologous polypeptide or amino acid sequence.

In one embodiment, such a chimeric molecule comprises a fusion of IL-22 with a tag polypeptide which provides an epitope to which an anti-tag antibody can selectively bind. The epitope tag is generally placed at the amino- or carboxyl-terminus of the IL-22 polypeptide. The presence of such epitope-tagged forms of the IL-22 polypeptide can be detected using an antibody against the tag polypeptide. Also, provision of the epitope tag enables the IL-22 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., 1988, Mol. Cell. Biol., 8:2159-2165); the c-myc tag and the 8F9, 3C7, 6E10, G4, and 9E10 antibodies thereto (Evan et al., 1985, Molecular and Cellular Biology, 5:3610-3616); and the Herpes Simplex virus glycoprotein D (gD) tag and its antibody (Paborsky et al., 1990, Protein Engineering, 3(6):547-553). Other tag polypeptides include the Flag-peptide (Hopp et al., 1988, BioTechnology, 6:1204-1210); the KT3 epitope peptide (Martin et al., 1992, Science, 255:192-194); an .quadrature.-tubulin epitope peptide (Skinner et al., 1991, J. Biol. Chem., 266:15163-15166); and the T7 gene 10 protein peptide tag (Lutz-Freyermuth et al., 1990, Proc. Natl. Acad. Sci. USA, 87:6393-6397).

In another embodiment, the chimeric molecule can comprise a fusion of the IL-22 polypeptide or a fragment thereof with an immunoglobulin or a particular region of an immunoglobulin. For a bivalent form of the chimeric molecule, such a fusion can be to the Fc region of an IgG molecule. These fusion polypeptides are antibody-like molecules which combine the binding specificity of a heterologous protein (an "adhesin") with the effector functions of immunoglobulin constant domains, and are often referred to as immunoadhesins. Structurally, the immunoadhesins comprise a fusion of an amino acid sequence of IL-22, or a variant thereof, and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD or IgM. In certain embodiments, the IL-22 Fc fusion protein exhibits modified effector activities.

The IL-22 polypeptide, or a fragment thereof, can be fused, for example, to an immunoglobulin heavy chain constant region sequence to produce an IL-22-Ig fusion protein (e.g., IL-22 Fc fusion protein). The IL-22 polypeptide can be human or murine IL-22. The immunoglobulin heavy chain constant region sequence can be human or murine immunoglobulin heavy chain constant region sequence.

B. Exemplary IL-22 Fc Fusion Protein

In one aspect, the invention provides isolated IL-22 fusion protein. In certain embodiments, the IL-22 fusion protein binds to and induces IL-22 receptor activity or signaling and/or is an agonist of IL-22 receptor activity.

In another aspect, an IL-22 Fc fusion protein comprises a polypeptide having at least 90%, 91%, 92%, 93%, 94%, 95%, 96%, 97%, 98%, 99%, or 100% sequence identity to the amino acid sequence of SEQ ID NO:4. In other embodiments, the IL-22 Fc fusion protein comprises a polypeptide having at least 90%, 91%, 92%, 93%, 94%, 95%, 96%, 97%, 98%, or 99% sequence identity contains substitutions (e.g., conservative substitutions), insertions, or deletions relative to the reference sequence, but an IL-22 Fc fusion protein comprising that sequence retains the ability to bind to IL-22 receptor. In certain embodiments, a total of 1 to 10 amino acids have been substituted, inserted and/or deleted in SEQ ID NOs:8, 10, 12, 14, 24 or 26. In certain embodiments, substitutions, insertions, or deletions occur in regions outside the IL22 (i.e., in the Fc). In certain particular embodiments, the C-terminus Lys residue of Fc is deleted. In certain other embodiments, the C-terminus Gly and Lys residues of Fc are both deleted.

In certain embodiments, IL-22 Fc fusion proteins variants having one or more amino acid substitutions are provided. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into the IL-22 Fc fusion protein and the products screened for a desired activity, e.g., retained/improved IL-22 receptor binding, decreased immunogenicity, or improved IL-22 receptor signaling.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

A useful method for identification of residues or regions of a protein that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the protein with its binding partner is affected. Further substitutions may be introduced at the amino acid locations demonstrating functional sensitivity to the initial substitutions. Alternatively, or additionally, a crystal structure of a protein complex (e.g., a cytokine-receptor complex) can be used to identify contact points between a protein and its binding partner. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues.

a) Glycosylation Variants

In certain embodiments, an Fc fusion protein provided herein is altered to increase or decrease the extent to which the fusion protein, especially the Fc portion of the fusion protein, is glycosylated. Addition or deletion of glycosylation sites to a protein may be conveniently accomplished by altering the amino acid sequence such that one or more glycosylation sites is created or removed.

Where the fusion protein comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody or the Fc region of an antibody may be made in order to create Fc variants with certain improved properties.

The amount of fucose attached to the CH2 domain of the Fc region can be determined by calculating the average amount of fucose within the sugar chain at Asn297, relative to the sum of all glycostructures attached to Asn 297 or N297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

b) Fc Region Variants

In certain embodiments, one or more amino acid modifications may be introduced into the Fc region of an Fc fusion protein provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an Fc variant that possesses some but not all effector functions, which make it a desirable candidate for applications in which the half life of the antibody or a fusion protein comprising an Fc region in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody or Fc lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody or Fc is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody or Fc variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an IL-22 Fc fusion protein comprises an Fc variant with one or more amino acid substitutions which reduce ADCC, e.g., substitution at position 297 of the Fc region to remove the N-glycosylation site and yet retain FcRn binding activity (EU numbering of residues).

In some embodiments, alterations are made in the Fc region that result in diminished C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

c) Cysteine Engineered Variants

In certain embodiments, it may be desirable to create cysteine engineered Fc fusion protein, in which one or more residues of the Fc region of an antibody are substituted with cysteine residues. In particular embodiments, the substituted residues occur at accessible sites of the Fc. By substituting those residues with cysteine, reactive thiol groups are thereby positioned at accessible sites of the Fc and may be used to conjugate the Fc to other moieties, such as drug moieties or linker-drug moieties, to create an immunoconjugate, as described further herein. For example, S400 (EU numbering) of the heavy chain Fc region can be substituted with Cysteine. See e.g., U.S. Pat. No. 7,521,541.

C. Recombinant Methods and Compositions

The IL-22 polypeptides can be prepared by routine recombinant methods, e.g., culturing cells transformed or transfected with a vector containing a nucleic acid encoding an IL-22 polypeptide, a fragment or variant thereof, or fusion protein comprising the same. Host cells comprising any such vector are also provided. By way of example, host cells can be CHO cells, *E. coli*, or yeast. A process for producing any of the herein described polypeptides is further provided and comprises culturing host cells under conditions suitable for expression of the desired polypeptide and recovering the desired polypeptide from the cell culture.

Host cells are transfected or transformed with expression or cloning vectors described herein for IL-22 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: A Practical Approach, M. Butler, ed. (IRL Press, 1991) and Sambrook et al., supra.

Methods of transfection are known to the ordinarily skilled artisan, for example, by $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., J. Bact, 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, can also be used. For various techniques for transforming mammalian cells, see Keown et al., Methods in Enzymology, 185:527-537 (1990) and Mansour et al., Nature, 336:348-352 (1988).

Recombinantly expressed polypeptides of the present invention can be recovered from culture medium or from host cell lysates. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of a polypeptide of the present invention. Various methods of protein purification can be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide produced.

Alternative methods, which are well known in the art, can be employed to prepare a polypeptide of the present invention. For example, a sequence encoding a polypeptide or portion thereof, can be produced by direct peptide synthesis using solid-phase techniques (see, e.g., Stewart et al., 1969, *Solid-Phase Peptide Synthesis*, W.H. Freeman Co., San Francisco, Calif.; Merrifield, J. 1963, *Am. Chem. Soc.*, 85:2149-2154. In vitro protein synthesis can be performed using manual techniques or by automation. Automated synthesis can be accomplished, for instance, using an Applied Biosystems Peptide Synthesizer (Foster City, Calif.) using manufacturer's instructions. Various portions of a polypeptide of the present invention or portion thereof can be chemically synthesized separately and combined using chemical or enzymatic methods to produce the full-length polypeptide or portion thereof.

In other embodiments, the invention provides chimeric molecules comprising any of the herein described polypeptides fused to a heterologous polypeptide or amino acid sequence. Examples of such chimeric molecules include, but are not limited to, any of the herein described polypeptides fused to an epitope tag sequence or an Fc region of an immunoglobulin.

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for IL-22-encoding vectors. *Saccharomyces cerevisiae* is a commonly used lower eukaryotic host microorganism.

Suitable host cells for the expression of glycosylated-IL-22 are derived from multicellular organisms. Examples of invertebrate cells include insect cells such as *Drosophila S2* and *Spodoptera* Sf9, as well as plant cells. Examples of useful mammalian host cell lines include Chinese hamster ovary (CHO) and COS cells. More specific examples include monkey kidney CV1 cells transformed by SV40 (COS-7, ATCC CRL 1651); human embryonic kidney cells (293 or 293 cells subcloned for growth in suspension culture, Graham et al., J. Gen Virol., 36:59 (1977)); Chinese hamster ovary cells/–DHFR (CHO, Urlaub and Chasin, Proc. Natl. Acad. Sci. USA, 77:4216 (1980)); mouse sertoli cells (TM4, Mather, Biol. Reprod., 23:243-251 (1980)); human lung cells (W138, ATCC CCL 75); human liver cells (Hep G2, HB 8065); and mouse mammary tumor cells (MMT 060562, ATCC CCL51). The selection of the appropriate host cell is deemed to be within the skill in the art.

The nucleic acid (e.g., cDNA or genomic DNA) encoding IL-22 can be inserted into a replicable vector for cloning (amplification of the DNA) or for expression. Various vectors are publicly available. The vector can, for example, be in the form of a plasmid, cosmid, viral particle, or phage. The appropriate nucleic acid sequence can be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The IL-22 polypeptides can be produced recombinantly not only directly, but also as a fusion polypeptide with a heterologous polypeptide, which can be a signal sequence or other polypeptide having a specific cleavage site at the N-terminus of the mature protein or polypeptide, as well as an IL-22 Fc fusion protein. In general, the signal sequence can be a component of the vector, or it can be a part of the IL-22 DNA that is inserted into the vector. The signal sequence can be a prokaryotic signal sequence selected, for example, from the group of the alkaline phosphatase, penicillinase, 1 pp, or heat-stable enterotoxin II leaders. For yeast secretion the signal sequence can be, e.g., the yeast invertase leader, alpha factor leader (including *Saccharomyces* and *Kluyveromyces* "—factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences can be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells is one that enables the identification of cells competent to take up the IL-22 nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [see, e.g., Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the IL-22 nucleic acid sequence to direct mRNA synthesis. Promoters recognized by a variety of potential host cells are well known. Promoters suitable for use with prokaryotic hosts include the quadrature-lactamase and lactose promoter systems [see, e.g., Chang et al., Nature, 275:615 (1978); Goeddel et al., Nature, 281:544 (1979)], alkaline phosphatase, a tryptophan (trn) promoter system [see, e.g., Goeddel, Nucleic Acids Res., 8:4057 (1980); EP 36,776], and hybrid promoters such as the tac promoter [see, e.g., deBoer et al., Proc. Natl. Acad. Sci. USA, 80:21-25 (1983)]. Promoters for use in bacterial systems also will contain a Shine-Dalgarno (S.D.) sequence operably linked to the DNA encoding IL-22.

Examples of suitable promoter sequences for use with yeast hosts include the promoters for 3-phosphoglycerate kinase [see, e.g., Hitzeman et al., J. Biol. Chem., 255:2073 (1980)] or other glycolytic enzymes [see, e.g., Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IL-22 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IL-22 polypeptides by higher eukaryotes can be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer can be spliced into the vector at a position 5' or 3' to the IL-22 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IL-22.

Still other methods, vectors, and host cells suitable for adaptation to the synthesis of IL-22 in recombinant vertebrate cell culture are described in Gething et al., Nature, 293:620-625 (1981); Mantei et al., Nature, 281:4046 (1979); EP 117,060; and EP 117,058.

Gene amplification and/or expression can be measured in a sample directly, for example, by conventional Southern blotting, Northern blotting to quantitate the transcription of mRNA [see, e.g., Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies can be employed that can recognize specific duplexes, including DNA duplexes, RNA duplexes, and DNA-RNA hybrid duplexes or DNA-protein duplexes. The antibodies in turn can be labeled and the assay can be carried out where the duplex is bound to a surface, so that upon the formation of duplex on the surface, the presence of antibody bound to the duplex can be detected.

Gene expression, alternatively, can be measured by immunological methods, such as immunohistochemical staining of cells or tissue sections and assay of cell culture or body fluids, to quantitate directly the expression of gene product. Antibodies useful for immunohistochemical staining and/or assay of sample fluids can be either monoclonal or polyclonal, and can be prepared in any mammal. Conveniently, the antibodies can be prepared against a native sequence IL-22 polypeptide or against a synthetic peptide based on the DNA sequences provided herein or against exogenous sequence fused to IL-22 DNA and encoding a specific antibody epitope.

Forms of IL-22 can be recovered from culture medium or from host cell lysates. If membrane-bound, it can be released from the membrane using a suitable detergent solution (e.g. Triton-X 100) or by enzymatic cleavage. Cells employed in expression of IL-22 can be disrupted by various physical or chemical means, such as freeze-thaw cycling, sonication, mechanical disruption, or cell lysing agents.

It may be desired to purify IL-22 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IL-22 polypeptide. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular IL-22 produced. The above-described general methods can be applied to the preparation of IL-2 Fc fusion protein as well.

Similarly, IL-22 Fc fusion proteins may be produced using recombinant methods and compositions, as described in, e.g., *Molecular Cloning: A Laboratory Manual* (Sambrook, et al., 1989, Cold Spring Harbor Laboratory Press) and *PCR Protocols: A Guide to Methods and Applications* (Innis, et al. 1990. Academic Press, San Diego, Calif.). In one embodiment, isolated nucleic acid encoding IL-22 Fc fusion proteins described herein is provided. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with) a vector comprising a nucleic acid that encodes an amino acid sequence comprising the IL-22 Fc fusion protein. In certain embodiment, the vector is an expression vector. In one embodiment, the host cell is eukaryotic, e.g. a Chinese Hamster Ovary (CHO) cell or lymphoid cell (e.g., Y0, NS0, Sp20 cell). In one embodiment, a method of making an IL-22 Fc fusion protein is provided, wherein the method comprises culturing a host cell comprising a nucleic acid encoding the IL-22 Fc fusion protein, as provided above, under conditions suitable for expression of the Fc fusion protein, and optionally recovering the Fc fusion protein from the host cell (or host cell culture medium).

For recombinant production of an IL-22 Fc fusion protein, nucleic acid encoding an Fc fusion protein, e.g., as described herein, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the fusion protein). In certain embodiments, when preparing the IL-22 Fc fusion proteins, nucleic acid encoding the IL-22 polypeptide or a fragment thereof can be ligated to nucleic acid encoding an immunoglobulin constant domain sequence at specified location on the constant domain to result in an Fc fusion at the C-terminus of IL-22; however N-terminal fusions are also possible.

As an example of constructing an IL-22 Fc fusion protein, the DNA encoding IL-22 is cleaved by a restriction enzyme at or proximal to the 3' end of the DNA encoding IL-22 and at a point at or near the DNA encoding the N-terminal end of the mature polypeptide (where use of a different leader is contemplated) or at or proximal to the N-terminal coding region for IL-22 full-length protein (where a native signal is employed). This DNA fragment then is readily inserted into DNA encoding an immunoglobulin light or heavy chain constant region and, if necessary, tailored by deletional mutagenesis. Preferably, this is a human immunoglobulin when the fusion protein is intended for in vivo therapy for humans.

In some embodiments, the IL-22-immunoglobulin chimeras are assembled as monomers, hetero- or homo-multimer, or as dimers or tetramers. Generally, these assembled immunoglobulins will have known unit structures as represented by the following diagrams. A basic four chain structural unit is the form in which IgG, IgD, and IgE exist. A four chain unit is repeated in the higher molecular weight immunoglobulins; IgM generally exists as a pentamer of, basic four-chain units held together by disulfide bonds. IgA globulin, and occasionally IgG globulin, may also exist in a multimeric form in serum. In the case of multimers, each four chain unit may be the same or different. See also Capon et al. U.S. Pat. No. 5,116,964, incorporated herein by reference in its entirety.

In the diagrams herein, "A" means at least a portion of a binding partner (such as IL-22) containing a binding site which is capable of binding its ligand or receptor (such as IL-22 R); X is an additional agent, which may be another functional binding partner (same as A or different), a multiple subunit (chain) polypeptide as defined above (e.g., an integrin), a portion of an immunoglobulin superfamily member such as a variable region or a variable region-like domain, including a native or chimeric immunoglobulin variable region, a toxin such as *pseudomonas* exotoxin or ricin, or a polypeptide therapeutic agent not otherwise normally associated with a constant domain; and $V_L$, $V_H$, $C_L$ and $C_H$ represent light or heavy chain variable or constant domains of an immunoglobulin. These diagrams are understood to be merely exemplary of general assembled immunoglobulin structures, and do not encompass all possibilities. It will be understood, for example, that there might desirably be several different "A"s or "X"s in any of these constructs.

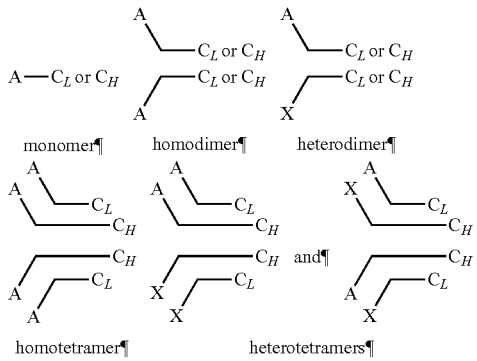

It will be understood that these diagrams are merely illustrative, and that the chains of the multimers are believed to be disulfide bonded in the same fashion as native immunoglobulins. According to this invention, hybrid immunoglobulins are readily secreted from mammalian cells transformed with the appropriate nucleic acid. The secreted forms include those wherein the binding partner epitope is present in heavy chain dimers, light chain monomers or dimers, and heavy and light chain heterotetramers wherein the binding partner epitope is present fused to one or more light or heavy chains, including heterotetramers wherein up to and including all four variable region analogues are substituted. Where a light-heavy chain non-binding partner variable-like domain is present, a heterofunctional antibody thus is provided.

Chains or basic units of varying structure may be utilized to assemble the monomers and hetero- and homo-multimers and immunoglobulins of this invention. Specific examples of these basic units are diagrammed below and their equivalents (for purposes of the attenuated formulae infra) are indicated.

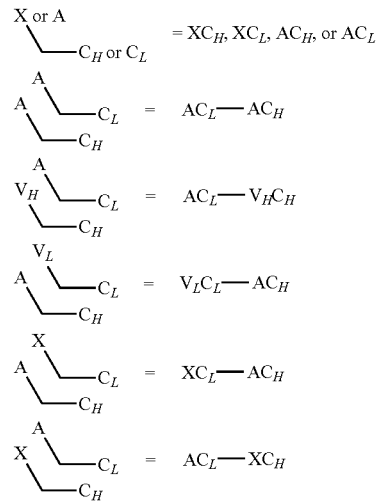

Various exemplary assembled novel immunoglobulins produced in accordance with this invention are schematically diagrammed below. In addition to the symbols defined above, n is an integer, and Y designates a covalent cross-linking moiety.

(a) $AC_L$;
(b) $AC_L$-$AC_L$;
(c) $AC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_H$—$V_LC_L$, $XC_L$-$AC_H$, or $AC_L$—$XC_H$];
(d) $AC_L$-$AC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_H$—$V_LC_L$, $XC_L$-$AC_H$, or $AC_L$—$XC_H$];
(e) $AC_L$—$V_HC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_H$—$V_LC_L$, $XC_L$-$AC_H$, or $AC_L$—$XC_H$];
(f) $V_LC_L$-$AC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_L$—$V_LC_L$, $XC_L$-$AC_H$, or $AC_L$—$XC_H$];
(g) $[A-Y]_n$—$[V_LC_L$—$V_HC_H]_2$;
(h) $XC_H$ or $XC_L$-[$AC_H$, $AC_L$-$AC_H$, $AC_L$—$VC_HC_H$, $LC_L$-$AC_H$, $XC_L$-$AC_H$, or $AC_L$—$XC_H$];
(i) $XC_L$—$XC_H$-[$AC_H$, $AC_L$-$AC_H$, $AC_L$—$V_HC_H$, $V_LC$-$AC_H$, $XC_L$-$AC_H$, or $AC_L$—$XC_H$];
(j) $XC_L$—$V_HC_H$-[$AC_H$, $AC_L$-$AC_H$, $AC_L$—$V_HC_H$, $V_LC_L$-$AC_H$, $XC_L$-$AC_H$, or $AC_L$—$XC_H$]2
(k) $XC_H$—$V_LC_L$-[$AC_H$, $AC_L$-$AC_H$, $AC_L$—$V_HC_H$, $V_LC_L$-$AC_H$, $XC_L$-$AC_H$, or $AC_L$—$XC_H$];
(l) $XC_L$-$AC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_H$—$V_LC_L$, $XC_L$-$AC_H$, or $AC_L$—$XC_H$];
(m) $AC_L$—$XC_H$-[$AC_H$, $AC_L$-$AC_H$, $AC_L$—$V_HC_H$, $V_LC_L$-$AC_H$, $V_LC_L$—$V_HC_H$, $XC_H$, $XC_L$, $XC_L$—$XC_H$, $XC_L$—$V_HC_H$, $XC_H$—$V_LC_L$, $XC_L$-$AC_H$, or $AC_L$—$XC_H$];

A, X, V or C may be modified with a covalent cross-linking moiety (Y) so to be $(A-Y)_n$, $(X-Y)_n$ etc.

The binding partner A (such as IL-22) may also be a multi-chain molecule, e.g. having chains arbitrarily denoted as $A_\alpha$ and $A_\beta$. These chains as a unit are located at the sites noted for the single chain "A" above. One of the multiple chains is fused to one immunoglobulin chain (with the remaining chains covalently or noncovalently associated with the fused chain in the normal fashion) or, when the ligand binding partner contains two chains, one chain is separately fused to an immunoglobulin light chain and the other chain to an immunoglobulin heavy chain.

Basic units having the structures as diagrammed below are examples of those used to create monomers, and hetero- and homo-multimers, particularly dimers and trimers with multi-chain ligand binding partners:

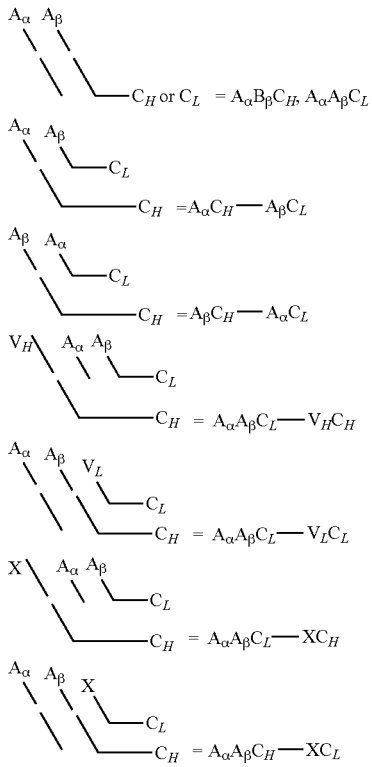

Various exemplary novel assembled antibodies having a two-chain ligand binding partner ("$A_\alpha$ and $A_\beta$") utilized in unit structures as above are schematically diagrammed below.

(n) $A_\alpha A_\beta C_L$-[$AC_H$, $AC_L$-$AC_H$, $AC_L$—$V_H C_H$, $V_L C_L$-$AC_H$, $V_L C_L$—$V_H C_H$, $XC_L$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(o) $A_\alpha A_\beta C_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(p) $A_\alpha C_L$-$A_\beta C_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(q) $A_\beta C_L$-$A_\alpha C_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(r) $A_\alpha A_\beta C_L$—$V_H C_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(s) $A_\alpha A_\beta C_H$—$V_L C_L$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(t) $A_\alpha A_\beta C_L$—$XC_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C_L$—$XC_H$, or $A_\alpha A_\beta C_H$—$XC_L$];

(u) $A_\alpha A_\beta C_H$-[$AC_H$, $AC_L$-$AC_H$, $AC_L$—$V_H C_H$, $V_L C_L$-$AC_H$, $V_L C_L$—$V_H C_H$, $XC_H$, $XC_L$, $XC_L$—$XC_H$, $XC_L$—$V_H C_H$, $XC_H$—$V_L C_L$, $XC_L$-$AC_H$, $AC_L$—$XC_H$, $A_\alpha A_\beta C_H$, $A_\alpha A_\beta C_L$, $A_\alpha C_L$-$A_\beta C_H$, $A_\beta C_L$-$A_\alpha C_H$, $A_\alpha A_\beta C_L$—$V_H C_H$, $A_\alpha A_\beta C_H$—$V_L C_L$, $A_\alpha A_\beta C$—$XC_H$, or $A_\alpha A_\beta C_H$—$XC_L$].

The structures shown in the above tables show only key features, e.g. they do not show joining (J) or other domains of the immunoglobulins, nor are disulfide bonds shown. These are omitted in the interests of brevity. However, where such domains are required for binding activity they shall be constructed as being present in the ordinary locations which they occupy in the binding partner or immunoglobulin molecules as the case may be.

DNA encoding immunoglobulin light or heavy chain constant regions is known or readily available from cDNA libraries or is synthesized. See for example, Adams et al., Biochemistry 19:2711-2719 (1980); Gough et al., Biochemistry 19:2702-2710 (1980); Dolby et al; P.N.A.S. USA, 77:6027-6031 (1980); Rice et al P.N.A.S USA 79:7862-7865 (1982); Falkner et al; Nature 298:286-288 (1982); and Morrison et al; Ann. Rev. Immunol. 2:239-256 (1984). DNA sequence encoding human IL-22 with the endogenous leader sequence is provided herein (SEQ ID NO:70). DNA sequences encoding other desired binding partners which are known or readily available from cDNA libraries are suitable in the practice of this invention.

DNA encoding an IL-22 Fc fusion protein of this invention is transfected into a host cell for expression. If multimers are desired then the host cell is transformed with DNA encoding each chain that will make up the multimer, with the host cell optimally being selected to be capable of assembling the chains of the multimers in the desired fashion. If the host cell is producing an immunoglobulin prior to transfection then one needs only transfect with the binding partner fused to light or to heavy chain to produce a heteroantibody. The aforementioned immunoglobulins having one or more arms bearing the binding partner domain and one or more arms bearing companion variable regions result in dual specificity for the binding partner ligand and for an antigen or therapeutic moiety. Multiply cotransformed cells are used with the above-described recombinant methods to produce polypeptides having multiple specificities such as the heterotetrameric immunoglobulins discussed above.

Although the presence of an immunoglobulin light chain is not required in the immunoadhesins of the present invention, an immunoglobulin light chain might be present either covalently associated to an IL-22-immunoglobulin heavy chain fusion polypeptide. In this case, DNA encoding an immunoglobulin light chain is typically co-expressed with the DNA encoding the IL-22-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989. Suitable host cells for cloning or expression of target protein-encoding vectors include prokaryotic or eukaryotic cells described herein. For example, IL-22 fusion protein may be produced in bacteria, in particular when glycosylation and Fc effector function are not needed or are detrimental. For expression of polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the Fc fusion protein may be isolated from the bacterial cell paste in a soluble fraction and can be further purified. As exemplified in the example section, further purification methods include without limitation purification using a Protein A column.

In addition to prokaryotes, eukaryotic microbes such as filamentous fungi or yeast are suitable cloning or expression hosts, including fungi and yeast strains whose glycosylation pathways have been "humanized," resulting in the production of an antibody with a partially or fully human glycosylation pattern. See Gerngross, *Nat. Biotech.* 22:1409-1414 (2004), and L1 et al., *Nat. Biotech.* 24:210-215 (2006).

Suitable host cells for the expression of glycosylated proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

D. IL-22 Agonists

In one aspect, the present invention provides IL-22 agonists for method embodiments. The IL-22 agonists have IL-22 biological activity as defined herein. In one embodiment, the IL-22 agonist is an antibody. In certain embodiments, an anti-IL-22 antibody is an agonistic antibody that promotes the interaction of IL-22 with IL-22R. In a particular embodiment, an IL-22 agonist is an antibody that binds IL-22BP and blocks or inhibits binding of IL-22BP to IL-22, and thereby induces or increases an IL-22 activity (e.g., binding to IL-22R). In another embodiment, an IL-22 agonist is an oligopeptide that binds to IL-22. Oligopeptides can be chemically synthesized using known oligopeptide synthesis methodology or can be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length. Such oligopeptides can be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. USA, 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In yet another embodiment, an IL-22 agonist of the present invention is an organic molecule that binds to IL-22, other than an oligopeptide or antibody as described herein. An organic molecule can be, for example, a small molecule. An organic molecule that binds to IL-22 can be identified and chemically synthesized using known methodology (see, e.g., PCT Publication Nos. WO00/00823 and WO00/39585). Such organic molecules are usually less than about 2000 daltons in size, alternatively less than about 1500, 750, 500, 250 or 200 daltons in size, wherein such organic molecules that are capable of binding to IL-22 of the present invention can be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). In a particular embodiment, an IL-22 agonist is an organic molecule that binds IL-22BP and blocks or inhibits binding of IL-22BP to IL-22, and thereby induces or increases an IL-22 activity (e.g., binding to IL-22R). In yet another embodiment, agonists of IL-22 are provided. Exemplary agonists include, but are not limited to, native IL-22 or IL-22R; fragments, variants, or modified forms of IL-22 or IL-22R that retain at least one activity of the native polypeptide; agents that are able to bind to and activate IL-22R; and agents that induce over-expression of IL-22 or IL-22R or nucleic acids encoding IL-22 or IL-22R.

E. Assays

IL-22 Fc fusion protein provided herein may be identified, screened for, or characterized for their physical/chemical properties and/or biological activities by various assays known in the art.

1. Binding Assays and Other Assays

In one aspect, an IL-22 Fc fusion protein of the invention is tested for its receptor binding activity, e.g., by known methods such as ELISA, western blotting analysis, cell surface binding by Scatchard, surface plasmon resonance. In another aspect, competition assays may be used to identify an antibody that competes with the IL-22 Fc fusion protein for binding to the IL-22 receptor. In a further aspect, an IL-22 Fc fusion protein of the invention can be used for detecting the presence or amount of IL-22 receptor or IL22-Binding Protein (soluble receptor) present in a biological sample. In a further aspect, an IL-22 Fc fusion protein of the invention can be used for detecting the presence or amount of IL-22 receptor present in a biological sample. In certain embodiments, the biological sample is first blocked with a non-specific isotype control antibody to saturate any Fc receptors in the sample.

2. Activity Assays

In one aspect, assays are provided for identifying biological activity of IL-22 Fc fusion protein. Biological activity of an IL-22 polypeptide or IL-22 Fc fusion protein may include, e.g., binding to IL-22 receptor, stimulating IL-22 signaling, and inducing STAT3, RegIII and/or PancrePAP expression. Further, in the case of a cardiovascular disease or condition, the biological activity may include affecting the formation of atherosclerotic plaques, in particular to inhibit formation of atherosclerotic plaque formation Inhibition of plaque formation can be assessed by any suitable imaging method known to those of ordinary skill in the art.

F. Conjugates

The invention also provides conjugates comprising an IL-22 Fc fusion protein described herein conjugated to one or more agents for detection, formulation, half-life extension, mitigating immunogenicity or tissue penetration. Exemplary conjugation includes without limitation PEGylation and attaching to radioactive isotopes.

In another embodiment, a conjugate comprises an IL-22 Fc fusion protein as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

G. Methods and Compositions for Detection

In certain embodiments, any of the IL-22 Fc fusion provided herein is useful for detecting the presence of IL-22 receptor in a biological sample. In certain embodiments, the method further comprises the step of blocking any Fc receptors in the sample with a non-specific isotype control antibody. The term "detecting" as used herein encompasses quantitative or qualitative detection. In certain embodiments, a biological sample comprises a cell or tissue, such as epithelial tissues.

In one embodiment, an IL-22 Fc fusion protein for use in a method of detection is provided. In a further aspect, a method of detecting the presence of IL-22 receptor in a biological sample is provided. In certain embodiments, the method comprises contacting the biological sample with an IL-22 Fc fusion protein as described herein under conditions permissive for binding of the IL-22 Fc fusion protein to IL-22 receptor, and detecting whether a complex is formed between the IL-22 Fc fusion protein and IL-22 receptor. In certain embodiments, the method further comprises the step of blocking any Fc receptors in the sample with a non-specific isotype control antibody. Such method may be an in vitro or in vivo method. In one embodiment, an IL-22 Fc fusion protein is used to select subjects eligible for therapy with IL-22 Fc fusion protein, e.g. where IL-22 receptor is a biomarker for selection of patients.

In certain embodiments, labeled IL-22 Fc fusion proteins are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

H. Pharmaceutical Formulations

The IL-22-based compositions (which in certain embodiments, include IL-22 Fc fusion proteins, and IL-22 polypeptide or agonists) herein will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. In one embodiment, the composition can be used for increasing the duration of survival of a human subject susceptible to or diagnosed with the disease or condition disease. Duration of survival is defined as the time from first administration of the drug to death.

Pharmaceutical formulations are prepared using standard methods known in the art by mixing the active ingredient having the desired degree of purity with one or more optional pharmaceutically acceptable carriers (*Remington's Pharmaceutical Sciences* 16th edition, Osol, A. Ed. (1980) and *Remington's Pharmaceutical Sciences* $20^{th}$ edition, ed. A. F Gennaro, 2000, Lippincott, Williams & Wilkins, Philadelphia, Pa.), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Optionally, but preferably, the formulation contains a pharmaceutically acceptable salt, preferably sodium chloride, and preferably at about physiological concentrations.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, benzalkonium chloride and propylparaben are preferred preservatives. Optionally, the formulations of the invention can include a pharmaceutically acceptable surfactant at a concentration of 0.005 to 0.02%.

The formulation herein can also contain more than one active compound as necessary for the particular indication being treated, preferably those with complementary activities that do not adversely affect each other. Such molecules are suitably present in combination in amounts that are effective for the purpose intended.

Exemplary lyophilized formulations are described in U.S. Pat. No. 6,267,958. Aqueous formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a steroid, TNF antagonist or other anti-inflammatory therapeutics Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the IL-22 Fc fusion protein, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

A pharmaceutical composition for topical administration can be formulated, for example, in the form of a topical gel. See e.g., U.S. Pat. No. 4,717,717, U.S. Pat. No. 5,130,298, U.S. Pat. No. 5,427,778, U.S. Pat. No. 5,457,093, U.S. Pat. No. 5,705,485, U.S. Pat. No. 6,331,309 and WO2006/138, 468. In certain embodiments, the composition can be formulated in the presence of cellulose derivatives. In certain other embodiments, the topical formulation can be reconstituted from lyophilized formulation with sufficient buffer or diluent before administration. In certain embodiments, IL-22 polypeptide or IL-22 Fc fusion protein is formulated for topical administration to a subject having a defect in epithelial wound healing. In certain particular embodiments, the epithelial wound healing occurs in the skin. In certain other particular embodiments, the subject is a human having a defect in wound healing. In certain other embodiments, the topical formulation comprising an IL-22 Fc fusion protein of the invention can be used to improve wound healing after internal or external surgical incisions.

In one embodiment of the invention, an IL-22 polypeptide or IL-22 Fc fusion protein for use in accelerating, promoting or improving wound healing is in a formulation of a topical gel, e.g., in a pre-filled syringe or container, or alternatively, the compound of the invention can be mixed with a gel matrix right before topical administration to a patient. In certain embodiments, an additional therapeutic agent is also administered topically, either concurrently or sequentially. Other routes of administration can also be optionally used, e.g., administered by any suitable means, including but not limited to, parenteral, subcutaneous, intraperitoneal, intrapulmonary, intracerobrospinal, subcutaneous, intra-articular, intrasynovial, intrathecal, oral, and intranasal administration. Parenteral infusions include intramuscular, intravenous, intraarterial, intraperitoneal, or subcutaneous administration.

Typically for wound healing, an IL-22 polypeptide or IL-22 Fc fusion protein is formulated for site-specific delivery. When applied topically, the IL-22 polypeptide or IL-22 Fc fusion is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, sprays, or suspensions, with or without purified collagen. The compositions also may be impregnated into sterile dressings, transdermal patches, plasters, and bandages, optionally in liquid or semi-liquid form. An oxidized regenerated cellulose/collagen matrices can also be used, e.g., PROMOGRAN Matrix Wound Dressing or PROMOGRAN PRISMA MATRIX.

Sustained-release preparations may be prepared. Suitable examples of sustained-release preparations include semipermeable matrices of solid hydrophobic polymers containing a polypeptide of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol), polylactides (U.S. Pat. No. 3,773,919), copolymers of L-glutamic acid and gamma ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), poly-lactic-coglycolic acid (PLGA) polymer, and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For obtaining a gel formulation, the IL-22 polypeptide or IL-22 Fc fusion protein formulated in a liquid composition may be mixed with an effective amount of a water-soluble polysaccharide or synthetic polymer to form a gel (e.g., a gelling agent) such as polyethylene glycol to form a formulation of the proper viscosity to be applied topically. The polysaccharide or gelling agent that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; Sodium carboxymethyl cellulose; POE-POP block polymers: poloxamer USP in various grades; Hyaluronic acid; Polyacrylic acid such as carbopol 940; starch and fractionated starch; agar; alginic acid and alginates; gum Arabic; pullulan; agarose; carrageenan; dextrans; dextrin; fructans; inulin; mannans; xylans; arabinans; chitosans; glycogens; glucans; and synthetic biopolymers; as well as gums such as xanthan gum; guar gum; locust bean gum; gum Arabic; tragacanth gum; and karaya gum; and derivatives, combinations and mixtures thereof. In one embodiment of the invention, the gelling agent herein is one that is, e.g., inert to biological systems, nontoxic, simple to prepare, and/or not too runny or viscous, and will not destabilize the IL-22 polypeptide or IL-22 Fc fusion held within it.

In certain embodiments of the invention, the polysaccharide is an etherified cellulose derivative, in another embodiment one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose (all referred to as cellulosic agents). In some embodiments, the polysaccharide is hydroxyethyl methylcellulose or hydroxypropyl methylcellulose.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

In certain embodiments, methylcellulose is employed in the gel, for example, it comprises about 1-5%, or about 1%, about 2%, about 3%, about 4% or about 5%, of the gel and the IL-22 polypeptide or IL-22 Fc fusion protein is present in an amount of about 50-2000 µg, 100-2000 µg, or 100-1000 µg per ml of gel. In certain embodiments, the effective amount of IL-22 polypeptide or IL-22 Fc fusion protein for wound healing by topical administration can be about 25 µg to about 500 µg, about 50 µg to about 300 µg, about 100 µg to about 250 µg, about 50 µg to about 250 µg, about 50 µg to about 150 µg, about 75 µg, about 100 µg, about 125 µg, about 150 µg, about 175 µg, about 200 µg, about 225 µg, about 250 µg, about 300 µg, or about 350 µg, per cm$^2$ wound area.

The formulations to be used for in vivo administration are generally sterile. Sterility may be readily accomplished, e.g., by filtration through sterile filtration membranes.

The present invention provides dosages for the IL-22-based therapeutics. For example, depending on the type and severity of the disease, about 1 µg/kg to 15 mg/kg (e.g. 0.1-20 mg/kg) of polypeptide is an initial candidate dosage for administration to the subject, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens can be useful. The progress of this therapy is easily monitored by conventional techniques and assays.

For the prevention or treatment of disease, the appropriate dosage of a polypeptide of the invention (when used alone or in combination with one or more other additional therapeutic agents) will depend on the type of disease to be treated, the type of polypeptide, the severity and course of the disease, whether the polypeptide is administered for preventive or therapeutic purposes, previous therapy, the subject's clinical history and response to the polypeptide, and the discretion of the attending physician. The polypeptide is suitably administered to the subject at one time or over a series of treatments. Depending on the type and severity of the disease, about 1 µg/kg to 20 mg/kg (e.g. 0.1 mg/kg-15 mg/kg) of the polypeptide can be an initial candidate dosage for administration to the subject, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the polypeptide would be in the range from about 0.05 mg/kg to about 20 mg/kg. Thus, one or more doses of about 0.5 mg/kg, 2.0 mg/kg, 4.0 mg/kg, 10 mg/kg, 12 mg/kg, 15 mg/kg, or 20 mg/kg (or any combination thereof) may be administered to the subject. In certain embodiments, about 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10 mg/kg, 12 mg/kg, 15 mg/kg, or 20 mg/kg (or any combination thereof) may be administered to the subject. Such doses may be administered intermittently, e.g. every week, every two weeks, or every three weeks (e.g. such that the subject receives from about two to about twenty, or e.g. about six doses of the polypeptide). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

The compounds of the invention for prevention or treatment of a cardiovascular disease or condition, metabolic syndrome, acute endotoxemia or sepsis, or diabetes are typically administered by intravenous injection.

Other methods of administration can also be used, which includes but is not limited to, topical, parenteral, as intravenous, subcutaneous, intraperitoneal, intrapulmonary, intranasal, ocular, intraocular, intravitreal, intralesional, intracerobrospinal, intra-articular, intrasynovial, intrathecal, oral, or inhalation administration. Parenteral infusions include intramuscular, intravenous, intraarterial, intraperitoneal, or subcutaneous administration. In addition, the compounds described herein are administered to a human subject, in accord with known methods, such as intravenous administration as a bolus or by continuous infusion over a period of time.

I. Therapeutic Methods and Compositions

Any of the IL-22 Fc fusion proteins or IL-22 polypeptides or IL-22 agonists provided herein may be used in therapeutic methods.

a) Inflammatory Bowel Disease

In one aspect, an IL-22 Fc fusion protein for use as a medicament is provided. In further aspects, an IL-22 Fc fusion protein for use in treating IBD, including UC and CD, is provided. In certain embodiments, an IL-22 Fc fusion protein for use in a method of treatment is provided. In certain embodiments, the invention provides an IL-22 Fc fusion protein for use in a method of treating an individual having UC or CD comprising administering to the individual an effective amount of the IL-22 Fc fusion protein. In one such embodiment, the method further comprises administering to the individual an effective amount of at least one additional therapeutic agent, e.g., as described below. In further embodiments, the invention provides an IL-22 Fc fusion protein for use in enhancing epithelial proliferation, differentiation and/or migration. In certain particular embodiments, the epithelial tissue is intestinal epithelial tissue. In certain embodiments, the invention provides an IL-22 Fc fusion protein for use in a method of enhancing epithelial proliferation, differentiation and/or migration in an individual comprising administering to the individual an effective amount of the IL-22 Fc fusion protein to enhance epithelial proliferation, differentiation and/or migration. In yet other embodiments, the invention provides an IL-22 Fc fusion protein for use in treating diabetes, especially type II diabetes, diabetic wound healing, metabolic syndromes and atherosclerosis. In certain embodiments, the invention provides an IL-22 Fc fusion protein for use in a method of treating diabetes, especially type II diabetes, diabetic wound healing, metabolic syndromes and atherosclerosis in an individual comprising administering to the individual an effective amount of the IL-22 Fc fusion protein. See Genentech applications, application Ser. No. 61/800,795, entitled "Using an IL-22 polypeptide for wound healing," and, application Ser. No. 61/801,144, entitled "Methods of treating cardiovascular conditions and metabolic syndrome using an IL-22 polypeptide," both filed on Mar. 15, 2013. The disclosures of both of the applications are incorporated herein by reference in their entireties. An "individual" or "subject" or "patient" according to any of the above embodiments is preferably a human.

In a further aspect, the invention provides for the use of an IL-22 polypeptide or IL-22 Fc fusion protein in the manufacture or preparation of a medicament. In one embodiment, the medicament is for treatment of IBD and wound healing. In a further embodiment, the medicament is for use in a method of treating IBD and wound healing comprising administering to an individual having IBD an effective amount of the medicament. In one such embodiment, the method further comprises administering to the individual an effective amount of at least one additional therapeutic agent, e.g., as described below. In a further embodiment, the medicament is for suppressing inflammatory response in the gut epithelial cells. In a further embodiment, the medicament is for use in a method of enhancing epithelial proliferation, differentiation and/or migration in an individual comprising administering to the individual an amount effective of the medicament to enhance epithelial proliferation, differentiation and/or migration. An "individual" according to any of the above embodiments may be a human.

In a further aspect, the invention provides a method for treating IBD, including UC and CD. In one embodiment, the method comprises administering to an individual having IBD an effective amount of an IL-22 polypeptide or an IL-22 Fc fusion protein. In one such embodiment, the method further comprises administering to the individual an effective amount of at least one additional therapeutic agent, as described below. An "individual" according to any of the above embodiments may be a human.

In a further aspect, the invention provides a method for enhancing epithelial proliferation, differentiation and/or migration in an individual. In one embodiment, the method comprises administering to the individual an effective amount of an IL-22 polypeptide or IL-22 Fc fusion protein to enhance epithelial proliferation, differentiation and/or migration. In one embodiment, an "individual" is a human.

b) Other Therapeutic Indications

The present invention provides IL-22-based therapeutic agents for cardiovascular diseases and conditions, metabolic syndrome, acute endotoxemia and sepsis, and diabetes. For the prevention, treatment or reduction in the severity of a given disease or condition, the appropriate dosage of a compound of the invention will depend on the type of disease or condition to be treated, as defined above, the severity and course of the disease or condition, whether the agent is administered for preventive or therapeutic purposes, previous therapy, the subject's clinical history and response to the compound, and the discretion of the attending physician. The compound is suitably administered to the subject at one time or over a series of treatments. Preferably, it is desirable to determine the dose-response curve and the pharmaceutical composition of the invention first in vitro, and then in useful animal models prior to testing in humans.

In one aspect, the present invention provides methods of treatment for a cardiovascular disease or disorder, metabolic syndrome, acute endotoxemia and sepsis, and an insulin-related disorder. In one embodiment, the method comprises administering to a subject in need a therapeutically effective amount of an IL-22 polypeptide, an IL-22 Fc fusion protein, or an IL-22 agonist. In another aspect, the invention provides a method for the delaying or slowing down of the progression of a cardiovascular disease or disorder, metabolic syndrome, and an insulin-related disorder. In one embodiment, the method comprises administering to subject diagnosed with the disease, condition, or disorder, an effective amount of an IL-22 polypeptide, IL-22 Fc fusion protein, or IL-22 agonist. In another aspect, the invention provides a method for preventing indicia of a cardiovascular disease or disorder, and an insulin-related disorder. In one embodiment, the method comprises administering an effective amount of an IL-22 polypeptide, IL-22 Fc fusion protein, or IL-22 agonist to a subject at risk of the disease, condition, or disorder, wherein the IL-22 polypeptide, IL-22 Fc fusion protein, or IL-22 agonist is effective against the development of indicia of the disease, condition, or disorder.

Cardiovascular Diseases and Conditions

In one aspect, the IL-22 polypeptides, IL-22 Fc fusion proteins and IL-22 agonists provide a preventative or prophylactic effect against the development of, or the progression of, clinical and/or histological and/or biochemical and/or pathological indicia (including both symptoms and signs) of cardiovascular diseases or conditions in a subject. In one embodiment, the disease or condition is atherosclerosis. In one embodiment, the indicia include atherosclerotic plaque formation and/or vascular inflammation. In another embodiment, the subject is at risk for cardiovascular disease. In general, a subject at risk will previously have had a cardiovascular disease or condition as described herein, or will have a genetic predisposition for a cardiovascular disease or condition.

The efficacy of the treatment of cardiovascular diseases and conditions can be measured by various assessments commonly used in evaluating cardiovascular diseases. For example, cardiovascular health can be assessed. Cardiovascular health can be evaluated by, but not limited to, e.g., blood tests (e.g., total cholesterol, LDL-C, HDL-C, triglyceride, C-reactive protein, fibrinogen, homocysteine, fasting insulin, ferritin, lipoprotein, LPS), blood pressure, auscultation, electrocardiogram, cardiac stress testing, cardiac imaging (e.g., coronary catheterization, echocardiogram, intravascular ultrasound, positron emission tomography, computed tomography angiography, and magnetic resonance imaging).

Metabolic Syndrome

In one aspect, the IL-22 polypeptides, IL-22 Fc fusion proteins and IL-22 agonists provide a therapeutic, preventative or prophylactic effect against the development of, or the progression of, clinical and/or histological and/or biochemical and/or pathological indicia (including both symptoms and signs) of metabolic syndrome (or metabolic disorder or disease) in a subject. In one or more embodiment, the subject is at risk for metabolic syndrome.

The efficacy of the treatment of metabolic syndrome can be measured by various assessments commonly used in evaluating metabolic syndrome. For example, obesity can be measured. As a further example, hyperglycemia, dyslipidemia, insulin resistance, chronic adipose tissue inflammation, and/or hypertension can be measured. Reduction in in levels of one or more of C-reactive protein, IL-6, LPS, and plasminogen activator inhibitor 1 can be measured. These measurements can be performed by any methods well known in the art.

Insulin-Related Disorders

For insulin-related disorders, the term "treatment" refers to both therapeutic treatment and prophylactic or preventative measures for the disorder, wherein the object is to prevent or slow down (lessen) the targeted pathologic condition or disorder. Those in need of treatment include those already with an insulin-related disorder as well as those prone to have such a disorder or those in whom the disorder is to be prevented.

In one aspect, the IL-22 polypeptides, IL-22 Fc fusion proteins and IL-22 agonists provide a preventative or prophylactic effect against the development of, or the progression of, clinical and/or histological and/or biochemical and/or pathological indicia (including both symptoms and signs) of an insulin-related disorder in a subject. In one embodiment, the disorder is Type I diabetes, Type II diabetes, or gestational diabetes. In one embodiment, the pathology or pathological indicia include one or more of: little or no insulin production by the pancreas (e.g., islet cells), insulin resistance, and hyperglycemia. In another embodiment, the subject is at risk for an insulin-related disorder. In general, a subject at risk has a genetic predisposition for an insulin-related disorder, has been exposed to a virus that triggers autoimmune destruction of islet cells (e.g., Epstein-Barr virus, coxsackievirus, mumps virus or cytomegalovirus), is obese, is pre-diabetic (higher than normal blood sugar levels), or has gestational diabetes.

The efficacy of the treatment of an insulin-related disorder can be measured by various assessments commonly used in evaluating such disorders. For example, both Type I and Type II diabetes can be evaluated with one or more of the following: a glycated hemoglobin test (A1C), a regular blood sugar test, and a fasting blood sugar test. Type I can also be evaluated by testing for autoantibodies in the blood and/or ketones in the urine. Type II can also be evaluated by testing for oral glucose tolerance.

Acute Endotoxemia and Sepsis

In one aspect, the IL-22 polypeptides, IL-22 Fc fusion proteins and IL-22 agonists provide a therapeutic, preventative or prophylactic effect against the development of, or the progression of, clinical and/or histological and/or biochemical and/or pathological indicia (including both symptoms and signs) of acute endotoxemia, sepsis, or both, in a subject. In one or more embodiment, the subject is at risk for acute endotoxemia, sepsis, or both.

The efficacy of the treatment of acute endotoxemia, sepsis, or both can be measured by various assessments commonly used in evaluating acute endotoxemia, sepsis, or both. For example, reduction in in levels of LPS or inflammatory markers can be measured. These measurements can be performed by any methods well known in the art.

Wound Healing

There are a variety of ways to measure wound healing. Often images are taken to calculate linear dimensions, perimeter and area. The NIH has a free program, Image J, that allows measurement of wound areas from an image. The final healing prognosis can be extrapolated from initial healing rates based on the migration of the periphery towards the center. This is done using a number of mathematical equations, the most common of which is a modified Gilman's equation. In addition to visual inspection, wound healing measurement can also be aided by spectroscopic methods or MRI. See e.g., Dargaville et al., Biosensors Bioelectronics, 2013, 41:30-42, Tan et al., 2007, British J. Radiol. 80:939-48. If healing is slow/inadequate, biopsies of the wound edges may be taken to rule out or determine infection and malignancy. In certain embodiments, the acceleration or improvement of wound healing can be assessed by comparing wound closure in IL-22-treated and control wounds. In certain embodiments, the acceleration or improvement of wound healing is at least 20%, 30%, 40%, 50%, 60%, 70%, 80% or 90% faster or better than the control.

In certain aspect, the invention provides methods for promoting/accelerating/improving healing of a wound with or without active infection, microbial contamination or colonization in the wound. The IL-22 polypeptides, IL-22 Fc fusion proteins or IL-22 agonists can be used for treating infected wounds or promoting/accelerating/improving infected wound healing. In certain embodiments, the IL-22 polypeptides, IL-22 Fc fusion proteins or IL-22 agonists can be used for treating wounds, or promoting/accelerating/improving wound healing, in the presence of infection. In some embodiments, the IL-22 polypeptides, IL-22 Fc fusion proteins or IL-22 agonists can be used for treating wounds or promoting/accelerating/improving wound healing in the presence of microbial contamination or colonization with risk for infection. In further embodiments, the patient in need of wound healing treatment can be a diabetic patient. Accordingly, in some embodiments, the wound is a diabetic wound, for example, diabetic foot ulcer. In some further embodiments, the wound is an infected diabetic wound, for example, infected diabetic foot ulcer.

In a further aspect, the invention provides pharmaceutical formulations comprising an IL-22 polypeptide, IL-22 Fc fusion protein or IL-22 agonist provided herein, e.g., for use in any of the above therapeutic methods. In one embodiment, a pharmaceutical formulation comprises an IL-22 polypeptide, IL-22 Fc fusion protein or IL-22 agonist provided herein and a pharmaceutically acceptable carrier. In another embodiment, a pharmaceutical formulation comprises an IL-22 polypeptide, IL-22 Fc fusion protein or IL-22 agonist provided herein and at least one additional therapeutic agent, e.g., as described below.

IL-22 Fc fusion protein of the invention can be used either alone or in combination with other agents in a therapy. For instance, an IL-22 polypeptide, IL-22 Fc fusion protein or IL-22 agonist of the invention may be co-administered with at least one additional therapeutic agent. In certain embodiments, an additional therapeutic agent is an immune suppressant that reduces the inflammatory response including without limitation methotrexate, TNF inhibitor, TNF antagonist, mesalazine, steroid, dexamethasone, and azathioprine, and combination thereof. Suitable additional therapeutic agents that reduce an inflammatory response include without limitation 5-aminosalicylic acid (5-ASA), mercaptopurine (also called 6-mercaptopurine or 6-MP) or combination thereof. In certain embodiments, the IL22 polypeptide or IL-22 Fc fusion may be co-administered with one or more additional therapeutic agents that reduce an inflammatory response (for example, 5-ASA, 6-MP, or an TNF antagonist) for the treatment of IBD. In certain other embodiments, the IL22 polypeptide or IL-22 Fc fusion may be co-administered with an integrin antagonist such as etrolizumab for the treatment of IBD. In one embodiment, the IL-22 polypeptide or IL-22 Fc fusion protein is used in combination with an IL-22 agonist.

For accelerating chronic wound healing, such as for the treatment of diabetic foot ulcer, the administration of an IL-22 polypeptide or fragments or variants thereof, IL-22 Fc fusion proteins or IL-22 agonists can be combined with one or more additional wound healing agents. Suitable additional wound healing agents include without limitation growth factors (e.g., EGF, FGF, IGF, PDGF, TGF, and VEGF), nerve growth factor (NGF), angiogenesis factors (e.g., HGF, TNF-α, angiogenin, IL-8, angiopoietins 1 and 2, Tie-2, integrin α5, matrix metalloproteinases, nitric oxide, COX-2), members of the platelet derived growth factor (PDGF) family (e.g., PDGF-A, PDGF-B, PDGF-C, and PDGF-D), members of the insulin growth factor (IGF) family (e.g., IGF-I, IGF-II), members of the transforming growth factor (TGF) family (e.g., TGF-α TGF-β) and anabolic oxygen (vacuum therapy). In certain embodiments, the IL-22 polypeptide or IL-22 Fc fusion can be co-administered with one or more additional wound healing agents described herein and/or one or more antibacterial agents or antibiotics suitable for use in topical administration. See WO2006/138468, incorporated herein by reference in its entirety. In such embodiments, the antibiotic can be sulfur antibiotic including without limitation silver sulfadiazine, i.e., silvadeen. The co-administered one or more additional agents can be administered concurrently, alternatively or sequentially with IL-22 polypeptide, IL-22 fusion protein or IL22 agonist.

In further exemplary embodiments, if the target is prevention or treatment of cardiovascular diseases or conditions or metabolic syndrome, the administration of an IL-22 polypeptide or fragments or variants thereof, IL-22 Fc fusion proteins or IL-22 agonists can be combined with or supplement the administration of the cholesterol-lowering agents such as statins (e.g., lovastatin, rosuvastatin, fluvastatin, atorvastatin, pravastatin, and simvastatin), bile acid binding resins (colestipol, cholestyramine sucrose, and colesevelam), ezetimibe, or a ezetimibe-simvastatin combination; anti-platelet agents such as cyclooxygenase inhibitors (aspirin), adenosine diphosphate (ADP) receptor inhibitors (clopidogrel, prasugrel, ticagrelor, ticlopidine), phosphodiesterase inhibitors (cilostazol), glycoprotein IIB/IIIA inhibitors (abciximab, eptifibatide, tirofiban), adenosine reuptake inhibitors (dipyridamole), thromboxane inhibitors (thromboxane synthase inhibitors, thromboxane receptor antagonists, terutroban); beta blockers such as alprenolol, bucindolol, carteolol, carvedilol, labetalol, nadolol, oxprenolol, penbutolol, pindolol, propranolol, sotalol, timolol, eucommia bark, acebutolol, atenolol, betaxolol, bisoprolol, celiprolol, esmolol, metoprolol, nebivolol, butaxamine, ICI-118, 551, and SR 59230A; angiotensin-converting enzyme (ACE) inhibitors such as captopril, zofenopril, dicarboxylate-containing agents (enalapril, ramipril, quinapril, perindopril, lisinopril, benazepril, imidapril, zofenopril), phosphonate-containing agents (fosinopril), casokinins, lactokinins, lactotripeptides (Val-Pro-Pro, and Ile-Pro-Pro produced by the probiotic *Lactobacillus helveticus* or derived from casein); calcium channel blockers such as dihydropyridines (e.g., amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, and pranidipine), phenylalkylamine (e.g., verapamil), benzothiazepines (e.g., diltiazem), mibefradil, bepridil, fluspirilene, and fendiline; diuretics such as high ceiling loop diuretics (e.g., furosemide, ethacrynic acid, torsemide and bumetanide), thiazides (e.g., hydrochlorothiazide acid), carbonic anhydrase inhibitors (e.g., acetazolamide and methazolamide), potassium-sparing diuretics (e.g., aldosterone antagonists: spironolactone, and epithelial sodium channel blockers: amiloride and triamterene), and calcium-sparing diuretics, and pharmaceutically acceptable salts, acids or derivatives of any of the above.

For insulin-related disorders or metabolic syndrome, the administration of an IL-22 polypeptide or fragments or variants thereof or IL-22 Fc fusion protein or IL-22 agonists can be combined with or supplement the administration of various therapeutic agents. In the case of Type I diabetes (insulin-dependent diabetes mellitus or IDDM), the IL-22 polypeptide, Fc fusion protein or agonist described herein are combined with one or more of regular insulin replacement therapy (including rapid-acting and long-acting insulin), immunosuppression treatment, islet transplantation and stem cell therapy. In one embodiment, the regular insulin replacement therapy includes, without limitation, regular insulin (e.g., Humulin R, Novolin R), insulin isophane (e.g., Humulin N, Novolin N), insulin lispro (e.g., Humalog), insulin aspart (e.g., NovoLog), insulin glargine (e.g., Lantus) and insulin detemir (e.g., Levemir). In other embodiments, the insulin replacement therapy further includes pramlintide (Symlin).

In the case of Type II diabetes (non-insulin dependent diabetes mellitus or NIDDM) or metabolic syndrome, the IL-22 polypeptide, Fc fusion protein and agonist described herein can be combined with one or more of insulin replacement therapy (as discussed above), an agent to lower glucose production by the liver, an agent to stimulate pancreatic production and release of insulin, an agent that blocks enzymatic break down of carbohydrates or increases insulin sensitivity. In one embodiment, the agent to lower glucose production is metformin (e.g., Glucophage, Glumetza). In another embodiment, the agent to stimulate pancreatic production and release of insulin is glipizide (e.g., Glucotrol, Glucotrol XL), glyburide (e.g., DiaBeta, Glynase) and glimepiride (e.g., Amaryl). In one other embodiment, the agent that blocks enzymatic break down of carbohydrates or increases insulin sensitivity is pioglitazone (e.g., Actos). In another embodiment, the IL-22 polypeptide, Fc fusion protein and agonist can be combined with one of the following replacements for metformin: sitagliptin (e.g., Januvia), saxagliptin (e.g., Onglyza), repaglinide (e.g., Prandin) and nateglinide (e.g., Starlix). Exenatide (e.g., Byetta) and liraglutide (e.g., Victoza). In another embodiment, the IL-22 polypeptide, Fc fusion protein and agonist are combined with an oral hypoglycemic agent, e.g., sulfonylureas.

In the case of gestational diabetes or metabolic syndrome, the IL-22 polypeptide, Fc fusion and agonist described herein are combined with an oral blood sugar control medication. In one embodiment, the medication is glyburide.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Such combination therapies noted above encompass combined administration (where two or more therapeutic agents are included in the same or separate formulations), and separate administration, in which case, administration of the IL-22 polypeptide or IL-22 Fc fusion protein of the invention can occur prior to, simultaneously, and/or following, administration of the additional therapeutic agent or agents. In one embodiment, administration of the IL-22 Fc fusion protein and administration of an additional therapeutic agent occur within about one month, or within about one, two or three weeks, or within about one, two, three, four, five, or six days, of each other.

An IL-22 polypeptide or IL-22 Fc fusion protein of the invention (and any additional therapeutic agent) can be administered by any suitable means, including parenteral, intrapulmonary, topical and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

IL-22 polypeptide or IL-22 Fc fusion protein of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The IL-22 polypeptide or IL-22 Fc fusion protein need not be, but is optionally formulated with one or more agents currently used to prevent or treat the disorder in question. The effective amount of such other agents depends on the amount of the fusion protein present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an IL-22 Fc fusion protein of the invention (when used alone or in combination with one or more other additional therapeutic agents) will depend on the type of disease to be treated, the type of Fc region, the severity and course of the disease, whether the fusion protein is administered for preventive or therapeutic purposes, previous therapy, the patient's clinical history and response to the IL-22 Fc fusion protein, and the discretion of the attending physician. The IL-22 Fc fusion protein is suitably administered to the patient at one time or over a series of treatments. Depending on the type and severity of the disease, about 1 µg/kg to 15 mg/kg (e.g. 0.1 mg/kg-10 mg/kg) or about 0.1 µg/kg to 1.5 mg/kg (e.g., 0.01 mg/kg-1 mg/kg) of the IL-22 Fc fusion protein can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the IL-22 Fc fusion protein would be in the range from about 0.05 mg/kg to about 10 mg/kg. Certain other dosages include the range from about 0.01 mg/kg to about 10 mg/kg, about 0.02 mg/kg to about 10 mg/kg, and about 0.05 mg/kg to about 10 mg/kg. Thus, one or more doses of about 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 2.0 mg/kg, 3.0 mg/kg, 4.0 mg/kg, 5 mg/kg, 6 mg/kg, 7 mg/kg, 8 mg/kg, 9 mg/kg or 10 mg/kg (or any combination thereof) may be administered to the patient. For topical wound healing, one or more doses of about 0.001 mg/cm$^2$-about 10 mg/cm$^2$ wound area, about 0.05 mg/cm$^2$-about 5 mg/cm$^2$ wound area, about 0.01 mg/cm$^2$-about 1 mg/cm$^2$ wound area, about 0.05 mg/cm$^2$-about 0.5 mg/cm$^2$ wound area, about 0.01 mg/cm$^2$-about 0.5 mg/cm$^2$ wound area, about 0.05 mg/cm$^2$-about 0.2 mg/cm$^2$ wound area, or about 0.1 mg/cm$^2$-about 0.5 mg/cm$^2$ wound area (or any combination thereof) may be administered to the patient. In certain embodiments, one or more doses of about 0.01 mg/cm$^2$, 0.02 mg/cm$^2$, 0.03 mg/cm$^2$, 0.04 mg/cm$^2$, 0.05 mg/cm$^2$, 0.06 mg/cm$^2$, 0.07 mg/cm$^2$, 0.08 mg/cm$^2$, 0.09 mg/cm$^2$, 0.1 mg/cm$^2$, 0.15 mg/cm$^2$, 0.2 mg/cm$^2$, 0.25 mg/cm$^2$, 0.3 mg/cm$^2$, 0.4 mg/cm$^2$, or 0.5 mg/cm$^2$ wound area may be administered to the patient. Such doses may be administered intermittently, e.g. every week or every three weeks (e.g. such that the patient receives from about two to about twenty, or e.g. about six doses of the IL-22 Fc fusion protein). An initial higher loading dose, followed by one or more lower doses may be administered. However, other dosage regimens may be useful. The progress of this therapy is easily monitored by conventional techniques and assays. Similar dosage ranges can be applied to an IL-22 polypeptide.

It is understood that any of the above formulations or therapeutic methods may be carried out using conjugate of the invention in place of or in addition to an IL-22 Fc fusion protein.

J. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an IL-22 Fc fusion protein of the invention. The label or package insert indicates that the composition is used for treating the condition of choice. Moreover, the article of manufacture may comprise (a) a first container with a composition contained therein, wherein the composition comprises an IL-22 Fc fusion protein of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include a conjugate of the invention in place of or in addition to an IL-22 Fc fusion protein.

K. Screening Assays and Animal Models

As exemplified in the Example sections, IL-22, IL-22 Fc fusion protein and IL-22 agonists can be evaluated in a variety of cell-based assays and animal models of IBD, cardiovascular diseases or conditions and metabolic syndrome.

Recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., Proc. Natl. Acad. Sci. USA 82, 6148-615 [1985]); gene targeting in embryonic stem cells (Thompson et al., Cell 56, 313-321 [1989]); electroporation of embryos (Lo, Mol. Cell. Biol. 3, 1803-1814 [1983]); sperm-mediated gene transfer (Lavitrano et al., Cell 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of appropriate pathology, such as cardiovascular disease pathology, for example by histological examination and/or imaging or ultrasound analysis to determine atherosclerotic plaque burden and vascular function (see Examples below). Blocking experiments can also be performed in which the transgenic animals are treated with IL-22, IL-22 Fc fusion protein or a candidate agonist to determine the extent of effects on atherosclerotic plaque formation, including the size, number, and degree of plaque formation. In these experiments, blocking antibodies which bind to the polypeptide of the invention are administered to the animal and the biological effect of interest is monitored.

Alternatively, "knock out" animals can be constructed which have a defective or altered gene encoding IL-22, as a result of homologous recombination between the endogenous gene encoding the IL-22 polypeptide and altered genomic DNA encoding the same polypeptide introduced into an embryonic cell of the animal. For example, cDNA encoding IL-22 can be used to clone genomic DNA encoding IL-22 in accordance with established techniques. A portion of the genomic DNA encoding IL-22 can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the IL-22 polypeptide.

Thus, the biological activity of IL-22 or its potential agonists can be further studied in murine IL-22 knock-out mice.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

The following are examples of methods and compositions of the invention. It is understood that various other embodiments may be practiced, given the general description provided above, and the examples are not intended to limit the scope of the claims.

Example 1 Cloning, Expression and Purification of the IL-22 Fc Fusion Protein

General molecular cloning and protein purification techniques can be applied in the following experiments.

i. Cloning

Full-length human IL-22 was cloned from a human colon cDNA library (Genentech). Constructs expressing human IgG1 or IgG4 IL-22Fc fusion protein were generated for this experiment using overlapping PCR technique using the following primers: IL-22 Fc fusion IgG1 forward primer: TTGAATTCCACCATGGGATGGTCATGTATCATC-CTTTTTCTAGTAGCAACTGCAACT GGAGTACAT-TCAGCGCCCATCAGCTCCCACTGCAGGC (SEQ ID NO:52), IL-22 Fc fusion IgG1 reverse primer AGGTC-GACTCATTTACCCGGAGACAGGGAGAGG (SEQ ID NO:53), IL-22 Fc fusion IgG4 forward primer: TTGAAT-TCCACCATGGGATGGTCATGTATCATC-CTTTTTCTAGTAGCAACTGCAACT GGAGTACAT-TCAGCGCCCATCAGCTCCCACTGCAGGC (SEQ ID NO:54), IL-22 Fc fusion IgG4 reverse primer: AGGTC-GACTTATTTACCCAGAGACAGGGAGAGG (SEQ ID NO:55). The PCR products were cloned into expression vectors pRK5.sm (Genentech). The leader sequence (or signal peptide) was cleaved in the cell and the mature IL-22 Fc fusion did not contain the leader sequence. The clones carrying artificial linkers were cloned with primers containing the linker sequences. The N297G mutation was further introduced by mutagenesis PCR using the following primers: IgG1 N297G forward primer: GCG GGA GGA GCA GTA CGG AAG CAC GTA CCG TGT GG (SEQ ID NO:56), IgG1 N297G reverse primer: CCA CAC GGT ACG TGC TTC CGT ACT GCT CCT CCC GC (SEQ ID NO:57), IgG4 N297G forward primer: ACA AAG CCG CGG GAG GAG CAG TTC GGA AGC ACG TAC CGT GTG GTC AGC GTC (SEQ ID NO:58), and IgG4 N297G reverse primer: GAC GCT GAC CAC ACG GTA CGT GCT TCC GAA CTG CTC CTC CCG CGG CTT TGT (SEQ ID NO:59). Sequences of all IL-22Fc constructs were confirmed by DNA sequencing.

ii. Cell Culture

CHO cells were grown in suspension by splitting the culture 2 times per week to $0.3 \times 10^6$ cells/ml in an incubator set at 37° C. and 5% $CO_2$.

iii. Transfection of IL-22 Fc Fusion Protein into CHO Cells and Protein Expression CHO cells were seeded at $1.23 \times 10^6$ cells/ml in 720 mL culture medium. The transfection complex (1.6 mL PEI+800 ug DNA in 80 mL serum free media) was incubated for 10 min before added to the cells. The culture was incubated at 33° C., 5% $CO_2$ for 24 hours. After further culturing for 14 days, the supernatant of the culture was harvested via centrifugation. Transient CHO conditioned media (supernatant from above) was purified using the MabSelect Sure (GE Healthcare) protein A affinity column. The eluate at low pH was neutralized to pH5.0 and further purified through a gel filtration column (GE Healthcare). The eluted peak was pooled, formulated and sterile filtered. The glycosylation status of the Fc region of the fusion protein was analyzed by Mass Spectrometry as discussed below.

iv. Establishment of Stable Clones Expressing IL-22 Fc Fusion Protein

The plasmid encoding IL-22 Fc fusion protein was introduced into CHO cells by transfection using Lipofectamine 2000 CD (Invitrogen). After transfection, the cells were centrifuged and re-plated into serum-free selective medium. Isolates were selected for secretion of IL-22 Fc. Clones with the highest titer, as identified by ELISA, were then pooled and scaled for production.

v. Expression of IL-22 Fc Fusion Protein in *E. coli*

*E. coli* fermentation feedstock was homogenized and conditioned to 0.4% w/w PEI pH 6.7 and centrifuged. Centrate was purified using a MabSelect Sure (GE Healthcare) protein A affinity column. The eluate at low pH was neutralized to pH 5.0 and further purified through an ion exchange chromatography. Fractions were pooled, formulated and sterile filtered.

Example 2 IL-22 Fc Fusion Protein Exhibited High Percentage of Afucosylation in the Fc Region In this study, the glycosylation status of the Fc portion of the IL-22 Fc fusion proteins was examined. Samples of purified IL-22 Fc fusion proteins from transiently transfected cells were digested with trypsin (1:25 trypsin:IL-22 Fc, w/w) for 2 hrs at 37° C. Samples were acidified with trifluoroacetic acid to a final concentration of 0.1% and injected onto a heated C18 column (PLRP-S, 1000 A 8 um, Agilent) equilibrated with 0.05% TFA in water. The digestion products were separated by a linear acetonitrile gradient (5 to 60%) over 20 min time. The column was directly connected to the electrospray orifice of an Agilent 6520B TOF Mass Spectrometer and the masses of the eluted fractions were determined in positive ion mode. Since the Fc portions of these fusion constructs are stable in trypsin under these digestion conditions, a direct comparison of the carbohydrate status of various IL-22 fusions could be made.

Figure 2C:
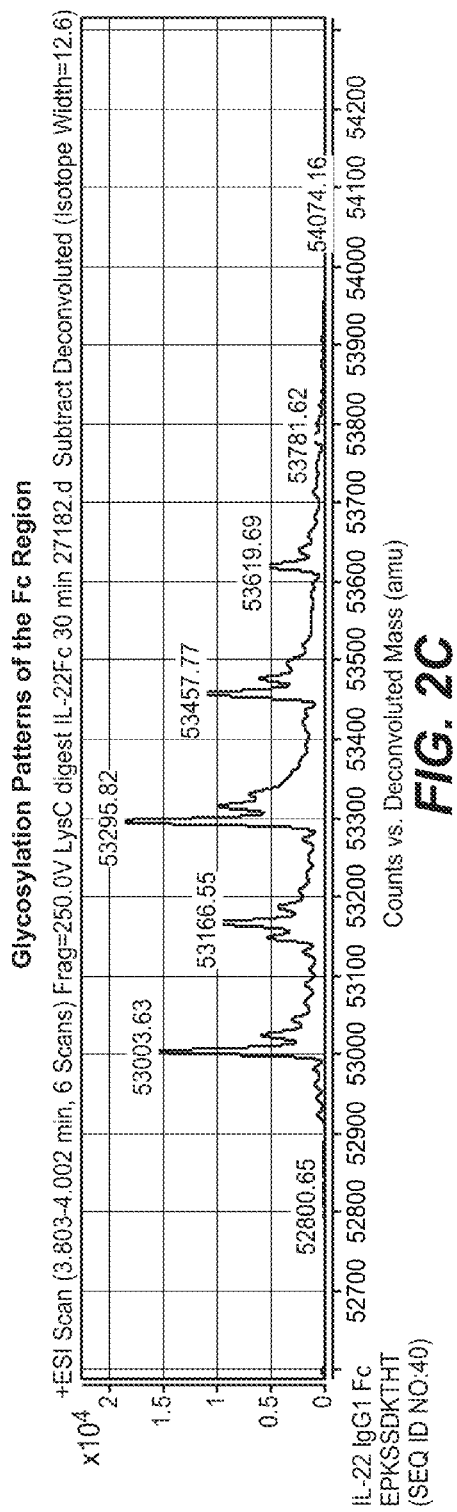
FIG. 2 shows mass spectrometry results of the glycosylation status of the Fc region of a typical human monoclonal IgG1 Fc (Panel A), IL-22 IgG1 Fc fusion containing the linker sequence EPKSCDKTHT (SEQ ID NO:33, Panel B), EPKSSDKTHT (SEQ ID NO:40, Panel C), and GGGDKTHT (SEQ ID NO:41, Panel D), and IL-22 IgG4 Fc fusion containing the linker sequence RVESKYGPP without or with the N297G mutation (SEQ ID NO:44, Panels E and F, respectively) and IL-22 IgG1 Fc fusion containing the linker sequence EPKSSDKTHT (SEQ ID NO:40) with the N297G mutation (Panel G).
Figure 2D:
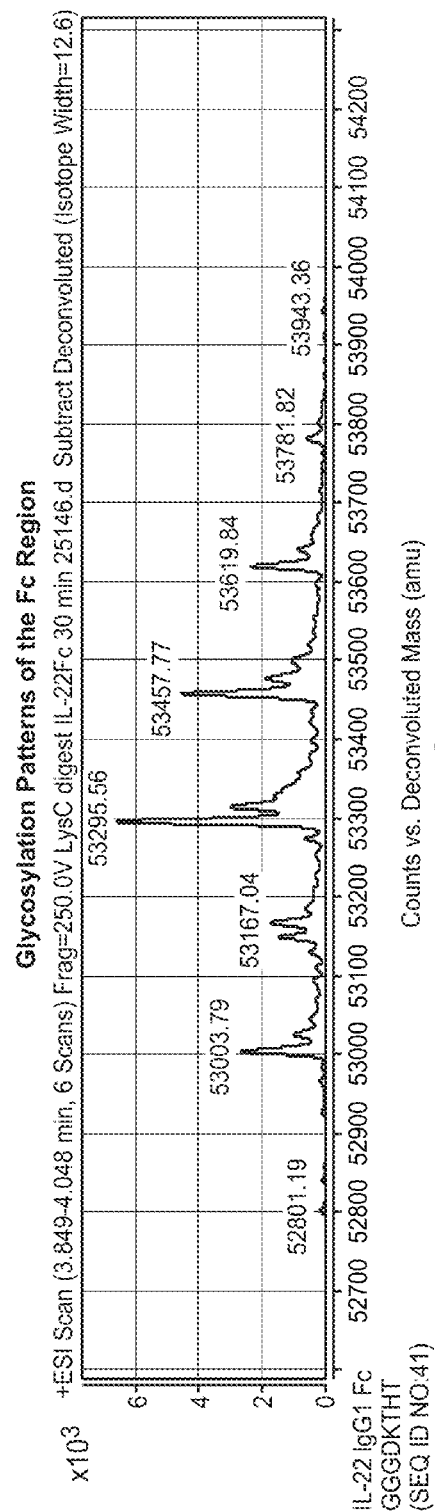
Figure 2G:
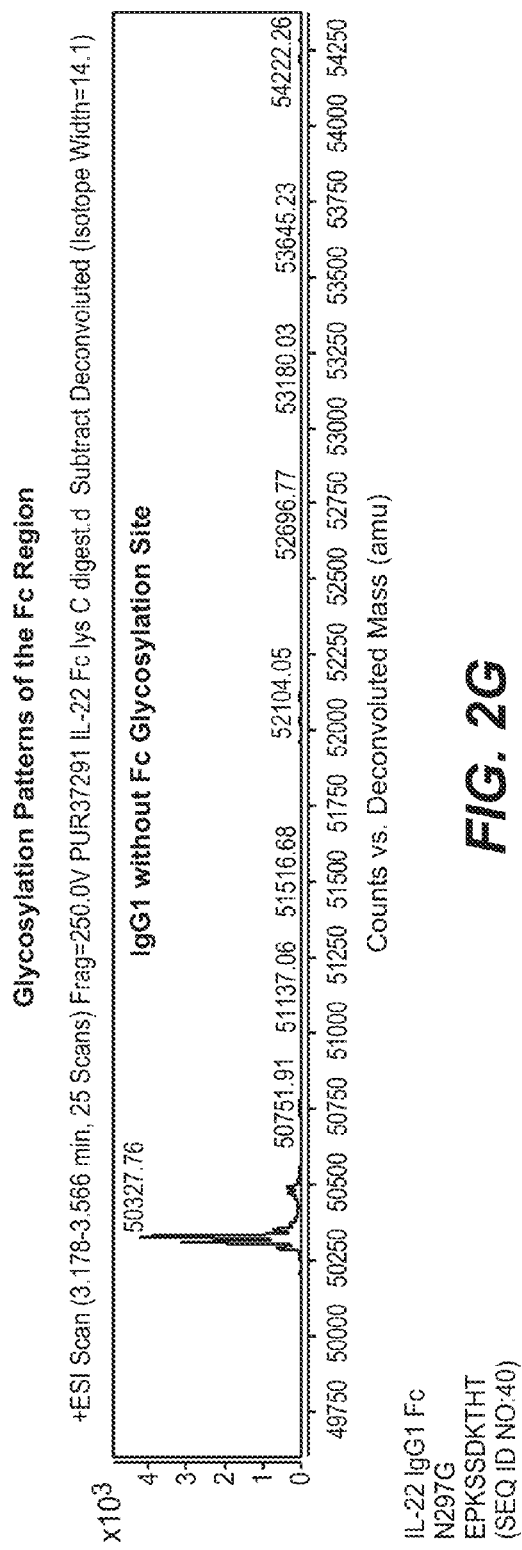

As shown in FIG. 2, both IL-22 IgG1 and IgG4 Fc fusion proteins showed abnormally high levels of afucosylation. The expected masses for a glycosylated Fc of a typical monoclonal IgG1 antibody would be those labeled as 53296, 53458 and 53620 Da of panel A in FIG. 2. Typically the core carbohydrate species on each arm of the Fc would each consist of the following carbohydrate composition: 4 N-acetyl glucosamine, 3 mannose and 1 fucose sugar species (as on the peak labeled 53296 in Panel A). The addition of one or two galactose sugars would produce the peaks labeled 53458 and 53620 Da, respectively (Panel A). A negligible amount of molecules containing sugar moieties that was missing fucose on one arm of the Fc was detected ("−1 fucose").

Surprisingly, human IL-22 IgG1 Fc fusion proteins of different constructs in which the CH2 domain is glycosylated all exhibited high level of afucosylation, including sugar moieties missing fucose on one arm ("−1 fucose") and both arms of Fc ("−2 fucose"). See FIG. 2, Panels B-D. These afucosylated molecules comprised as high as about 30% of the total species observed. Afucosylation can increase the undesirable effector activities of the IL-22 IgG1 Fc fusion.

IgG4 is known to have less effector function as compared to IgG1. Unexpectedly, results of Mass Spectrometry analysis also showed the "−1 fucose" and "−2 fucose" glycosylated species in the trypsin-digested Fc regions of human IL-22 IgG4 Fc fusion protein. These afucosylated molecules comprised more than 50% of the total species observed. FIG. 2, Panel E. Afucosylated antibodies have much enhanced ADCC or CDC cytotoxicity activities, a property not desirable with these IL-22 Fc fusion proteins.

Subsequently, two additional IL-22 Fc molecules, one containing IgG1 Fc and the other IgG4 Fc were constructed in which the residue in the Fc that would normally be glycosylated (N297) was mutated to a glycine (N297G) thereby preventing attachment of the normal core sugar. These were shown to be devoid of any sugar on their Fc portions and both had their expected Fc molecular weights based on their amino acid sequences (FIG. 2, Panels F and G).

In summary, the Fc region of the human IL-22 Fc fusion proteins, either IgG1 or IgG4 Fc fusion, showed high levels of afucosylation, which can result in increased ADCC or CDC activities, a property not desirable for use as IL-22 therapeutics. Thus, the non-glycosylated variants were tested in further studies.

Example 3 IL-22 IgG1 and IgG4 Fc Fusion Protein In Vitro Activity Assay

IL-22 engages IL-22 receptor complex and activates Jak-Stat signaling pathway. STAT3 activation is a predominant event in IL-22 mediated signaling pathway. In this experiment, the in vitro activities of IL-22 Fc fusion proteins were measured using a luciferase reporter assay. HEK 293 cells were engineered to overexpress human IL-22 receptor complex IL22R1 and IL10R2. On day 1, $1 \times 10^5$ 293 cells were seeded in 24-well plates in 0.4 ml Dulbecco's modified Eagle Medium (DMEM)+10% Fetal Bovine Serum (FBS). On day 2, cells were transfected with a STAT3-driven luciferase reporter and a *Renilla* luciferase control using Lipofectamine 2000 (Invitrogen) in 0.1 ml reduced serum media (Gibco Poti-MEM with reduced serum reduced by at least 50%). The STAT3 luciferase reporter construct contains STAT3-responsive luciferase reporter construct containing tandem repeats of the sis-inducible element (SIE) and the firefly luciferase reporter gene. On day 3, IL-22 Fc fusion proteins produced by either transient or stable CHO clones were titrated into different concentrations in 0.5 ml media, and added on top of transfected cells. On day 4, media were removed and cells were lysed with 100 ul passive lysis buffer (provided by the Dual-Luciferase Reporter 1000 Assay System). Twenty microliter of cell lysates were transferred into 96-well plate and analyzed with Dual-Luciferase Reporter 1000 Assay System on luminometer (Promega). The EC50 was calculated based on the dose-dependent activity in GraphPad Prism software (La Jolla, Calif.). The EC50 values for different IL-22 Fc fusion constructs are shown in Table 2 below.

TABLE 2

| IL-22 Fc Constructs | Fc isotype | Linker | Production | EC50 (pM) |
|---|---|---|---|---|
| 1 | huIgG1 | DKTHT (SEQ ID NO: 32) | CHO | 150-200 |
| 2 | huIgG1 | EPKSCDKTHT (SEQ ID NO: 33) | CHO | 350-500 |
| 3 | huIgG1 | VEPKSCDKTHT (SEQ ID NO: 34) | CHO | 100-150 |
| 4 | huIgG1 | KVEPKSCDKTHT (SEQ ID NO: 35) | CHO | 50-75 |

TABLE 2-continued

| IL-22 Fc Constructs | Fc isotype | Linker | Production | EC50 (pM) |
|---|---|---|---|---|
| 5 | huIgG1 | KKVEPKSCDKTHT (SEQ ID NO: 36) | CHO | 25-50 |
| 6 | huIgG1 | DKKVEPKSCDKTHT (SEQ ID NO: 37) | CHO | 25-50 |
| 7 | huIgG1 | VDKKVEPKSCDKTHT (SEQ ID NO: 38) | CHO | 25-50 |
| 8 | huIgG1 | KVDKKVEPKSCDKTHT (SEQ ID NO: 39) | CHO | 2.5-5 |
| 9 | huIgG1 | GGGDKTHT (SEQ ID NO: 41) | CHO | 50-75 |
| 10 | huIgG1 | GGGSTHT (SEQ ID NO: 63) | CHO | 50-100 |
| 11 | huIgG1 | EPKSSDKTHT (SEQ ID NO: 40) | CHO | 50-100 |
| 12 | huIgG1 | DKKVEPKSSDKTHT (SEQ ID NO: 64) | CHO | 25 |
| 13 | huIgG1 | KVDKKVEPKSSDKTHT (SEQ ID NO: 65) | CHO | 25 |
| 14 | huIgG1 | DKTHT (SEQ ID NO: 32) N297A | CHO | 150-200 |
| 15 | huIgG1 | EPKSSDKTHT (SEQ ID NO: 40) N297A | CHO | 50-100 |
| 16 | huIgG1 | DKTHT (SEQ ID NO: 32) (N297G) | CHO | 150-200 |
| 17 | huIgG1 | EPKSSDKTHT (SEQ ID NO: 40) (N297G) | CHO | 50-100 |
| 18 | huIgG1 | KKVEPKSSDKTHT (SEQ ID NO: 66) (N297G) | CHO | 20 |
| 19 | huIgG4 | SKYGPP (SEQ ID NO: 43) | CHO | 150-200 |
| 20 | huIgG4 | SKYGPP (SEQ ID NO: 43) N297G | CHO | 75-100 |
| 21 | huIgG4 | RVESKYGPP (SEQ ID NO: 44) | CHO | 25-50 |
| 22 | huIgG4 | RVESKYGPP (SEQ ID NO: 44) N297G | CHO | 50-75 |
| 23 | huIgG1 | ELKTPLGDTTHT (SEQ ID NO: 42) (IgG3 linker) | CHO | 50-75 |
| 24 | huIgG1 | EPKSSDKTHT (SEQ ID NO: 40) | E. coli | 16 |
| 25 | huIgG1-monomeric IL-22 | EPKSSDKTHT (SEQ ID NO: 40) | E. coli | 82 |

A large number of IL-22 Fc fusion proteins were constructed with linkers of different length and sequences to examine the activities, stability and yield of each design. Linkers with native IgG sequences are preferred to minimize potential risk of immunogenicity; however, linkers with exogenous sequences that showed good in vitro activity were considered and encompassed by the current invention.

The IL-22 IgG1 Fc fusion protein containing the DKTHT linker (SEQ ID NO:32) was tested in the STAT3 luciferase assay. See Table 2. To improve EC50 of the fusion protein, the linker length was increased from 5 to 10 amino acids containing the native IgG1 sequence EPKSCDKTHT (SEQ ID NO:33). The resulting IL-22 Fc fusion protein, however, exhibited reduced in vitro activity. See Table 2. Surprisingly, an increase in the linker length even by one amino acid VEPKSCDKTHT (SEQ ID NO:34) improved the activity of the IL-22 fusion protein. Further increases in the linker length resulted in further improvement in activity. See Table 2.

In separate experiments, the Cys in EPKSCDKTHT was changed to Ser to remove the potential of disulfide bond formation. As shown in Table 2, IL-22 Fc fusion with the linker EPKSSDKTHT (SEQ ID NO:40) showed improved activity as compared to the parent linker sequence with the Cys residue. Longer linker sequence incorporating the upstream sequences (into the CH1 domain of IgG1) further improved activity. Constructs with N297G mutation showed similar EC50 values when compared with the wild type counterparts. IL-22 IgG1 (N297G) Fc fusion protein (SEQ ID NO:12) and IL-22 IgG4 (N297G) Fc fusion protein (SEQ ID NO:8) were chosen for further studies.

Figure 4:
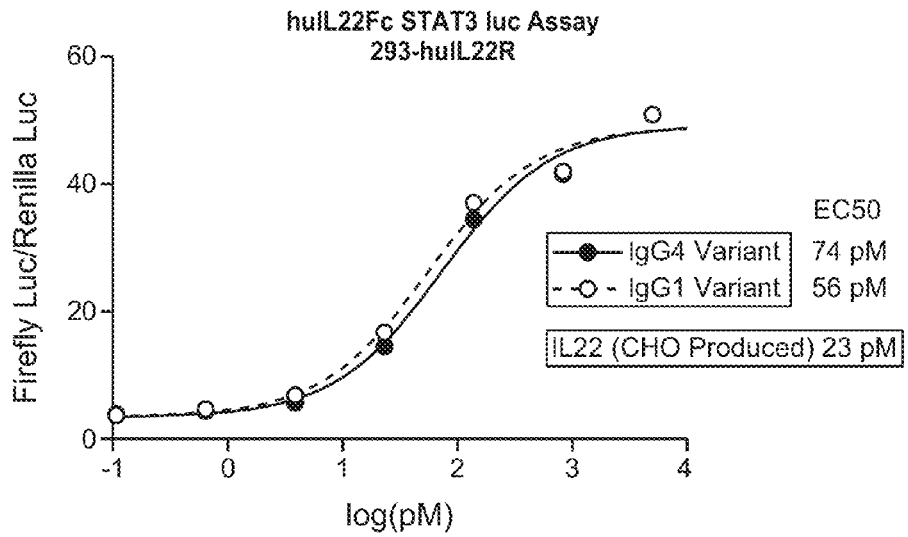
FIG. 4 presents a graph showing the results of STAT3 luciferase assay. Luciferase activity stimulated by IL-22 IgG4 Fc fusion or IL-22 IgG1 Fc fusion was measured in 293 cells expressing human IL-22R. The results show that IL-22 IgG4 and IL-22 IgG1 Fc fusion exhibited similar in vitro activity.

The in vitro activities of human IL-22 IgG1 (N297G) Fc fusion protein (SEQ ID NO:12) or IL-22 IgG4 (N297G) Fc fusion protein (SEQ ID NO:8) expressed from stable clones were tested in the same assay. Data in FIG. 4 show representative results. Both IL-22 IgG1 and IgG4 Fc fusion proteins induced STAT3 activity at a dose-dependent manner. Both IL-22 Fc fusion proteins showed similar potency. IL-22 Fc fusion proteins expressed from transiently transfected cells showed similar results (data not shown). As a control, native IL-22 protein produced in CHO cells was tested in the same assay, and exhibited two to three folds higher potency than the IL-22 Fc fusion proteins.

In summary, both IgG1 and IgG4 IL-22 Fc fusion proteins exhibited in vitro activity demonstrated by STAT3 luciferase assay. Further, IL-22 Fc fusion proteins with linkers of different length and sequences were shown to activate IL-22R mediated luciferase activity.

Example 4 IL-22 Fc Fusion Proteins Reduced Symptoms of DSS-Induced Colitis in Mice Dextran Sodium Sulfate (DSS)-induced colitis is a commonly-accepted mouse colitis model. Oral administration of DSS-containing water rapidly damages colon epithelial cells and causes substantial body weight loss and colon epithelial structure disruption characterized by either immunohistochemical (IHC) staining or histology clinical score by pathologist. In this proof of concept study, the effect of IL-22 Fc fusion protein on DSS-induced colitis was tested.

In C57BL/6 mice, colitis was induced with drinking water containing 3.5% DSS for five consecutive days starting from day 0. Mouse IL-22 IgG2a Fc (SEQ ID NO:60), a surrogate for human IL-22 Fc fusion protein was dosed through intraperitoneal route at 5 mg/Kg on day −1, 1, 4, and 6. Body weight of the animals was measured daily. On day 8, all animals were sacrificed and colon histology was studied through both IHC staining and manual histological score.

Figure 5A:
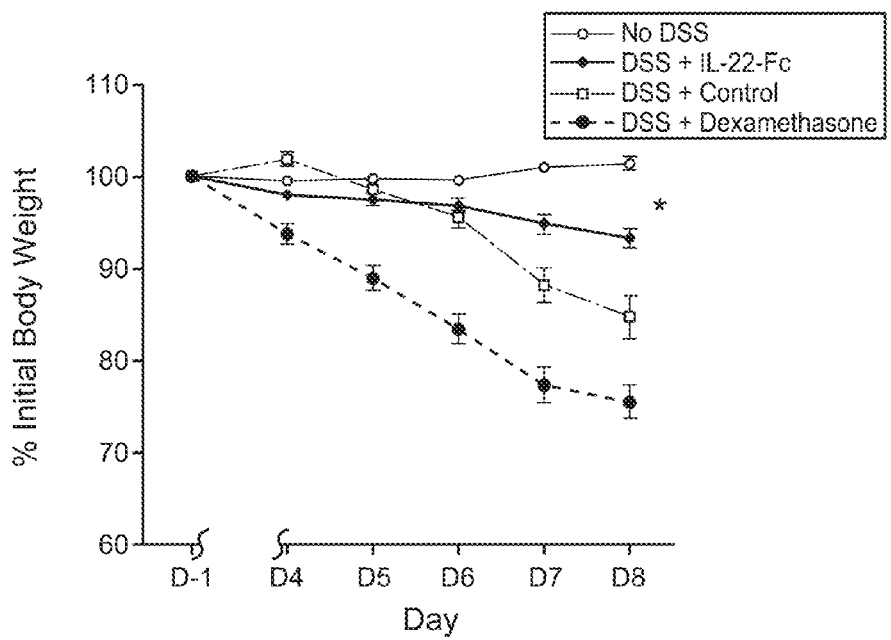
FIG. 5 shows the therapeutic effects of mouse IL-22 Fc fusion protein in the dextran sodium sulfate (DSS)-induced mouse IBD model. Mouse IL-22 Fc fusion protein improved colon histology in the DSS-induced IBD mice (FIG. 5B) and the improvement was translated to reduced colon histology score (FIG. 5C). IL-22 Fc fusion protein treatment resulted in reduced weight loss of the mice during treatment as compared to dexamethasone, currently the best standard of care in this model (FIG. 5A).
Figure 5C:
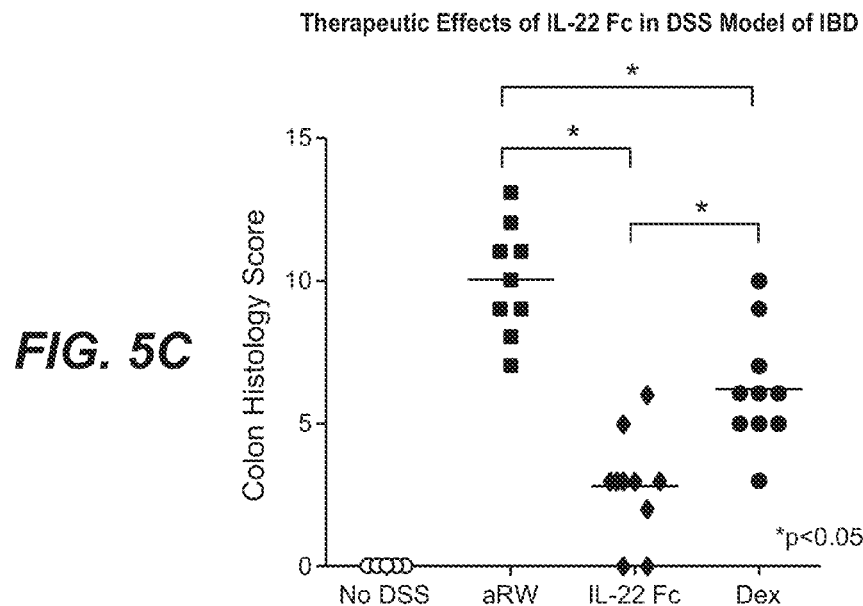

As shown in FIG. 5, DSS induced colitis is associated with dramatic body weight loss (FIG. 5A), colonic epithelial damage and colon inflammation (FIG. 5B) and high histology score (FIG. 5C). IL-22Fc treatment significantly prevented weight loss, restored epithelial integrity, diminished inflammation and reduced histology score. See FIG. 5. The efficacy of IL-22 Fc exceeded the effect of dexamethasone, the steroid standard of care (SOC) that caused significant body weight loss in this study.

Example 5 IL-22 Fc Fusion Protein Pharmacokinetics Study

The pilot safety and PKPD study in cynomolgus monkeys was approved by the Institutional Animal Care and Use Committee (IACUC). The study was conducted at Charles River Laboratories (CRL) Preclinical Services (Reno, Nev.). A total of 15 male cynomolgus monkeys (4-5 kg) from CRL stock were randomly assigned to five groups (n=3/group). Animals in group 1 were given an intravenous (i.v.) dose of the control vehicle on Days 1 and 8. Animals in groups 2 and 3 were given a single i.v. bolus dose of IL22-Fc IgG1 at 0.15 and 1.5 mg/kg, respectively, on Days 1 and 8. Animals in groups 4 and 5 were given a single i.v. bolus dose of IL22-Fc IgG4 at 0.15 and 1.5 mg/kg, respectively, on Days 1 and 8. Serum samples were collected at various time points for PK and PD analysis out to Day 43 and concentrations of IL22-Fc were assessed by ELISA.

For analysis of human IL-22-Fc in cynomolgus monkey serum, mouse anti-human IL-22 mAb (Genentech) was used as a capture antibody in an ELISA assay. The recombinant IL-22 Fc fusion protein was used to develop a standard curve. Plate-bound IL-22-Fc was detected during a 1 hour incubation with HRP-conjugated anti-human-Fcγ-pan murine mAb (Genentech) diluted to 500 ng/mL in assay buffer. After a final wash, tetramethyl benzidine peroxidase substrate (Moss, Inc., Pasadena, Md.) was added, color was developed for 15 minutes, and the reaction was stopped with 1 M phosphoric acid. The plates were read at 450 nm with a 620 nm reference using a microplate reader. The concentrations of IL-22 Fc fusion were calculated from a four-parameter fit of the IL-22 Fc fusion standard curve.

For PK data calculations, Study Day 1 was converted to PK Day 0 to indicate the start of dose administration. All time points after the in life dosing day are calculated as Study Day minus 1. The serum concentration data for each animal were analyzed using 2 compartment analysis with WinNonlin®, Version 5.2.1 (Pharsight; Mountain View, Calif.).

The plasma concentrations of IL22-Fc showed a bi-exponential decline after i.v. dosing (0.15 mg/kg and 1.5 mg/kg) with a short distribution phase and a long terminal elimination phase. See FIG. 6. The two-compartment model with linear elimination of IL-22 Fc from the central compartment described the pharmacokinetic profiles for both the doses well, suggesting negligible target mediated disposition at these dose ranges.

Figure 6:
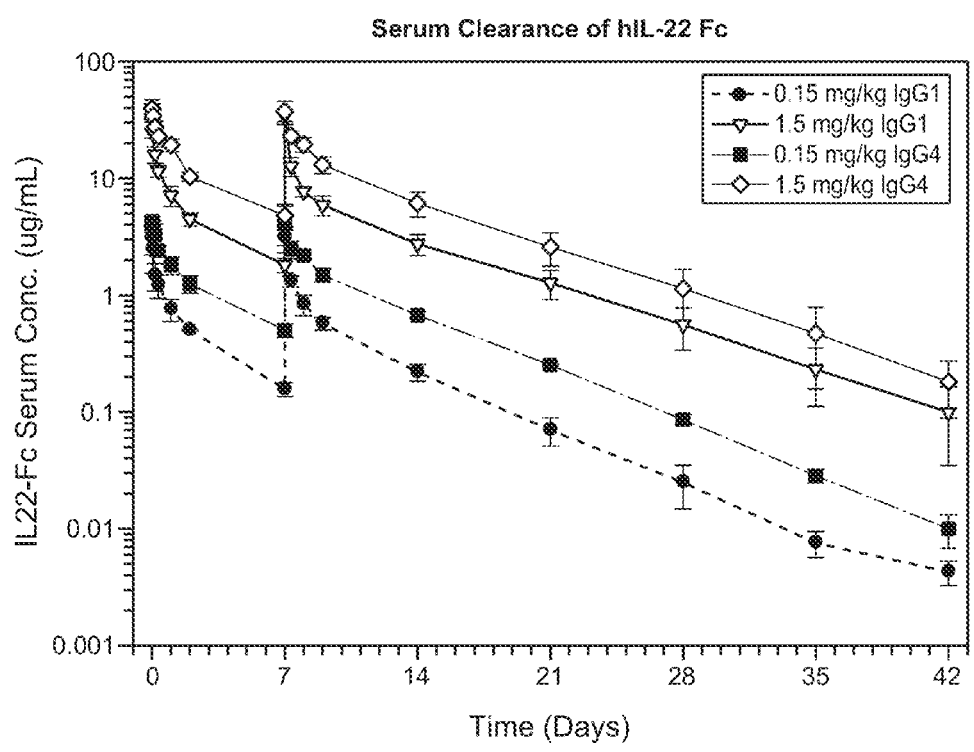
FIG. 6 shows the rate of serum clearance of human IL-22 IgG4 and IgG1 Fc fusion proteins in cynomolgus monkeys dosed at 0.15 mg/kg and 1.5 mg/kg on day 0 and day 7.

The maximum serum concentration ($C_{max}$) and area-under-serum-concentration-time-curve (AUC) estimated by the two-compartmental analysis were roughly linear and dose-proportional. See Table 3. The dose-proportional kinetics suggested IL-22R saturation at the doses tested. As shown in FIG. 6, the IL-22 IgG4 Fc fusion unexpectedly showed a 2-fold slower CL and greater than 2-fold higher exposure compared to the IgG1 Fc fusion. Without limiting to particular mechanisms, the faster clearance (CL) of IgG1 fusion may be due to less stability of the IgG1 fusion construct because the greater than 2-fold faster CL of the IL-22 IgG1 Fc fusion appeared to be mainly driven by a larger volume of distribution. The Beta half-lives of 4-5 days were similar between IgG1 and IgG4 fusions.

TABLE 3

| Group | AUC (day · µg/mL) | $C_{max}$ (ug/mL) | CL (mL/day/kg) | Beta_HL* (day) |
|---|---|---|---|---|
| 0.15 mg/kg IgG1 | 4.47 ± 0.603 | 2.70 ± 0.607 | 34.0 ± 4.26 | 4.02 ± 0.478 |
| 1.5 mg/kg IgG1 | 51.1 ± 9.70 | 30.5 ± 4.14 | 30.1 ± 6.18 | 5.33 ± 0.580 |
| 0.15 mg/kg IgG4 | 11.3 ± 0.752 | 3.99 ± 0.432 | 13.3 ± 0.853 | 4.61 ± 0.394 |
| 1.5 mg/kg IgG4 | 102 ± 18.9 | 33.4 ± 4.02 | 15.0 ± 2.58 | 5.80 ± 0.770 |

*Beta half-life

Example 6 Assessment of In Vivo Activity of IL-22Fc in Cynomolgus Monkey

Cynomolgus monkeys (*Macaca fascicularis*) were dosed intravenously with IL-22 Fc fusion of isotype IgG1 or IgG4 as indicated, at doses of 0.15 mg/kg or 1.5 mg/kg. IL-22 binding to IL-22 receptor triggers the expression of several genes including Serum Amyloid A (SAA), RegIII/Pancreatitis Associated Protein (PAP, also called PancrePAP), and Lipopolysaccharide Binding Protein (LPS-BP). In this study, IL-22 Fc fusion protein in vivo activities were analyzed by measuring the expression of SAA, PancrePAP, and LPS-BP. Serum samples were obtained over a time course pre- and post-dose, as indicated in the graph. Circulating levels of monkey SAA were quantified in serum using a commercial enzyme-linked immunosorbent assay (ELISA) kit (catalog #3400-2) available from Life Diagnostics (West Chester, Pa.). Circulating levels of RegIII/PAP were quantified in serum using a commercial ELISA kit (catalog PancrePAP) produced by Dynabio (Marseille, France).

Levels of Lipoprotein Binding Protein (LBP) in serum samples were determined by using a qualified ELISA. Biotinylated-Lipoprotein (Enzo Life Sciences, Farmingdale, N.Y.) was coated on a Streptavidin coated microtiter plate (Thermo; Rockland, Ill.). Recombinant human LBP (R&D Systems, Inc., Minneapolis, Minn.) was used as a standard in the assays. Bound LBP analyte was detected with an anti-LBP mouse monoclonal antibody (Thermo, Rockland, Ill.). Horseradish peroxidase (HRP)-conjugated F(ab')$_2$ fragment goat anti-mouse IgG, Fc (Jackson ImmunoResearch, West Grove, Pa.) was used for detection. The colorimetric signals were visualized after addition of 3,3',5,5'-tetramethylbenzidine (TMB) substrate (Kirkegaard & Perry Laboratories, Gaithersburg, Md.). The reaction was stopped by addition of 1 M phosphoric acid and absorbance was measured at 450 nm using 650 nm as reference on a plate reader (Molecular Devices, Sunnyvale, Calif.). All ELISA samples were run according to manufacturer's specifications and were prepared either at a single dilution in duplicate or at four serial dilutions in singlicate and concentrations were interpolated from a standard curve. The mean value of each sample was reported.

Figure 7A:
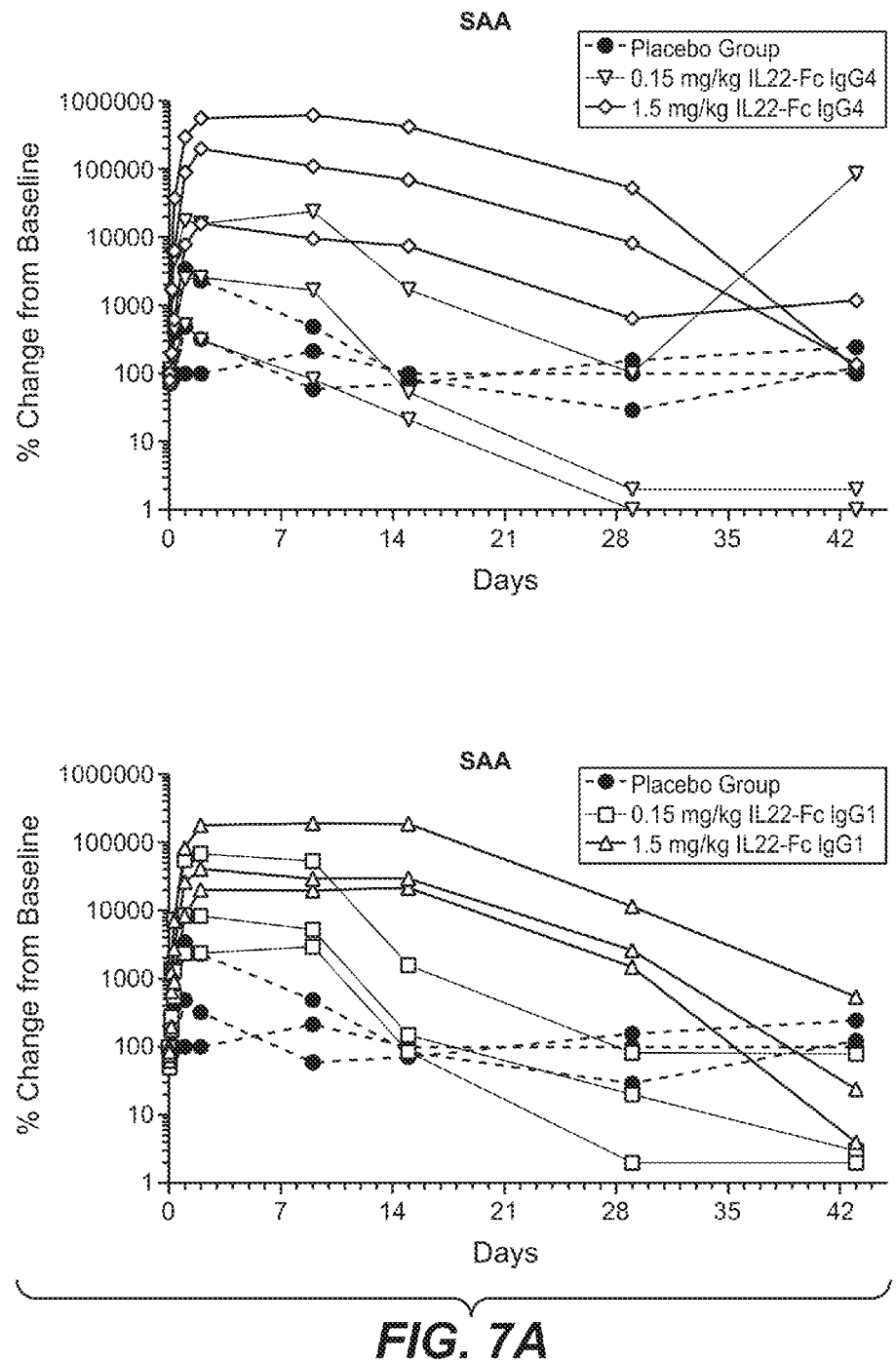
FIG. 7A shows dose-dependent increases in serum amyloid A (SAA), FIG. 7B shows does-dependent increases in lipopolysaccharide binding protein (LPS-BP), FIG. 7C shows dose-dependent increases in RegIII/Pancreatitis Associated Protein (PAP or PancrePAP), following hIL-22 Fc administration.
Figure 7B:
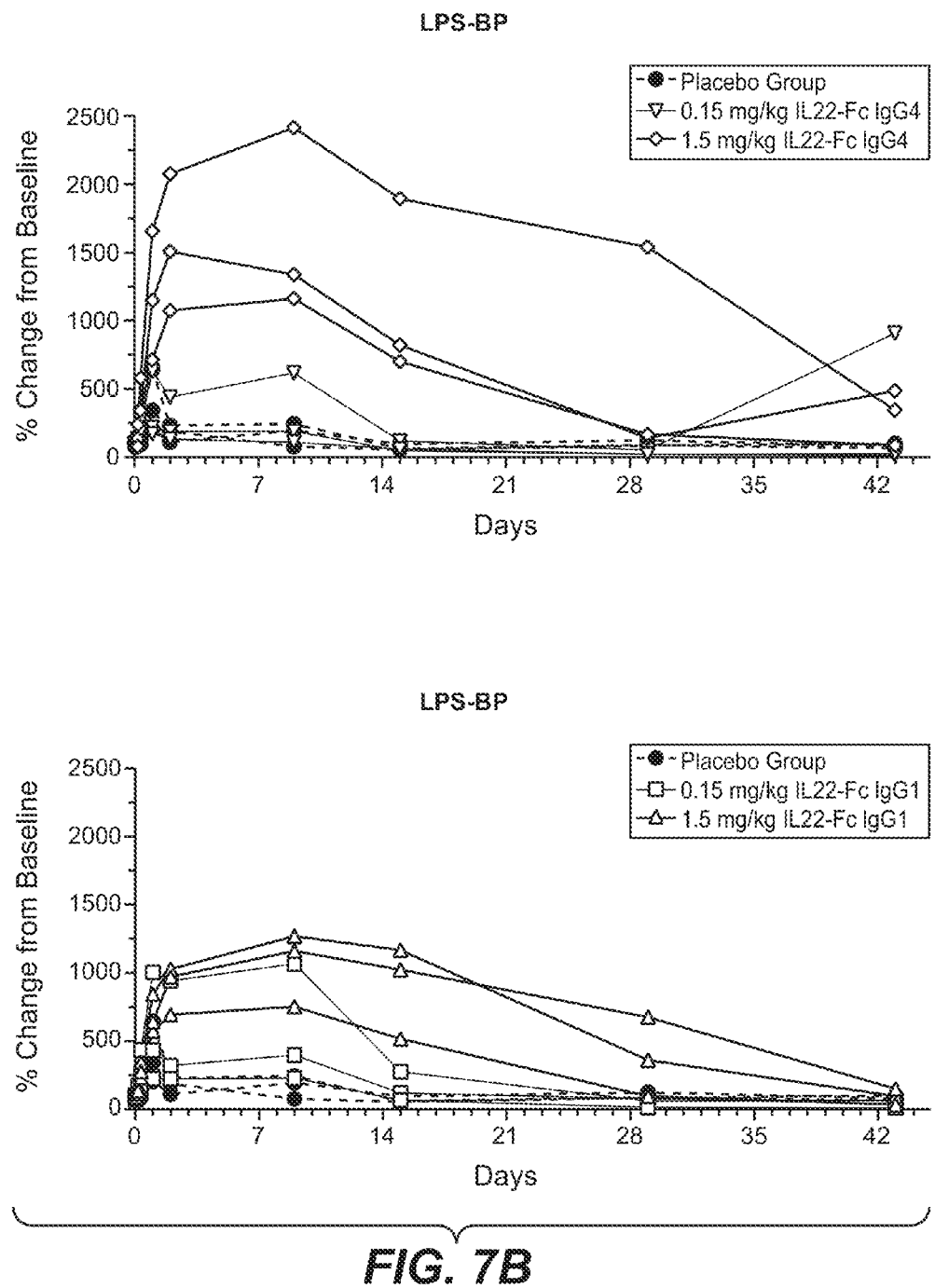
FIG. 7 shows the serum levels of three IL-22R downstream genes in cynomolgus monkeys after dosing at 0.15 mg/kg and 1.5 mg/kg at day 1 and day 8 (same dosing regimen as day 0 and day 7 in FIG. 6.
Figure 7C:
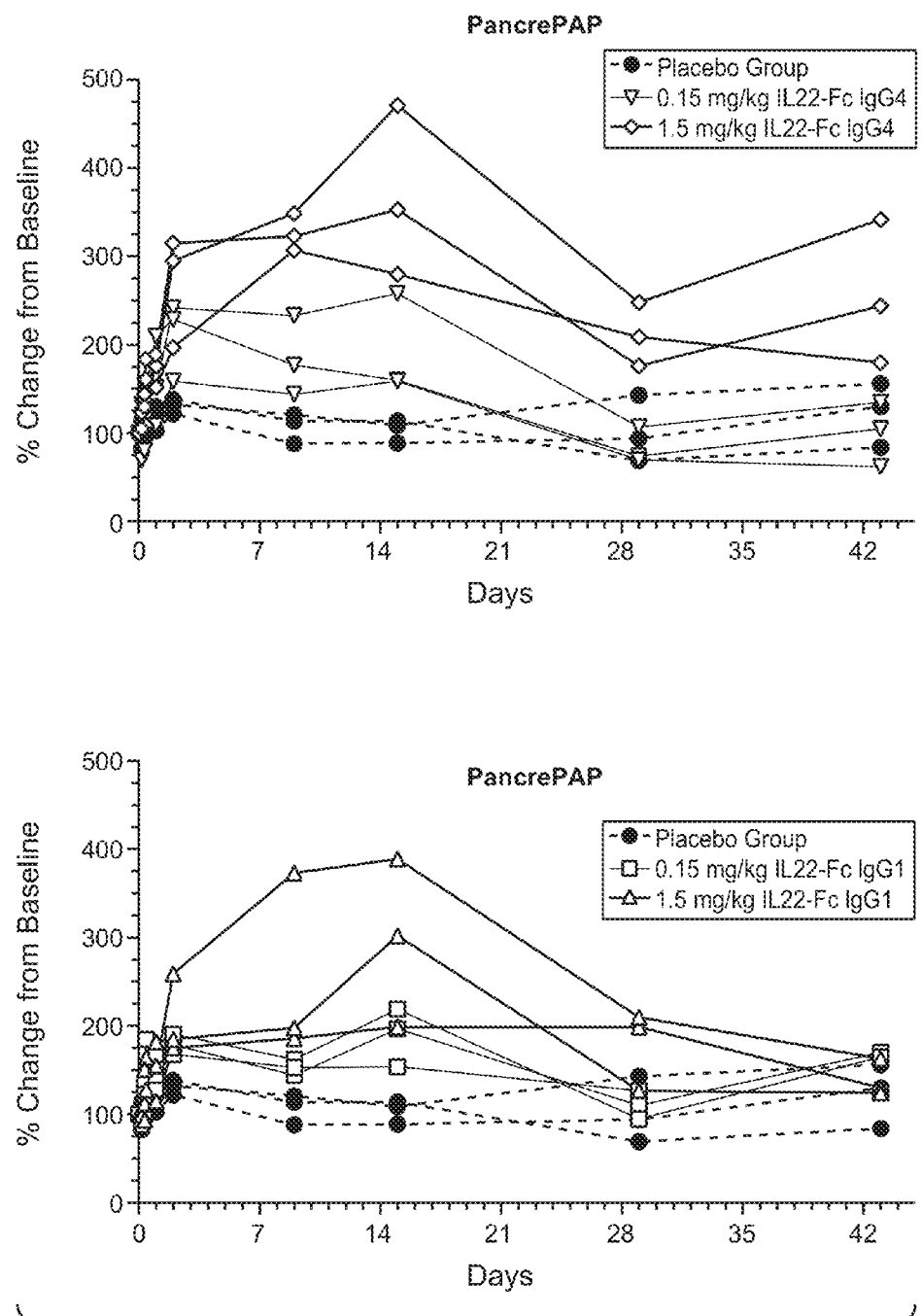

As shown in FIG. 7, SAA, LPS-BP, and RegIII/PAP serum protein levels were induced by IL-22Fc in vivo. Dose-dependent responses were observed in vivo in non-human primates, indicating IL-22R engagement and suggesting saturation by IL-22Fc. In the majority of cases, no increase in the serum protein levels was observed 24 hours after the second dose, suggesting that serum SAA, LPS-BP, and RegIII/PAP proteins had reached the maximal levels. Serum levels of all three proteins declined slowly over the 35-day recovery period, returning to baseline in most animals. The exception being the RegIII/PAP levels in the IgG4 high dose group, which appeared to stay elevated throughout the 42-day course. This may reflect improved PK and increased exposure by AUC for the IL-22 IgG4 Fc fusion protein as compared to IL-22 IgG1 Fc fusion protein.

Example 7 IL-22 Treatment of Atherogenic Prone Mice (Ldlr−/−Apobec1−/−)

Recent studies have revealed IL-22's role in host defense against pathogenic microbes. Its beneficial effects on mucosal tissue homeostasis and immunity led us to speculate that IL-22 treatment could alleviate endotoxemia and its pathological consequences including atherogenic dyslipidemia, systemic inflammation and ultimately slowing the progression of atherosclerotic disease and related disorders including diabetes.

To test this hypothesis atherogenic prone mice (Ldlr−/−Apobec1−/−) were treated with an IL-22-Fc construct. These mice lack the LDL receptor and synthesis exclusively apoB100. This model is unique in that it recapitulates much of the pathophysiology associated with human familial hypercholesterolemia. Specifically, on a chow diet, these mice develop elevated LDL cholesterol, a lipid profile with a distribution of cholesterol similar to humans, and progressive plaque formation. Further, Ldlr−/−Apobec−/− mice have measurable risk factors that contribute to its cardiovascular disease, including insulin resistance, systemic inflammation, progressive plague burden, and endothelial cell dysfunction. Here we demonstrate that the 3 months of treatment with the IL-22-Fc fusion protein can dramatically improve the cardiovascular health of these animals and reduce atherosclerotic progression.

Material and Methods

Mouse IL-22-Fc Constructs.

The IL-22-Fc construct and polypeptide used herein was typically a mouse IL-22-mouse-Fc fusion protein (SEQ ID NO:73) as shown in FIG. 32A (and DNA sequence encoding it as shown in FIG. 32B, SEQ ID NO:72). Protein was produced in CHO cells by transient transfections of plasmid DNA. The fusion protein was purified by running the cell supernatant over a protein A column followed by ion-exchange chromatography to eliminate aggregates. Serum half-life was estimated by injecting a single dose of 10 mg/kg IL-22-Fc in a C57B6 mouse followed by obtaining serum from the mice at specified time intervals. The serum levels of IL-22-Fc was determined by a sandwich ELISA using anti IL-22 mAbs. For the in vivo studies using the Lrlr−/−Apobec1−/− double KO mice a mouse IL-22-Fc construct was utilized. While mouse sequences are presented and have been used in the examples, it is expected that in various embodiments human sequences can replace the mouse sequences.

Mouse Studies.

Ldlr−/−Apobec1−/− double KO mice were bred in the Genentech breeding facility and the WT C57BL/6 mice were purchased from Jackson Laboratory. Mice were maintained in a pathogen-free animal facility at 21° C. under standard 12 hr light/12 hr dark cycle with access to chow: a standard rodent chow (Labdiet 5010, 12.7% calories from fat) or a high fat, high carbohydrate diet (Harlan Teklad TD.03584, 58.4% calories from fat) and water ad libitum. db/db mice in C57BLKS/J background were females and other mice used in the study were all males. The mouse IL-22-Fc or Control IgG antibody were administered through intraperitoneal (ip) route starting at the age 6 months at 50 µg/week for three months (total of 12 weekly doses).

Analysis of Atherosclerotic Burden.

High resolution x-ray micro computed tomography was used to quantify atherosclerotic lesion volume and atherosclerotic plaque composition. Animals were euthanized with inhalation of carbon dioxide, then perfused via the cardiac left ventricle with ten milliliters of phosphate buffered saline then ten milliliters of ten percent neutral buffered formalin. The aortas were dissected and immersed in ten percent neutral buffered formalin for a minimum of twenty four hours and transferred to a solution of twenty percent iodine based x-ray contrast agent, Isovue 370 (Bracco Diagnostics Inc., Princeton, N.J.) in ten percent neutral buffered formalin for a minimum of twelve hours. After blotting dry, the aortas were perfused and immersed in soy bean oil (Sigma-Aldrich, St. Louis, Mo.), a low x-ray intensity background imaging media. Micro computed tomography images were obtained using the µCT40 (Sanco Medical, Basserdorf, Switzerland) with image acquisition energy of 45 kV, a current of 160 µA, an integration time of 300 milliseconds with three averages and image resolution of twelve micrometers. The resulting images were analyzed with Analyze (AnalyzeDirect Inc., Lenexa, Kans.) by employing semi-automated morphological filtering and user defined regions to determine object volumes and object composition.

Assessment of Vascular Function.

Vascular function was determined by ultrasound examination of the femoral artery to flow mediated dilatation and nitroglycerin mediated dilatation. Animals were anesthetized with two percent isoflurane, and kept at thirty seven degrees Celsius for twenty minute ultrasound exam. Nair was used to remove the hair from the ventral surface of the hind limbs and allow for ultrasound imaging using the Vevo770 with a fifty five megahertz imaging probe (VisualSonics, Toronto, Canada). For flow mediated dilatation, a baseline image of the femoral artery was collected then a rubber band was used as a temporary tunicate to occlude femoral artery blood flow for four minutes. The rubber band was then released for reflow of the femoral artery and an image was acquired every minute for four minutes and analyzed for femoral artery maximum diameter using manufactures supplied software tools. For nitroglycerin mediated dilatation, a baseline image of the femoral artery was collected then an intraperitoneal injection of 20 micrograms of nitroglycerin (Baxter, Deerfield, Ill.) was administered and an image was acquired every minute for four minutes and analyzed for femoral artery maximum diameter using manufactures supplied software tools.

Total Cholesterol, Triglyceride and Lipoprotein Determination.

Fresh sera samples were used to determine the total cholesterol, triglyceride, and lipoprotein distribution per manufactures instructions using the Cholestech LDX analysis system (Inverness Medical, Princeton, N.J.).

Sera Lipopolysaccharide Measurement.

Frozen sera samples were thawed and diluted one hundred fold in endotoxin free water and incubated at ninety degrees Celsius for ten minutes in a hot water bath. Samples were then run per manufactures instructions on the Endosafe-PTS system (Charles River Laboratories, Wilmington Mass.).

GTT: Glucose Tolerance Test.

The Glucose Tolerance Test (GTT) was conducted at the end of the dosing period with 1 g/kg i.p. glucose injection after overnight fast (14 hrs). Glucose levels were measured using One Touch Ultra glucometer. Food consumption was calculated during the study by individually housing the mice over 4 days of acclimatizing period followed by the measurement of one week period.

Measurement of Serum Cytokine Levels.

Serum cytokine levels were measured using Luminex 23 Multiplex panel (BioRad) through automated method. Some of the results were independently confirmed by Individual ELISA kits (R&D). Total cholesterol and free fatty acids (FFA) (Roche) were determined by using enzymatic reactions.

Results:

Ldlr-/-Apobec1-/- Mice Accurately Modeled Atherogenic Dyslipedia and were Sensitive to Inflammatory Challenges.

Figure 8:
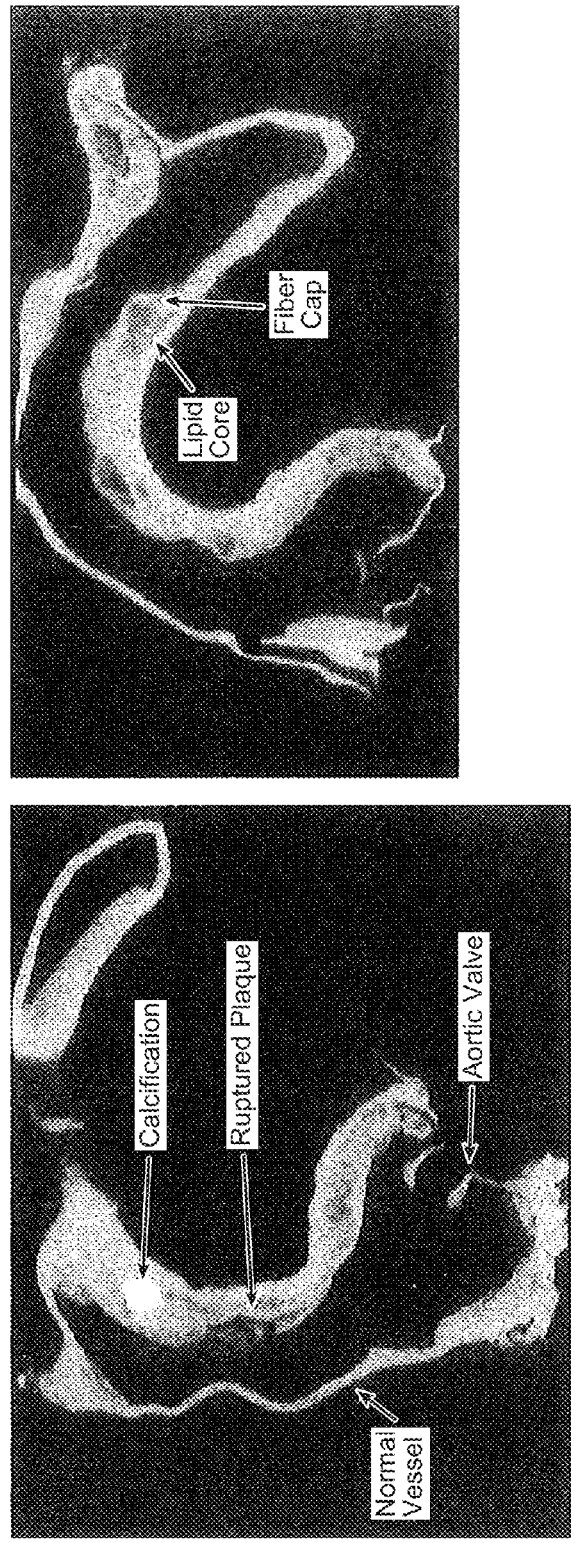
FIG. 8 shows a high resolution MicroCT demonstrating the atherosclerotic plaque burden in the aorta arch and brachiocephalic artery of an 8 month old Ldlr−/−Apobec1−/− mouse on high fat diet.
Figure 9A:
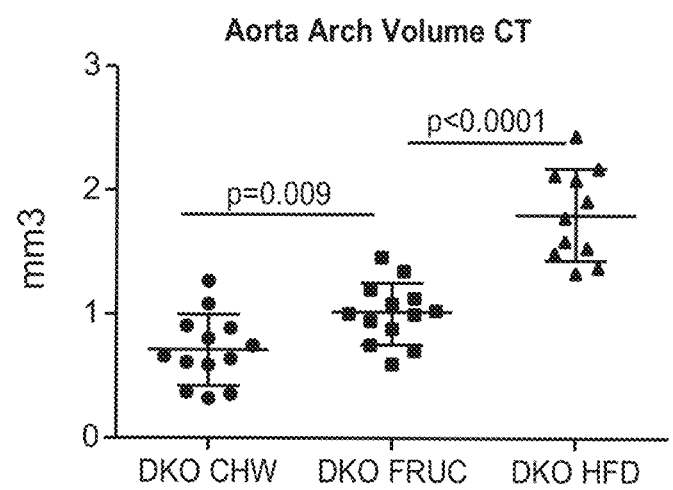
FIG. 9 shows that Ldlr−/−Apobec1−/− mice were sensitive to dietary challenges and showed a substantially increased level of atherosclerosis as measured from microCT (A), but with only modestly increased serum LDL levels (B).
Figure 9B:
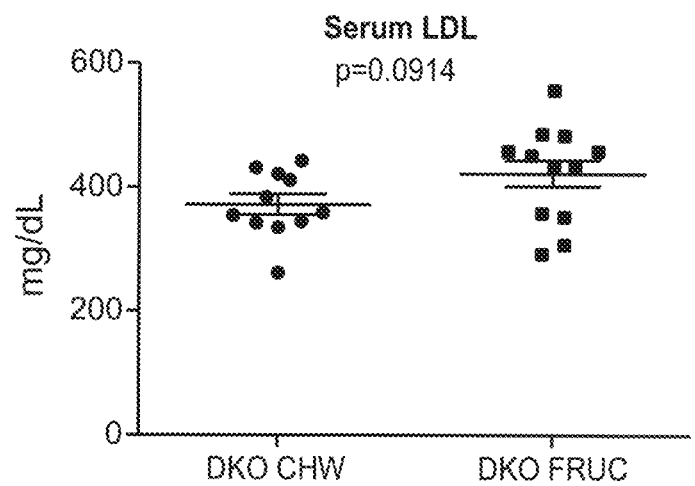
Figure 10A:
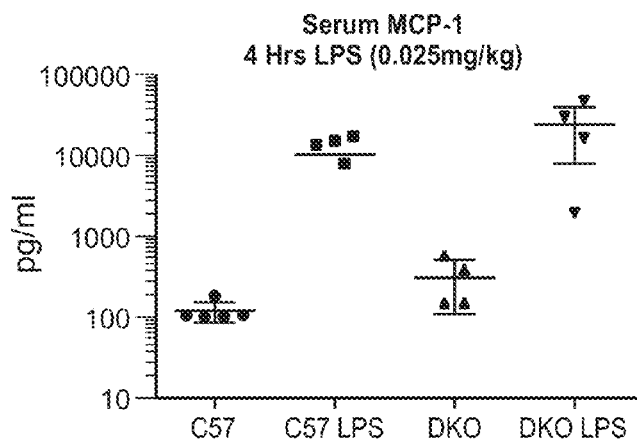
FIG. 10 shows the response of Ldlr−/−Apobec1−/− mice to an acute low grade inflammation stimulus, demonstrating an increase in sera MCP-1 (A) and IL-6 (B) greater than observations in wt C57 mice and accompanied by loss of vascular function as assessed by flow mediated dilation and infusion of nitroglycerine (C).
Figure 10B:
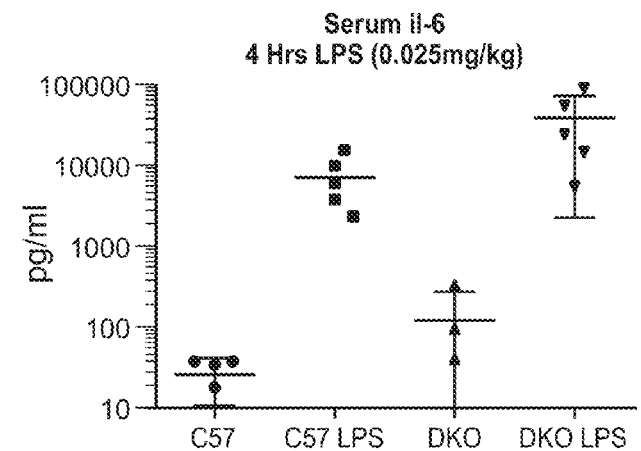
Figure 10C:
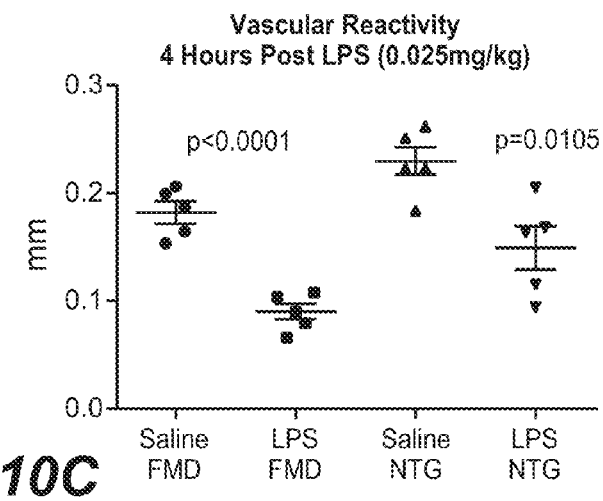
Figure 11A:
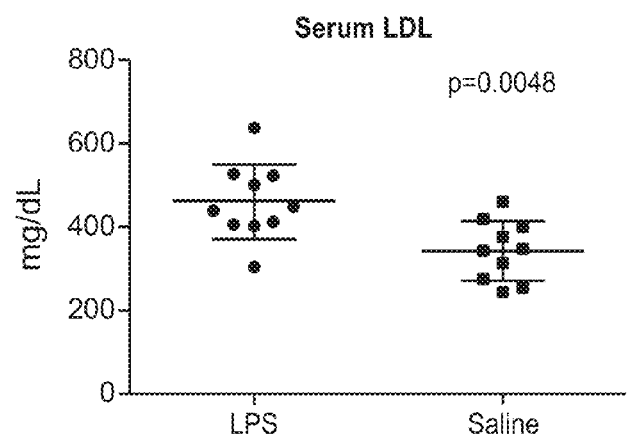
FIG. 11 shows that chronic endotoxin exposure results in dyslipidemia (A) and greater plaque burden (B) and instability (C).
Figure 11B:
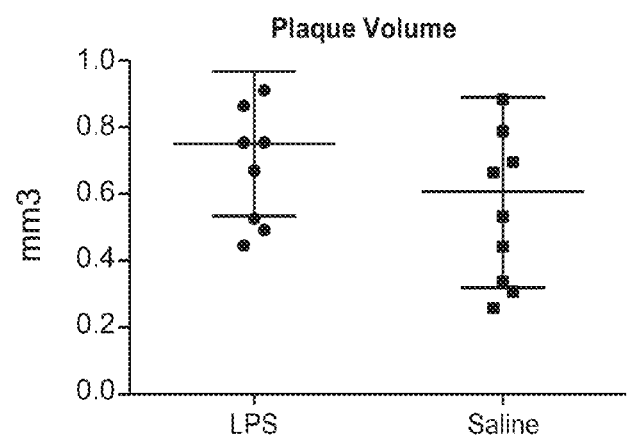
Figure 11C:
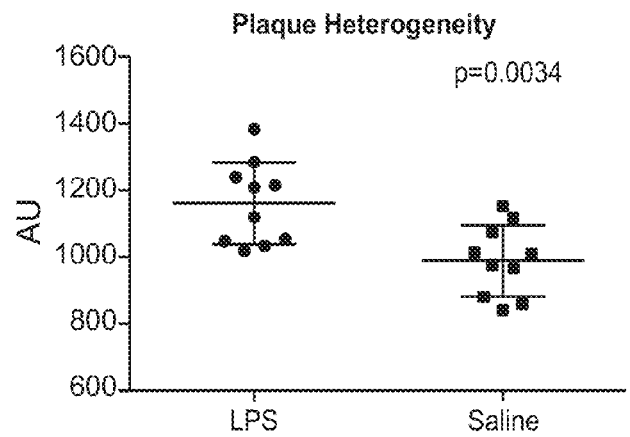

The Ldlr-/-Apobec1-/- mouse model displays lipoprotein levels and extensive atherosclerotic lesions characteristic of atherosclerotic disease in humans (Powell-Braxton et al. (1998). Nat Med 4(8): 934-8). MicroCT analysis of the aortic arch of Ldlr-/-Apobec1-/- mice revealed signs of atherosclerotic disease as determined using an automated image processing techniques on prepared samples that included the ascending aorta, arch of the aorta, descending aorta and part of the brachiocephalic artery. This technique also demonstrated a high degree of heterogeneity reflecting the regional variation in severity and progression of atherosclerosis burden that included lipid core, regions of ruptured plaque and calcification (FIG. 8). The heterogeneity of the CT signal reflects the underlying pathology of the lesions consistent with the complex plaque pathology of the human disease. To characterize this model and demonstrate its sensitivity to diet induced atherogenesis, the cohort of mice were treated with either a high fat diet or adding fructose to their drinking water (8% w/v) for 2 months. The Ldlr-/-Apobec1-/- mice demonstrated sensitivity to these dietary alterations with only modestly increased serum LDL but with a significant increase in total atherosclerosis burden as compared to mice on standard chow diet (FIG. 9). This demonstrates that the increase in atherosclerosis burden is likely due to inflammation rather than LDL increase. Further, an acute low grade inflammation stimulation with LPS challenge (0.025 mg/Kg) resulted in a marked elevation of proinflammatory markers in the Ldlr-/-Apobec1-/- compared with wt controls (FIG. 10). The Ldlr-/-Apobec1-/- mice were also exposed to chronic LPS dosing (750 ng, ip) for 8 weeks and assessed for serum lipid profile and plaque burden. As shown in FIG. 11, chronic endotoxin exposure results in dyslipidemia and greater plaque instability.

Figure 12A:
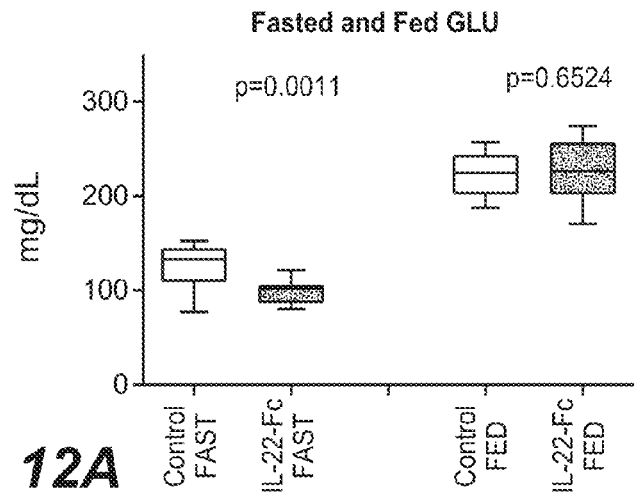
FIG. 12 shows fasting blood glucose was reduced in the IL-22-Fc treated group compared to controls (A) and glucose clearance was improved with IL-22-Fc treatment as seen from the glucose tolerance test (B, C).
Figure 12B:
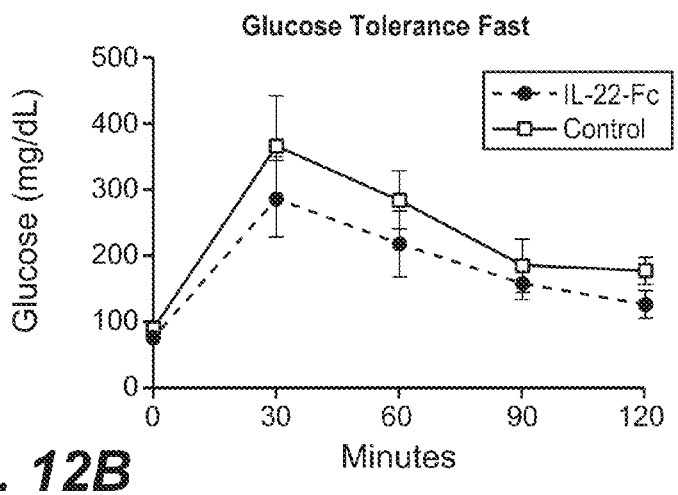
Figure 12C:
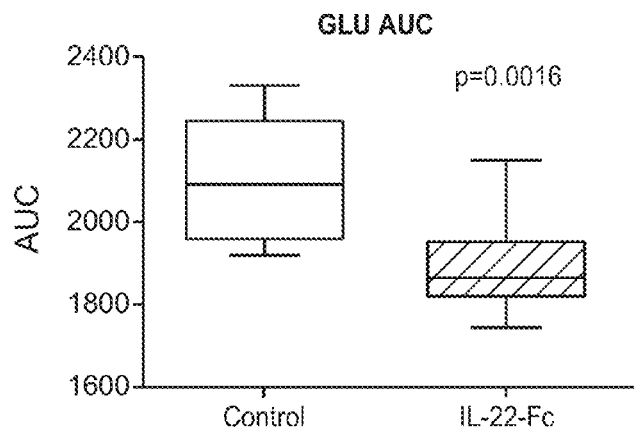
Figure 13A:
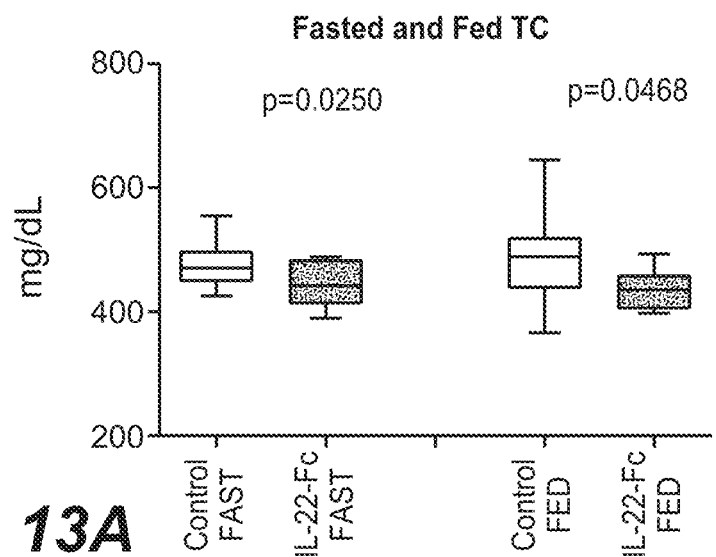
FIG. 13 shows reduction in total cholesterol occurs after treatment with IL-22-Fc. In Ldlr−/−Apobec1−/− mice total cholesterol was elevated, in both the fasting and fed conditions, and was reduced in the IL-22-Fc group compared with the controls as measured at the end of the treatment period (A). Plasma triglycerides levels were also reduced upon IL-22-Fc treatment with a marked reduction in the fed state (B).
Figure 13B:
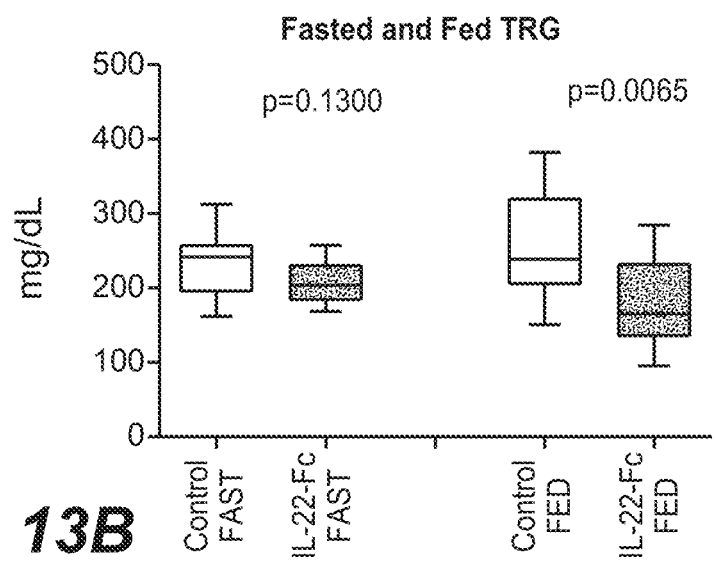
Figure 14A:
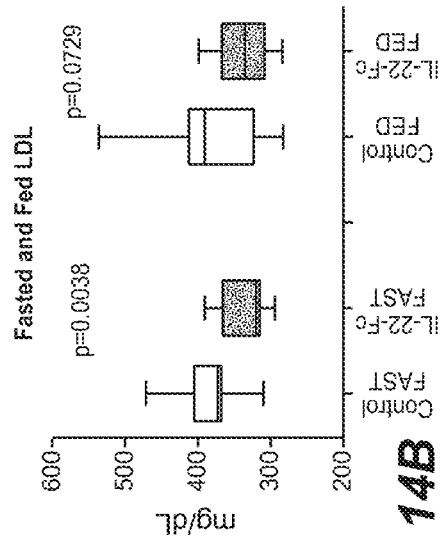
FIG. 14 shows the hyperlipidemia seen in the Ldlr−/−Apobec1−/− mouse was reduced following IL-22-Fc treatment. LDL was reduced in both the fasting and fed state (A), HDL was raised (B), and LDL/HDL ratio were reduced in both fast and fed (C). vLDL was reduced under fed conditions (D). Results of HDL (E), LDL (F) and LDL/HDL ratio (G) were depicted after 5 days with mice given two doses.
Figure 14B:
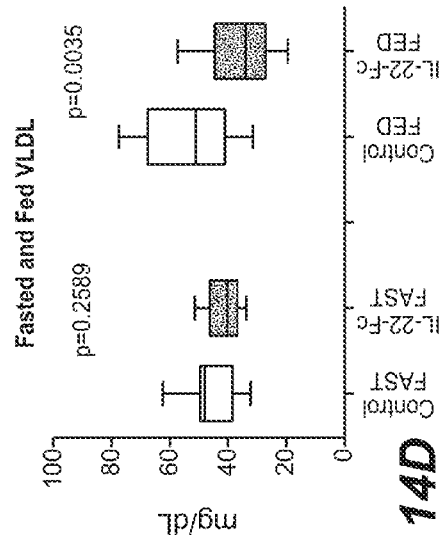
Figure 14C:
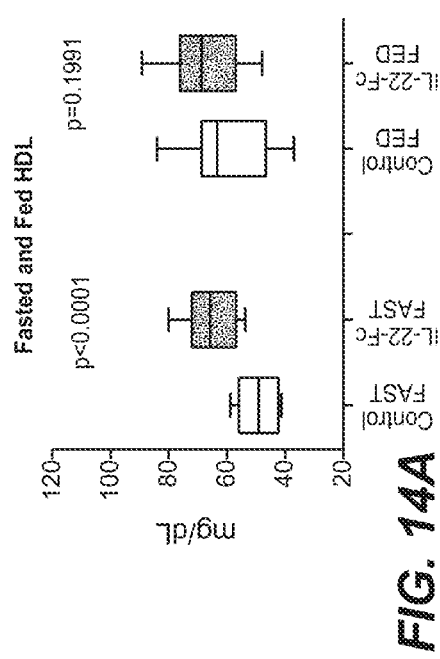
Figure 14D:
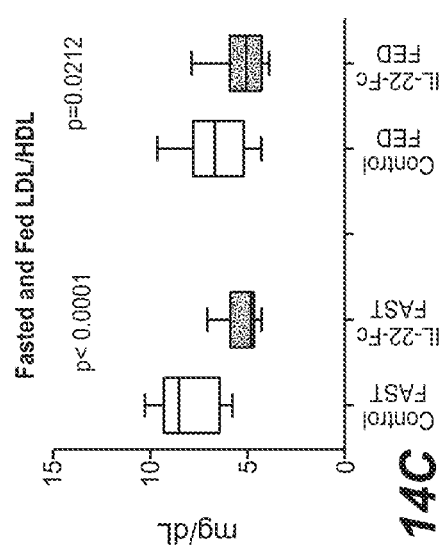
Figure 14E:
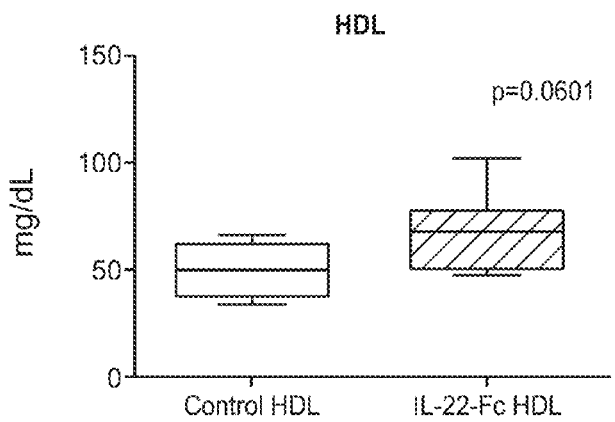
Figure 14F:
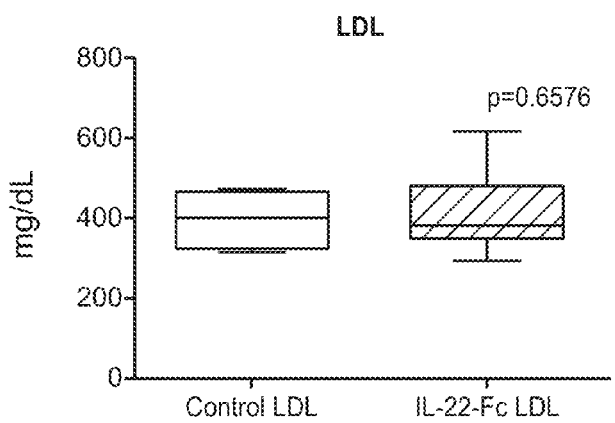
Figure 14G:
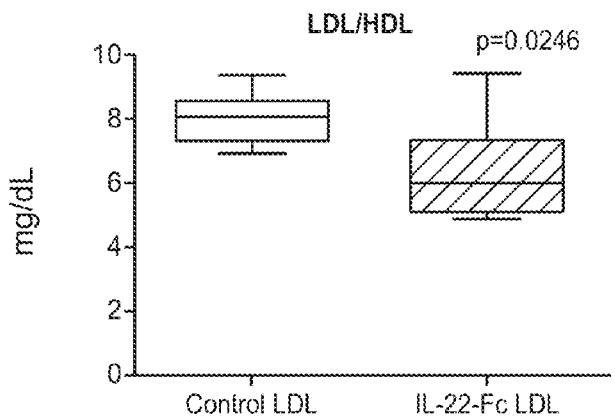
Figure 15:
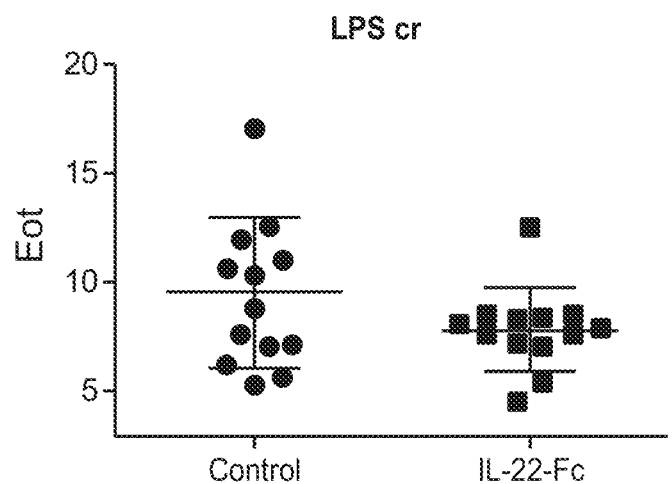
FIG. 15 shows that plasma LPS levels were reduced after IL-22-Fc treatment.
Figure 16:
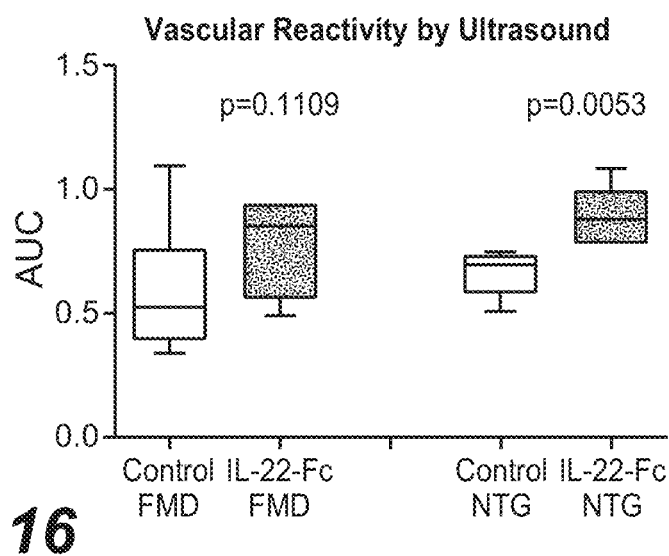
FIG. 16 shows improved endothelial function measure by vascular reactivity after IL-22-Fc treatment.
Figure 17A:
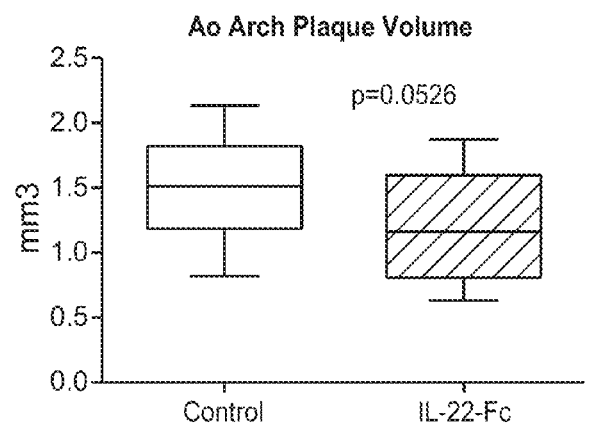
FIG. 17 depicts the quantitative analysis of plaque burden performed using contrast-enhanced microCT on postmortem samples of the dissected aortic arch, ascending and descending aorta (A), the brachiocephalic artery (B) and aortic valve (C).
Figure 17B:
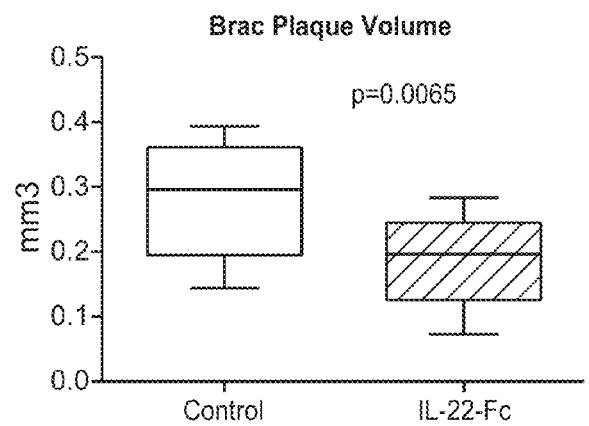
Figure 17C:
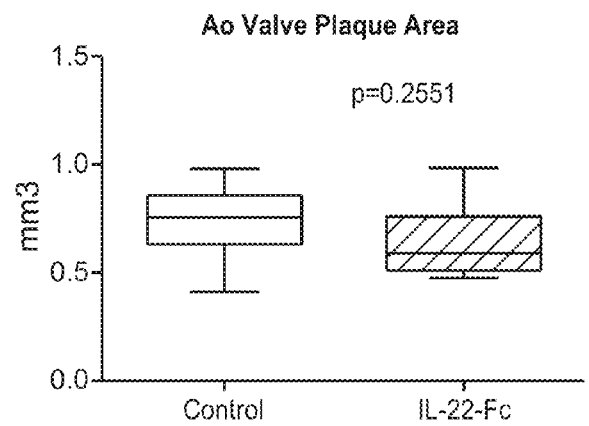
Figure 18A:
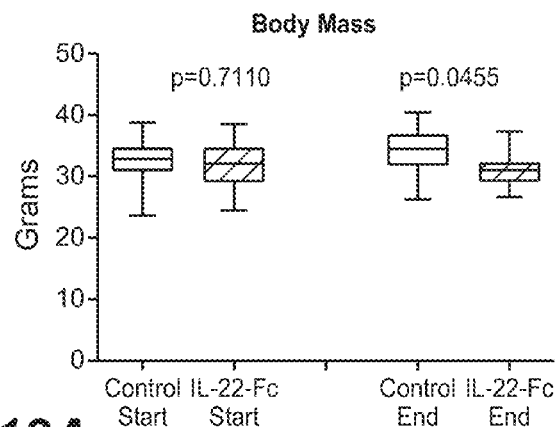
FIG. 18 shows body weights (A) and food intake (B) following IL-22-Fc treatment.
Figure 18B:
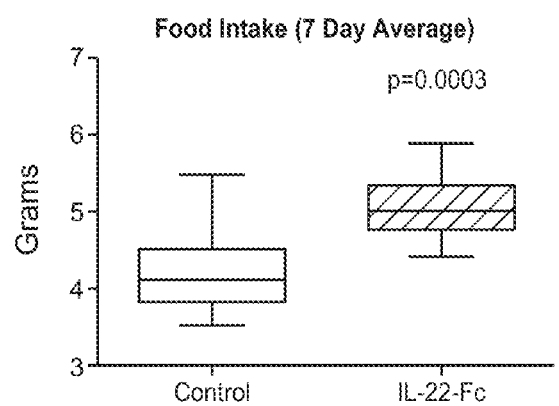

Upon treatment with IL-22-Fc, improvements in atherogenic dyslipidemia and symptoms of metabolic syndrome were seen in the Ldlr-/-Apobec1-/- mice. These mice develop characteristics of metabolic syndrome, including insulin resistance, on a chow diet. With IL-22-Fc treatment, fasting blood glucose was reduced compared to controls and glucose clearance was improved in the treatment group compared to control group (FIG. 12). Thus, glucose homeostasis was improved with a normalization of glucose tolerance (GTT) and improvement in fasting glucose (FIG. 12). Both fasted and fed hypercholesterolemia were reduced (FIG. 13A) as were fed TG levels (FIG. 13B) and the lipid profiles were improved (FIG. 14). Plasma LPS levels were reduced after IL-22-Fc treatment (FIG. 15). In addition to the reduction in dyslipidemia and insulin sensitization, improvement in endothelial function measured by vascular reactivity was seen (FIG. 16). Consistent with an improvement in dyslipidemia, CT analysis of plaque volume showed a reduction in total atherosclerotic burden in the aortic arch and in the brachiocephalic artery and aorta valves (FIGS. 17A-C). The improvement in lipid profile and insulin resistance was not due to a reduction in caloric intake since the food intake, measured over a 7 day period, increased despite a modest but statistically significant reduction in body weight that occurred during the 3 months treatment (FIG. 18). Body weight in the control group did not change during the 3 month treatment protocol and the IL-22-Fc treatment group showed a significant reduction of body weight between the start and end of study (FIG. 18A). The average daily food intake measured over a 7 day period during the course of the treatment study was elevated in the IL-22-Fc treatment group compared to control group (FIG. 18B).

Example 8 Peripheral Artery Disease Model

Stimulation of IL-22 regulated pathways by IL-22-Fc to reduce atherosclerotic progression is a potentially novel form of therapy for subjects with cardiovascular disease and related disorder including diabetes and chronic kidney disease. Because cardiovascular disease, typically, is not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. The same strategy described above can be used to validate IL-22 as a target using a mouse peripheral artery disease model. The IL-22-Fc constructs are prepared and evaluated as described above. All necessary controls are also used. IL-22 agonists/ antagonists are evaluated and the results will validate IL-22 pathways as a target for drug discovery and development.

A peripheral artery disease (PAD) model based upon femoral artery ligation to create ischemic damage is used. The efficacy of the IL-22-Fc constructs are evaluated similar to the procedures described previously (Couffinhal et al., Am. J. Pathol. 152:1667 (1998); Takeshita et al., Lab. Invst. 75:487 (1996); Isner et al., Human Gene Therapy 7:959 (1996)). To test the ability of an IL-22-Fc to modulate such a peripheral arterial disease, the following experimental protocol is used: a) Using a rodent (as in the above described method), one side of the femoral artery is ligated to create ischemic damage to a muscle of the hindlimb (the other non-damaged hindlimb functions as the control); b) an IL-22-Fc polypeptide (or fragment thereof) is delivered to the animal either intravenously and/or intramuscularly (at the damaged limb) at least 3× per week for 2-3 weeks at a range of dosages; and c) the ischemic muscle tissue is collected after at 1, 2, and 3 weeks post-ligation for an analysis of biomarkers and histology. Generally, (as above) parameters for evaluation include determining viability and vascularization of tissue surrounding the ischemia, while more specific evaluation parameters may include, e.g., measuring skin blood flow, skin temperature, and factor VIII immunohistochemistry, and/or endothelial alkaline phosphatase reaction. Polypeptide expression during the ischemia, is studied using any art known in situ hybridization technique. Biopsy is also performed on the other side of normal muscle of the contralateral hindlimb for analysis as a control.

Alternatively, other mouse models are used (Pownall et al. US 2011/0118173 A1). There are several mouse models of atherosclerosis that will be used to test atheroprotection. These include the apo A-I KO, apo E KO, cystathionine beta-synthase and apolipoprotein E, and the apo A-I/SR-BI double KO. These mouse models of atherosclerosis will be treated with IL-22-Fc by injection, oral dosage, or ex vivo treatment. Measurement of blood cholesterol levels after treatment with IL-22-Fc will show an immediate decrease in total plasma cholesterol and an increased amount of neo HDL and the subsequent appearance of mature forms of HDL, which contains cholesterol extracted from peripheral tissue over an appropriate period of hours.

Example 9 Effect of Recombinant IL-22 Fc in Diabetic Mouse Models

In our initial studies to look at the effect of IL-22-Fc in metabolic syndromes, we noted that IL-22R KO mice were more susceptible to diet induced obesity and insulin resistance. In subsequent experiments we observed a loss of body fat following treatment with recombinant IL-22-Fc. In view of these data we chose to test the role of recombinant IL-22-Fc in diabetic mouse models. Efficacy end points such as fed and fasted glucose, body weight and glucose and insulin tolerance were evaluated in this study.

Figure 19:
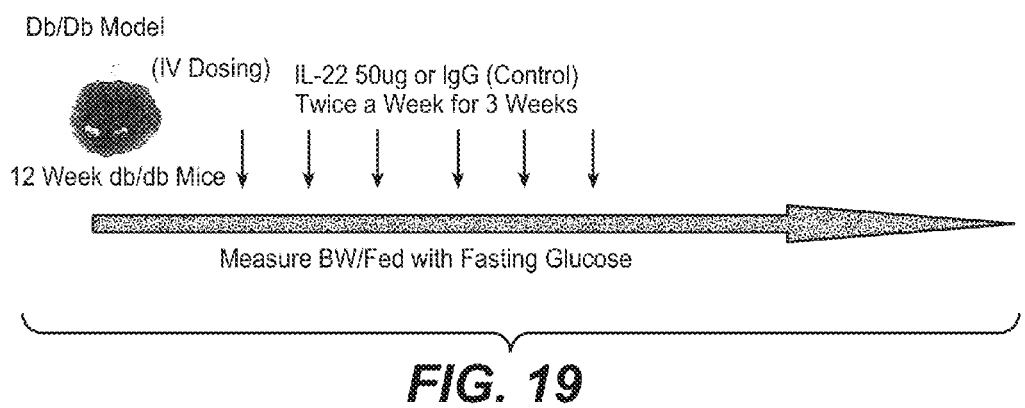
FIG. 19 depicts a schematic of diabetic mouse model treatment regimen.

Mice (10 animals/group) were treated with either Recombinant IL-22-Fc or anti Ragweed antibody as an isotype IgG control, giving 2 doses/week for 3 weeks (FIG. 19):

Group 1: db/db mice (BKS.Cg-Dock7(m)+/+ Lepr(db)/J FAT): anti-Ragweed antibody (50 µg)
Group 2: db/db mice: Recombinant IL-22-Fc (50 µg)
Group 3: Diet Induced Obesity (DIO) mice: anti-Ragweed antibody (50 µg)
Group 4: Diet Induced Obesity (DIO) mice: Recombinant IL-22-Fc (50 µg)

12 week old female db/db were purchased from Jackson Laboratory and used in the experiment. Prior to the study mice were acclimated (daily handling) for 7-10 days after arrival and housed single before the start of the experiment. Over days −5 to day −1 blood was collected (3-5 µl) via tail nick for base-line glucose measurement daily. On day 0 proteins were administered by i.p. injection (150 µl) in PBS, followed by twice weekly doses for 3 weeks. Blood (3-5 ul) was again collected via tail nick for glucose measurement on day 2, 4, 8, 10, 14, 18 and 21. For measuring pK, 30 ul of blood was collected via orbital bleed under anesthesia on Days 2, 7, 13 and 20.

Figure 20B:
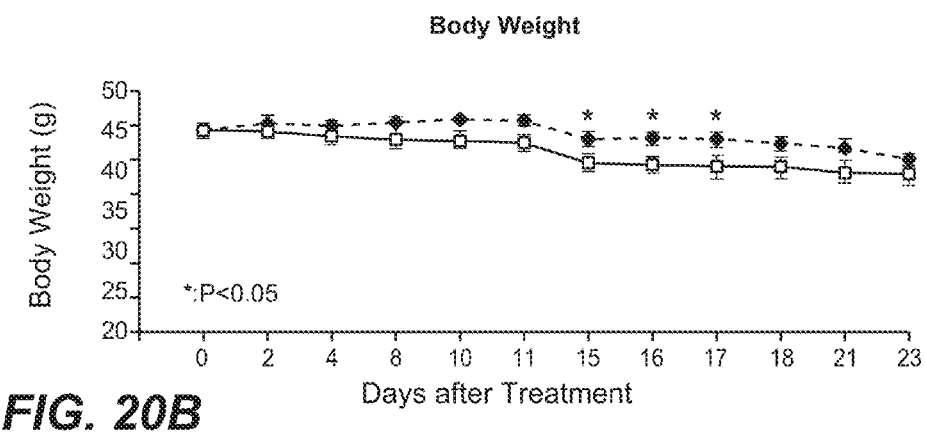
Figure 20C:
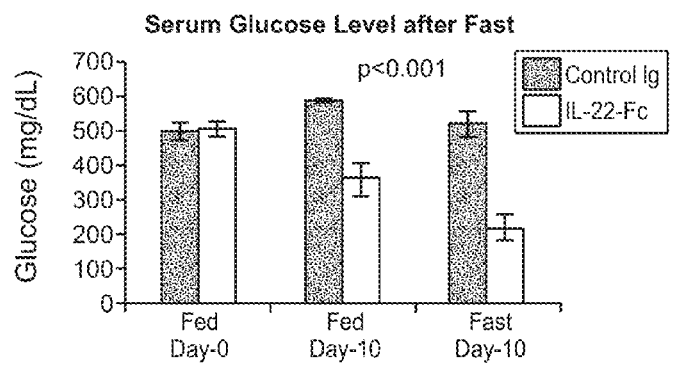

Recombinant IL-22-Fc or isotype IgG control antibody was dosed twice a week through Intraperitoneal route for three weeks. The body weight and fed glucose were measured every 2 days until the end of study at day 23 and glucose measurements were done through tail nick and measured using glucometer (FIGS. 20A-B). In order to access the fed and fasting glucose level, on day 10 the fed glucose measurement was done in the morning and mice from both groups were fasted for 4 hours (hrs) and glucose measurements were taken using Glucometer (FIG. 20C). IL-22-Fc exposure resulted in a significant glucose lowering effect in db/db mice.

Figure 21:
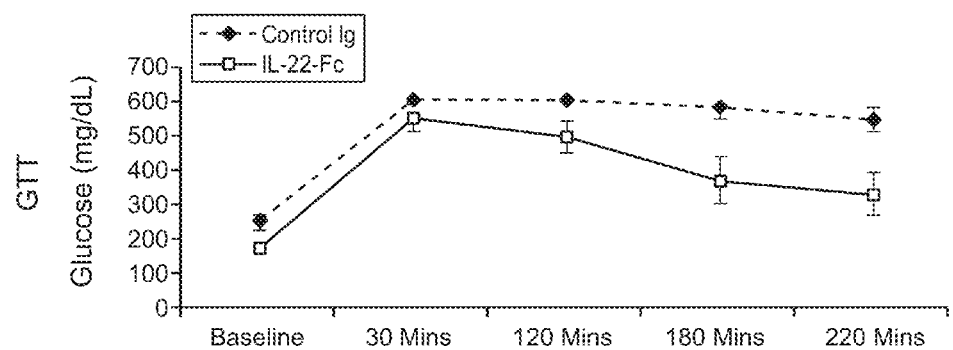
FIG. 21 shows IL-22Fc treatment improves glucose tolerance and insulin sensitivity based on the Glucose Tolerance Test (GTT). p<0.05

Glucose Tolerance Test (GTT) was performed after 2 weeks of treatment with IL-22-Fc or IgG control at 50 µg/dose twice a week. The mice were fasted overnight (14 hrs). Fasting glucose level were measured in the morning and served as a baseline. Body weight was measured and blood was collected (3-5 µl) via tail nick for glucose measurement. Glucose solution at 1.5 mg/Kg body weight was administered intraperitoneally and glucose measurement was taken every 30 mins. The glucose values were represented in the graph for 30, 120, 180 and 220 mins. One more GTT was performed on day 21 following overnight fasting on day 20. Mice were weighed daily. All the groups were euthanized on day 23 and tissues were collected for histology. IL-22-Fc treatment demonstrated significant improvement in glucose tolerance and insulin sensitivity (FIG. 21).

Figure 22A:
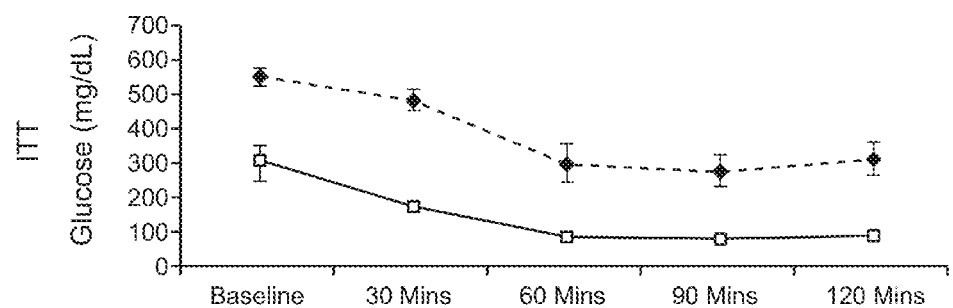
FIGS. 22A-B show that IL-22Fc treatment improved insulin sensitivity based on the Insulin Tolerance Test (ITT) as measured through mg/dL glucose levels (A) and % glucose reduction (B).
Figure 22B:
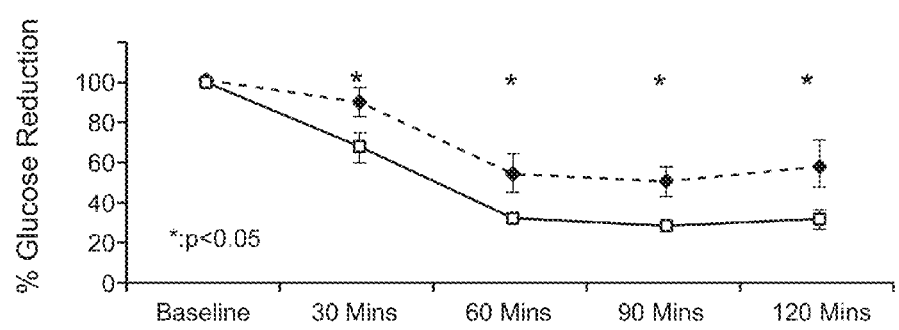

Insulin Tolerance Test (ITT) was performed after on Day 20 of the mice treated with IL-22-Fc or IgG control at 50 µg/dose twice a week. The mice were fasted for 4 hrs and baseline glucose level was taken. 1 mU/Kg body weight was administered intraperitoneally and blood glucose levels were monitored by tail nicks every 30 mins. In order to calculate % glucose reduction, baseline glucose level following 4 hrs fasting is normalized to 100%. IL-22-Fc treatment was shown to significantly improve insulin sensitivity measured through Insulin Tolerance test (FIGS. 22A-B).

IL-22R is highly expressed in pancreas especially in acinar cells, although its expression status in β islet cells is still unclear. The insulin signal in pancreas from IL-22 Fc or control protein treated db/db mice was examined. Histological assessment of the diabetic mice was also carried out to evaluate insulin expression in the islet cells and the level of hepatic periportal steatosis in IL-22-Fc treated animals. Immunohistochemistry for insulin and glucagon was performed on formalin fixed paraffin embedded pancreas tissues as previously reported (Wu et al. 2011, *Science translational medicine* 3, 113ra126, doi:10.1126/scitranslmed.3002669) using rabbit anti-glucagon (Cell Signaling Technologies #2760) with Alexa Fluor 555-conjugated goat anti-rabbit secondary antibody, or guinea pig anti-insulin (DAKO A0564) with Alexa Fluor 647-conjugated goat anti-guinea pig secondary antibody. The percent insulin area per islet area was calculated by dividing the insulin positive area by the islet area minus the nuclear area.

IL-22-Fc appears to increase insulin expression in islets in db/db mice (FIG. 23A) and quantitative analysis revealed a significant increase of both insulin-signal intensity (FIG. 23 B and FIG. 24) and insulin positive area in IL-22-Fc treated animals (FIG. 25), while IL-22 Fc did not increase glucagon-signal intensity (FIG. 23 C). The insulin positive area showed a 2.16 fold increase with IL-22-Fc treatment compared to treatment with Herceptin control (95% confidence interval 1.25 to 3.72). The number and area of islet were not affected by IL-22 Fc treatment. But the β cell area per islet and the intensity of insulin staining from IL-22 Fc treated pancreas was significantly elevated (FIGS. 23 and 52).

Figure 23A:
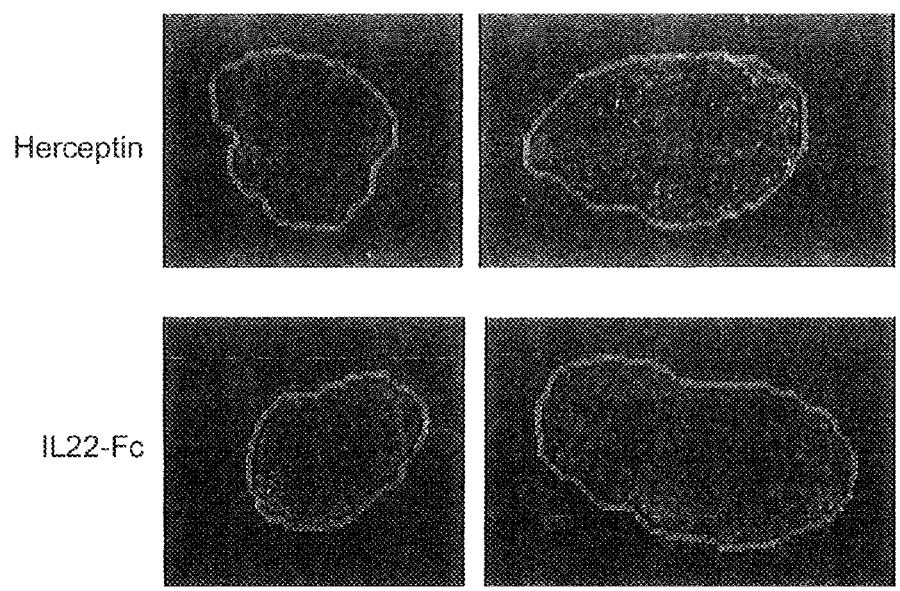
FIGS. 23A-F show that IL-22Fc increased insulin expression in islets. (A) Green shows glucagon, red shows insulin. The circled area surrounded by red line shows islet area. Bar, 50 μm. (B) Average insulin staining intensity. (C) Average glucagon staining intensity. (D) Fed insulin levels in HFD-fed mice. (E) Fasted insulin levels in HFD-fed mice. (F)
Figure 23B:
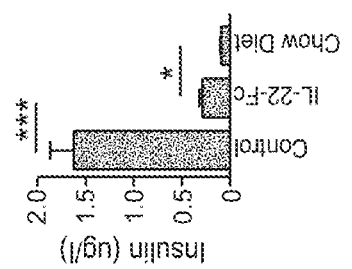
Figure 23C:
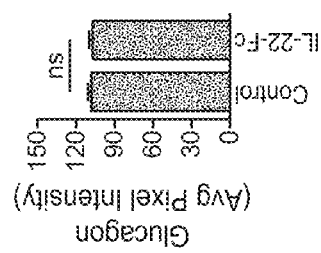
Figure 23D:
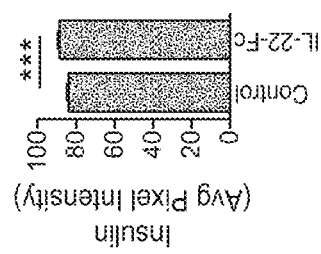
Figure 23E:
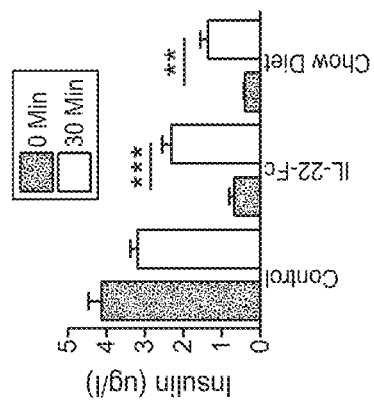
Figure 23F:
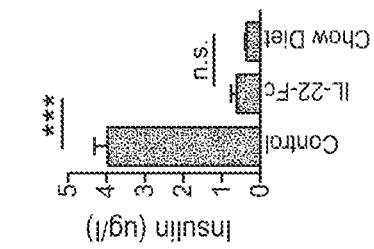

The pancreas beta cells of obese mice showed signs of degranulation and degeneration (data not shown). Statistically significant higher insulin staining was observed in beta cells of obese mice treated with IL22, as compared to untreated obese mice (FIG. 23A, B). The increase was probably due to increased insulin storage in the IL22 treatment group. Despite the higher level of pancreas insulin seen in IL22 treated obese mice, serum insulin levels in these mice were actually reduced as compared to obese mice without IL22 treatment, either in fed or fasted condition (FIG. 23D, E). But the IL22 treated obese mice responded to glucose by releasing insulin in a pattern more resembling wild type mice on chow diet, as compared to untreated obese mice (FIG. 23F). Thus, IL22 improved glucose homeostasis in obese mice potentially by increasing granulation and improving the control mechanism of insulin release in the obese mice.

Next, the effect of IL-22 Fc on insulin homeostasis was examined. HFD-fed mice were treated with IL-22 Fc twice per week for 8 weeks. The results show that (FIGS. 23D and E). The data presented in FIG. 23F show insulin levels in mice 0 or 30 min after glucose injection. HFD-fed mice treated with IL-22 Fc, but not control HFD mice, responded to glucose injection by increasing serum insulin levels, similar to wild type mice on Chow diet (normal diet). See FIG. 23 F. Thus, IL-22 improved glucose homeostasis in obese mice and improved insulin secretion in response to glucose.

As a comparison, we looked at IL-22 receptor KO mice and their susceptibility to diet induced obesity (DIO) and insulin resistance. The IL-22 R KO mouse is described in FIG. 43 and below. IL-22 receptor KO mice and littermate control mice were put on 60% High Fat Diet from week 7 of age for 10 weeks. To assess the high fat diet (HFD) induced glucose tolerance, mice were fasted overnight and glucose tolerance test was performed next day morning. For this experiment, seven week old IL-22 R KO mice and littermate age matched control animals (WT: served as wildtype) were put on 60% HFD for 10 weeks. Mice were intraperitoneally injected with 1.5 mg/kg body weight of glucose and blood glucose levels were monitored every 30 mins for a period of 2 hrs. Total area under curve for individual mice were calculated and graphically represented. The data demonstrate that glucose levels are significantly higher in the IL-22R KO mice based on the total area under the curve (FIG. 27A-B), suggesting that the IL-22 receptor plays a role in HFD induced glucose tolerance. The IL-22 receptor KO mice did in fact put on more body weight following HFD feeding compared to Littermate WT control mice (FIG. 28).

Example 10 IL-22 Treatment of Atherogenic Prone Mice (Ldlr−/−Apobec1−/−), Resulting in Reduction in Serum LPS and Serum LDL/HDL Nine month old Ldlr−/−, Apobec1−/− (dko) mice were injected intraperitoneally with 50 ug of fusion protein IL-22Fc or 50 µg anti-ragweed control antibody (n=6 per group). Forty eight hours later, the animals were euthanized and serum was harvested. Lipid profiles were analyzed using Cholestech LDX assay, and Endotoxin was analyzed using the Limulus amebocyte lysate assay. Serum LPS was reduced by 50% (p=0.0052) and serum LDL/HDL was reduced by 30% (p=0.049) with IL-22-Fc as compared to anti-ragweed Fc control antibody (FIG. 29).

In summary, mice treated with IL-22 Fc fusion protein had rapid positive changes in lipid profile and reduction in circulating endotoxin.

Example 11 IL-22Fc Accelerated Wound Closure in Murine Diabetic Wound Healing Model, by Either Systemic or Topical Administration Protocol The IL-22-Fc constructs were typically a mouse IL-22-mouse-IgG2a fusion protein (SEQ ID NOs:72 and 73) as shown in FIGS. 32A-B.

Mice used in the study: IL-22R KO mice and littermate control wild-type (WT) mice were bred in the Genentech animal facility. The IL-22R KO mice is described in FIG. 43 and below. The 9 weeks old Diabetic female mice BKS.Cg-Dock7(m)+/+ Lepr(db)/J FAT (db/db) and BKS.Cg-Dock7(m)+/− Lepr(db)/J lean (control BKS) were used. Mice were randomized in the study based on body weight and fed glucose level.

The wound healing protocol was strictly followed according to IACUC Rodent Survival Surgery Guidelines. Sterile technique was used through-out the procedure (including sterile gloves, mask, gown, and drape). Following induction of a surgical plane of anesthesia, the dorsal portion of the animals back (from the scapular area to the lumbar area) was shaved, stubble removed with hair remover lotion (Nair or equivalent), following rinse off with sterile water and prepped with betadine scrub followed by alcohol rinse. The animal was placed in ventral recumbency then using a 6 mm punch to mark the area of skin to be removed (with sterile marker on the tip of the punch, then touch to skin). One 6 mm diameter full thickness skin wounds was made 1 cm left and right of midline. The underlying perichondrium was removed with periosteal elevator and a fine scissors.

Following this a 0.5 mm thick silicone frame, 10-12 mm inside diameter, was placed around the circular wound with superglue). Then a 2 cm square of Tegaderm™ (3M, St. Paul, Minn.) or Opsite® (Smith & Nephew, Inc., St. Petersburg, Fla.) adhesive was placed over the wound and frame and the animal is allowed to recover from anesthesia.

Opsite® dressings were removed every other day, wounds were inspected, treatments applied topically (20 uL of test material or saline), and fresh dressing applied. Wound gap was calculated by measuring wound diameter from day 0 through end of the study.

In some studies fed glucose level was recorded following tail nick and using commercial Onetouch® glucometer (lifeScan, Inc., Milpitas, Calif.).

Results

IL-22R−/− Mice Exhibited Defects in Dermal Wound Healing Response

The role of IL-22 signaling in dermal wound healing response was studied in IL-22R KO (lacking signaling of IL-22 and its family members IL-20 and IL-24). FIG. 33 shows the wound gap curve of both IL-22RKO mice (n=10) and IL-22RWT control mice (n=10) over 14 days. A 6 mm diameter wound was generated on day 0 and the gap was measured every 2 days staring from Day 4. Wound gap of IL-22R KO mice showed significant delay in the closure compared to WT littermate control at day 8 through day 14. At the end of the study (day 14) 100% of the WT mice wounds were closed, compared to only 30% of mice in the IL-22RKO mice (p=0.005). The differences in the wound gap between IL-22RKO and WT control mice are deemed statistically significant at P<0.05.

Wound Healing Defect in Obese Diabetic Mice

The dermal wound healing response in diabetic condition was modeled in the preclinical study using leptin receptor KO diabetic mice (BKS.Cg-Dock7(m)+/+ Lepr(db)/J FAT) (db/db) and WT control lean mice. Circular wounds (6 mm) were generated at the back of a mouse and the wound gap closure was recorded every 2 days starting from day 4. FIG. 34 shows the wound gap closure (in mm) measured from day 0 through Day 27. Throughout the study period, diabetic, obese db/db mice wounds displayed significant delay statistically (P<0.0001) in the wound closure compared to Lean mice. By day 14 100% of WT mice wounds were closed while none of the db/db mice wounds are closed even at day 27 (FIG. 35A). IL-22 expression was induced as measured by RNA levels in wild type mice days after wound excision, but not in db/db mice. See FIG. 35B, IL-22Fc Accelerated Wound Closure in the Diabetic Wound Healing Model As IL-22R−/− mice display defects in the wound closure, it was hypothesized that IL-22 may influence in the wound closure. FIG. 36 showed the schematic diagram of the study design. 9-week-old female obese db/db mice were used to model diabetic wound healing. In addition to IL-22Fc (murine), anti-ragweed antibody as Fc control protein and anti-FGFR1 antibody were used as positive control. Since anti-FGFR1 antibody has been demonstrated to normalize blood glucose level in this preclinical model, it was used as a control antibody. FIG. 36 shows schematic diagram of the study design. Treatment groups were:

Anti-Ragweed antibody (intra peritoneal (i.p.) 50 ng/dose, 8 dose)

IL-22Fc (intra peritoneal (i.p.) 50 ng/dose, 8 dose)

Anti-FGFR1 antibody (intra peritoneal (ip) 0.5 mg/kg on day 0 and day 14).

Both IL-22Fc and anti FGFR1 showed statistically significant ($P \leq 0.001$) effect in lowering glucose level in the diabetic mice compared with anti-ragweed treatment (FIG. 37). The data (FIG. 38) shows that systemic administration of IL-22 Fc had striking effect in wound closure rate compared to control anti Ragweed antibody treatment. The differences in the wound gap was significant from starting from day 16 ($P \leq 0.05$) and the wounds in IL-22Fc treated mice was completely covered by day 27. The Fc control antibody as well as anti FGFR1 treated mice failed to close wounds completely even at day 27. FIG. 39 shows the wound gap measurements of individual mice at day 19, 21 and 27 where the differences in the wound gap between IL-22 Fc treated groups compared to other 2 groups are very significant statistically ($P \leq 0.001$).

Comparison of IL-22 Fc Topical Vs. Systemic Treatment

FIG. 40 shows the schematic diagram of study design. In this study we compared 2 modes of treatment—topical vs. systemic treatment. The groups were:

Anti-Ragweed antibody (topical 50 µg/dose, 8 doses)

IL-22Fc (topical 50 ug/dose, 8 doses)

IL-22Fc (intra peritoneal (i.p.) 50 µg/dose, 8 doses).

The Graph in FIG. 41 shows both IL-22-Fc topical as well as IL-22-Fc systemic administration accelerated the wound closure compared to control antibody treatment. The wound gap measurements were statistically significantly ($P \leq 0.001$) different from day 16 through day 22. No significant difference was observed with wound closure rate between 11-22 Fc topical and systemic treatment groups. See also FIG. 42.

Example 12 Obese Mice Exhibited Reduced IL-22 Induction

In the following experiments, the regulation of IL-22 during immune responses was examined in obese mice. The major leukocyte sources of IL-22 are innate lymphoid cells (ILCs) and T helper subsets, especially Th17 and Th22 cells. The IL-22 production from CD4+ T cells upon antigen challenge in leptin receptor deficient db/db mice was examined.

Protocol

In Vivo Treatment with OVA and Flagellin.

To activate CD4 T cell in vivo, 100 µg OVA emulsified in complete Freund's adjuvant (CFA) was injected subcutaneously at lower back of the animals, and the inguinal lymph nodes were harvested on day 7. To activate TLR5, 3 µg ultra-pure flagellin (InvivoGen) was injected intravenously, and serum samples were harvested at 2 h.

Mice.

Leptin receptor deficient mice (db/db; BKS.Cg-Dockr+/+ Lepr$^{db}$/J or B6.BKS(D)-Lepr$^{db}$/J), Leptin deficient mice (ob/ob; B6.Cg-Lep$^{ob}$/J), and their respective lean control mice, as well as high-fat diet mice (C57BL/6J 60% DIO) and the chow-diet control mice were purchased from Jackson Laboratory. IL-22 deficient mice (Zheng et al, 2007, Nature 445, 648-651) and IL-22Ra1 deficient mice (described in FIG. 43 and below) were generated by Lexicon Pharmaceuticals and backcrossed with C57BL/6 stain more than 10 times. Where indicated, mice were fed with adjusted calories diet (HFD, containing 60% fat, Harlan) starting at the age of 4-6 weeks old. For metabolism studies 12-18 weeks old mice were used, whereas 5-6 weeks old mice were used for C. rodentium infection studies. All animal experiments were approved by the Genentech Institutional Animal Care and Use Committee.

Naïve CD4 T Cell Purification and Differentiation.

Naïve CD4 T cells were sorted and stimulated as previously described (Rutz, et al. 2011, Nature Immunol. 12:1238-45), and cultured under specific condition for each subset similarly to the way as described previously. Id. For IL-22 induction, anti-IL-4 (10 µg/ml), anti-IFN-γ (10 µg/ml), and recombinant IL-6 (20 ng/ml) were used; where indicated, recombinant mouse leptin (1 µg/ml, R&D systems) was added.

Intracellular Staining and IL-22 ELISA.

Lymphocytes purified from draining lymph nodes were stained for IL-22 and IL-17A as previously described (Zheng et al., supra) using phycoerythrin (PE)-anti-IL-22 (1H8PWSR, eBioscience) and fluorescein isothiocyanate (FITC)-anti-IL-17A (17B7, eBioscience). IL-22 ELISA was performed as previously described (Zheng et al., supra) using monoclonal anti-IL-22 antibodies (20E5 and 14B7, Genentech).

RNA Isolation and Real-Time PCR.

Colon were harvested and processed, and mRNA was isolated with RNeasy mini plus kit (Qiagen). Il22, Il22ra1, and Reg3b mRNA level were evaluated using real-time PCR analysis as previously reported (Ota et al. 2011, Nature immunol. 12, 941-948). Results were normalized to those of the control housekeeping gene Rpl19 (encoding ribosomal protein L19) and are reported as $2^{\Delta CT}$. The primer and probe sequence for Il22 and Reg3b were reported previously. Id. For Il22ra1, 5'-AGG TCC ATT CAG ATG CTG GT-3' (SEQ ID NO:74), 5'-TAG GTG TGG TTG ACG TGG AG-3' (SEQ ID NO:75) and 5'-FAM-CCA CCC CAC ACT CAC ACC GG-TAMRA-3' (SEQ ID NO:76) were used.

Statistical Analysis

All statistical analysis was done with two-tailed unpaired Student's t-test. P value less than 0.05 was considered as statistically significant.

Results

Figure 45A:
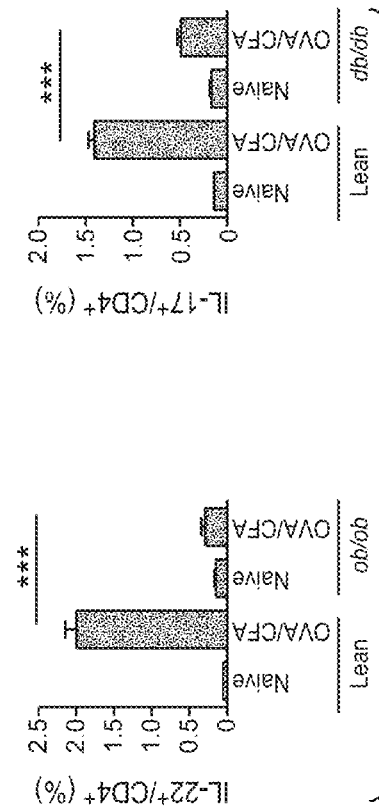
Figure 45B:
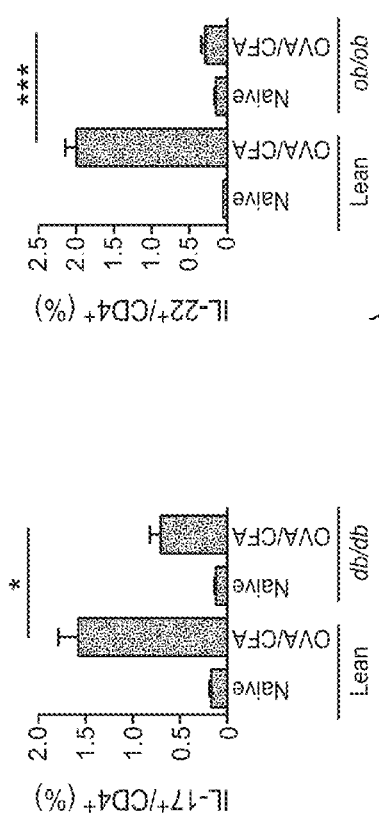
Figure 45C:
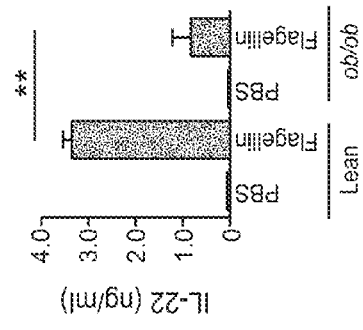

After immunizing the mice with ovalbumin (OVA) in Complete Freund's Adjuvant (CFA), the IL-22 expressing CD4 T cells were detected ex vivo with intracellular cytokine staining IL-22$^{+}$ T cells were significantly reduced in db/db mice (FIGS. 44 A-B). Consistent with previous reports, IL-17$^{+}$ CD4 T cells were also significant reduced in db/db mice (FIG. 45A). Similar results were observed in leptin deficient ob/ob mice as well (FIG. 45B). Leptin can regulate Th cells, such as Th1 cells and Treg cells. However, a direct effect of Leptin on IL-22 production from in vitro differentiated Th22 cells was not observed (FIG. 45C). Moreover, similar reduction of IL-22 producing T cells was also observed in immunized DIO (diet-induced obesity, or HFD-fed) C57BL/6 (FIGS. 44C and D), suggesting obesity but not lack of Leptin signaling might be accountable for the reduced IL-22 production in CD4$^{+}$ T cells. Activation TLR5 pathway by flagellin could stimulate IL-22 production from ILCs.

Figure 45D:
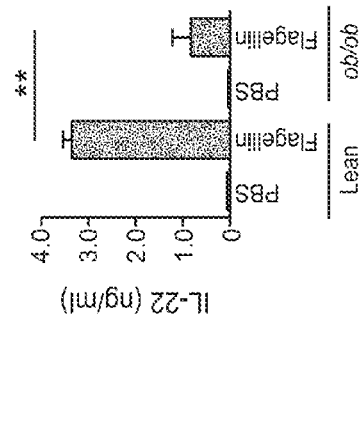
Figure 45E:
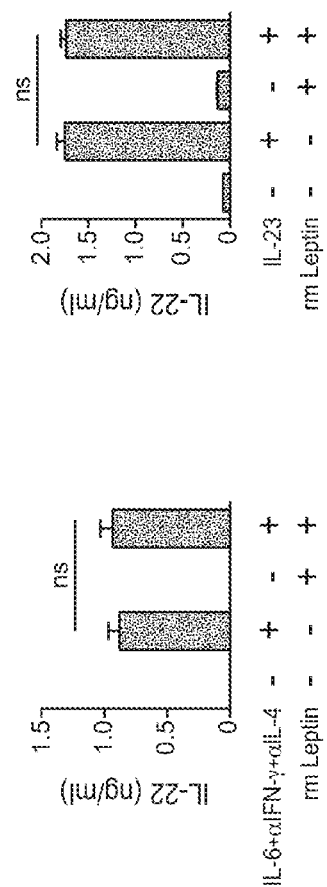

In db/db mice (FIG. 44E), ob/ob mice (FIG. 45E), and DIO mice (FIG. 44F), serum IL-22 level was significantly lower than that of WT mice upon in vivo challenge with flagellin. Consistent with the results from T cells, leptin itself did not enhance IL-22 production from ILCs in vitro (FIG. 45D). Taken together, these data suggested that there is a general defect in IL-22 induction from both ILCs and T cells in obese mice.

Example 13 The Mucosal Defense was Compromised in Leptin Deficient Mice and Restored by IL-22 Fc Fusion Protein IL-22 produced by ILCs and T cells is essential for host defense against *Citrobecter rodentium* infection in colon. The IL-22 induction in the colon from db/db and ob/ob mice infected with *C. rodentium* was analyzed. *C. rodentium* was cultured overnight and mice were orally inoculated with $2 \times 10^9$ CFU of bacteria as described (Zheng et al. 2008, Nature medicine 14, 282-289, doi:10.1038/nm1720). Bacterial burden was analyzed as follows: the spleen and liver of infected mice were harvested, weighted, and homogenized in 0.1% NP40/PBS in C-tube with gentle MACS (Miltenyi Biotec). Serially diluted homogenates were plated on MacConkey agar (Remel), and *C. rodentium* colonies were identified as pink colonies after overnight incubation at 37° C. Where indicated, the mice were injected intramuscularly with IL-22-Fc (150 µg/dose) or equivalent amount of mouse isotype control 3 times per week. Histology analysis of colon from mice infected with *C. rodentium* was performed as reported previously (Ota et al. 2011, Nature immunology 12, 941-948, doi:10.1038/ni.2089), and scored for epithelial changes (proliferation, blebbing, enterocyte shedding), inflammation, and mucosal thickening. Clinical scores were determined for four anatomic regions—proximal, middle and distal colon and rectum—on a scale from 0-5 with 0=normal colon and 5=severe disease. Regional scores were summed to get a final colon disease severity score for each animal.

Figure 46A:
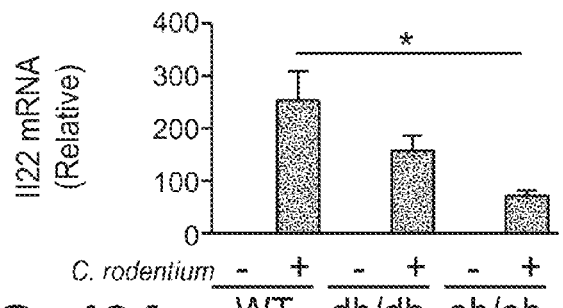
Figure 46B:
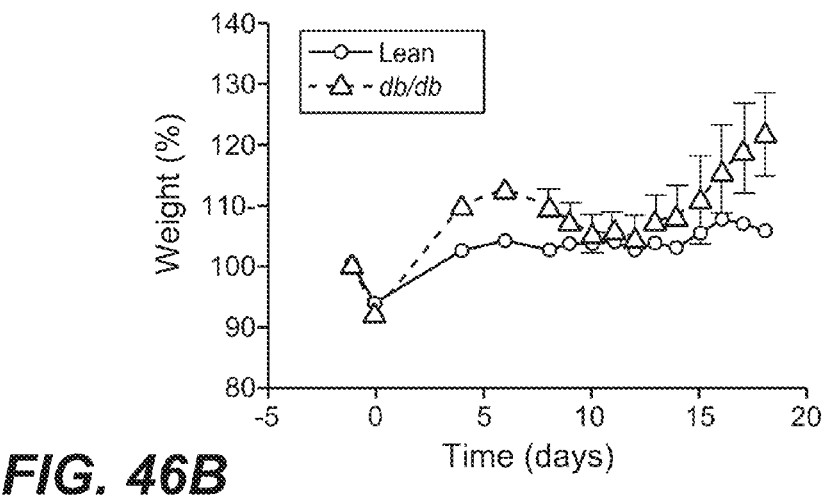
Figure 46C:
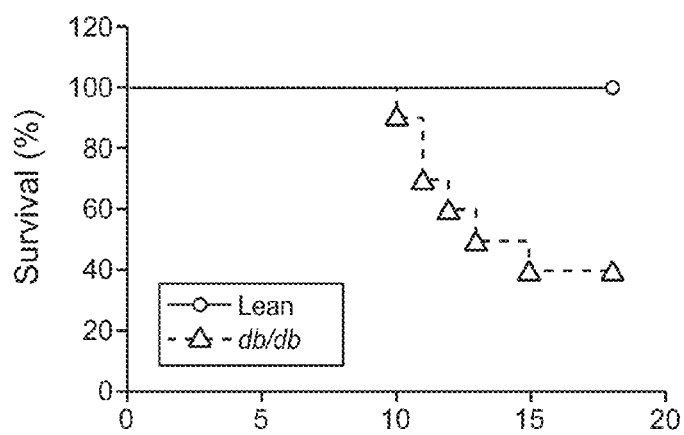
Figure 46D:
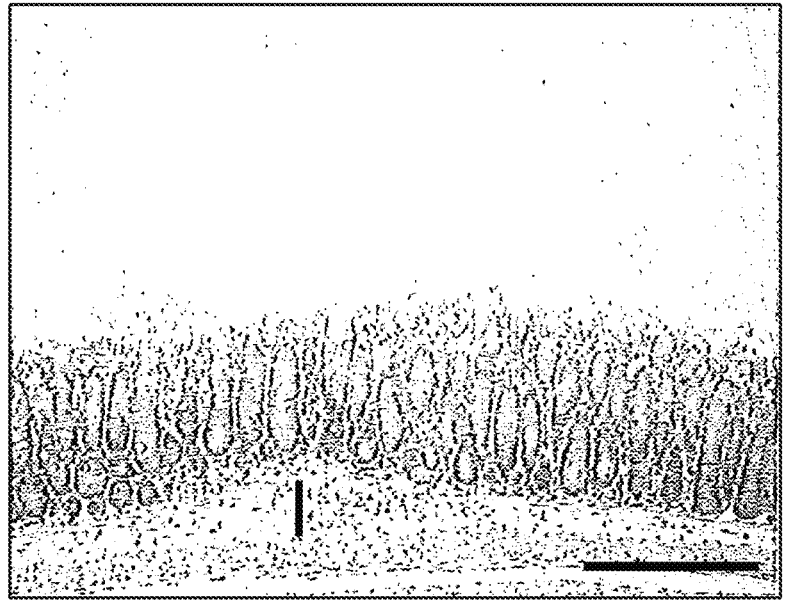
Figure 46E:
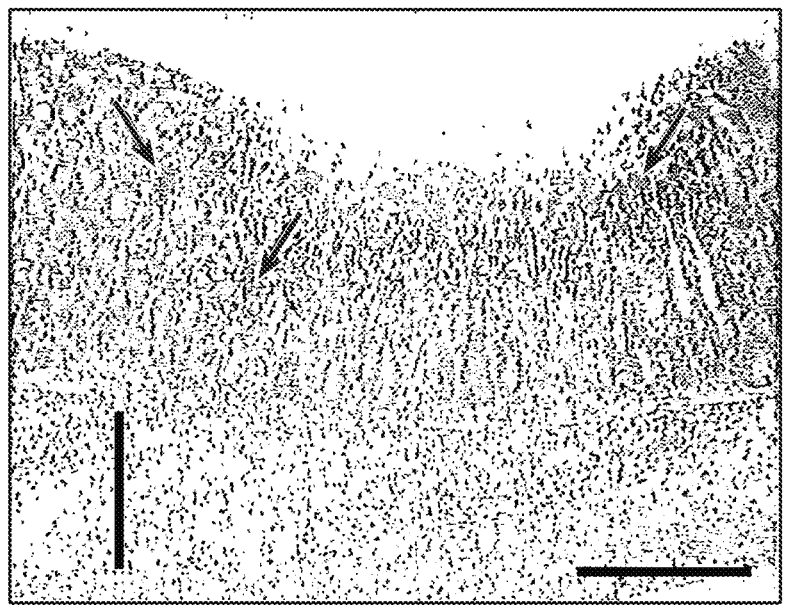
Figure 46F:
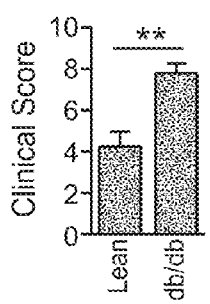
Figure 46G:
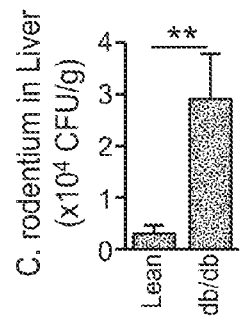
Figure 46H:
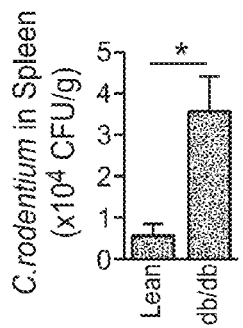

Corroborating with above results, the peak induction of IL-22 on day 4 in the colon in db/db and ob/ob mice was also significantly reduced, but not completely abolished (FIG. 46A). In db/db mice after oral inoculated with *C. rodentium* there was no significant weight loss (FIG. 46B). Surprisingly, the infected db/db mice started to die 10 days after bacterial inoculation, and about 60% to 100% db/db mice succumbed during the second week of the infection in repeated experiments (FIG. 46C). Histological analysis of the colon sections from db/db mice revealed increased inflammatory cell infiltration and severe epithelial damages, including epithelial shedding at the mucosal surface (FIGS. 46 D-F). In addition, these mice showed patchy submucosal edema and multifocal bacterial colonies, which were often associated with localized necrosis. Significantly elevated bacterial burdens were also detected in both the liver and spleen of db/db mice (FIGS. 46 G-H). Similar defects in mucosal defense were observed in ob/ob mice as well (FIG. 54). It was unexpected that db/db mice had such a significant defect in controlling *C. rodentium* infection; especially given the induction IL-22 by *C. rodentium* infection was only partially defective in these mice (see FIG. 46A).

It has been reported that Leptin deficient mice also have defects in B cell functions, and antibody against *C. rodentium* is required for eventually eliminating the bacteria from the host during the later phase of the infection. The production of anti-*C. rodentium* antibody in these mice was thus examined. The serum samples were harvested by bleeding from submandibular vein on day 10 after the infection. ELISA plate was coated with heat-killed *C. rodentium* or with a goat anti-mouse Ig capturing antibody. Coated plate was washed with washing buffer (0.05% Tween 20 in PBS), blocked for 2 h with blocking buffer (0.5% BSA, 15 ppm Proclin in PBS), and washed prior to the addition of serially diluted standard mouse monoclonal IgG (SouthernBiotech), or serum samples. After 2 h incubation at room temperature, plate was washed and the Ig were detected with goat anti-mouse IgG conjugated with horseradish peroxidase (HRP) (SouthernBiotech), diluted 1/4,000 in assay diluent (0.5% BSA, 0.05% Tween 20, 15 ppm Proclin in PBS), and incubated for 2 h at room temperature. After washing, TMB peroxidase substrate (Sigma-Aldrich) was added to each well. Absorbance was read at 650 nm in plate reader (Molecular Devices).

Figure 46I:
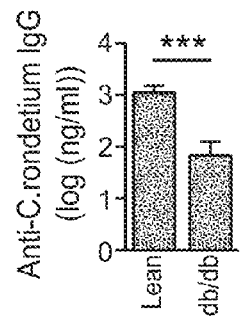
Figure 46J:
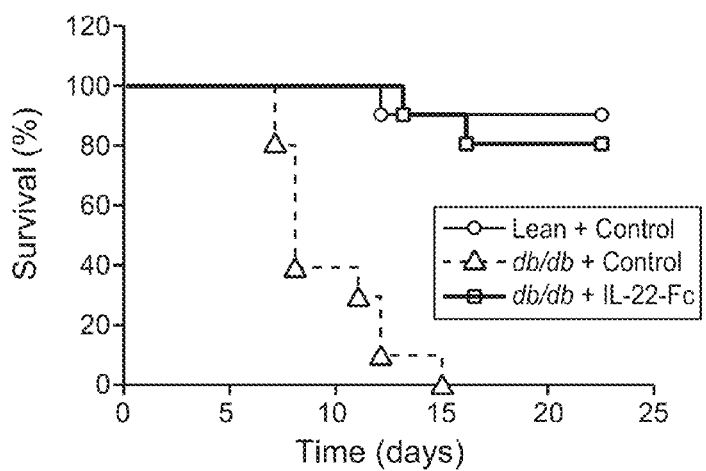

The titer of anti-*C. rodentium* IgG antibody was significantly reduced in the survived db/db mice on day 14 after the infection (FIG. 46I). However, the reduced anti-*C. rodentium* IgG production alone should also not result in the observed early mortality, since Rag2 deficient mice, which completely lack B cells and antibody production, can survive much longer after infection (Zheng et al. 2008, Nature medicine 14, 282-289). Therefore, the failed host defense against *C. rodentium* in db/db mice were likely caused by defects in both the adaptive antibody response and the induction of IL-22 from ILCs. Next, experiment was carried out to examine whether IL-22 was able to restore the mucosal immunity in db/db mice during *C. rodentium* infection with the administration of exogenous IL-22-Fc. As shown in FIG. 46 J, while the majority of the control IgG-treated db/db mice perished, almost all IL-22 Fc treated db/db mice survived the infection (FIG. 46J), supporting that IL-22 Fc was able to therapeutically restore the mucosal immune defects in db/db mice.

Example 14 IL-22 Fc Reduced Glucose Levels in Obese Mice and High Fat Diet-Fed Normal Mice As described in Example 9 above, IL-22 Fc reduced glucose levels in db/db mice that already developed hyperglycemia (FIG. 20A). The therapeutic benefit was persistent during the course of IL-22-Fc administration. After 3 weeks of treatment, the glucose level in these mice dropped below 200 mg/dl, close to the normal glucose level in WT mice, while the control protein treated db/db mice sustained their high glucose level. The reduction of glucose in IL-22 Fc treated mice was more obvious when the mice were fasted (FIG. 20C). IL-22 Fc treatment also resulted in a trend of weight loss or delayed weight gain compared to control treatment. However, at the end of this study, the weight difference between the two groups did not reach statistical significance in these mice (FIG. 20B). Corroborating with these data, IL-22 Fc treatment led significantly improved glucose tolerance and insulin sensitivity in glucose tolerance test and insulin tolerance test (FIG. 21 and FIG. 22, respectively).

To confirm general beneficial functions of exogenous IL-22 in modulation of metabolic disorders, IL-22 Fc was administered for 4 weeks to C57BL/6 mice that had been fed with HFD for at least 8 weeks to induce glucose intolerance. For the glucose tolerance test (GTT), mice were fasted overnight, and injected i.p. with glucose solution at 1.5 mg/kg. For the insulin tolerance test (ITT), mice were injected i.p. with insulin solution at 1.0 unit/kg. Blood glucose was measured before and after the injection. Blood glucose was measured by Contour (Bayer).

Figure 47A:
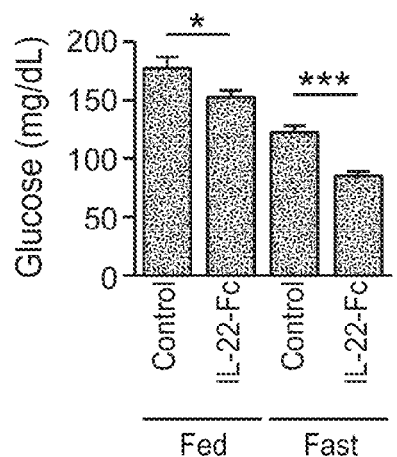
Figure 47B:
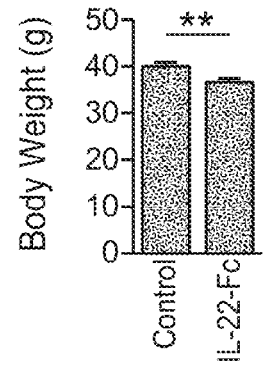

Consistent with the results from db/db mice, IL-22 Fc treatment significantly reduced serum glucose level, especially after fasting (FIG. 47A). There was also a reduced body weight (or delayed weight gain) in the IL-22 Fc treated group at the end of the study (FIG. 47B). In addition, IL-22

Figure 47C:
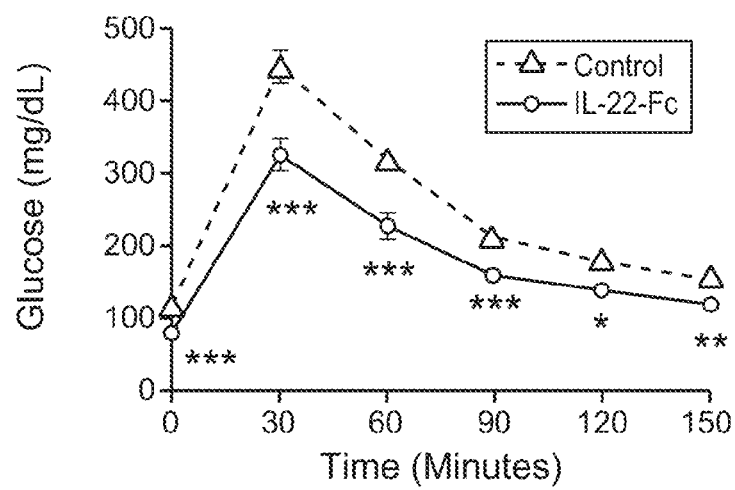
Figure 48C:
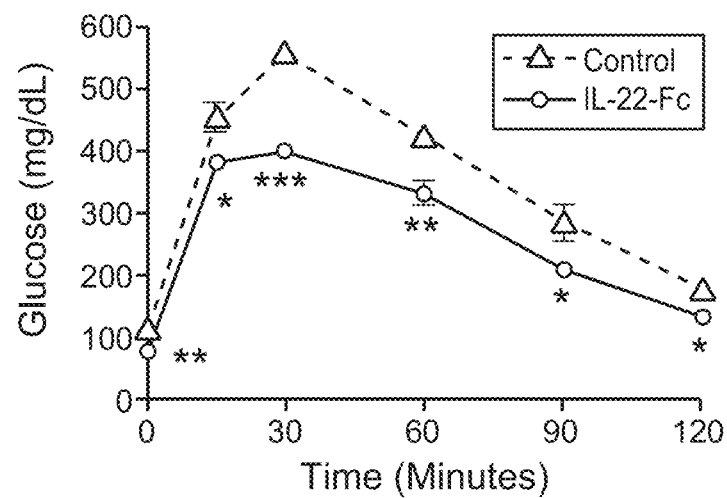
Figure 48D:
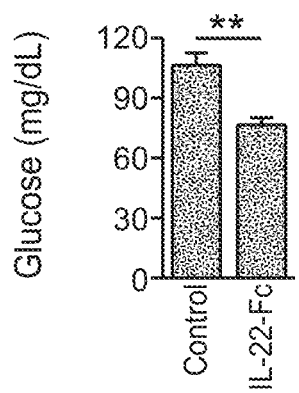
Figure 48E:
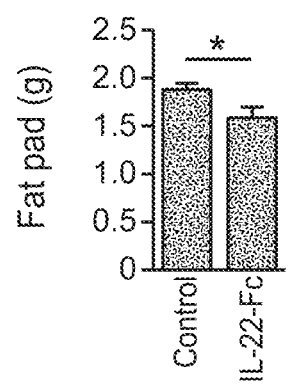

Fc reduced glucose intolerance and insulin resistance in HFD-fed C57BL/6 mice (FIGS. 47C and D). Similar results were obtained when mice were concurrently administrated with IL-22 Fc at the beginning of feeding with HFD (FIG. 48). Taken together, the data demonstrated that IL-22 Fc was a potential therapy to normalize serum glucose concentration, and alleviate glucose intolerance and insulin resistance in obese mice.

Example 15 IL-22 Fc Reduced Food Consumption and Increased Expression of PYY in Obese and HFD-Fed Mice The reduction of food consumption could reverse hyperglycemia and insulin resistance in diabetic mice. Indeed, db/db mice treated with IL-22 Fc showed significant reduction of food intake in comparison with the control group (FIG. 49A). Pair-feeding experiments were performed to ensure the same food intakes in the IL-22 Fc and control treated mice (FIG. 50). Food consumption was measured for ad lib-fed group daily during the study. The supplied food for pair-fed group was restricted to match the previous day food consumption of ad lib-fed group. Correspondingly, the treatment and measurement of pair-fed group was one day after ad lib-fed group.

Even under this condition, IL-22 Fc significantly reduced serum glucose although at a later time point (FIG. 49B), and reversed glucose tolerance in db/db mice (FIG. 49C), suggesting that modulating food consumption by IL-22 was not the only mechanism for its therapeutic effect in metabolic disease. Similar results were observed in HFD-fed mice (data not shown). To further understand how IL-22 regulated food consumption and metabolism, the expression of intestine hormones, PYY, which is known to inhibit food intake was examined.

Mice were injected i.p. with 50 μg IL-22-Fc on day 0 and 2. On day 4 mice were fasted overnight and re-fed for 1 h on day 5. Blood samples were collected on day 2 before treatment and on day 5 after feeding. All serum samples were mixed with Protease inhibitor (Sigma), DPPIV inhibitor (Millipore) and Pefabloc (Roche) immediately after collection. PYY was measured with PYY ELISA kit (Abnova) following manufacture's instruction. The results show that IL-22 Fc treatment significantly increased PYY concentration in the serum of db/db and HFD-fed mice (FIGS. 49 D and E). To demonstrate that IL22's effect on food intake was mediated through promoting PYY production, food intake in mice treated with PYY inhibitor BIIE0246 was examined. C57BL/6 mice on normal diet were either untreated or treated with IL-22 Fc on day 2 and day 4. After overnight fasting, food intake during a 4-hour feeding was measured. The results show that the reduction of food intake in IL-22 Fc treated mice was reversed by BIIE0246 (data not shown), indicating that the effect of IL-22 Fc on reduced food intake was mediated through the induction of PYY.

Example 16 IL-22 Fc Reduced Serum LPS and Liver ALT and AST and Increased Lipid Metabolism in Obese Mice Since IL-22 receptor is expressed in many organs including liver and pancreas that regulate metabolism, the therapeutic benefits of IL-22 in metabolic diseases are likely mediated by various mechanisms. Metabolic endotoxemia contributes to inflammatory status and insulin resistance and modulation of gut microbiota enhance glucose tolerance. Serum endotoxin was measured by Limulus Amebocyte Lysate assay kit, QCL-1000 (Lonza), following manufacture's instruction. ALT and AST were measured by Cholestech LDX (Alere). The results shown in FIG. 49F demonstrate that IL-22 Fc treatment resulted in significant reduction of the LPS amount in the serum from db/db mice.

Figure 51F:
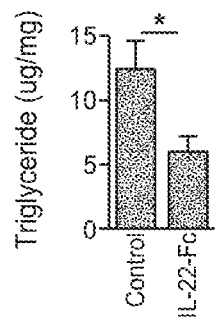
Figure 51G:
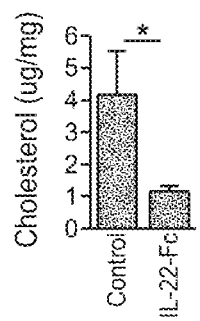
Figure 51H:
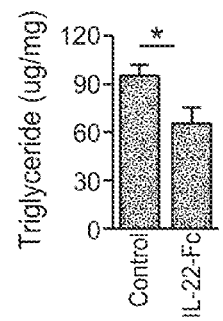
Figure 51I:
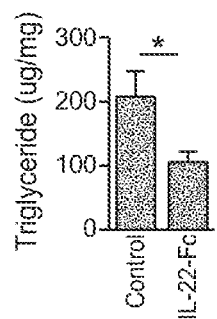
Figure 51J:
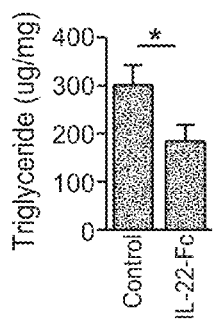

IL-22 can repress genes involved in lipogenesis and ameliorate liver steatosis. Serum ALT and AST levels were next examined. Blood glucose was measured by Contour (Bayer). ALT and AST were measured by Cholestech LDX (Alere). As shown in FIGS. 51A and B, IL-22 Fc treatment lowered ALT and AST levels in the serum in db/db (FIG. 51A) and HFD-fed (FIG. 51B) mice. The abdominal fat was also significantly dropped with IL-22 Fc treatment in HFD-fed mice (FIG. 51C). In addition, genes responsible for lipid metabolism were induced by IL-22 in primary adipocytes (FIG. 51D). Next, the effect of IL-22 on triglyceride and cholesterol in liver and adipose tissue were examined. The results show that IL-22 Fc reduced triglyceride, cholesterol, and free fatty acid (FFA) (FIG. 51E), as well as hepatic triglyceride (FIG. 51F), hepatic cholesterol (FIG. 51G) and triglyceride in white adipose tissue (FIG. 51H) in HFD-fed mice. Similarly, IL-22 reduced triglyceride in the liver and white adipose tissue in db/db mice (FIG. 51I and FIG. 51J). Further experiments show that IL-22 Fc treatment reduced inflammatory cytokines such as TNFα and IL-1β as compared to no treatment in obese mice (data not shown). H&E staining of liver sections revealed a decrease in hepatic periportal steatosis with IL-22 Fc fusion protein treatment (FIG. 26).

IL-22 signals through IL-22R1 and IL-10R2 chains. IL-22R1 can also be paired with IL-20R2 chain and be utilized by IL-20 and IL-24. It has been shown that all these ligands induced very similar downstream biological effects from skin epidermis (Sa et al., 2007, *J Immunol* 178, 2229-2240). Thus, both the IL-22 and IL-22R1 deficient mice were examined to avoid potential redundancy of other cytokines in HFD induced diabetes. The generation of IL-22R knock out mice is illustrated in FIG. 43 A. The deletion of IL-22R1 in the KO mice was confirmed by the absence of IL-22R1 mRNA in the IL-22R KO mice, and the lack of RegIIIb mRNA expression in response to IL-22 Fc in the IL-22R KO mice. See FIGS. 43 B and C. In addition, administration of IL-22-Fc to IL-22R KO mice did not induce pStat3 (data not shown).

No difference was observed in glucose tolerance and body weight in IL-22 deficient mice from those of WT littermate controls (FIG. 53). When IL-22R1 deficient mice were treated with high fat diets for three months, however, these mice developed significantly more severe glucose tolerance and gained more weight (FIGS. 49G, H and I), supporting a critical role of IL-22R pathway in controlling metabolism. The possibility of IL-20 and IL-24 redundancy in reducing metabolic syndrome was examined. In this experiment, db/db mice were treated with IL-20 Fc, IL-22 Fc or IL-24 Fc. The result indicates that only IL-22 Fc reduced serum glucose level (FIG. 55B) and improved glucose tolerance in a GTT assay on day 20 (FIG. 55C) in db/db mice, while treatment of db/db mice with IL-20 Fc or IL-24 Fc did not. The reduction of body weight was not statistically significant. Further experiments show that although IL-20 Fc and IL-24 induced pStat3 in primary adipocytes, these cytokines failed to induce pStat3 in liver tissue from db/db mice that had become insensitive to insulin (data not shown). Treatment of IL-22 Fc in the IL-22R KO mice had no effect in a glucose tolerance test, confirming that the effect of IL-22 Fc was exerted through the IL-22 R signaling (data not shown).

The studies presented here indicate critical functions of IL-22 in regulating metabolic processes. IL-22R1 deficient mice were predisposed to development of metabolic syndromes. Exogenous IL-22 was not only able to restore the mucosal immune defects in preclinical diabetic models, but also helped to normalize glucose and lipid metabolisms. IL-22, thus, can provide a novel therapeutic approach to treat human metabolic disorders.

Example 17 Comparison of VGEF and IL-22 in Promoting Wound Healing in db/db Mice In this experiment, the effect of IL-22 on promoting or improving wound healing was analyzed and compared with that of VEGF. Female BKS.Cg-Dock7$^m$+/+ Lepr$^{db}$/J db/db mice of 11 weeks of age were purchased from Jackson Laboratory, Bar Harbor, Me. All experimental animal studies were conducted under the approval of the Institutional Animal Care and Use Committees of Genentech Lab Animal Research. Under isoflurane anesthesia the dorsal skin was shaved then depilatory cream was applied to remove the remaining stubble. After the skin is cleaned and prepped with povidone-iodine followed by alcohol swabs, a circular, full-thickness wound was created on the dorsal skin of each mouse using a disposable 6 mm biopsy punch (Miltex, Inc.). The wound was covered with a Tegaderm film before and after treatment.

Figure 56B:
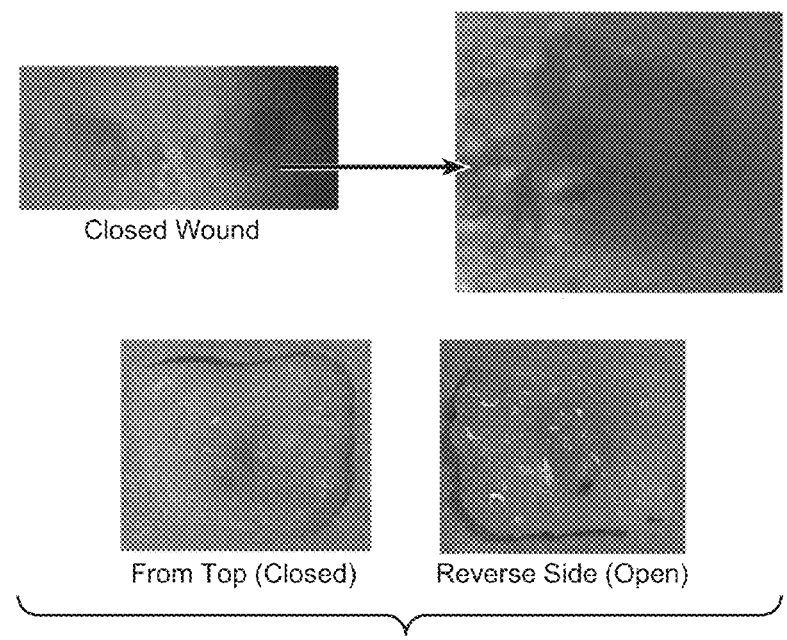
Figure 57A:
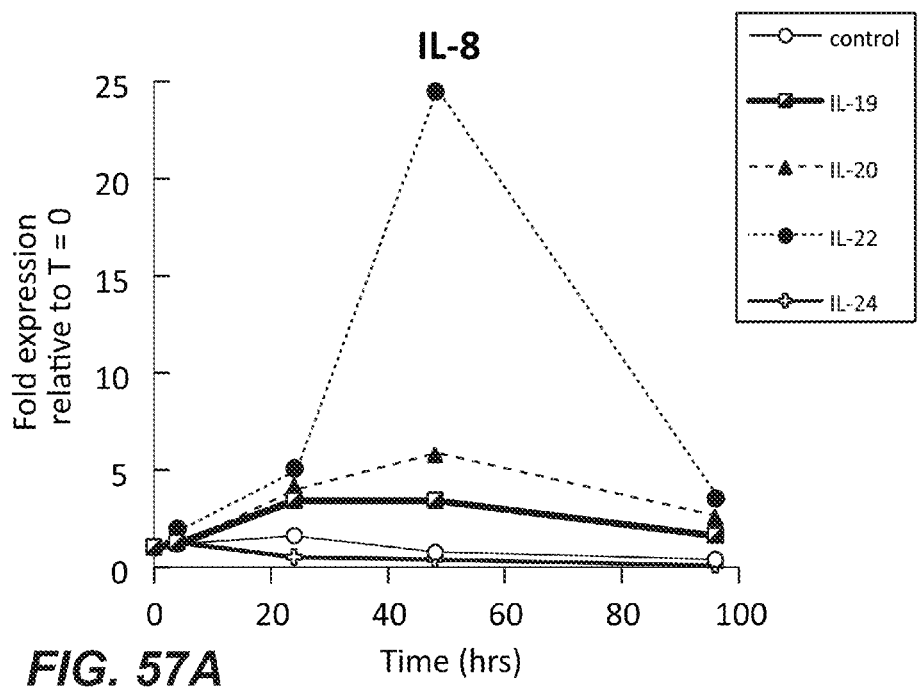
Figure 57B:
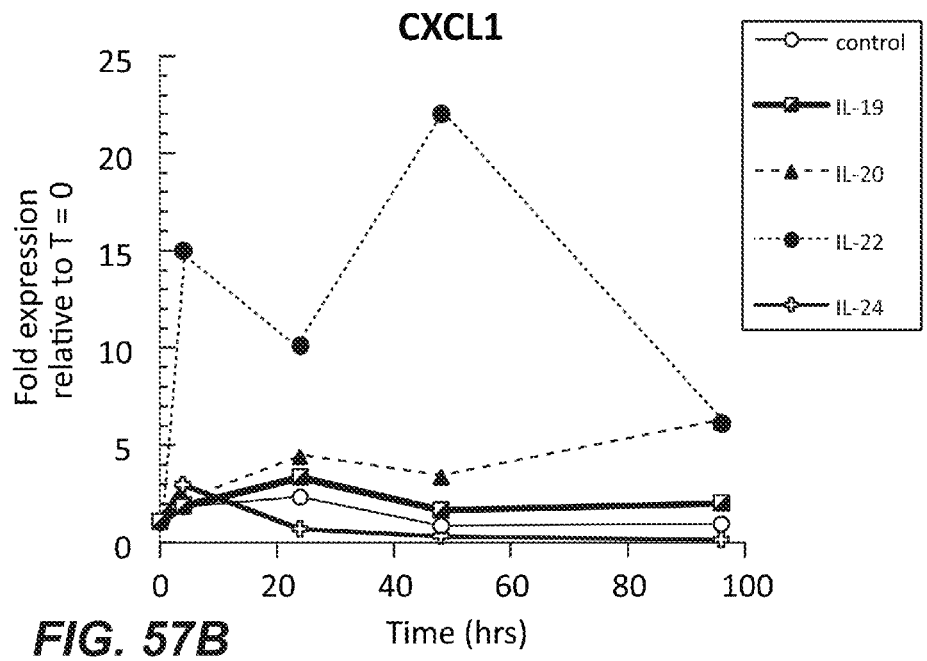
Figure 57C:
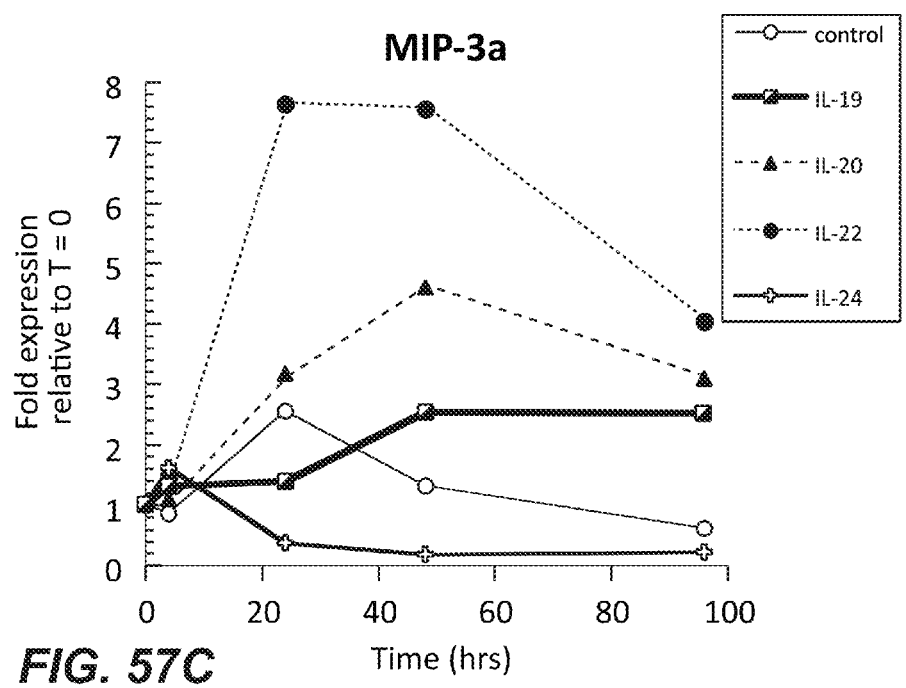
Figure 57D:
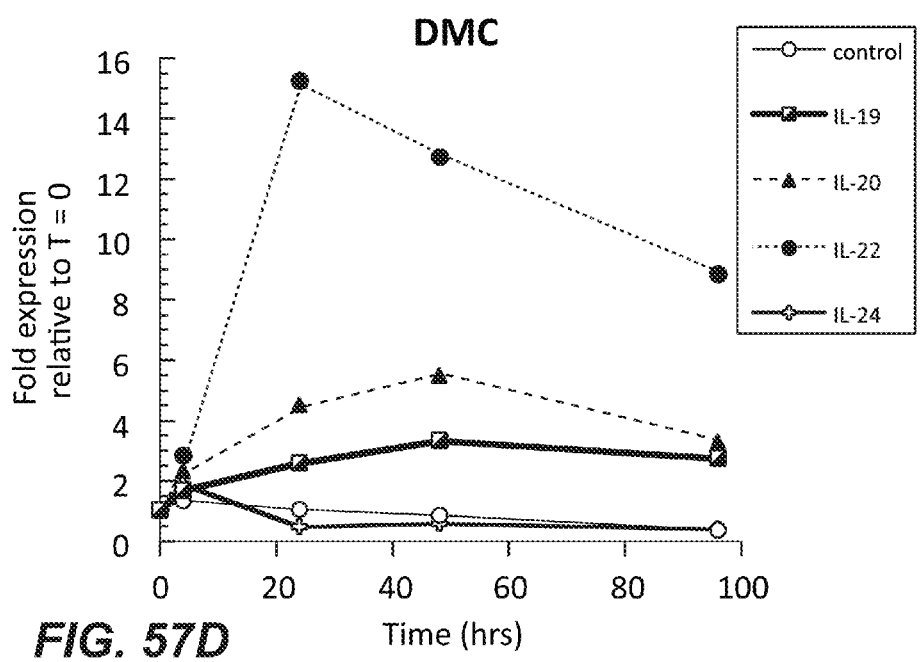
Figure 57E:
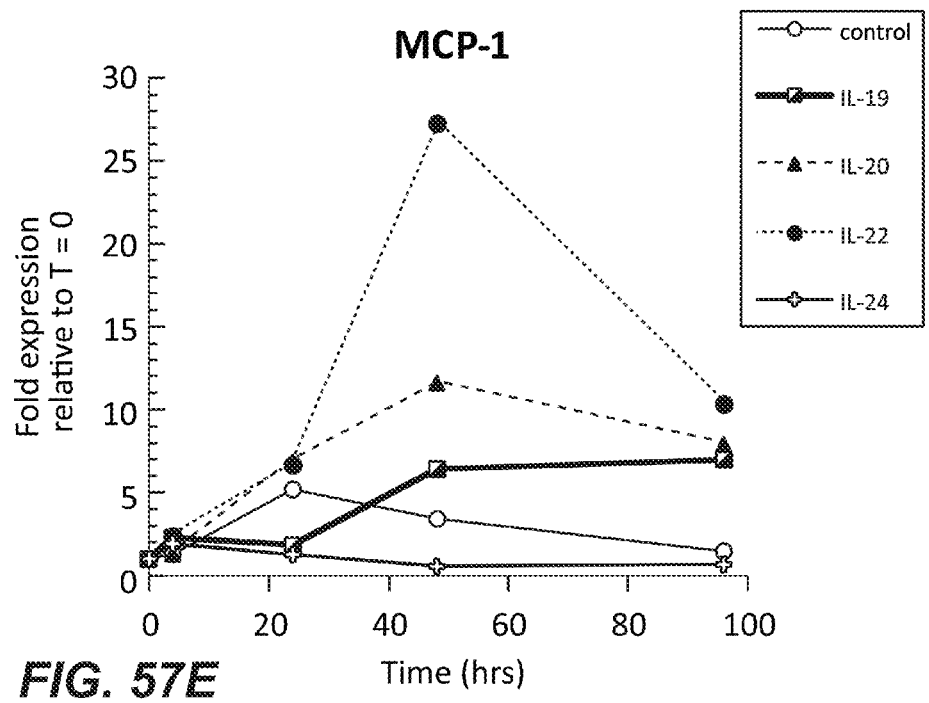

The results in FIG. 56 show that VEGF appeared to achieve faster surface closure as compared with IL-22; however, when the dermis side of the skin was examined, wounds treated with VEGF remained open even on day 21 (FIG. 56B). The ability of VEGF and IL-22 Fc in promoting angiogenesis at the wound site was also analyzed. In this experiment, two 6 mm wounds were excised in db/db mice on day 0. On day 2, 4, 6, 8, 10 and 12, either control anti-ragweed antibody or IL-22 Fc (50 µg) or VEGF (20 µg) in saline was administered topically onto the wounds. On day 6 and 12, three mice from each group were taken down for histology and immunohistochemistry analysis and BrdU staining. On day 16, one mouse was taken down for BrdU staining. On day 18, 20 and 22, one mouse from each group was taken down for each time point for immunohistochemistry analysis and CD31 whole tissue staining. The results indicate that both VEGF and IL22-Fc, but not the control anti-ragweed antibody, promoted blood vessel formation at the wound site as analyzed by CD31 tissue immunostaining (data not shown).

Next, we analyzed IL-22-induced and other IL-10 family member-induced cytokine and chemokine expression in reconstituted epidermis. The reconstituted epidermis was EpiDerm RHE tissue models maintained in EPI-100-NMM medium purchased from MatTek. See Sa et al. 2007, *J. Immunol.* 178:2229-2240. The results show that IL-22 prominently induced expression of IL-8, CXCL-1, MIP 3a, DMC, and MCP-1 in reconstituted human epidermis, though inductions by IL-19, IL-20 or IL-24 were also observed (FIG. 57). In view of the effect of IL-22 on wound healing described herein, IL-19, IL-20, and IL-24 may also play a role in accelerating wound healing.

Example 18 IL-22 Provides Superior Efficacy in the Treatment of Infected Wound than VEGF and PDGF in a Splinted Wound Model in db/db Mice In the mouse wound healing model, contraction accounts for a large part of wound closure in mice because mice skin is mobile. To more closely resemble the wound healing process in human, a mouse splinted wound model was established in which a silicon ring was glued to the skin and anchored with sutures around the wound to prevent local skin contraction (see representative images in FIG. 59B). See e.g., Zhao et al., 2012, Wound Rep. Reg. 20:342-352 and Brubaker et al., 2013, J. Immunol., 190:1746-57. In this model, wounds healed through granulation and re-epithelialization processes, similar to the wound healing processes in humans. To splint the wound, Krazy glue (Elmer's Products, Inc.) was applied to one side of the sterile silicone splint (Grace Bio-Labs, Inc.) and the splint was carefully placed around the wound with the glue side down so that the wound was centered within the splint. The glue bonded to the skin on contact and served as a splint for the entire course of the study. The splint was further anchored to the skin with four interrupted 6.0 monofilament nylon suture (Ethicon, Inc.). Digital image of the wound was taken before the wound was covered with a Tegaderm transparent film. Further, microbial infection on the open wound can delay wound healing, and chronic wounds, such as chronic wounds observed in diabetic patients, are often infected wounds.

Using the splinted wound model, the effect of IL-22 Fc on infected wound was examined in db/db mice. Wounds excised as described above in wild type or db/db mice were inoculated topically with $0.5\times10^6$ CFU, $1\times10^6$ CFU (plaque forming unit) or $2\times10^6$ CFU of *Staphylococcus aureus* two days after wound excision. As shown in FIG. 58, db/db mice exhibited delayed wound healing as compared to wild type mice, and wound healing was further delayed when the wound was infected by bacteria in these mice as compared to control.

In separate experiments, IL-22's wound healing effect was compared with other agents in the splinted infected wound model. Two days after wound excision, the methicillin-resistant *S. aureus* strain USA300 NRS 384 (NARSA) at $1\times10^6$ CFU in 30 ul saline was inoculated onto the wound surface and covered again with a Tegaderm film. Topical treatment began 48 hours after *S. aureus* infection with 30 ug of either IL22-Fc or VEGF (Lot #110308, Genentech) or PDGF (Lot #0507CY420, PeproTech, Inc.) in 30 ul of saline 3 times a week thereafter. Digital images of the wound were recorded before treatment and twice a week after treatment until closure of the wounds. Percentage of wound closure was calculated from the wound images using ImageJ, a java-based image processing program developed at the NIH.

As shown in FIG. 59, IL-22 Fc promoted faster wound healing than VEGF when same amount of the compounds was applied to infected wounds in the splinted wound model, which more closely resembled wound healing in human. Next, different doses of VEGF and IL-22 Fc were tested on infected wounds. In this experiment, one 6 mm diameter splinted excisional wound was created in db/db mice with blood glucose >300 mg/dl. At each wound $1\times10^6$ CFU of *S. aureus* USA 300 was inoculated. Varying doses of VEGF or IL-22 Fc in saline were administered topically three times per week until wound closure. Saline was used as a control. At wound closure, mice were sacrificed and samples were subjected to histology, immune-histochemistry, and PCR analysis and CFU count. The results in FIG. 60 show that IL-22 Fc at the amount of 30 µg demonstrated better infected wound healing efficacy than 60 µg VEGF. Thus, the faster surface closure by VEGF observed in a non-splinted wound model was likely due to mouse skin contraction and the effects of IL-22 Fc on promoting keratinocyte proliferation and re-epithelializatin were likely masked by mouse skin contraction.

Similar results are shown in FIG. 61, in which IL-22 Fc was demonstrated of having superior efficacy than VEGF and PDGF when the same amount (30 µg) of each compound was applied to the wound. Complete wound closure in IL-22 Fc treated infected splinted wound was seen on day 15. In VEGF- or PDGF-treated mice, however, complete closure of infected splinted wound was not seen until day 25, same as untreated uninfected wound. Wound closure in the control group, i.e., untreated infected wound, was not seen until day 29. Without being limited to specific mechanism(s), the superiority of IL-22 Fc in promoting wound healing than VEGF or PDGF can be due to its effects on re-epithelialization, promoting keratinocyte proliferation, induction of neovascularization, induction of proteases to facilitate tissue remodeling and, repair and the antimicrobial activities.

Next, we tested whether IL-22 Fc can be administered in a gel formulation for wound healing. The exemplary gel formulation used in this experiment contained 10 mM sodium phosphate at pH 7.1 with 0.5 mg/g Methionine and 3% Hydroxypropyl methylcellulose (HPMC E4M premium from Dow Chemicals), with or without 1 mg/g IL-22 Fc. The gel solution and IL-22 Fc solution were mixed prior to being applied topically to the splinted wound. The formulation containing IL-22 Fc also contained a small amount of sucrose (<20 mM) and P20 (<0.002%) carried from the original protein formulation. The results shown in FIG. 62 demonstrate that IL-22 Fc in both solution and gel formulation promoted wound healing in a non-infected splinted wound.

The specification is considered to be sufficient to enable one skilled in the art to practice the invention. Although the foregoing invention has been described in some detail by way of illustration and example for purposes of clarity of understanding, the descriptions and examples should not be construed as limiting the scope of the invention. Indeed, various modifications of the invention in addition to those shown and described herein will become apparent to those skilled in the art from the foregoing description and fall within the scope of the appended claims.

What is claimed is:

1. A method of treating IBD, the method comprising administering to a subject in need thereof a therapeutically effective amount of an IL-22 Fc fusion protein comprising an IL-22 polypeptide linked to an IgG4 Fc region by a linker, wherein the Fc region is not glycosylated, and wherein the linker consists of the amino acid sequence RVESKYGPP (SEQ ID NO: 44).

2. A method of treating IBD, the method comprising administering to a subject in need thereof a therapeutically effective amount of an IL-22 Fc fusion protein consisting of the amino acid sequence of SEQ ID NO:16.

3. The method of claim 2 or 1, wherein the IBD is ulcerative colitis.

4. The method of claim 2 or 1, wherein the IBD is Crohn's disease.

5. A method of treating IBD, the method comprising administering to a subject in need thereof a therapeutically effective amount of an IL-22 Fc fusion protein consisting of the amino acid sequence of SEQ ID NO:8.

6. A method of treating inflammatory bowel disease (IBD), the method comprising administering to a subject in need thereof a therapeutically effective amount of an IL-22 Fc fusion protein, the IL-22 Fc fusion protein comprising an IL-22 polypeptide linked by a linker to an IgG4 Fc region that is not glycosylated, wherein the IL-22 Fc fusion protein binds to IL-22 receptor and comprises an amino acid sequence having at least 98% sequence identity to the amino acid sequence of SEQ ID NO:8, and wherein the linker consists of the amino acid sequence RVESKYGPP (SEQ ID NO: 44).

7. The method of claim 6, wherein the amino acid sequence of the IL-22 Fc fusion protein has at least 99% sequence identity to the amino acid sequence of SEQ ID NO:8.

8. The method of claim 6, wherein the IL-22 Fc fusion protein comprises the amino acid sequence of SEQ ID NO:10.

9. The method of claim 6, wherein the IL-22 Fc fusion protein comprises the amino acid sequence of SEQ ID NO:16.

10. The method of claim 6, wherein the IL-22 polypeptide is a human IL-22 polypeptide.

11. The method of claim 6, wherein the IL-22 polypeptide comprises the amino acid sequence of SEQ ID NO:4.

12. The method of claim 6, wherein the IL-22 receptor is a human IL-22 receptor.

13. The method of claim 6, wherein the amino acid residue at position 297 as in the EU index of the IgG4 Fc region is Gly.

14. The method of claim 6, wherein the amino acid residue at position 297 as in the EU index of the IgG4 Fc region is Ala.

15. The method of claim 6, wherein the IL-22 Fc fusion protein is a dimeric IL-22 Fc fusion protein.

16. The method of claim 6, wherein the IL-22 Fc fusion protein is a monomeric IL-22 Fc fusion protein.

17. The method of claim 6, wherein the IL-22 Fc fusion protein is administered in a formulation comprising a pharmaceutically acceptable carrier.

18. The method of claim 6, wherein the subject is administered at least one additional therapeutic agent.

19. The method of claim 6, wherein the IL-22 Fc fusion protein is administered intravenously.

20. The method of claim 6, wherein the IL-22 Fc fusion protein is administered subcutaneously.

21. The method of claim 6, wherein the IL-22 Fc fusion protein is administered intraperitoneally.

22. The method of claim 6, wherein the IBD is ulcerative colitis.

23. The method of claim 6, wherein the IBD is Crohn's disease.

24. The method of claim 6, wherein the subject is a human.

25. A method of treating IBD, the method comprising administering to a subject in need thereof a therapeutically effective amount of an IL-22 Fc fusion protein comprising the amino acid sequence of SEQ ID NO:8.

26. The method of any one of claims 5, 2, 1 wherein the subject is a human.

27. A method of treating ulcerative colitis, the method comprising administering to a subject in need thereof a therapeutically effective amount of an IL-22 Fc fusion protein comprising the amino acid sequence of SEQ ID NO:8.

28. A method of treating ulcerative colitis, the method comprising administering to a subject in need thereof a therapeutically effective amount of an IL-22 Fc fusion protein consisting of the amino acid sequence of SEQ ID NO:8.

29. A method of treating Crohn's disease, the method comprising administering to a subject in need thereof a therapeutically effective amount of an IL-22 Fc fusion protein comprising the amino acid sequence of SEQ ID NO:8.

30. A method of treating Crohn's disease, the method comprising administering to a subject in need thereof a therapeutically effective amount of an IL-22 Fc fusion protein consisting of the amino acid sequence of SEQ ID NO:8.

* * * * *

UNITED STATES PATENT AND TRADEMARK OFFICE
CERTIFICATE OF CORRECTION

PATENT NO. : 10,160,793 B2
APPLICATION NO. : 14/214161
DATED : December 25, 2018
INVENTOR(S) : Justin Scheer et al.

It is certified that error appears in the above-identified patent and that said Letters Patent is hereby corrected as shown below:

On the Title Page

Page 2, under FOREIGN PATENT DOCUMENTS, in JP 2011-50310, replace "2011-50310" with --2011-503102--.

Page 4, under OTHER PUBLICATIONS, in Lowman et al., replace "!Biochem" with --Biochem--.

Page 5, under OTHER PUBLICATIONS, in So jar et al., replace "Soj ar" with --Sojar--;

in Zhao et al., replace "biofllm" with --biofilm--;

in Brandi et al., replace "Brandi" with --Brandl--;

in Fisher, replace "523" with --S23--.

In the Specification

Column 2, Line 43, replace "2):5419-20" with --2):S419-20--.

Column 17, Line 45, replace "(1-J)" with --(I-J)--;

Line 49, replace "13" with --β--.

Column 21, Line 41, replace "IL-22Ra1" with --IL-22Rα1--.

Column 38, Line 28, replace "IL-221 g" with --IL-22 lg--;

Line 35, replace "formation Inhibition" with --formation. Inhibition--.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,160,793 B2

Column 44, Line 28, replace "H is" with --His--.

Column 47, Line 24, replace "5400" with --S400--.

Column 54, Line 41, replace "$XC_L$" with --$XC_H$--;

Line 43, replace "$VC_HC_H$, $LC_L$" with --$V_HC_H$, $V_LC_L$--.

Column 55, Line 28, replace "$A_\alpha A_\beta C_L$" with --$A_\alpha A_\beta C_H$--;

Line 45, replace "$XC_L$" with --$XC_H$--.

Column 56, Line 4, replace "$A\alpha A_\beta C_L$" with --$A_\alpha A_\beta C_L$--.

Column 57, Line 30, replace "L1" with --Li--.

Column 59, Lines 37-38, replace "formation Inhibition" with --formation. Inhibition--.

Column 80, Line 20, replace "EPKS $\overline{S}$ DKTHT" with --EPKS$\underline{S}$DKTHT--.

Column 90, Line 52, replace "P<0.0001" with --$P \leq 0.0001$--.

Column 91, Line 4, replace "ng" with --µg--;

Line 6, replace "ng" with --µg--;

Line 36, replace "11-22" with --IL-22--;

Line 58, replace "Dockr" with --Dock7$^m$--;

Line 64, replace "IL-22Ra1" with --IL-22Rα1--;

Line 48, replace "staining IL-22" with --staining. IL-22--.

Column 92, Line 32, replace "Rp119" with --Rpl19--.

Column 93, Line 18, replace "gentle MACS" with --gentleMACS--.

In the Claims

Column 177, Line 57, Claim 3, replace "claim 2 or 1" with --claim 1 or 2--;

Line 59, Claim 4, replace "claim 2 or 1" with --claim 1 or 2--.

Column 180, Line 5, Claim 26, replace "claims 5, 2, 1 wherein" with --claims 1, 2, and 5, wherein--.